US011648261B2

(12) United States Patent
Peyman

(10) Patent No.: US 11,648,261 B2
(45) Date of Patent: *May 16, 2023

(54) METHOD OF TREATING, REDUCING, OR ALLEVIATING A MEDICAL CONDITION IN A PATIENT

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/180,784

(22) Filed: Feb. 20, 2021

(65) Prior Publication Data
US 2021/0228619 A1 Jul. 29, 2021

Related U.S. Application Data

(63) Continuation-in-part of application No. 16/861,128, filed on Apr. 28, 2020, now Pat. No. 10,925,889, which is a continuation-in-part of application No. 16/246,618, filed on Jan. 14, 2019, now Pat. No. 11,045,352, which is a continuation-in-part of application No. 15/816,140, filed on Nov. 17, 2017, now Pat. No. 10,278,920, which is a continuation-in-part of application No. 15/653,053, filed on Jul. 18, 2017, now Pat. No. 10,206,569, which is a continuation-in-part of application No. 15/631,219, filed on Jun. 23, 2017, now Pat. No. 10,195,081, which is a continuation-in-part of application No. 15/285,375, filed on Oct. 4, 2016, now Pat. No. 9,744,029, which is a continuation-in-part of application No. 15/230,445, filed on Aug. 7, 2016, now Pat. No. 9,937,033, which is a continuation-in-part of application No. 14/709,801, filed on May 12, 2015, now Pat. No. 9,427,355.

(60) Provisional application No. 63/131,761, filed on Dec. 29, 2020, provisional application No. 63/106,319, filed on Oct. 27, 2020, provisional application No. 63/077,677, filed on Sep. 13, 2020, provisional application No. 63/055,770, filed on Jul. 23, 2020, provisional application No. 63/039,959, filed on Jun. 16, 2020, provisional application No. 63/016,258, filed on Apr. 27, 2020, provisional application No. 62/839,738, filed on Apr. 28, 2019, provisional application No. 62/617,251, filed on Jan. 14, 2018, provisional application No. 62/423,734, filed on Nov. 17, 2016, provisional application No. 62/363,382,
(Continued)

(51) Int. Cl.
A61P 31/14 (2006.01)
A61K 9/00 (2006.01)
A61K 31/706 (2006.01)
A61K 31/4045 (2006.01)
A61K 31/727 (2006.01)
A61K 31/5415 (2006.01)
A61K 31/225 (2006.01)
A61K 31/343 (2006.01)
A61K 31/353 (2006.01)
A61K 45/06 (2006.01)
A61K 33/30 (2006.01)
A61K 9/50 (2006.01)
C07K 16/08 (2006.01)

(52) U.S. Cl.
CPC .......... *A61K 31/727* (2013.01); *A61K 9/0053* (2013.01); *A61K 9/5031* (2013.01); *A61K 9/5036* (2013.01); *A61K 31/225* (2013.01); *A61K 31/343* (2013.01); *A61K 31/353* (2013.01); *A61K 31/5415* (2013.01); *A61K 33/30* (2013.01); *A61K 45/06* (2013.01); *C07K 16/08* (2013.01)

(58) Field of Classification Search
None
See application file for complete search history.

(56) References Cited

U.S. PATENT DOCUMENTS 3,760,807 A 9/1973 Neefe
4,563,779 A 1/1986 Kelman
(Continued)

FOREIGN PATENT DOCUMENTS

CA 2662943 A1 10/2009
EP 1616568 A2 1/2016
(Continued)

OTHER PUBLICATIONS

Xu, Jimin, et al. "Broad spectrum antiviral agent niclosamide and its therapeutic potential." ACS infectious diseases 6.5 (Mar. 3, 2020): 909-915. (Year: 2020).*
(Continued)

*Primary Examiner* — Bethany P Barham
*Assistant Examiner* — Peter Anthopolos
(74) *Attorney, Agent, or Firm* — The Law Office of Patrick F. O'Reilly III, LLC

(57) ABSTRACT

A method of treating, reducing, or alleviating a medical condition in a patient is disclosed herein. The method includes administering to a patient in need thereof a biocompatible drug comprising one or more antiviral medications together with one or more cell pathway inhibitors, the patient having at least one of a respiratory tract inflammatory disease, a central nervous system inflammatory disease, and vasculitis. The one or more antiviral medications preventing an attachment of viruses to cell walls, blocking a penetration of the viruses into cells, and/or inhibiting virus replication by damaging nucleic acids of the viruses. The one or more cell pathway inhibitors blocking an inflammatory response of inflamed tissue without inhibiting an immune response of the patient.

23 Claims, 34 Drawing Sheets

Related U.S. Application Data filed on Jul. 18, 2016, provisional application No. 62/360,439, filed on Jul. 10, 2016, provisional application No. 62/360,281, filed on Jul. 8, 2016, provisional application No. 62/353,632, filed on Jun. 23, 2016, provisional application No. 62/065,714, filed on Oct. 19, 2014, provisional application No. 61/991,785, filed on May 12, 2014.

(56) References Cited

U.S. PATENT DOCUMENTS

| | | |
|---|---|---|
| 4,665,913 A | 5/1987 | L'Esperance, Jr. |
| 4,718,418 A | 1/1988 | L'Esperance, Jr. |
| 4,793,344 A | 12/1988 | Cumming et al. |
| 4,799,931 A | 1/1989 | Lindstrom |
| 4,840,175 A | 6/1989 | Peyman |
| 4,842,599 A | 6/1989 | Bronstein |
| 4,903,695 A | 2/1990 | Warner et al. |
| 4,994,058 A | 2/1991 | Raven et al. |
| 5,171,318 A | 12/1992 | Gibson et al. |
| 5,336,261 A | 8/1994 | Barrett et al. |
| 5,552,452 A | 9/1996 | Khadem |
| 5,702,441 A | 12/1997 | Zhou |
| 5,964,748 A | 10/1999 | Peyman |
| 6,102,946 A | 8/2000 | Nigam |
| 6,110,166 A | 8/2000 | Juhasz |
| 6,180,687 B1 | 1/2001 | Hammer |
| 6,197,019 B1 | 3/2001 | Peyman |
| 6,537,545 B1 | 3/2003 | Karageozian et al. |
| 6,551,307 B2 | 4/2003 | Peyman |
| 7,001,374 B2 | 2/2006 | Peyman |
| 7,004,902 B2 | 2/2006 | Luce |
| 7,044,945 B2 | 5/2006 | Sand |
| 7,083,802 B2 | 8/2006 | Peyman |
| 7,598,288 B2 | 10/2009 | Hellberg et al. |
| 8,632,489 B1 | 1/2014 | Ahmed |
| 8,911,768 B2 | 12/2014 | Whitcup et al. |
| 8,986,738 B2 * | 3/2015 | Meinert ............... A61K 9/0073 424/489 |
| 9,249,424 B2 | 2/2016 | Wolf et al. |
| 9,301,925 B2 | 4/2016 | Xu et al. |
| 9,370,446 B2 | 6/2016 | Peyman |
| 9,427,355 B1 | 8/2016 | Peyman |
| 9,486,357 B2 | 11/2016 | Peyman |
| 9,814,567 B2 | 11/2017 | Peyman |
| 9,861,521 B2 | 1/2018 | de Juan, Jr. et al. |
| 9,931,171 B1 | 4/2018 | Peyman |
| 10,980,756 B1 * | 4/2021 | Glick ................. A61K 31/4706 |
| 2001/0027314 A1 | 10/2001 | Peyman |
| 2002/0006394 A1 | 1/2002 | Redmond et al. |
| 2002/0071856 A1 | 6/2002 | Dillingham |
| 2002/0123744 A1 | 9/2002 | Reynard |
| 2003/0035843 A1 | 2/2003 | Livesey et al. |
| 2004/0029855 A1 | 2/2004 | Klaveness et al. |
| 2004/0049174 A1 | 3/2004 | Peyman |
| 2004/0234457 A1 * | 11/2004 | Rennie ................... A61K 45/06 424/46 |
| 2005/0070942 A1 | 3/2005 | Perez |
| 2005/0246018 A1 | 11/2005 | Grubbs |
| 2006/0110428 A1 | 5/2006 | deJuan et al. |
| 2006/0135477 A1 | 6/2006 | Haitjema |
| 2006/0166919 A1 | 7/2006 | Shepard et al. |
| 2007/0135754 A1 | 6/2007 | Akiyama et al. |
| 2007/0142908 A1 | 6/2007 | Xu |
| 2007/0255404 A1 | 11/2007 | Pinchuk |
| 2009/0171305 A1 | 7/2009 | El Hage |
| 2009/0177139 A1 | 7/2009 | Boyden et al. |
| 2009/0196903 A1 | 8/2009 | Kliman |
| 2009/0208577 A1 | 8/2009 | Xu et al. |
| 2009/0253661 A1 | 10/2009 | Peyman |
| 2009/0263899 A1 | 10/2009 | Steinfeld et al. |
| 2009/0287005 A1 | 11/2009 | Baker, Jr. et al. |
| 2010/0087920 A1 | 4/2010 | Marmo |
| 2010/0198348 A1 | 8/2010 | Hiles et al. |
| 2010/0210996 A1 | 8/2010 | Peyman |
| 2010/0215717 A1 | 8/2010 | Soker et al. |
| 2011/0076734 A1 | 3/2011 | Zhou et al. |
| 2011/0152219 A1 | 6/2011 | Stagni et al. |
| 2011/0166650 A1 | 7/2011 | Busin |
| 2011/0208300 A1 | 8/2011 | de Juan, Jr. et al. |
| 2011/0250688 A1 | 10/2011 | Hasan |
| 2012/0203161 A1 | 8/2012 | Herekar |
| 2012/0213841 A1 | 8/2012 | Peyman |
| 2012/0226139 A1 | 9/2012 | Peyman |
| 2012/0226351 A1 | 9/2012 | Peyman |
| 2012/0245683 A1 | 9/2012 | Christie et al. |
| 2013/0218167 A1 | 8/2013 | Coffey et al. |
| 2015/0134049 A1 | 5/2015 | Austen, Jr. et al. |
| 2015/0223930 A1 | 8/2015 | Shiuey |
| 2015/0342875 A1 | 12/2015 | Haffner |
| 2015/0366706 A1 | 12/2015 | Belkin et al. |
| 2016/0022495 A1 | 1/2016 | Feingold |
| 2016/0081852 A1 | 3/2016 | Peyman |
| 2016/0081920 A1 | 3/2016 | Csaky |
| 2016/0117443 A1 | 4/2016 | Van Ooijen et al. |
| 2016/0287700 A1 * | 10/2016 | Griffin ............... A61K 31/5415 |
| 2016/0331868 A1 | 11/2016 | Grubbs et al. |
| 2016/0346389 A1 | 12/2016 | Friedman et al. |
| 2017/0007395 A1 | 1/2017 | Peyman |
| 2019/0054183 A1 | 2/2019 | Yang et al. |
| 2019/0083518 A1 | 3/2019 | Borody |
| 2020/0222557 A1 | 7/2020 | Berlin |
| 2021/0330685 A1 * | 10/2021 | Ellis ....................... A61P 31/18 |

FOREIGN PATENT DOCUMENTS

| | | |
|---|---|---|
| WO | 89/04153 A1 | 5/1989 |
| WO | 92/16172 A1 | 10/1992 |
| WO | 01/58495 A2 | 8/2001 |
| WO | 2004/108064 A2 | 12/2004 |
| WO | 2008/055118 A2 | 5/2008 |

OTHER PUBLICATIONS

Pulivendala, Gauthami, Swarna Bale, and Chandraiah Godugu. "Inhalation of sustained release microparticles for the targeted treatment of respiratory diseases." Drug delivery and translational research 10.2 (Dec. 23, 2019): 339-353. (Year: 2019).*

Cagno, Valeria, et al. "Methylene Blue has a potent antiviral activity against SARS-CoV-2 in the absence of UV-activation in vitro." bioRxiv (Aug. 14, 2020). (Year: 2020).*

Belen-Apak, F. B., and F. Sarialioglu. "The old but new: Can unfractioned heparin and low molecular weight heparins inhibit proteolytic activation and cellular internalization of SARS-CoV2 by inhibition of host cell proteases?." Medical hypotheses 142 (Apr. 20, 2020): 109743. (Year: 2020).*

Diao, Bo, et al. "Human kidney is a target for novel severe acute respiratory syndrome coronavirus 2 (SARS-CoV-2) infection." MedRxiv (Apr. 10, 2020). (Year: 2020).*

Tandukar, Srijan, and Paul M. Palevsky. "Continuous renal replacement therapy: who, when, why, and how." Chest 155.3 (2019): 626-638. (Year: 2019).*

Sarkar, Prasanta Kumar, and Chitrangada Das Mukhopadhyay. "Ayurvedic metal nanoparticles could be novel antiviral agents against SARS-CoV-2." International Nano Letters (Jan. 6, 2021): 1-7. (Year: 2021).*

Baum, Alina, et al. "REGN-COV2 antibodies prevent and treat SARS-CoV-2 infection in rhesus macaques and hamsters." Science 370.6520 (2020): 1110-1115. (Year: 2020).*

Sanders, James M., et al. "Pharmacologic treatments for coronavirus disease 2019 (COVID-19): a review." JAMA (Apr. 13, 2020): 1824-1836. doi:10.1001/jama.2020.6019 (Year: 2020).*

Carnevale, Sergio, Paolo Beretta, and Patrizia Morbini. "Direct endothelial damage and vasculitis due to SARS-CoV-2 in small bowel submucosa of COVID-19 patient with diarrhea." Journal of Medical Virology. Jun. 3, 2020. https://doi.org/10.1002/jmv.26119 (Year: 2020).*

Sarkar, K. "US FDA-approved ointment found to treat, kill viral infections including Covid-19." Hindustan Times (Aug. 22, 2020). (Year: 2020).*

(56) References Cited

OTHER PUBLICATIONS

Moriguchi, Takeshi, et al. "A first case of meningitis/encephalitis associated with SARS-Coronavirus-2." International journal of infectious diseases 94 (Apr. 3, 2020): 55-58. https://doi.org/10.1016/j.ijid.2020.03.062 (Year: 2020).*

Duan, Kai, et al. "Effectiveness of convalescent plasma therapy in severe COVID-19 patients." Proceedings of the National Academy of Sciences 117.17 (Apr. 6, 2020): 9490-9496. https://doi.org/10.1073/pnas.2004168117 (Year: 2020).*

Hodgson, John. "The pandemic pipeline." Nat Biotechnol 38.5 (Mar. 20, 2020): 523-532. (Year: 2020).*

Uddin, Mohammed, et al. "SARS-CoV-2/COVID-19: Viral Genomics, Epidemiology, Vaccines, and Therapeutic Interventions." Preprints.org (Apr. 1, 2020). doi: 10.20944/preprints202004.0005.v1 (Year: 2020).*

Buyting, Sonya. "Treating the coronavirus: improvising now, but with real hope on the horizon." CBC/Radio-Canada (Feb. 7, 2020). (Year: 2020).*

J. I. Barraquer, "Keratomileusis and Keratophakia for the Correction of Congenital Hypermetropia and Aphakia", Bulletins et Memoires de la Societe Francaise D'Ophthalmologie, vol. 95, pp. 380-390 (1984).

Wollensak et al., "Riboflavin/Ultraviolet-A—induced Collagen Crosslinking for the Treatment of Keratoconus", American Journal of Ophthalmology, vol. 135, pp. 620-627 (2003).

M. A. Bamashmus, M. F. Saleh, M. A. Awadalla, "Reasons For Not Performing Keratorefractive Surgery in Patients Seeking Refractive Surgery in a Hospital-Based Cohort in Yemen", Middle East Afr J Ophthalmol, Oct.-Dec. 2010;17(4): pp. 349-353.

Goins et al., "Photodynamic biologic tissue glue to enhance corneal wound healing after radial keratotomy" (Nov. 1997), Journal of Cataract and Refractive Surgery, vol. 23, Issue 9, pp. 1331-1338. (Abstract only).

First office action on the merits (Non-Final Rejection) in U.S. Appl. No. 14/709,801, dated Jan. 11, 2016.

Second office action on the merits (Final Rejection) in U.S. Appl. No. 14/709,801, dated May 4, 2016.

Notice of Allowance in U.S. Appl. No. 14/709,801, dated Jul. 19, 2016.

First office action on the merits (Non-Final Rejection) in U.S. Appl. No. 15/230,445, dated Jul. 11, 2017.

Notice of Allowance in U.S. Appl. No. 15/230,445, dated Dec. 4, 2017.

First office action on the merits (Non-Final Rejection) in U.S. Appl. No. 15/816,140, dated Oct. 22, 2018.

Notice of Allowance in U.S. Appl. No. 15/816,140, dated Feb. 19, 2019.

PCT Form 210, International Search Report for PCT/US2019/030931, dated Jul. 17, 2019.

PCT Form 237, Written Opinion of the International Searching Authority for PCT/US2019/030931, dated Jul. 17, 2019.

Darwish et al. "Subbasal Nerve Fiber Regeneration after LASIK and LASEK Assessed by Noncontact Esthesiometry and in Vivo Confocal Microscopy: Prospective Study." Journal of Cataract & Refractive Surgery, vol. 33, No. 9, Sep. 2007, pp. 1515-1521, doi:https://doi.org/10.1016/j.jcrs.2007.05.023.

Townes-Anderson et al. "Fasudil, a Clinically Used ROCK Inhibitor, Stabilizes Rod Photoreceptor Synapses after Retinal Detachment." Translational Vision Science & Technology, vol. 6, No. 3, ser. 22, Jun. 2017. 22, doi:10.1167/tvst.6.3.22.

Abegunde et al. "Doxycycline plus Ivermectin versus Ivermectin Alone for Treatment of Patients with Onchocerciasis." The Cochrane Database of Systematic Reviews, U.S. National Library of Medicine, Jan. 15, 2016, www.ncbi.nlm.nih.gov/pmc/articles/PMC5029467/.

Hegde et al. "A Skin-Depth Analysis of Integrins: Role of the Integrin Network in Health and Disease." Cell Communication & Adhesion, vol. 20, No. 6, Nov. 2013, pp. 155-169, doi:https:1/doi.org/10.3109/15419061.2013.854334.

Todorich et al. "Simultaneous Dexamethasone Intravitreal Implant and Anti-VEGF Therapy for Neovascular Age-Related Macular Degeneration Resistant to Anti-VEGF Monotherapy." Journal of Vitreoretinal Diseases, vol. 1, No. 1, Jan. 26, 2017, pp. 65-74, doi:10.1177/2474126416683299.

Tao et al. "Treatment of Burn Scars in Fitzpatrick Phototype III Patients with a Combination of Pulsed Dye Laser and Mon-Ablative Fractional Resurfacing 1550 Nm Erbium:Glass/1927 Nm Thulium Laser Devices." Scars, Burns & Healing, SAGE Publications, Feb. 23, 2018, www.ncbi.nlm.nih.gov/pmc/articles/PMC5965338/.

Stepp et al. "Wounding the Cornea to Learn How It Heals." Experimental Eye Research, U.S. National Library of Medicine, Apr. 2014, www.ncbi.nlm.nih.gov/pmc/articles/PMC4072315/.

Loewen. Ocular Surgery News. "How Many Medications Should Be Tried to Lower IOP before Moving on to SLT or Glaucoma Filtering Surgery?" Healio Ocular Surgery News, Healio, Oct. 25, 2010, www.healio.com/ophthalmology/glaucoma/news/print/ocular-surgery-news/%7Bd9857d89-570c-4b52-af40-26bfd5273ddc%7D/how-many-medications-should-be-tried-to-lower-iop-before-moving-on-to-slt-or-glaucoma-filtering-surgery.

Li et al. "Intranasal Delivery of FSD-C10, a Novel Rho Kinase Inhibitor, Exhibits Therapeutic Potential in Experimental Autoimmune Encephalomyelitis." Immunology, Blackwell Science Inc, Oct. 2014, www.ncbi.nlm.nih.gov/pmc/articles/PMC4172138/.

First office action on the merits (Non-Final Rejection) in U.S. Appl. No. 15/941,641, dated Sep. 27, 2018.

Notice of Allowance in U.S. Appl. No. 15/941,641, dated Mar. 21, 2019.

"KY02111", MedChemExpress Website, Web page <https://www.medchemexpress.com/KY02111.html?src=google-product&gclid-EAlalQobChMI0OP38Ony5wIVFvbjBx3joQOGEAAYASAAEgJOkfD_BwE>, 3 pages, dated at least as early as Feb. 27, 2020, retrieved from MedChemExpress website on Feb. 27, 2020.

"WAY 316606", APExBIO Website, Web page <http://www.apexbt.com/way-316606.html?gclid=EAlalQobChMIIsj51Ory5wIVxMDACh3qogldEAAYASAAEgISkfD_BwE>, 4 pages, dated at least as early as Feb. 27, 2020, retrieved from APExBIO website on Feb. 27, 2020.

"IWP-2", MedChemExpress Website, Web page <https://www.medchemexpress.com/IWP-2.html>, 3 pages, dated at least as early as Feb. 27, 2020, retrieved from MedChemExpress website on Feb. 27, 2020.

"LGK974", MedChemExpress Website, Web page <https://www.medchemexpress.com/LGK974.html?src=google-product&gclid-EAlalQobChMlylHI4_zy5wIVOYZbCh15nws7EAAYASAAEgKTTPD_BwE>, 3 pages, dated at least as early as Feb. 27, 2020, retrieved from MedChemExpress website on Feb. 27, 2020.

"C59", Abeam Website, Web page <https://www.abcam.com/c59-wnt-antagonist-wnt-signaling-pathway-inhibitor-ab142216.html>, 3 pages, dated at least as early as Feb. 27, 2020, retrieved from Abcam website on Feb. 27, 2020.

First office action on the merits (Non-Final Rejection) in U.S. Appl. No. 16/246,618, dated Nov. 27, 2019.

Second office action on the merits (Final Rejection) in U.S. Appl. No. 16/246,618, dated Mar. 5, 2020.

Third office action on the merits (Non-Final Rejection) in U.S. Appl. No. 16/246,618, dated Jul. 1, 2020.

Fourth office action on the merits (Final Rejection) in U.S. Appl. No. 16/246,618, dated Nov. 13, 2020.

Notice of Allowance in U.S. Appl. No. 16/246,618, dated Feb. 23, 2021.

First office action on the merits (Non-Final Rejection) in U.S. Appl. No. 16/861,128, dated Oct. 27, 2020.

Notice of Allowance in U.S. Appl. No. 16/861,128, dated Jan. 4, 2021.

Wang et al., Lancet 2020;295: 1569-78. (Year: 2020).

Laporte et al., Virology 2017, 24:16-24. (Year: 2017).

Ma et al., Clinical Immunology 214 (2020) 108408 (available online Apr. 1, 2020). (Year: 2020).

Sedger, https://theconversation.com/in-the-fight-against-coronavirus-antivirals-are-as-important-as-a-vaccine-heres-where-the-science-is-up-to-133926 (last accessed Oct. 24, 2020). (Year: 2020).

(56) References Cited

OTHER PUBLICATIONS

Farkas, Internet Book of Critical Care (IBCC), https://emcrit.org/ibcc/covid19/ (last accessed Oct. 24, 2020). (Year: 2020).
Singh et al., Ther Adv Infectious Dis 2017, vol. 4(4) 105-131 (Year: 2017).

* cited by examiner

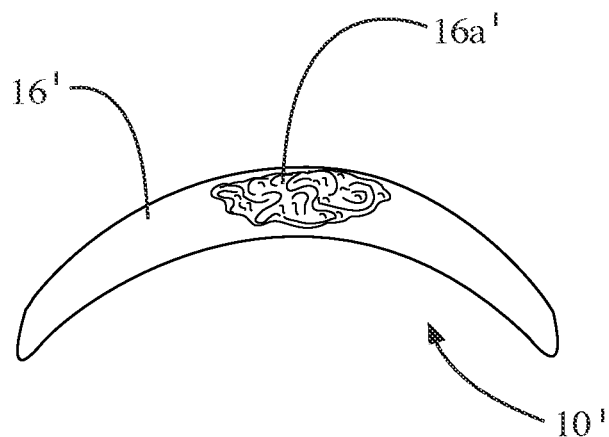
FIG. 2A
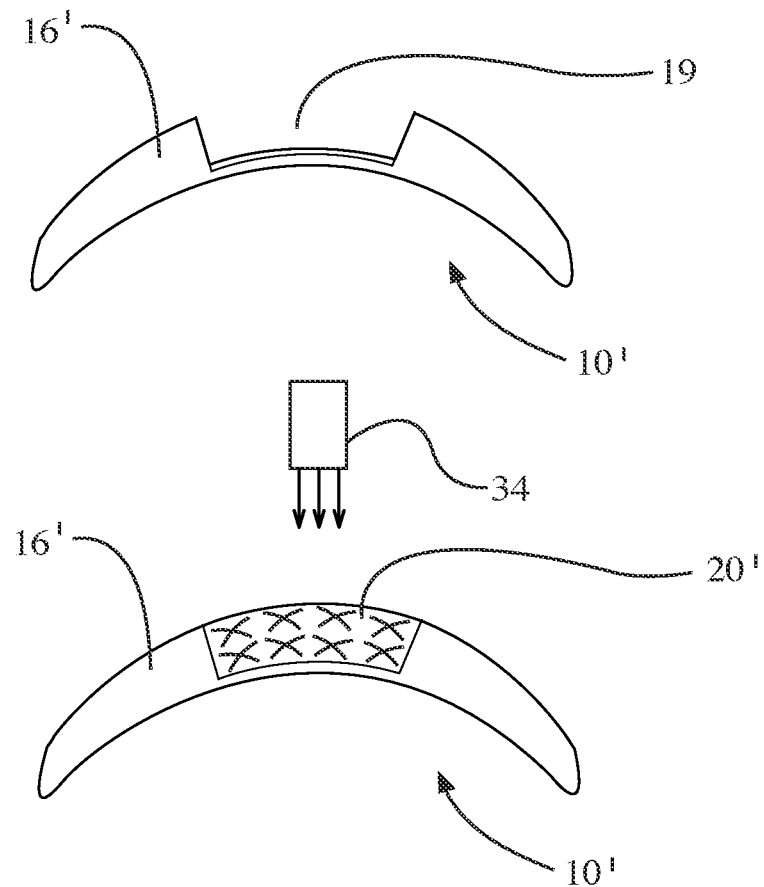
FIG. 2B
FIG. 2C

Detail "A"

Detail "B"

Detail "C"

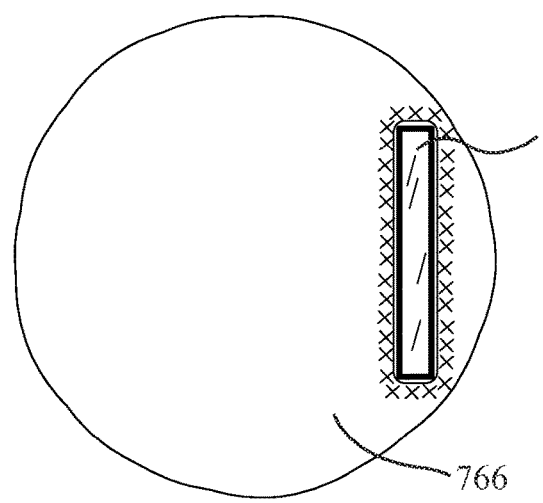
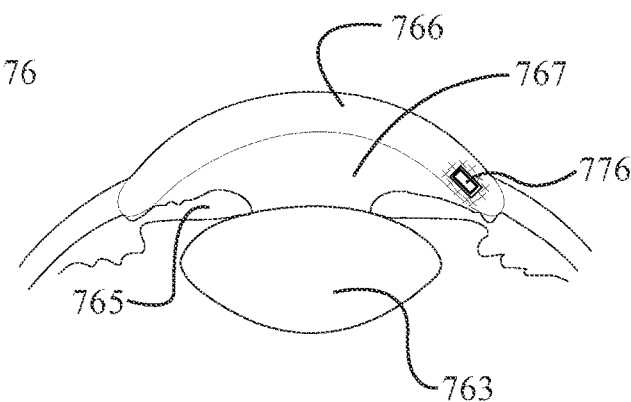
FIG. 69A    FIG. 69B
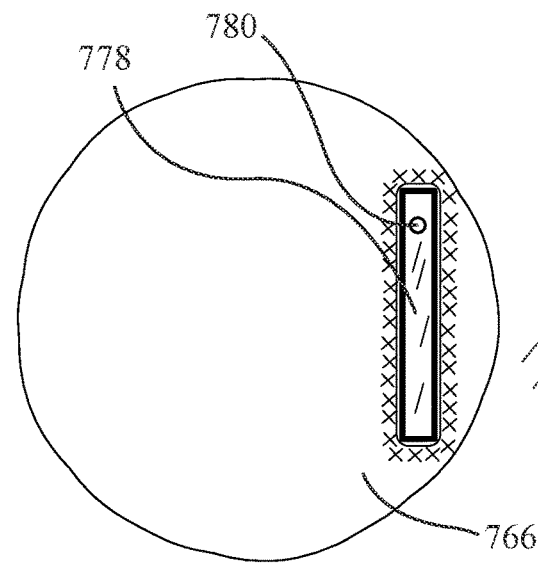
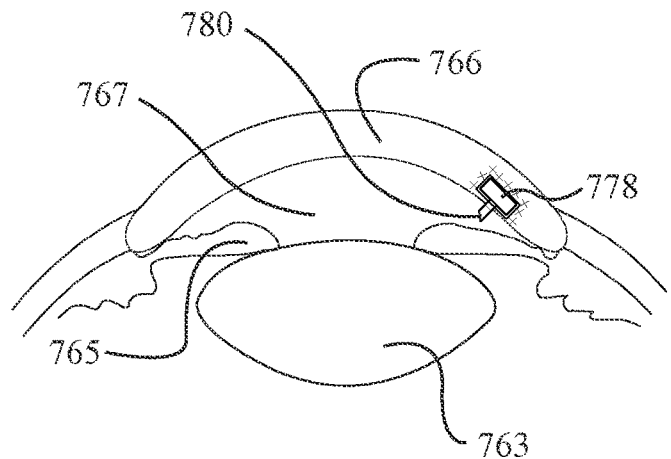
FIG. 70A    FIG. 70B

METHOD OF TREATING, REDUCING, OR ALLEVIATING A MEDICAL CONDITION IN A PATIENT

CROSS-REFERENCE TO RELATED APPLICATIONS

This patent application claims priority to U.S. Provisional Patent Application No. 63/039,959, entitled "Treatment And Prevention Methods For Respiratory Infections", filed on Jun. 16, 2020, U.S. Provisional Patent Application No. 63/055,770, entitled "Treatment And Prevention Methods For Respiratory Infections", filed on Jul. 23, 2020, U.S. Provisional patent Application No. 63/077,677, entitled "Treatment And Prevention Methods For Respiratory Infections", filed on Sep. 13, 2020, U.S. Provisional Patent Application No. 63/106,319, entitled "Treatment And Prevention Methods For Respiratory Infections", filed on Oct. 27, 2020, and U.S. Provisional Patent Application No. 63/131,761, entitled "Treatment And Prevention Methods For Respiratory Infections", filed on Dec. 29, 2020, and is a continuation-in-part of application Ser. No. 16/861,128, entitled "Method Of Treating, Reducing, Or Alleviating A Medical Condition In A Patient", filed Apr. 28, 2020, which claims priority to U.S. Provisional Patent Application No. 62/839,738, entitled "Method Of Treating, Reducing, Or Alleviating A Medical Condition In A Patient", filed on Apr. 28, 2019, and to U.S. Provisional Patent Application No. 63/016,258, entitled "Treatment Methods For Respiratory Infections", filed on Apr. 27, 2020, and Ser. No. 16/861,128 is a continuation-in-part of application Ser. No. 16/246,618, entitled "Methods For Treatment Of Dry Eye And Other Acute Or Chronic Inflammatory Processes", filed Jan. 14, 2019, which claims priority to U.S. Provisional Patent Application No. 62/617,251, entitled "Methods For Treatment Of Dry Eye And Other Acute Or Chronic Inflammatory Processes", filed on Jan. 14, 2018, and Ser. No. 16/246,618 is a continuation-in-part of application Ser. No. 15/816,140, entitled "Drug Delivery Implant And A Method Using The Same", filed Nov. 17, 2017, which claims priority to U.S. Provisional Patent Application No. 62/423,734, entitled "Drug Delivery Implant And A Method Using The Same", filed on Nov. 17, 2016, and Ser. No. 15/816,140 is a continuation-in-part of application Ser. No. 15/653,053, entitled "Corneal Intraocular Pressure Sensor And A Surgical Method Using The Same", filed Jul. 18, 2017, which claims priority to U.S. Provisional Patent Application No. 62/363,382, entitled "Corneal Intraocular Pressure Sensor And A Surgical Method Using The Same", filed on Jul. 18, 2016, and Ser. No. 15/653,053 is a continuation-in-part of application Ser. No. 15/631,219, entitled "Method of Prevention of Capsular Opacification and Fibrosis After Cataract Extraction and/or Prevention of Fibrosis Around a Shunt or Stent After Glaucoma Surgery", filed Jun. 23, 2017, which claims priority to U.S. Provisional Patent Application No. 62/353,632, entitled "Method of Prevention of Capsular Opacification and Fibrosis After Cataract Extraction and/or Prevention of Fibrosis Around a Shunt or Stent After Glaucoma Surgery", filed on Jun. 23, 2016, and Ser. No. 15/631,219 is a continuation-in-part of application Ser. No. 15/285,375, entitled "Method of Preventing Capsular Opacification and Fibrosis Utilizing an Accommodative Intraocular Lens Implant", filed Oct. 4, 2016, now U.S. Pat. No. 9,744,029, which claims priority to U.S. Provisional patent Application No. 62/360,439, entitled "Method of Preventing Capsular Opacification and Fibrosis with the Creation of an Accommodative Intraocular Lens", filed on Jul. 10, 2016, and Ser. No. 15/285,375 is a continuation-in-part of application Ser. No. 15/230,445, entitled "Corneal Lenslet Implantation With A Cross-Linked Cornea", filed Aug. 7, 2016, now U.S. Pat. No. 9,937,033, which claims priority to U.S. Provisional Patent Application No. 62/360,281, entitled "Method of Altering the Refractive Properties of an Eye", filed on Jul. 8, 2016, and Ser. No. 15/230,445 is a continuation-in-part of application Ser. No. 14/709,801, entitled "Corneal Transplantation With A Cross-Linked Cornea", filed May 12, 2015, now U.S. Pat. No. 9,427,355, which claims priority to U.S. Provisional Patent Application No. 61/991,785, entitled "Corneal Transplantation With A Cross-Linked Cornea", filed on May 12, 2014, and to U.S. Provisional Patent Application No. 62/065,714, entitled "Corneal Transplantation With A Cross-Linked Cornea", filed on Oct. 19, 2014, the disclosure of each of which is hereby incorporated by reference as if set forth in their entirety herein.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

INCORPORATION BY REFERENCE OF MATERIAL SUBMITTED ON A COMPACT DISK

Not Applicable.

BACKGROUND OF THE INVENTION

1. Field of the Invention

The invention generally relates to methods of treating, reducing, or alleviating a medical condition in a patient. More particularly, the invention relates to combination therapy for the treatment of various medical conditions, which include respiratory infections.

2. Background

Corneal scarring is a major cause of blindness, especially in developing countries. There are various causes for corneal scarring, which include: bacterial infections, viral infections, fungal infections, parasitic infections, genetic corneal problems, Fuch's dystrophy, and other corneal dystrophies. A corneal transplant is often required if the corneal scarring is extensive, and cannot be corrected by other means. However, there can be major complications associated with a corneal transplant, such as corneal graft rejection wherein the transplanted cornea is rejected by the patient's immune system.

A normal emmetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emmetropic eye, or a cornea or lens having a refractive power stronger than that of the cornea and lens of an emmetropic eye. This stronger refractive power causes the far point to be projected in front of the retina.

Conversely, a hypermetropic or hyperopic eye has an axial length shorter than that of a normal emmetropic eye, or a lens or cornea having a refractive power less than that of a lens and cornea of an emmetropic eye. This lesser refractive power causes the far point to be focused behind the retina.

An eye suffering from astigmatism has a defect in the lens or shape of the cornea converting an image of the point of light to a line. Therefore, an astigmatic eye is incapable of sharply focusing images on the retina.

While laser surgical techniques, such as laser-assisted in situ keratomileusis (LASIK) and photorefractive keratectomy (PRK) are known for correcting refractive errors of the eye, these laser surgical techniques have complications, such as post-operative pain and dry eye. Also, these laser surgical techniques cannot be safely used on patients with corneas having certain biomechanical properties. For example, corneal ectasia may occur if these laser surgical techniques are applied to patients having thin corneas (e.g., corneas with thicknesses that are less than 500 microns).

Therefore, what is needed is a method for corneal transplantation that reduces the likelihood that the implanted cornea will be rejected by the patient. Moreover, a method is needed for corneal transplantation that is capable of preserving the clarity of the transplanted cornea. Furthermore, there is a need for a method of corneal transplantation that reduces the likelihood that the transplanted cornea will be invaded by migrating cells. Also, what is needed is a method for corneal lenslet implantation for modifying the cornea to better correct ametropic conditions. In addition, a method is needed for corneal lenslet implantation that prevents a lens implant from moving around inside the cornea once implanted so that the lens implant remains centered about the visual axis of the eye.

Moreover, many cataract patients experience complications following their cataract surgery. For example, opacification of the lens capsule affects about 80-90% of the eyes after cataract surgery because of proliferation of the remaining cells in the lens capsule. This post-surgery opacification requires a laser disruption of the posterior capsule for the patient to see. Also, conventional monofocal intraocular lenses do not permit accommodation. As such, patients with monofocal intraocular lenses typically require reading glasses after cataract surgery.

Therefore, it is apparent that a need also exists for treatment of cell proliferation of the lens capsule after cataract extraction, and for an accommodative intraocular lens implant that enables the cataract patient to see both far and near objects without the need for supplemental lenses, such as reading glasses.

Furthermore, cataract patients who additionally have glaucoma pose difficult challenges for the treating ophthalmologist. When glaucoma is associated with a cataract in the same patient, the two surgeries must often be performed at the same time. However, unfortunately, both conditions can have their own complications. For example, as mentioned above, opacification of the lens capsule affects about 80-90% of the eyes after cataract surgery because of proliferation of the remaining cells in the lens capsule. This post-surgery opacification requires a laser disruption of the posterior capsule for the patient to see. Similarly, after glaucoma surgery, the connecting hole from the eye to the subconjunctival space may become plugged by fibrous proliferation occurring after surgery in an attempt to reject the shunt after the surgery or even a shunt in place, as a response of the surgical procedure creating a hole in the eye wall to drain the intraocular fluid.

Therefore, it is apparent that a need further exists for treatment of cell proliferation of the lens capsule after cataract extraction, and for treatment of fibrous cell proliferation after glaucoma surgery with or without a drainage tube.

Glaucoma is a disease that affects the eye and is considered one of the major causes of blindness in the world. There are many forms of glaucoma, having different pathogenesis. Among these are open angle glaucoma (OAG) where the anterior chamber located between the cornea and the iris is open, closed angle glaucoma where the anterior chamber angle is closed, and secondary glaucoma caused by different etiologies, but often an inflammatory process proceeds its occurrence. The glaucoma can be congenital or acquired, and some have genetic predisposition. Regardless of its pathogenesis, the hallmark of the disease is mostly an increased intraocular pressure (IOP), except for in the low tension glaucoma where the IOP appears to be normal, but the patient has the other symptoms of glaucoma. The other characteristic findings in glaucoma eyes are the cupping of the optic nerve head, and the loss of the nerve fiber layer of the retina and ganglion cells of the retina. These can lead to, or can also be considered a consequence of a degenerative process affecting potentially the retinal ganglion cells and an imbalance of the IOP and intracranial pressure leading to gradual loss of the visual field that can be constricted with time or completely lost resulting in blindness.

There are many treatment modalities in managing the disease processes. Since the IOP is, in most cases, elevated beyond a normal level of 10-20 mmHg, routine checking of the IOP including potentially a 24-hour or more measuring of these values during the day and night is needed to find out if there are any pressure variations during the course of the day, especially during sleep where the IOP generally is raised. These pressure variations can obviously compromise the retinal nerves and circulation, even if the pressure is within a normal range of 10-20 mmHg, such as in patients with low tension glaucoma. Thus far, the measurement of the IOP has been sporadic because it is limited by a patient's visit to the doctor's office.

The treatment for glaucoma has been mostly medicinal, that is by applying antiglaucoma medication(s) as eye drops to reduce the intraocular pressure. If the IOP cannot be controlled, either by laser surgery of the angle or ciliary body processes where the fluid is produced, then alternatively, one tries to drain the intraocular fluid to outside of the eye through a stent or shunt opening with one end in the anterior chamber and the other end located in the subconjunctival space or connecting the intraocular fluid via a shunt tube from the inside the eye to the choroidal space. In some situations, the surgeon makes a small hole in the eye wall connecting the anterior chamber fluid or aqueous directly to the subconjunctival space. There are a number of variations of this surgery having the same goal of reducing the IOP to a normal level. The glaucoma can also be associated with a cataract and not seldom requires doing the two surgeries at the same time. However, unfortunately both conditions can have their own complications (e.g., opacification of the lens capsule after cataract surgery affecting about 80-90% percent of the eyes because of proliferation of the remaining cells in the lens capsule, and requiring a laser disruption of the posterior capsule for the patient to see). Similarly, after glaucoma surgery, the connecting hole from the eye to the subconjunctival space can become plugged by fibrous proliferation occurring after surgery with or without a shunt tubing.

Recently, efforts have been made experimentally to measure the intraocular pressure via a contact lens positioned on the surface of the cornea for a duration of 24 hours with a pressure sensor and transmit the information wirelessly to a receiver mounted on an eye glass frame. The disadvantage of this contact lens system is that the system provides the measurement of the IOP indirectly from the eye cavity and depends on how the corneal curvature is deformed in response to the IOP. Also, the contact lens can be worn only for a short time because, otherwise it can interfere with the corneal oxygenation that happens mostly from the outside air and nutrition of the cornea that is, in part, supplied by the tear film that is compromised by placement of a static contact lens on the cornea. The chances of a corneal abrasion is increased by the described shortcomings, and for the patient, the placement and removal of the contact lens is particularly difficult in elderly patients.

Another recent effort has implanted such a system inside the lens capsule of the eye, by removing the natural crystalline lens, but leaving the lens capsule intact so that the device can be positioned inside the lens capsule and measure the IOP, and then transmit it outside the eye to a receiver. Because the system disposed in the lens capsule requires a battery to operate, the eventual need to replace the battery necessitates another surgical procedure to be performed later. Also, the initial surgical procedure has its own serious complications, and often is not justified when one is dealing with young patients or children. In addition, this process creates capsular opacification, it deprives the patient from the use of his or her natural lens, and can have the lifelong potential complication of inflammation that aggravates the existing glaucoma itself.

Therefore, it is apparent that a need further exists for an intraocular pressure measurement device and a method using the same that eliminates the shortcomings of the aforedescribed procedures.

Further, conventional ocular drug delivery systems include medication dissolved or suspended in a physiological solutions applied as drops to the cornea and conjunctiva bathing the superficial structure of the eye. The drops can have also particulate matter for faster tissue penetration or slow release of medication potentially lasting 1-2 days or months, etc. The medication, when applied as drops, partially penetrates the barrier of the corneal epithelium and reaches in sufficient concentration in the aqueous fluid of the anterior chamber. The aqueous is constantly produced in the eye from the ciliary body epithelium in the back or the iris in the posterior chamber and moves through the pupil in the anterior chamber, and is removed from the eye through the trabecular meshwork located in the angle of the eye between the iris and the cornea. A part of the aqueous mixes with the vitreous. In general, topically-applied medication reaches the back of the eye in lower concentrations and slower than when injected in the vitreous cavity.

The injection of medication in the eye cavity, in the form of solution or micro-particulates, can bypass the ocular barrier and effectively treat the retinal and choroidal diseases, for months. Therefore, they have to be reinjected frequently in chronic disease of the eye.

The polymeric slow release systems release the medication inside the eye and have been implanted in the vitreous cavity, over or under the retina, providing medication only to the back of the eye for a period of 3 months to a year.

In general, a drug delivery device has been implanted in most places of the eye, except in the cornea. A non-biodegradable device can be injected in the vitreous cavity if they are very small otherwise, they can move around scratching the retina or move to the anterior chamber damaging the corneal endothelial cells. However, they can be sutured in the sclera with their anchoring section, while the drug delivery section is located inside the eye, i.e., in the vitreous cavity to release the medication.

These devices, in general, initiate a foreign body response associated with fibroblast cell migration around the device, and the device becomes encapsulated, making the amount of drug release unpredictable through the thick fibrotic scar tissue.

Similarly, stem cellular drug delivery devices, such as ciliary body neurotrophic factors that produce needed factors for the retinal survival in certain degenerative diseases can be only be implanted inside the vitreous cavity where it is considered an immune-privileged space. Otherwise, it becomes encapsulated by the scar tissue and become less effective. The vitreous cavity is considered an immune privileged space meaning that blood vessels have no access to it to produce a cellular immune response that would attack and destroy the stem cells or surround a device with a fibrous membrane which would make the system useless.

To date, in general, the cornea has not been considered a suitable location to implant a slow release drug delivery device because of concern that it becomes vascularized affecting the transparency of cornea, which is vital for passing the light through it to reach the photoreceptors of the retina creating sensation of vision.

Therefore, it is apparent that a need exists for a drug delivery implant and a method using the same that is capable of effectively delivering medications to the cornea of the eye and to parts of the body other than the cornea of the eye.

Further, it is known that on the cell surface membrane, Wnt proteins bind to receptors of the Frizzled and LRP protein families causing accumulation of beta-catenin in the cytoplasm and its translocation in the nucleus that forms a complex with transcriptional cofactor (TCF) to activate the transcription of Wnt targeted genes.

The Wnt pathway is considered canonical when it is dependent on beta-catenin, or non-canonical when it is independent. The canonical Wnt/β-catenin plays an important role in the expression of several inflammatory molecules during acute or chronic inflammatory diseases affecting mucosal surfaces of the body.

It is known that innate immunity protects the host cells from invasion and infection and development of an adaptive immune response. However, uncontrolled inflammation causes damage to the tissue.

Conventional oral medication or topical medications used for the mucosa have contained steroids, systemic medication, such as hormonal therapy and or omega-3 oil along with systemic medications, have unwanted side effects and are not tolerated by many patients.

As such, an improved treatment method is needed for an inflammatory process that involves the conjunctiva, sclera, optic nerve, nasal, oral and throat including dry eye syndrome, mucosal form of lichen planus, psoriasis, and inflammatory bowel diseases, plantar fasciitis, skin form of lichen planus or chronic pain caused by inflammatory disease affecting the nerves such as in diabetes or after surgery or trauma, etc.

Respiratory infections also involve inflammatory processes. Respiratory infections are mostly manifested as bacterial or viral infections affecting the nose, throat, epiglottis, trachea, and the lungs. Often these infections in the end stage can cause serious damage to the lungs as pneumonia and superinfection and serious consequences.

In an upper respiratory Infection (URI), the bacterial culprit is group A streptococcal bacteria producing sinusitis and or bronchitis. The common symptoms are redness of the throat and tonsils and moderately elevated temperature of about 38 degrees C. and enlarged cervical nodes. One of the symptoms of laryngotracheitis is roughness of the voice, etc. and positive culture of the organism.

The viral infection is caused often by influenza virus, Epstein Barr virus, Herpes virus, etc. and can be diagnosed by available rapid tests for antibody or polymerase chain reaction (PCR) viral proteins (e.g., enzyme assays for reverse transcriptase in retroviruses), or virus particles (e.g., by electron microscopy or Raman surface enhance spectroscopy, QuantiFERON-virus Gold test (QFV-G) and Surface-enhanced Raman scattering (SERS) for rapid detection of multiple viral antigens using magnetic capture of SERS-active nanoparticles as known in the art). In Surface Enhanced Raman Spectroscopy (SERS), antibody conjugated magnetic or paramagnetic and gold nanoparticles/virus complex is enhanced by an external magnetic field detected by SERS where the signal of the specific virus, e.g., COVID-19 or its mutations, gene, bacteria present in blood, dry blood, serum, or nasal, throat swab, etc. is enhanced by laser excitation and recognized using principal component analysis (PCA) and hierarchical cluster analysis (HCA) as known in the art at low picomolar concentration. In a hospitalized patient, a blood culture, sputum, nasal, skin, mouth conjunctival mucosa or urogenital mucosa, aqueous, vitreous, CSF, joint fluid, etc. might be taken to verify the extent of the localized or systemic involvement of the viruses or bacteria, etc. The use of a single strand of DNA/antibody or aptamer coated nanoparticles can be used to recognize the RNA expression of RNA viruses, etc. Management of these cases is done in general by oral and systemic antibiotics, penicillin, fluoroquinolones (e.g., levofloxacin, moxifloxacin etc.), tetracycline and its derivatives and antivirals, etc. Hospitalization might be required in advanced cases affecting the lung with the symptom of dyspnea. The viral infection of the upper respiratory tract is caused by a variety of viruses, among them, the most common are Rhinoviruses, Coxsackie viruses, Adenoviruses and Coronaviruses and Respiratory syncytial virus (RSV) and Epstein Barr Virus (EBV) causing a variety of disease manifestations, such as infectious mononucleosis, or Cytomegalovirus. Rhinoviruses cause a number of common cold infections in adults and are seasonal, appearing in fall and winter. These cause approximately 30-50% of colds in adults. The Adenovirus causes conjunctivitis and laryngitis. *H. influenzae* type b (Hib) often causes epiglottitis in children, whereas influenza, Human parainfluenza viruses (HPIVs) viruses and RSV cause laryngitis and some cause pelvic inflammatory diseases of various types. Most of the viral infections are initiated by close contact, travel, or in patients with immune suppression. In general vaccination can reduce a number of these infections. Some viruses are seen more often in male patients than females, or during menstrual cycles etc. and some with preference in children, yet others in the elderly. Some of the viruses produce epidemic diseases such as Middle East respiratory syndrome, pandemic H1N1, and H7N9, thus affecting a large number of the population and can be diagnosed by diagnosed by polymerase chain reaction (PCR) panels, etc. Therapy with antibiotics is ineffective in majorities of viral infections unless it is accompanied by a bacterial superinfection. However some viruses, such as influenza viruses and COVID-19 grow in the presence of the bacteria, therefore in these cases administration of some antibiotics such as tetracycline derivatives, a metalloproteinase inhibitor, as inhalation combined with antiviral work synergistically. The antiviral therapies are effective, such as administration of ribavirin in lung transplant patients with Motavizumab. However, they are not affordable for common viral infections, a second-generation anti-RSV antibody, or intravenous immunoglobin (RI-002).

Although influenza and parainfluenza viruses are often self-limited, unfortunately they can be associated with life threatening consequences in patients after lung transplantation or immunosuppressed patients, and may have a high mortality rate similar to RSV disease, and 20% of patients with SARS-CoV-2, COVID-19 or its mutations, have multi-organ failure due to cytokine storm.

Among viruses that cause epidemic or pandemic disease are severe acute respiratory syndrome coronavirus (SARS-CoV-2) and COVID-19 or its mutations, an RNA virus involving bird and mammals which was found initially in the Wuhan Seafood Wholesale market. By now (SARS-CoV-2), COVID-19 or its mutations, has affected every country in every continent. It is a highly contagious virus and survives 3-7 hours, and sometimes more hours on surfaces.

The (SARS-CoV-2) COVID-19 coronavirus affects the bronchoalveolar cell linings as seen with other Coronaviruses. The viruses utilize certain protease proteins of these cells membrane to enter in the cell cytoplasm and utilize the genetic machinery of the cell to multiply. The incubation time varies between 3-7 days or more, while the patient remains relatively asymptomatic. The transmission occurs by contact or aerosolized droplet sputum by sneezing or being close (less than 6 feet) from an infected person. Thus, one person can transmit the virus to many others. In addition, many patients who have recovered can still transmit the virus to others. At present, at least six or more different coronal viruses have been recognized. Among these are SARS-CoV coronavirus causing severe acute respiratory syndrome or MERS-CoV Middle Eastern respiratory syndrome and some that live in bats.

The mechanism of cell entry of the virus into the cell involves using the receptor binding domain (RBD) of the S protein of the virus to attach to the human receptor ACE2 of the alveoli cell where serine protease cleaves the S protein of the virus and causes the binding of the virus to the cell membrane and facilitates entry in the cell. Among the symptoms of coronavirus, a high fever of 100 Fahrenheit or more, is a common finding in addition to cough, shortness of breath, chills, headache, sore throat, muscle pain and gastrointestinal symptoms, loss of smell or taste, urticaria or discoloration of the foot or toes, etc., followed by laboratory finding of leukopenia, lymphocytopenia and thrombocytopenia, coagulopathy, increase in antiphospholipid antibodies, multiple infarcts, increased C-reactive protein greater than >10 mg/L, elevated lactate dehydrogenase (LDH), elevated creatinine, specifically in patients with cytokine storm, similarly increased IFNγ and increased pro-inflammatory ferritin, D-dimer. Cytokine storm induces damage to many organs, such as heart, kidney, etc. A cytokine storm is often associated with macrophage activation syndrome (MAS) and hemophagocytic lymphohistiocytosis (sHLH), increase in cytokines, such as tumor necrosis factor (TNF)-α, interferon (IFN)-γ, interleukin (IL)-1(3, IL-2, IL-6, IL-7, IL-12, IL-18, and granulocyte colony-stimulating factor (GCSF). Interestingly, one finds also the anti-inflammatory stimuli, such as regulatory T cells, cytokines IL-10, transforming growth factor (TGF)-β. The latter can lead to pulmonary fibrosis when the patient has recovered, whereas the presence of IL-2, IL-6, IL-7, TNFα, IFNγ, and GCSF, indicates significant lung injury. Comorbidity conditions are old age, male sex, asthma, heart disease, diabetes, kidney disease, etc.

At present, there is no definite therapy for the SARS-CoV-2, COVID-19 or its coronavirus mutations. In general, the early stages are treated palliative. Since fever is a relatively an early symptom, aspirin and Tylenol are useful, but do not affect the replication of the virus. Protection against infection includes self-isolation quarantine, the use of a mask and gloves, and prevention of the virus spreads by sanitizing drops and handwashing. At present, patients with dyspnea, are treated with inhalation of oxygen through the nose or by ventilator, increasing the tissue oxygenation to a level of 92-96%. If a higher level is required, one has recommended the use of nonrebreather mask, with a flow rate up to 6-10 L while providing 100% $FiO_2$ (fraction of inspired oxygen (FiO20).

Inflammatory disease of the brain is called encephalitis. It is caused by viral or bacterial invasion of the brain through the circulation, but most independently through the nasal mucosa and lamina cribrosa, a thin layer of bone that separates the brain and cerebrospinal fluid from the nasal cavity, directly through the olfactory nerve that begins one side inside from the nasal cavity with its receptors between the nasal epithelial cells, and ends with the olfactory bulb located inside the skull under the brain and another nerve "the trigeminal nerve" that transmits sensation of touch or pain from the facial skin, or mouth, throat, and nasal mucosa to trigeminal ganglion cells located at the brain.

The olfactory neurons are close to the nasal cavity and have access to the subarachnoid space in the brain, therefore virus can migrate from the nasal cavity to the olfactory bulb and migrate to brain, thalamus, cerebrum, and cerebellum.

All viruses show a tropism for the olfactory epithelium, bovine herpesvirus 5 and equine herpesvirus 9 spread from the nasal mucosa to the central nervous system (CNS) via the olfactory nerves, herpesvirus 6 has been found in the nasal mucosa in healthy controls, multiple sclerosis patients, and patients with a loss of smell.

The bony structure of skull protects the brain which is surrounded by meninges, consisting of dura mater, arachnoid and pita matter. The cerebrospinal fluid is produced in the brain ventricle existing through the venous system of the meninges and through the lamina cribrosa, etc. and the lymphatic system of the nose.

The thigh junction of the endothelial cells and pericytes, astrocytes and epithelial cells of the arachnoid mainly prevent passage of the blood and its components including the potentially invasive pathogens in the brain substance.

The brain is composed of many ganglion cells, microglia, astrocytes, dendritic cells, oligodendrocytes, etc. of which the neuronal cells and glial cells build the majority of cells. The cerebrospinal fluid (CSF) contains many migrating mononuclear cells, such as monocytes, and dendritic cells, T cells, B cells, macrophages, the T-cell exit the subarachnoid space access the lymphatic system that drains in the nasal mucosal lymphatic system.

The viral and microbial pathogens can gain access to the brain passing through the damaged endothelial cells of the brain or spinal cord vessels through the circulation or alternatively through the olfactory or trigeminal nerves directly bypassing all barriers of the brain.

The neurotrophic viruses often invade the nasal mucosa where they proliferate then gain preferentially access to the olfactory nerve and the brain and its vasculature inducing vasculitis and encephalitis, followed by the release of cytokines and enzymes such as metalloproteinases, etc. enhances the degradation of the blood brain barrier (BBB), with poring blood plasma, fibrinogen that is converted into fibrin in the brain, increased intraocular pressure, headache, changes in mental cognition, and difficulty of interaction and death of the neuronal cells.

Viruses constitute the majority of the pathogens involved in cases of encephalitis. The infection produces a combined inflammation of the brain substance and its vasculature (Vasculitis). Other viruses beside herpes virus that cause encephalitis are, influenza viruses, Epstein-Barr viruses, measles virus, enteroviruses, varicella-zoster virus and arboviruses, Japanese encephalitis virus, West Nile virus, and Murray Valley encephalitis virus.

In some cases, the encephalitis (brain inflammation) is caused by viruses which gain access to the brain through the circulation. However, more commonly, the nasal cavity and its mucosa are affected initially, and the viruses multiply there, before spreading to the vascular endothelial cells or brain through the lamina cribrosa, a thin plate of bone between the nasal cavity and brain.

The pathogens induce vasculitis, breakdown of the blood brain barrier leading to further invasion of the bacteria or viruses affecting the ganglion cell function, stimulating glial cell and immune cells, proliferation and migration in the affected area.

Viral encephalitis occurs after nasal invasion by the viruses, such as common cold, influenza viruses, coronaviruses, SARS-CoV-2, COVID-19 or their mutations, influenza viruses, herpes simplex, varicella zoster, shingles, but also measles, rubella and mumps, or Epstein-Barr virus (EBV), Ebola virus, enteroviruses, cytomegalovirus, other viruses such as Zika chikungunya, and arboviruses that are transmitted via mosquitos' bites and subsequently affect the CNS, etc. or via circulation. Herpes simplex type 1 virus can become as deadly as some other viruses, such as Ebola if not treated rapidly. Sever inflammatory process specifically in bacterial infection produces brain abscess.

Conjunctivitis is one of the most common infectious diseases of the eye affecting the conjunctiva, cornea or the lid, kwon as keratoconjunctivitis, or blepharoconjuctivitis. The acute inflammation is initiated by invading bacterial or viral organism such as streptococcal or staphylococcal bacteria, etc. Bacterial conjunctivitis is associated with trichiasis, chronic blepharitis or dry eye. The most commonly viral pathogens are adenoviruses causing pinkeye or adenoviral epidemic keratoconjunctivitis (EKC) or herpes simplex virus (HSV) viruses. Other viral infection causing conjunctivitis are varicella-zoster virus (VZV), picornavirus (enterovirus 70, Coxsackie A24), Poxvirus (molluscum contagiosum, vaccinia), and human immunodeficiency virus (HIV) or rarely, influenza virus, SARS-CoV-2, COVID-19 or their mutations, Epstein-Barr virus, paramyxovirus (measles, mumps, Newcastle), or rubella, Most of viral conjunctivitis, are contagious and can be transmitted to others and to majorities of body's organs.

The COVID-19 virus or its mutations can induce numerous inflammatory disorders in the including conjunctivitis scleritis, or nodular conjunctivitis and scleritis, uveitis and retinitis, and/or optic nerve vasculitis.

The infection can be caused by the virus invasion directly, or the inflammation is caused by the presence of the cytokine released causing hyperemia of the conjunctiva. The diagnosis is done by detection of the virus using PCR from the conjunctival fluid, saliva anterior chamber fluid or vitreous samples or from the nasal fluid which is drained in the nose through the nasolacrimal duct or to the throat and lung, etc.

The patients with conjunctivitis have typically some pain, itching, watery or thick discharge associated with redness of the conjunctiva, photophobia, keratitis and lid swelling.

Conjunctivitis can also be caused as an allergic response to an external antigen in children or adults known as vernal conjunctivitis often seen in warm season appearing as dot-like swelling involving the pre-corneal or limbal conjunctiva.

Giant papillary conjunctivitis is seen in people who do not tolerate wearing contact lens. The symptoms involve the upper conjunctiva, usually under the upper lid. It is associated with increased mucus production and itching resembling venereal disease.

BRIEF SUMMARY OF EMBODIMENTS OF THE INVENTION

Accordingly, the present invention is directed to a method of treating, reducing, or alleviating a medical condition in a patient that substantially obviates one or more problems resulting from the limitations and deficiencies of the related art.

In accordance with one or more embodiments of the present invention, there is provided a method of treating, reducing, or alleviating a medical condition in a patient. The method includes administering to a patient in need thereof a biocompatible drug comprising one or more antiviral medications together with one or more cell pathway inhibitors, the patient having at least one of a respiratory tract inflammatory disease, a central nervous system inflammatory disease, and vasculitis, the one or more antiviral medications preventing an attachment of viruses to cell walls, blocking a penetration of the viruses into cells, and/or inhibiting virus replication by damaging nucleic acids of the viruses, and the one or more cell pathway inhibitors blocking an inflammatory response of inflamed tissue without inhibiting an immune response of the patient. The administration of the biocompatible drug to the patient treats the at least one of the respiratory tract inflammatory disease, the central nervous system inflammatory disease, and the vasculitis, reduces the symptoms associated with the at least one of the respiratory tract inflammatory disease, the central nervous system inflammatory disease, and the vasculitis, and/or alleviates the at least one of the respiratory tract inflammatory disease, the central nervous system inflammatory disease, and the vasculitis.

In a further embodiment of the present invention, the patient has a respiratory tract inflammatory disease, and the respiratory tract inflammatory disease is selected from the group consisting of influenza, parainfluenza, severe acute respiratory syndrome, a coronavirus disease, an Epstein-bar virus disease, a herpes virus disease, a bacterial infection, and combinations thereof.

In yet a further embodiment, the patient has a respiratory tract inflammatory disease, and the respiratory tract inflammatory disease comprises a coronavirus, the coronavirus being selected from the group consisting of COVID-19, mutations of COVID-19, mutations of the SARS CoV-2 virus, and combinations thereof.

In still a further embodiment, the biocompatible drug further comprises a semifluorinated alkane and polymeric slow release nanoparticles or microparticles used as a carrier of the biocompatible drug; and the biocompatible drug with the semifluorinated alkane and the polymeric slow release nanoparticles or microparticles is administered by inhalation or as a topical ointment to the patient to treat the at least one of the respiratory tract inflammatory disease, the central nervous system inflammatory disease, and the vasculitis, the semifluorinated alkane evaporating quickly upon administration to the patient so as to leave the polymeric slow release nanoparticles or microparticles with the biocompatible drug at a desired treatment location.

In yet a further embodiment, the polymeric slow release nanoparticles or microparticles are conjugated with a viral specific antibody while carrying at least two antiviral medications for intranasal inhalation or topically as an ointment to specifically target one or more viruses, the viral specific antibody being obtained from plasma/serum of patients who have recovered from a viral infection or the viral specific antibody being produced in a tissue culture using dead viruses cultured with T-cell lymphocytes or natural killers that produce the viral specific antibody in addition to producing exosomes or extracellular vesicles (ECV) that are both able to be harvested.

In still a further embodiment, the biocompatible drug is administered through the nasal mucosa to reach branches of the trigeminal nerve or olfactory nerve for delivery of the biocompatible drug to the brain, brain vasculature, and the cerebrospinal fluid where the semifluorinated alkane rapidly evaporates at body temperature in the tissue leaving the polymeric slow release nanoparticles or microparticles with the biocompatible drug at the desired treatment location.

In yet a further embodiment, the one or more antiviral medications are selected from the group consisting of amantadine, Lopinavir, linebacker and equivir, Arbidol, a nanoviricide, remdesivir, Favipiravir, Ebselen, oseltamivir, oseltamivir, indinavir, molnupiravir, MK-4482/EIDD-2801, ribavirin, Oya1, Glidesivir, Xofluza, interferon, umifenovir, tamivir, baloxavir, and combinations thereof; and the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, TGF beta inhibitors, and combinations thereof.

In still a further embodiment, the biocompatible drug further comprises one or more protease inhibitors in combination with the one or more antiviral medications and the one or more cell pathway inhibitors.

In yet a further embodiment, the at least one of the respiratory tract inflammatory disease, the central nervous system inflammatory disease, and the vasculitis comprises at least one of a viral infection of the lung, a viral brain encephalitis, and a brain vasculitis; and the method further comprises administering tocilizumab or tamoxifen in combination with the one or more antiviral medications and the one or more cell pathway inhibitors to treat the viral infection of the lung, the viral brain encephalitis, and/or the brain vasculitis; and administering the one or more cell pathway inhibitors through nose inhalation by spraying, aerosolization, or nebulization to reach both brain and lung tissue, and to reduce the inflammatory process and eliminate the side effects of the viral infection of the lung, the viral brain encephalitis, and/or the brain vasculitis.

In still a further embodiment, the method further comprises administering interferon or pegylated interferon in combination with the one or more antiviral medications and the one or more cell pathway inhibitors to the patient, where the interferon or pegylated interferon acts as an antiviral in the upper and lower respiratory tract, thereby blocking the replication of the RNA and DNA of the viruses at an early stage of viral infection.

In yet a further embodiment, the method further comprises administering a TMPRSS2 inhibitor, an ACE-2 inhibitor, and/or a neuropilin inhibitor in combination with the one or more cell pathway inhibitors to the patient where the TMPRSS2 inhibitor, the ACE-2 inhibitor, and/or the neuropilin inhibitor inhibits entry of the virus into the cell.

In still a further embodiment, the method further comprises administering a low molecular weight heparin or synthetic heparin mimetics in combination with a macrolide to the patient to enhance nerve repair and prevent blood coagulation so as to combat an overactive immune response.

In yet a further embodiment, the macrolide comprises cyclosporine A.

In still a further embodiment, the method further comprises administering a polyphenol and/or a derivative of a polyphenol that binds to heparan sulfate, thereby preventing viral attachment to cell receptors. In this further embodiment, the polyphenol and/or the derivatives of the polyphenol are selected from the group consisting of Epigallocatechin gallate (EGCG), green tea, and catechin.

In yet a further embodiment, the method further comprises administering a polyclonal antibody cocktail so as to effectively treat multiple proteins of a mutated virus.

In still a further embodiment, the method further comprises administering methylene blue, which acts as antioxidant and converts methemoglobin to hemoglobin and acts as an antiviral at a concentration of 0.25-2 mg/liter or less than 1 nM concentration, together with the one or more antiviral medications and the one or more cell pathway inhibitors; administering low molecular weight heparin to the patient to prevent blood coagulation; and performing dialysis, hemodialysis, or serum electrophoresis to remove unwanted toxins and creatinine and simultaneously acting to prevent blood clotting after administration of the methylene blue and the low molecular weight heparin.

In yet a further embodiment, the methylene blue together with the one or more antiviral medications and the one or more cell pathway inhibitors are administered using ultra small pluralities of gold nanoparticles to enhance viral damage.

In still a further embodiment, the method further comprises administering dimethyl fumarate orally, by injection, or by inhalation to prevent pyroptosis of cells resulting from an excessive immune response.

In yet a further embodiment, the method further comprises administering mycophenolic acid or metalloproteinase inhibitors to blocking an excessive immune response of inflamed tissue.

In still a further embodiment, the method further comprises administering an anti-vascular endothelial growth factor medication in combination with the one or more antiviral medications, wherein the anti-vascular endothelial growth factor medication blocks the release of the vascular endothelial growth factor from affected capillary endothelial cells or inflamed alveoli cells and prevents exhaustion of a cellular immune response.

In yet a further embodiment, the method further comprises administering prophylactically the one or more antiviral medications and methylene blue as a nasal spray, in aerosolized or nebulized form, or as a vapor, together with zinc in a saline solution orally in aliginate, chitosan encapsulated beads, or polycaprolactone, or nasally in a saline solution, to damage the invading viruses before entering the nasal mucosa along with an antibiotic or antiviral ointment applied to the nasal passages to kill the viruses in the nose and respiratory tract.

It is to be understood that the foregoing general description and the following detailed description of the present invention are merely exemplary and explanatory in nature. As such, the foregoing general description and the following detailed description of the invention should not be construed to limit the scope of the appended claims in any sense.

BRIEF DESCRIPTION OF THE SEVERAL VIEWS OF THE DRAWINGS

The invention will now be described, by way of example, with reference to the accompanying drawings, in which:

FIG. 2A is a partial side cross-sectional view of an eye having internal corneal scar tissue;

FIG. 2B is a partial side cross-sectional view of the eye of FIG. 2A, wherein the scarred corneal tissue has been externally removed from the eye;

FIG. 2C is a partial side cross-sectional view of the eye of FIG. 2A, wherein a cross-linked donor cornea is shown being implanted in the location previously occupied by the scarred corneal tissue;

FIG. 69A is a front view of a cornea of an eye illustrating a generally linear drug delivery implant disposed in a cross-linked pocket in the peripheral portion of the cornea;

FIG. 69B is a partial side cross-sectional view of the eye of FIG. 69A illustrating the generally linear drug delivery implant disposed in the cross-linked pocket in the peripheral portion of the cornea;

FIG. 70A is a front view of a cornea of an eye illustrating a drug delivery implant disposed in a cross-linked pocket in the peripheral portion of the cornea, wherein the implant comprises a needle fluidly coupling the implant to the anterior chamber of the eye; and FIG. 70B is a partial side cross-sectional view of the eye of FIG. 70A illustrating the tubular drug delivery implant with the needle extending into the anterior chamber of the eye with the aqueous fluid of the eye.

Throughout the figures, the same elements are always denoted using the same reference characters so that, as a general rule, they will only be described once.

DETAILED DESCRIPTION OF EMBODIMENTS OF THE INVENTION

A first illustrative embodiment of a corneal transplant procedure with a cross-linked cornea is shown in FIGS. 1A-1D. The corneal transplant procedure illustrated in FIGS. 1A-1D involves full corneal replacement of the scarred or diseased cornea by the donor cornea. In other words, FIGS. 1A-1D illustrate a penetrating keratoplasty procedure wherein the full thickness of the scarred or diseased cornea is replaced with a cross-linked donor cornea (i.e., a full-thickness corneal transplant).

Figure 1A:
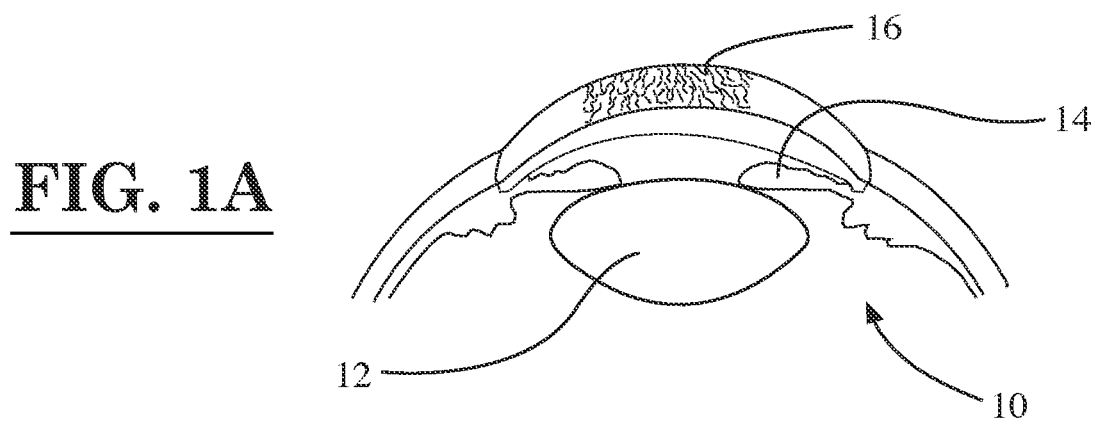
FIG. 1A is a partial side cross-sectional view of an eye having a scarred cornea, wherein substantially the entire thickness of the cornea is scarred.

Referring initially to FIG. 1A, it can be seen that substantially the entire thickness of the cornea 16 of the eye 10 is scarred and/or diseased (i.e., scarred, diseased, or scarred and diseased). FIG. 1A also illustrates the lens 12 and iris 14 of the eye 10, which are located posteriorly of the cornea 16. In this embodiment, it is necessary to replace substantially the entire thickness of the cornea 16 with a donor cornea.

Figure 1B:
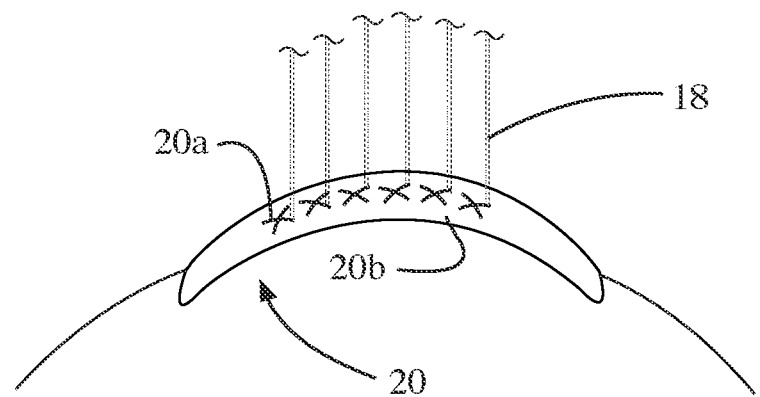
FIG. 1B is a partial side cross-sectional view of a donor cornea undergoing cross-linking.

In FIG. 1B, the cross-linking 18 of the clear donor cornea 20 is diagrammatically illustrated. As depicted in FIG. 1B, only the front portion 20a of the donor cornea 20 is cross-linked. That is, the cross-linking does not extend all the way to the rear portion 20b of the donor cornea 20. It is to be understood that the cross-linking 18 of the donor cornea 20 may also be done after implanting the donor cornea into the eye of the patient, rather than before implantation as shown in the illustrative example of FIGS. 1A-1D. Also, it is to be understood that all or just a part of the donor cornea 20 may be cross-linked.

In the illustrative embodiments described herein (i.e., as depicted in FIGS. 1A-1D, 2A-2C, and 3A-3C), the cross-linking of the clear donor cornea may comprise the steps of: (i) applying a photosensitizer to the donor cornea, the photosensitizer facilitating cross-linking of the donor cornea; and (ii) irradiating the donor cornea with ultraviolet light so as to activate cross-linkers in the donor cornea and thereby strengthen the donor cornea. The photosensitizer may comprise riboflavin or a solution comprising a liquid suspension having nanoparticles of riboflavin. The cross-linker may have between about 0.1% Riboflavin to about 100% Riboflavin or any other suitable range or specific percentage therein. The ultraviolet radiation or rays used to irradiate the donor cornea may be between about 370 nanometers and about 380 nanometers (or between 370 nanometers and 380 nanometers). The radiation is preferably about 3 mW or more as needed and emanates from a laser source at about a 3 cm distance from the donor cornea for about 30 minutes or less. The time of the exposure can vary depending on the light intensity, focus, and the concentration of riboflavin. However, the ultraviolet radiation can be applied at any suitable distance, time or wavelength. Preferably, cross-linking the donor cornea does not significantly change the refractive power of the donor cornea; however, if desired, cross-linking can change the refractive power of the donor cornea to any suitable degree.

In addition to Riboflavin, other suitable cross linking agents are low carbon carbohydrates, such as pentose sugar (e.g., ribose) or hexose sugar (e.g., glucose), or complex carbohydrates. Other crosslinking agents may include Transaminidases, transglutaminases or a naturally-derived cross-linker named malic acid derivative (MAD) concentrations higher than 30 mM, commercially available cross-linkers such as 1-ethyl-3-(3('-dimethylaminopropyl) carbodiimide (EDC), or ethyl-3(3-dimethylamino) propyl carbodiimide (EDC), etc. The cross-linking may also be done postoperatively by the application of other crosslinking agents, such as Triglycidylamine (TGA) synthesized via reacting epichlorhydrin and a carbodiimide, or the oxidized glycogen hexoses. The ribose, glucose and similar agents may penetrate the cornea easily using drops, gel, or the slow release mechanisms, nanoparticle, microspares, liposome sets. In addition, the crosslinkers may be delivered with Mucoadhesives.

In one or more embodiments, all or part of the donor cornea is cross-linked. Also, in one or more embodiments, a very high concentration of Riboflavin may be used because the in vitro cross-linking process may be stopped whenever needed prior to the transplantation of the donor cornea in the host eye. In addition, the power of the ultraviolet (UV) laser may also be increased so as to cross-link the tissue of the donor cornea faster. The use of a high concentration of Riboflavin, and the increasing of the ultraviolet (UV) laser power, are not possible during an in vivo cross-linking procedure because the aim of such an in vivo procedure is to protect the cells of the host cornea. Also, the in vivo process cannot be controlled as efficiently as in the vitro crosslinking of the corneal transplant.

In one or more embodiments, the donor cornea may be extracted from a human cadaver, or the cornea may be reconstructed as known in tissue engineering in vitro and three-dimensionally (3D) printed. Cross-linking of a culture-grown cornea eliminates the cellular structure inside the cornea. If needed again, the healthy corneal endothelium of the patient may be grown in vitro for these tissues by placing them on the concave surface of the cornea and encouraging their growth under laboratory control conditions prior to the transplantation.

In the embodiments where the donor cornea is tissue culture grown, the cornea may be formed from mesenchymal fibroblast stem cells, embryonic stem cells, or cells derived from epithelial stem cells extracted from the same patient, or a mixture of these cells. Using known tissue culture techniques, the cells may produce a transparent corneal stroma. This culture-grown corneal stroma will not have a corneal epithelium or a corneal endothelium. Thus, it eliminates the complexity of developing a full thickness cornea in the tissue culture. This stromal transplant may be used as a lamellar or partial thickness replacement of the existing host cornea. This transplant may also be used to augment or add to the thickness of the host cornea. This transparent corneal stroma may be transplanted either prior to, or after being cross-linked using various cross-linking methods.

In one or more embodiments, the cross-linked donor cornea may be sized and precisely cut with a femtosecond laser to the desired shape and curvature to replace the removed host cornea so that the refractive errors of the recipient are also automatically corrected with the cross-linked cornea.

Figure 1C:
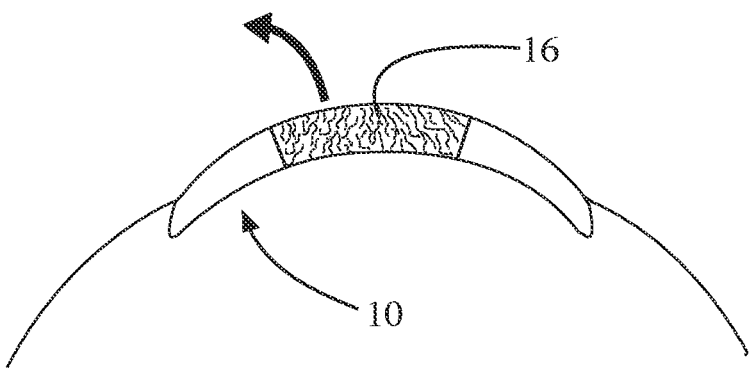
FIG. 1C is a partial side cross-sectional view of the eye of FIG. 1A, wherein the scarred cornea is shown being removed.

Now, referring to FIG. 1C, it can be seen that the scarred and/or diseased cornea 16 is shown being removed from the eye 10. The scarred and/or diseased cornea 16 may be removed from the eye 10 by using various suitable means, such as mechanical means or cutting using a laser. When mechanical means are used to remove the scarred and/or diseased cornea 16 from the eye 10, the scarred and/or diseased cornea 16 may initially be cut away or dissected from the remainder of the eye 10 using a sharp mechanical instrument (e.g., a surgical micro-knife, a needle, a sharp spatula, a pair of micro-scissors), and then subsequently removed or extracted with a pair of micro-forceps. When laser cutting is used to remove the scarred and/or diseased cornea 16 from the eye 10, the scarred and/or diseased cornea 16 may be cut away using a suitable laser, such as a femtosecond laser. Also, in some embodiments, the mechanical means for cutting and extraction (e.g., the surgical micro-knife and/or pair of micro-scissors) may be used in combination with the laser means (e.g., the femtosecond laser).

In one or more embodiments, the donor cornea may be shaped and cut with the femtosecond laser prior to the cross-linking thereof so as to replace part or all of the recipient cornea which is cut with the femtosecond laser. In these one or more embodiments, the entire donor and host cornea together may be cross-linked with Riboflavin and UV radiation. These procedures may also be performed on a culture-grown transplant cornea.

Figure 1D:
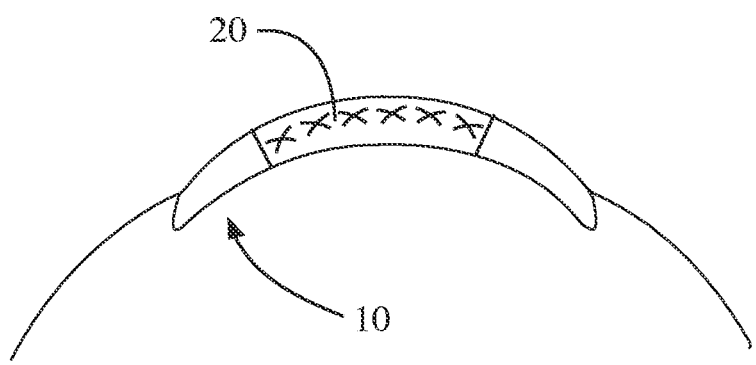
FIG. 1D is a partial side cross-sectional view of the eye of FIG. 1A, wherein the cross-linked donor cornea is shown being implanted in the location previously occupied by the scarred cornea.

Then, as shown in FIG. 1D, after the scarred and/or diseased cornea 16 has been removed from the eye 10, the cross-linked donor cornea 20 is implanted into the eye 10 of the patient in the location previously occupied by the scarred and/or diseased cornea 16. After implantation of the cross-linked donor cornea 20, sutures or a suitable adhesive may be utilized to secure the cross-linked donor cornea 20 in place on the eye 10. When sutures are used for holding the donor cornea 20 in place, the sutures may comprise nylon sutures, steel sutures, or another suitable type of non-absorbable suture. When the cornea 16 is subsequently ablated after the implantation of the donor cornea, as will be described hereinafter, additional sutures may be required after ablation.

In one or more embodiments, a biodegradable adhesive is used in a corneal transplantation procedure with the cross-linked donor cornea 20 described above, or with a non-cross-linked corneal transplant. In these one or more embodiments, the biodegradable adhesive obviates the need for a suture in the corneal transplant procedure. Sutures generally distort the surface of the cornea and can produce an optically unacceptable corneal surface. Also, the use of the biodegradable adhesive obviates the need for glues requiring exothermic energy. Glues that use an exothermic effect, such as Fibronectin, need thermal energy to activate their adhesive properties. This thermal energy, such as that delivered by a high-powered laser, produces sufficient heat to coagulate the Fibronectin and the tissue that it contacts. Any thermal effect on the cornea produces: (i) corneal opacity, (ii) tissue contraction, and (iii) distortion of the optical surface of the cornea. The tissue adhesion created by these glues, including Fibronectin or fibrinogen, is flimsy and cannot withstand the intraocular pressure of the eye.

In fact, sutures are superior to these types of adhesives because the wound becomes immediately strong with sutures, thereby supporting the normal intraocular pressure of between 18 and 35 mmHg. In contrast to the use of a suture in which distortion that is caused by suture placement can be managed by cutting and removing the suture, the distortion caused by the coagulated corneal tissue cannot be corrected.

Other glues, such as cyanoacrylate, become immediately solid after coming into contact with the tissue or water. These glues produce a rock-hard polymer, the shape of which cannot be controlled after administration. Also, the surface of the polymer created by these glues is not smooth. Thus, the eyelid will rub on this uneven surface, and the uneven surface scratches the undersurface of the eyelid when the eyelid moves over it. In addition, the cyanoacrylate is not biodegradable or biocompatible. As such, it causes an inflammatory response if applied to the tissue, thereby causing undesirable cell migration and vascularization of the cornea.

Thus, by using a biocompatible and absorbable acrylate or other biodegradable glues that do not need exothermic energy for the process of adhesion (i.e., like fibronectin or fibrinogen), one is able to maintain the integrity of the smooth corneal surface. In one or more embodiments, the biocompatible and biodegradable adhesive may be painted only at the edges of the transplant prior to placing it in the host or diseased cornea. In these embodiments, the biocompatible and biodegradable adhesive only comes into contact with the host tissue at the desired predetermined surface to create a strong adhesion. The adhesion may last a few hours to several months depending on the composition of the molecule chosen and the concentration of the active component.

Other suitable biodegradable adhesives or glues that may be used in conjunction with the transplant include combinations of gallic acid, gallic tannic acid, Chitosan, gelatin, polyphenyl compound, Tannic Acid (N-isopropylacrylamide (PNIPAM), and/or Poly(N-vinylpyrrolidone) with polyethylene glycol (PEG). That is, polyethylene glycol (PEG) may be mixed with any one or plurality of gallic acid, gallic tannic acid, Chitosan, gelatin, polyphenyl compound, Tannic Acid (N-isopropylacrylamide (PNIPAM), and Poly(N-vinylpyrrolidone), so as to form a molecular glue. These adhesives are suitable for the use on the cornea because they create a tight wound that prevents leakage from the corneal wound and maintain the normal intraocular pressure shortly after their application and also do not distort the wound by causing traction on the tissue.

In addition, other suitable biodegradable adhesives or glues, which may need an external source of energy, that are able to be used in conjunction with the transplant include combinations of riboflavin, lactoflavin, gallic acid, gallic tannic acid, Chitosan, gelatin, polyphenyl compound, Tannic Acid (N-isopropylacrylamide (PNIPAM), dopamine, and/or Poly(N-vinylpyrrolidone) with polyethylene glycol (PEG). That is, polyethylene glycol (PEG) may be mixed with any one or plurality of riboflavin, lactoflavin, tannic acid, dopamine, gallic tannic acid, Chitosan, gelatin, polyphenyl compound, Tannic Acid (N-isopropylacrylamide (PNIPAM), and Poly(N-vinylpyrrolidone), so as to form a molecular glue. These adhesives are also suitable for the use on the cornea because they create a tight wound that prevents leakage from the corneal wound and maintain the normal intraocular pressure shortly after their application and also do not distort the wound by causing traction on the tissue.

In one or more embodiments, the donor cornea may be temporarily sutured to the host cornea by only a few single sutures to the host cornea. Then, the sutures may be removed immediately after donor cornea is fixed to the host cornea with a suitable adhesive.

A second illustrative embodiment of a corneal transplant procedure with a cross-linked cornea is shown in FIGS. 2A-2C. Unlike the first embodiment described above, the corneal transplant procedure illustrated in FIGS. 2A-2C does not involve full corneal replacement of the scarred or diseased cornea by the donor cornea. Rather, FIGS. 2A-2C illustrate a lamellar keratoplasty procedure wherein only a portion of the cornea 16' of the eye 10' contains scarred and/or diseased tissue (i.e., a full-thickness corneal section is not removed). In the procedure of FIGS. 2A-2C, an internal scarred and/or diseased portion 16a' of the cornea 16' is externally removed from the eye 10' of a patient.

Referring initially to FIG. 2A, it can be seen that only an internal portion 16a' of the cornea 16' is scarred and/or diseased. As such, in this embodiment, it is not necessary to replace the entire thickness of the cornea 16 with a donor cornea as was described above in conjunction with FIGS. 1A-1D, but rather just a portion of the cornea 16'.

Next, referring to FIG. 2B, it can be seen that the scarred and/or diseased portion 16a' has been externally removed from the cornea 16' of the eye 10' such that the cornea 16' comprises a cavity 19 disposed therein for receiving the donor cornea. Because an external approach was utilized for removing the scarred and/or diseased portion 16a' of the cornea 16', the cavity 19 comprises a notch-like void in the outside or anterior surface of the cornea 16'. As described above for the first embodiment, the scarred and/or diseased corneal portion 16a' may be removed from the remainder of the cornea 16' using various suitable means, such as mechanical means or the laser cutting means (e.g., femtosecond laser) described above.

Finally, as shown in FIG. 2C, after the scarred and/or diseased portion 16a' has been removed from the remainder of the cornea 16' of the eye 10', the cross-linked donor cornea or cross-linked donor corneal portion 20' is implanted into the eye 10' of the patient in the location previously occupied by the scarred and/or diseased corneal portion 16a'. As described above, after implantation of the cross-linked donor corneal portion 20' into the eye 10', sutures or a suitable adhesive (e.g., the biocompatible and biodegradable adhesive described above) may be utilized to secure the cross-linked donor corneal portion 20' in place on the host cornea of the eye 10'.

After the cross-linked donor corneal portion 20' is implanted into the eye 10' of the patient, a portion of the cornea 16' may be ablated so as to change the refractive properties of the eye (e.g., to give the patient perfect or near perfect refraction). The ablation of the portion of the cornea 16' may be performed using a suitable laser 34, such as an excimer laser. The ablation by the laser causes the ablated tissue to essentially evaporate into the air. Also, the ablation of the portion of the cornea 16' may be done intrastromally, as with LASIK (laser-assisted in situ keratomileusis), or on the surface of the cornea, as with PRK (photorefractive keratectomy). The ablation may be performed a predetermined time period after the corneal transplantation so as to enable the wound healing process of the recipient's cornea to be completed. It is to be understood that the ablation, which follows the corneal transplantation, may be performed in conjunction with any of the embodiments described herein.

It is also to be understood that, in some alternative embodiments, the ablation may be performed prior to the transplantation of the donor cornea, rather than after the transplantation of the donor cornea. For example, in one or more alternative embodiments, a lenticle may be precisely cut in the tissue of a culture-grown stroma of a donor cornea by using a femtosecond laser so that when implanted into the host cornea, it corrects the residual host eye's refractive error.

Figure 3A:
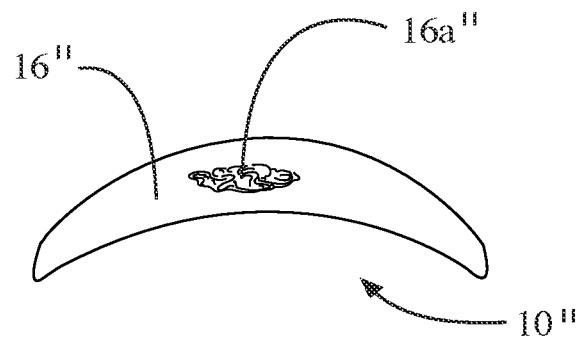
FIG. 3A is a partial side cross-sectional view of an eye having internal corneal scar tissue.
Figure 3B:
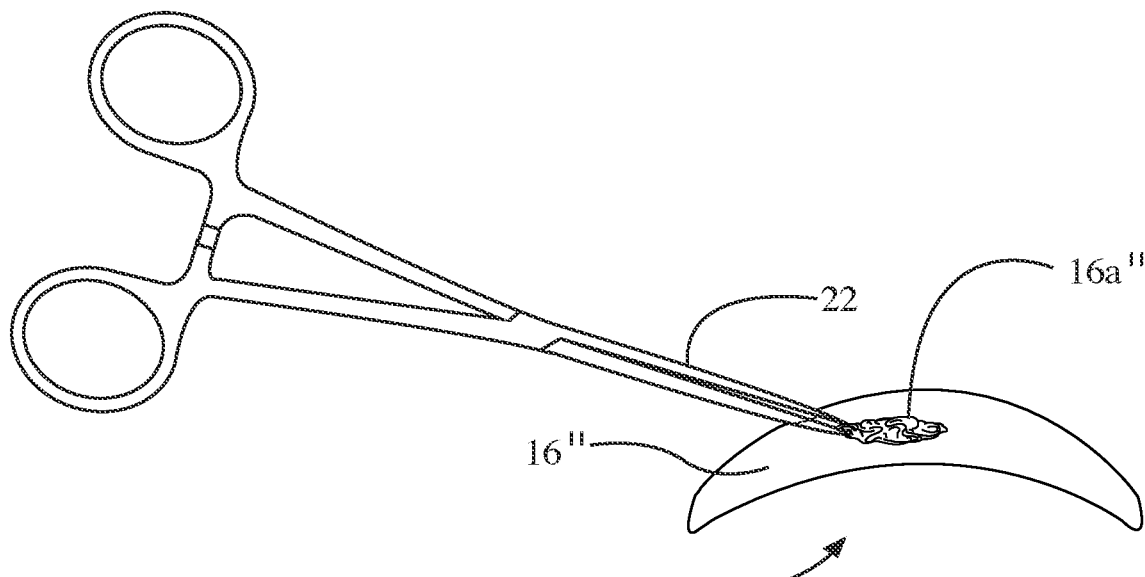
FIG. 3B is a partial side cross-sectional view of the eye of FIG. 3A, wherein the scarred corneal tissue is shown being internally removed from the eye.
Figure 3C:
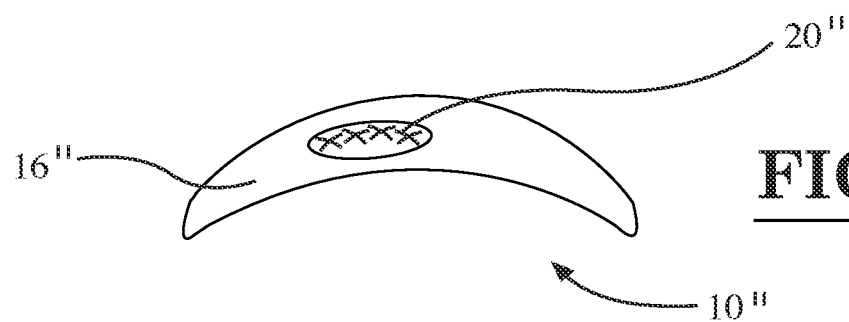
FIG. 3C is a partial side cross-sectional view of the eye of FIG. 3A, wherein a cross-linked donor cornea is shown being implanted in the location previously occupied by the scarred corneal tissue.

A third illustrative embodiment of a corneal transplant procedure with a cross-linked cornea is shown in FIGS. 3A-3C. Like the second embodiment described above, the corneal transplant procedure illustrated in FIGS. 3A-3C only involves replacing a scarred and/or diseased portion 16a" of the cornea 16" with a donor corneal portion. Thus, similar to the second embodiment explained above, FIGS. 3A-3C illustrate a lamellar keratoplasty procedure wherein only a portion of the cornea 16" of the eye 10" contains scarred and/or diseased tissue (i.e., a full-thickness corneal section is not removed). Although, in the procedure of FIGS. 3A-3C, an internal scarred and/or diseased portion 16a" of the cornea 16" is internally removed from the eye 10" of a patient, rather than being externally removed as in the second embodiment of FIGS. 2A-2C.

Referring initially to FIG. 3A, it can be seen that only an internal portion 16a" of the cornea 16" of the eye 10" is scarred and/or diseased. As such, in this embodiment, like the preceding second embodiment, it is not necessary to replace the entire thickness of the cornea 16" with a donor cornea, but rather just a portion of the cornea 16".

Next, referring to FIG. 3B, it can be seen that the scarred and/or diseased portion 16a" is being internally removed from the remainder of the cornea 16" using a pair of forceps 22 (i.e., mechanical means of removal are illustrated in FIG. 3B). Advantageously, because an internal approach is being utilized for removing the scarred and/or diseased portion 16a" of the cornea 16", the cornea 16" will not comprise the notch-like cavity 19 disposed in the outside or anterior surface of the cornea, which was described in conjunction with the preceding second embodiment. As described above for the first and second embodiments, the scarred and/or diseased corneal portion 16a" may be removed from the remainder of the cornea 16" using other suitable alternative means, such as laser cutting techniques (e.g., using a femtosecond laser). Advantageously, the femtosecond laser is capable of cutting inside the tissue without involving the surface of the tissue. The cut part of the tissue can then be removed by other means (e.g., micro-forceps).

Finally, as shown in FIG. 3C, after the scarred and/or diseased corneal portion 16a" has been removed from the remainder of the cornea 16" of the eye 10", the cross-linked donor cornea or cross-linked donor corneal portion 20" is implanted into the eye 10" of the patient in the location previously occupied by the scarred and/or diseased corneal portion 16a". After implantation of the cross-linked donor corneal portion 20", sutures or a suitable adhesive (e.g., the biocompatible and biodegradable adhesive described above) may be utilized to secure the cross-linked donor corneal portion 20" in place on the host cornea of the eye 10". Advantageously, the cross-linked donor corneal portion 20", which is strengthened by the cross-linking performed thereon, reinforces the cornea 16" and greatly reduces the likelihood of corneal graft rejection.

It is to be understood that the scarred and/or diseased corneal portion 16a" that is removed from the cornea 16" may also be replaced with stroma stem cells or mesenchymal stem cells, which can be contained in a medium, and then injected in the internal cavity previously occupied by the scarred and/or diseased corneal tissue 16a".

In one or more embodiments, mesenchymal stem cells also may be injected inside the donor cornea before or after transplantation. In addition, in one or more embodiments, daily drops of a Rho Kinase inhibitor may be added to the host eye after the surgery. The use of a medication, such as a Rho Kinase inhibitor, with the stem cells will encourage stem cell proliferation.

A fourth illustrative embodiment of a corneal transplant procedure with a cross-linked cornea is shown in FIGS. 4A-4E. Like the second and third embodiments described above, the corneal transplant procedure illustrated in FIGS. 4A-4E only involves replacing a scarred and/or diseased portion 16a''' of the cornea 16''' with a donor corneal portion. Thus, similar to the second and third embodiments explained above, FIGS. 4A-4E illustrate a lamellar keratoplasty procedure wherein only a portion of the cornea 16''' of the eye 10''' contains scarred and/or diseased tissue (i.e., a full-thickness corneal section is not removed). Although, in the procedure of FIGS. 4A-4E, a different-shaped scarred and/or diseased portion 16a''' of the cornea 16''' is removed.

Figure 4A:
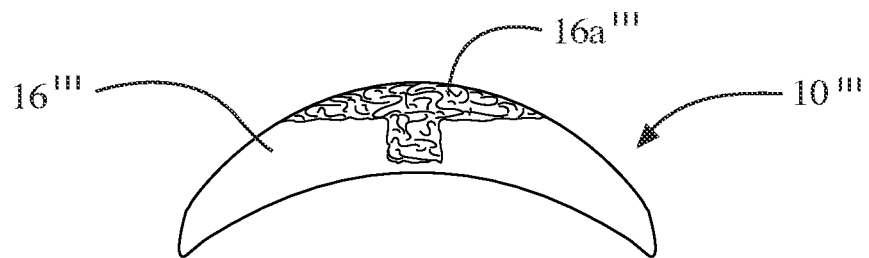
FIG. 4A is a partial side cross-sectional view of an eye having a T-shaped corneal scar and/or diseased tissue portion.

Referring initially to FIG. 4A, it can be seen that only a portion 16a''' of the cornea 16''' having a T-shape or "top hut" shape is scarred and/or diseased. As such, in this embodiment, it is not necessary to replace the entire thickness of the cornea 16''' with a donor cornea as was described above in conjunction with FIGS. 1A-1D, but rather just a portion 16a''' of the cornea 16'''. In this illustrative embodiment, the back side of the cornea 16''' is maintained (see e.g., FIG. 4D).

Figure 4B:
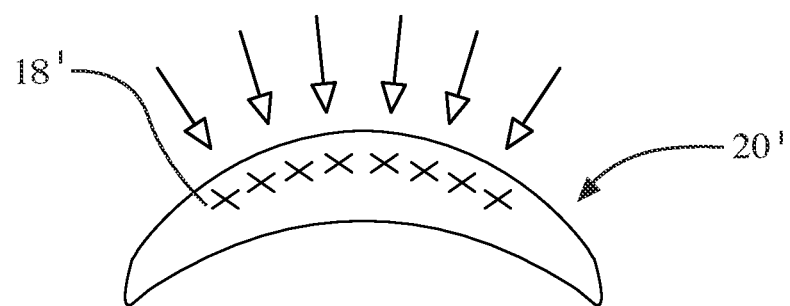
FIG. 4B is another partial side cross-sectional view of a donor cornea undergoing cross-linking.
Figure 4C:
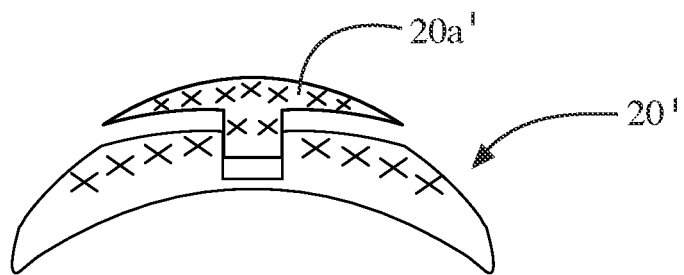
FIG. 4C is a partial side cross-sectional view illustrating a T-shaped portion of the cross-linked donor cornea being cut out from a remainder of the donor cornea.
Figure 5A:
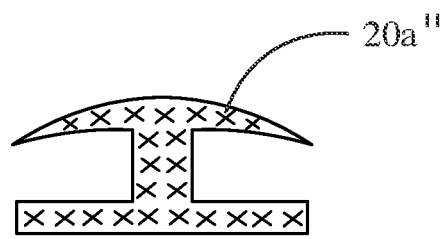
FIG. 5A illustrates an alternative configuration for the cross-linked donor cornea implant, wherein the donor cornea implant has a dumbbell shape.
Figure 5B:
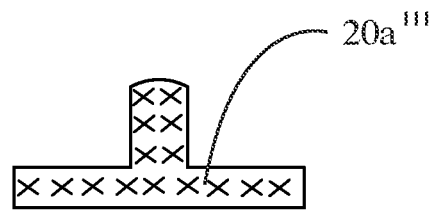
FIG. 5B illustrates another alternative configuration for the cross-linked donor cornea implant, wherein the donor cornea implant has a reversed or upside down T-shape.

In FIG. 4B, the cross-linking 18' of the clear donor cornea 20' is diagrammatically illustrated. As mentioned above, it is to be understood that all or just a part of the donor cornea 20' may be cross-linked. Then, in FIG. 4C, it can be seen that a portion 20a' of the clear donor cornea 20', which has a T-shape or "top hut" shape that matches the shape of the scarred and/or diseased portion 16a''' of the cornea 16''', is cut out from the remainder of the clear donor cornea 20' such that it has the necessary shape. In one or more embodiments, the portion 20a' may be cut from the clear donor cornea 20' and appropriately shaped using a femtosecond laser. As shown in FIGS. 5A and 5B, other suitably shaped cross-linked corneal portions may be cut from the clear donor cornea 20', such as a dumbbell-shaped corneal portion 20a" (see FIG. 5A) or a corneal portion 20a''' having a reversed T-shape or "reversed top hut" shape (see FIG. 5B), in order to accommodate correspondingly shaped scarred and/or diseased areas in the host cornea.

Figure 4D:
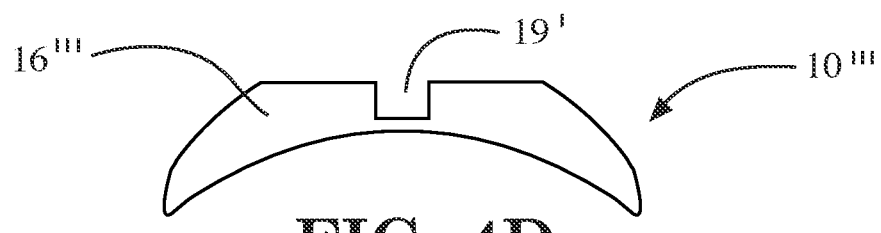
FIG. 4D is a partial side cross-sectional view of the eye of FIG. 4A, wherein the T-shaped scarred and/or diseased portion of corneal tissue has been removed from the eye.

Next, referring to FIG. 4D, it can be seen that the scarred and/or diseased portion 16a''' having the T-shape or "top hut" shape has been removed from the cornea 16''' of the eye 10''' such that the cornea 16''' comprises a cavity 19' disposed therein for receiving the donor cornea. As described above for the first three embodiments, the scarred and/or diseased corneal portion 16a''' may be removed from the remainder of the cornea 16''' using various suitable means, such as mechanical means or the laser cutting means (e.g., femtosecond laser) described above.

Figure 4E:
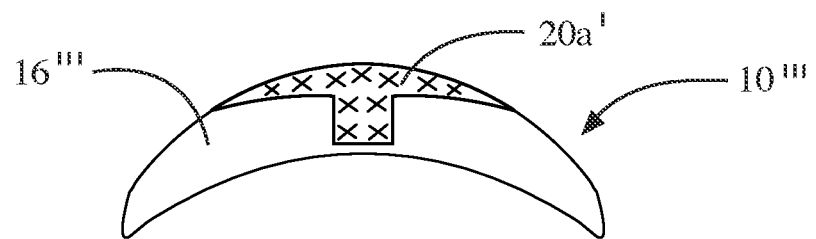
FIG. 4E is a partial side cross-sectional view of the eye of FIG. 4A, wherein the cross-linked T-shaped donor cornea portion is shown being implanted in the location previously occupied by the scarred and/or diseased corneal tissue portion.

Finally, as shown in FIG. 4E, after the scarred and/or diseased portion 16a''' has been removed from the remainder of the cornea 16''' of the eye 10''', the cross-linked donor corneal portion 20a' is implanted into the eye 10''' of the patient in the location previously occupied by the scarred and/or diseased corneal portion 16a'''. Because the shape of the transplant corresponds to that of the removed portion 16a''' of the cornea 16''', the transplant sits comfortably in its position in the host cornea. As described above, after implantation of the cross-linked donor corneal portion 20a' into the eye 10''', sutures or a suitable adhesive (e.g., the biocompatible and biodegradable adhesive described above) may be utilized to secure the cross-linked donor corneal portion 20a' in place on the host cornea 16''' of the eye 10'''. For example, if a biocompatible and biodegradable adhesive is used to secure the cross-linked donor corneal portion 20a' in place in the cornea 16''' of the eye 10''', the edges of the donor corneal portion 20a' are coated with the biocompatible and biodegradable adhesive so as to give the transplant a reliable stability. In this case, it is desirable to have the attachment of the transplant maintained by the biocompatible and biodegradable adhesive for a period of months (i.e., it is desirable for the transplant to be secured in place by the biocompatible and biodegradable adhesive for as long as possible).

An illustrative embodiment of a corneal lenslet implantation procedure with a cross-linked cornea is shown in FIGS. 6A-6C and 7A-7C. Similar to the second, third, and fourth embodiments described above, FIGS. 6A-6C and 7A-7C illustrate a lamellar keratoplasty procedure wherein only a portion of the cornea 16''' of the host eye 10''' is removed during the procedure (i.e., a full-thickness corneal section is not removed). Although, the procedure of FIGS. 6A-6C and 7A-7C differs in several important respects from the abovedescribed procedures. In this embodiment, the corneal transplant is cross-linked in vitro. Then, using a femtosecond laser or an excimer laser, the surgeon carves out or ablates a three-dimensional (3D) corneal cross-linked augment from the donor cornea 20''' that exactly compensates for the refractive error of the recipient of the transplant. That is, the corneal cross-linked augment or inlay may be cut to the desired shape using a femtosecond laser, or the inlay may be shaped in vitro using an excimer laser prior to its implantation in the cornea 16'''' of the host eye 10''''. After making an internal pocket 28 in the recipient cornea 16'''' of the host eye 10'''' with a femtosecond laser, the cross-linked transplant is folded and implanted in a predetermined fashion inside the host's corneal pocket 28 to provide stability to the eye 10'''' having keratoconus, keratoglobus, a thin cornea or abnormal corneal curvature, thereby preventing future corneal ectasia in this eye 10'''' and correcting its refractive errors. Advantageously, the procedure of this embodiment comprises a lamellar cross-linked corneal transplantation, which additionally results in simultaneous correction of the refractive error of the eye 10'''' of the patient. As used herein, the term "lenslet" refers to a lens implant configured to be implanted in a cornea of an eye. The lens implant may be formed from an organic material, a synthetic material, or a combination of organic and synthetic materials.

Figures 6A, 6B, 6C:
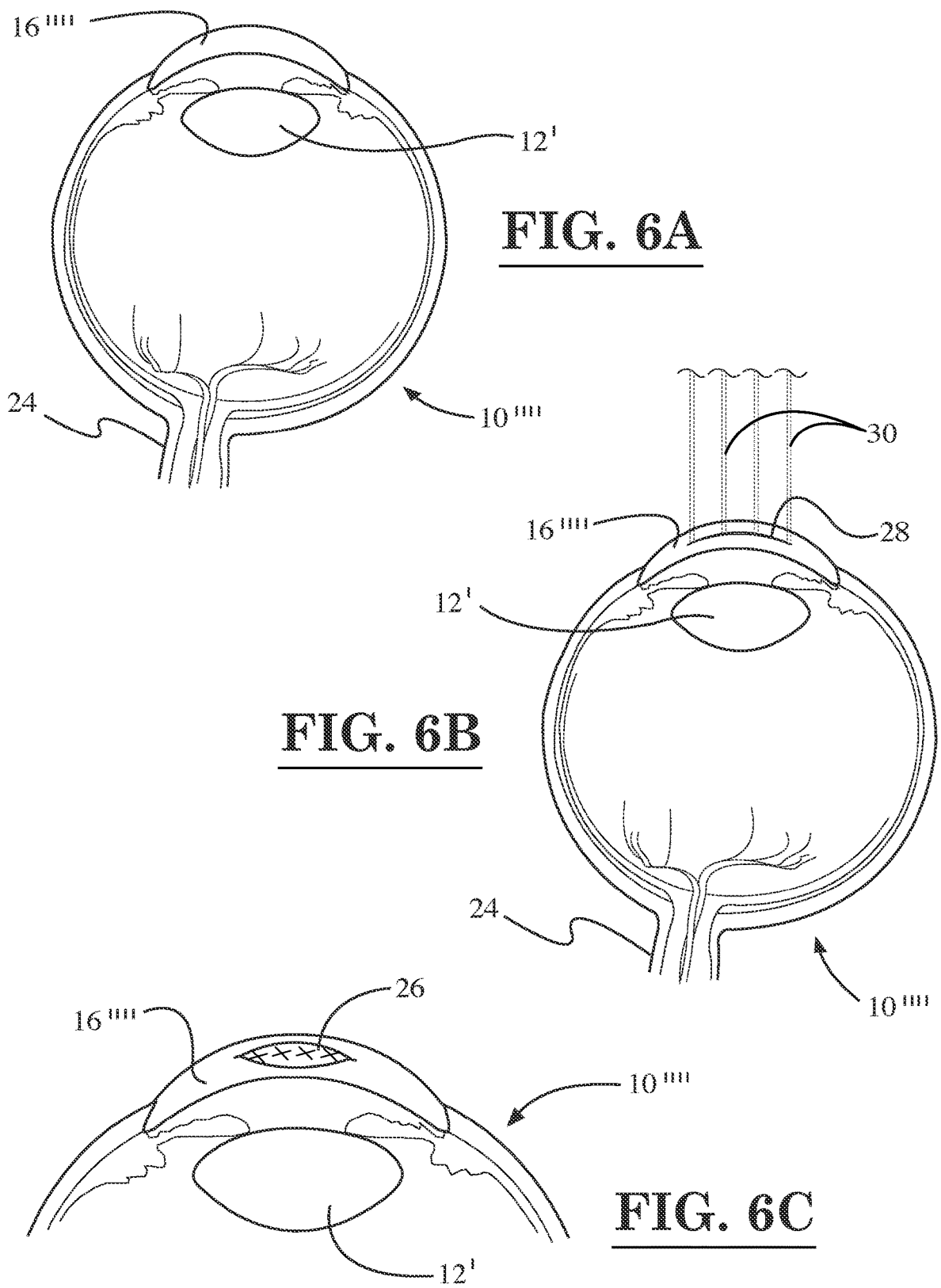
FIG. 6A is a side cross-sectional view of a host eye prior to an transplant procedure.
FIG. 6B is another side cross-sectional view of the host eye of FIG. 6A, which illustrates a creation of a corneal pocket therein.
FIG. 6C is another side cross-sectional view of the host eye of FIG. 6A, which illustrates an implantation of the cross-linked lamellar lenslet into the host eye.
Figure 7A:
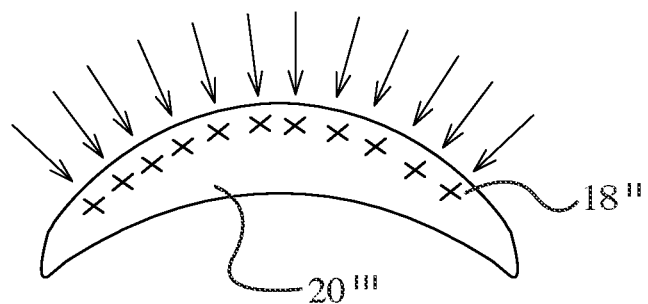
FIG. 7A is a partial side cross-sectional view of a donor cornea being cross-linked prior to being shaped for use in a transplant procedure.
Figure 7B:
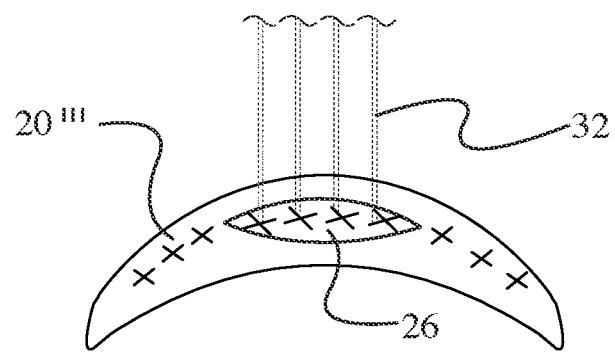
FIG. 7B is another partial side cross-sectional view of the donor cornea of FIG. 7A, which illustrates the cutting of a cross-linked lamellar lenslet from a remainder of the cross-lined donor cornea.

Now, with reference to FIGS. 6A-6C and 7A-7C, the illustrative embodiment will be described in further detail. The host eye 10'''' with lens 12', cornea 16'''', and optic nerve 24 is shown in FIG. 6A, while the donor cornea 20''' is depicted in FIG. 7A. The donor cornea 20''' of FIG. 7A may be a cross-linked cornea of a cadaver or a tissue culture-grown cornea that has been cross-linked. Turning to FIG. 6B, it can be seen that an internal corneal pocket 28 is created in the cornea 16'''' of the host eye 10'''' (e.g., by using a suitable laser, which is indicated diagrammatically in FIG. 6B by lines 30).

Figure 7C:
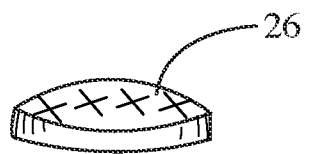
FIG. 7C is a side cross-sectional view of the cross-linked lamellar lenslet after it has been appropriately shaped and removed from the donor cornea of FIGS. 7A and 7B.

In FIG. 7A, the cross-linking 18'' of the donor cornea 20''' is diagrammatically illustrated. As mentioned in the preceding embodiments, it is to be understood that all or just a part of the donor cornea 20''' may be cross-linked. Then, after the donor cornea 20''' of FIG. 7A has been cross-linked (e.g., by using a photosensitizer in the form of riboflavin and UV radiation as described above), it can be seen that a cross-linked lamellar lenslet 26 is cut out from the remainder of the donor cornea 20''' (e.g., by using a suitable laser, which is indicated diagrammatically in FIG. 7B by lines 32) such that it has the necessary shape for implantation into the host eye 10''''. As explained above, the cross-linked lamellar lenslet 26 may be cut from the donor cornea 20''' and appropriately shaped using a femtosecond laser or an excimer laser. The cross-linked lamellar lenslet 26 is capable of being prepared to any requisite shape using either the femtosecond laser or the excimer laser. FIG. 7C illustrates the shaped cross-linked lamellar lenslet 26 after it has been removed from the remainder of the donor cornea 20'''.

Finally, as shown in FIG. 6C, the cross-linked lamellar lenslet 26 is implanted into the cornea 16'''' of the host eye 10'''' of the patient in the location where the pocket 28 was previously formed. Because the shape of the transplant corresponds to that of the pocket 28 formed in the eye 10'''', the transplant sits comfortably in its position in the host cornea 16''''. As described above, after implantation of the cross-linked lamellar lenslet 26 into the eye 10'''', the refractive errors of the eye 10'''' have been corrected because the cross-linked lamellar lenslet 26 has been appropriately shaped to compensate for the specific refractive errors of the host eye 10'''' prior to its implantation into the eye 10''''. In addition, as explained above, the implantation of the cross-linked lamellar lenslet 26 provides additional stability to an eye having keratoconus, keratoglobus, a thin cornea, or abnormal corneal curvature.

Another illustrative embodiment of a corneal lenslet implantation procedure with a cross-linked cornea is shown in FIGS. 8-14. In general, the procedure illustrated in these figures involves forming a two-dimensional cut into a cornea of an eye; creating a three-dimensional pocket in the cornea of the eye, cross-linking the interior stroma, and inserting a lenslet or lens implant into the three-dimensional pocket after the internal stromal tissue has been cross-linked.

Figure 8:
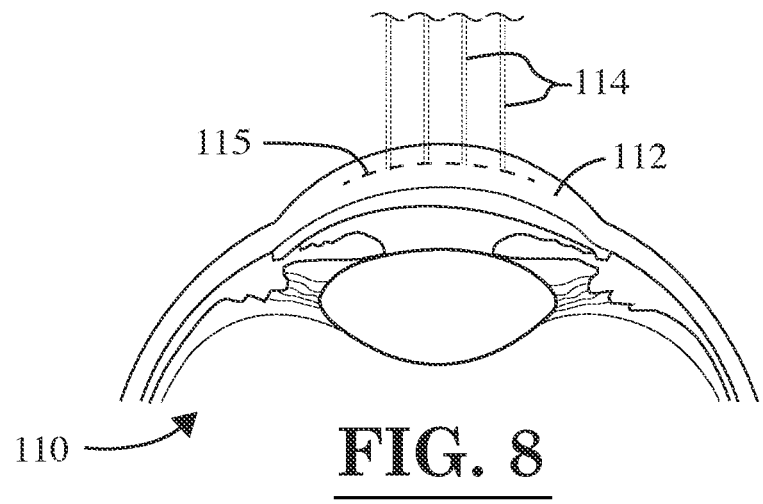
FIG. 8 is a partial side cross-sectional view illustrating the formation of a two-dimensional cut into a cornea of an eye, according to another embodiment of the invention.

Initially, in FIG. 8, the forming of a two-dimensional cut 115 into the cornea 112 of the eye 110 is diagrammatically illustrated. In particular, as shown in the illustrative embodiment of FIG. 8, the two-dimensional cut 115 is formed by making an intrastromal incision in the cornea 112 of the eye 110 using a femtosecond laser (i.e., the incision is cut in the cornea 112 using the laser beam(s) 114 emitted from the femtosecond laser). Alternatively, the two-dimensional cut 115 may be formed in the cornea 112 of the eye 110 using a knife.

Figure 9:
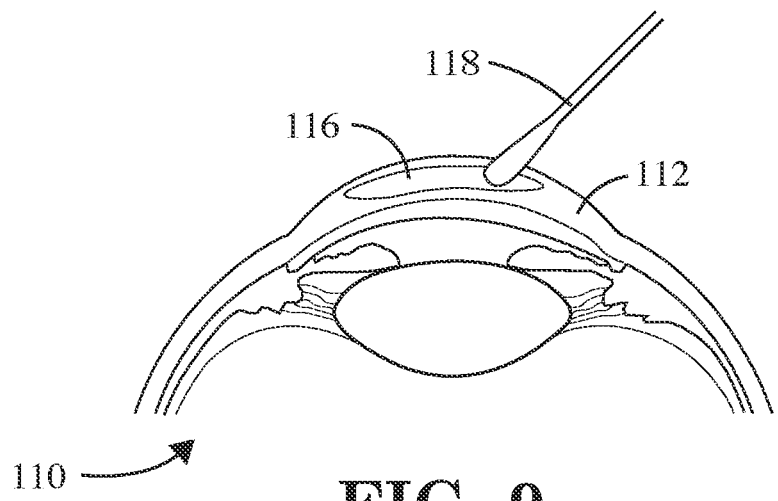
FIG. 9 is another partial side cross-sectional view of the eye of FIG. 8, which illustrates the creation of a three-dimensional pocket in the cornea of the eye.

Then, in FIG. 9, the forming of a three-dimensional corneal pocket 116 in the cornea 112 of the eye 110 is diagrammatically illustrated. In particular, as shown in the illustrative embodiment of FIG. 9, the three-dimensional corneal pocket 116 is formed by using a spatula 118. The formation of the intracorneal pocket 116 in the cornea 112 of the eye 110 allows one to gain access to the tissue surrounding the pocket 116 (i.e., the interior stromal tissue surrounding the pocket 116).

Turning again to FIGS. 8 and 9, in the illustrative embodiment, the corneal pocket 116 formed in the cornea 112 of the eye 110 may be in the form of an intrastromal corneal pocket cut into the corneal stroma. A femtosecond laser may be used to form a 2-dimensional cut into the cornea 112, which is then opened with a spatula 118 to create a 3-dimensional pocket 116. In one embodiment, a piece of the cornea 112 or a cornea which has a scar tissue is first cut with the femtosecond laser. Then, the cavity is cross-linked before filling it with an implant or inlay 128 to replace the lost tissue with a clear flexible inlay or implant 128 (see FIG. 12).

In one embodiment, a three-dimensional (3D) uniform circular, oval, or squared-shaped corneal pocket 116 is cut with a femtosecond laser and the tissue inside the pocket is removed to produce a three-dimensional (3D) pocket 116 to be cross-linked with riboflavin and implanted with a prepared implant.

Figure 10:
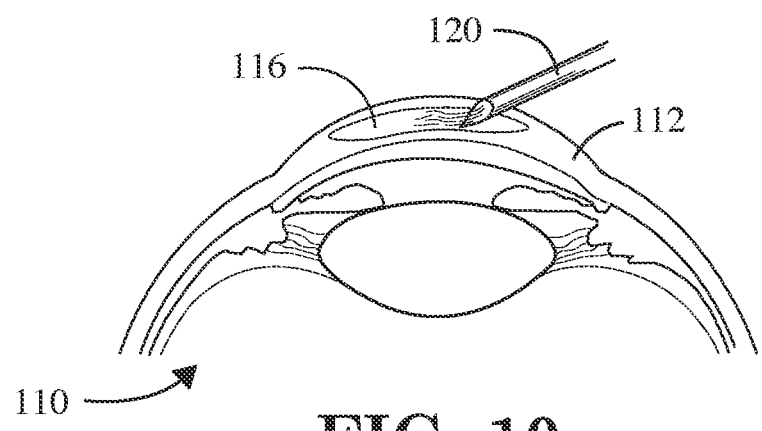
FIG. 10 is yet another partial side cross-sectional view of the eye of FIG. 8, which illustrates the injection of a photosensitizer into the three-dimensional pocket in the cornea of the eye.

After the pocket 116 is formed using the spatula 118, a photosensitizer is applied inside the three-dimensional pocket 116 so that the photosensitizer permeates the tissue surrounding the pocket 116 (see FIG. 10). The photosensitizer facilitates the cross-linking of the tissue surrounding the pocket 116. In the illustrative embodiment, the photosensitizer is injected with a needle 120 inside the stromal pocket 116 without lifting the anterior corneal stroma so as to cover the internal surface of the corneal pocket 116. In one or more embodiments, the photosensitizer or cross-linker that is injected through the needle 120 inside the stromal pocket comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 116 may be aspirated through the needle 120 until all, or substantially all, of the excess portion of the photosensitizer is removed from the pocket 116 (i.e., the excess cross-linker may be aspirated through the same needle so that the pocket 116 may be completely emptied or substantially emptied).

Figure 11A:
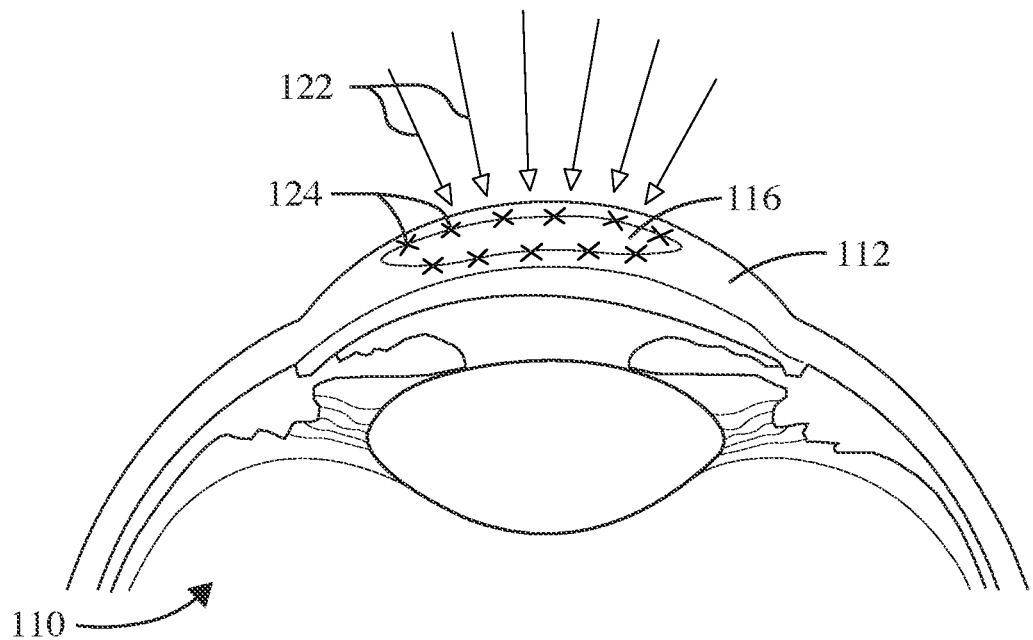
FIG. 11A is still another partial side cross-sectional view of the eye of FIG. 8, which illustrates the irradiation of the stromal tissue surrounding the three-dimensional pocket of the eye using ultraviolet radiation delivered from outside of the cornea.

Next, turning to the illustrative embodiment of FIG. 11A, shortly after the photosensitizer is applied inside the pocket 116, the cornea 112 of the eye 110 is irradiated from the outside using ultraviolet (UV) radiation 122 so as to activate cross-linkers in the portion of the tissue surrounding the three-dimensional pocket 116, and thereby stiffen the cornea 112, prevent corneal ectasia of the cornea 112, and kill cells in the portion of the tissue surrounding the pocket 116. In the illustrative embodiment, the ultraviolet light used to irradiate the cornea 112 may have a wavelength between about 370 nanometers and about 380 nanometers (or between 370 nanometers and 380 nanometers). Also, in the illustrative embodiment, only a predetermined anterior stromal portion 124 of the cornea 112 to which the photosensitizer was applied is cross-linked (i.e., the surrounding wall of the corneal pocket 116), thereby leaving an anterior portion of the cornea 112 and a posterior stromal portion of the cornea 112 uncross-linked. That is, in the illustrative embodiment, the entire corneal area inside the cornea 112 exposed to the cross-linker is selectively cross-linked, thereby leaving the anterior part of the cornea 112 and the posterior part of the stroma uncross-linked. The portion of the cornea 112 without the cross-linker is not cross-linked when exposed to the UV radiation. In an alternative embodiment, the cornea 112 may be irradiated using wavelengths of light other than UV light as an alternative to, or in addition to being irradiated using the ultraviolet (UV) radiation 122 depicted in FIG. 11A. Also, microwave radiation may be used synergistically or additively to correct non-invasively the remaining refractive error(s) of the cornea.

Figure 11B:
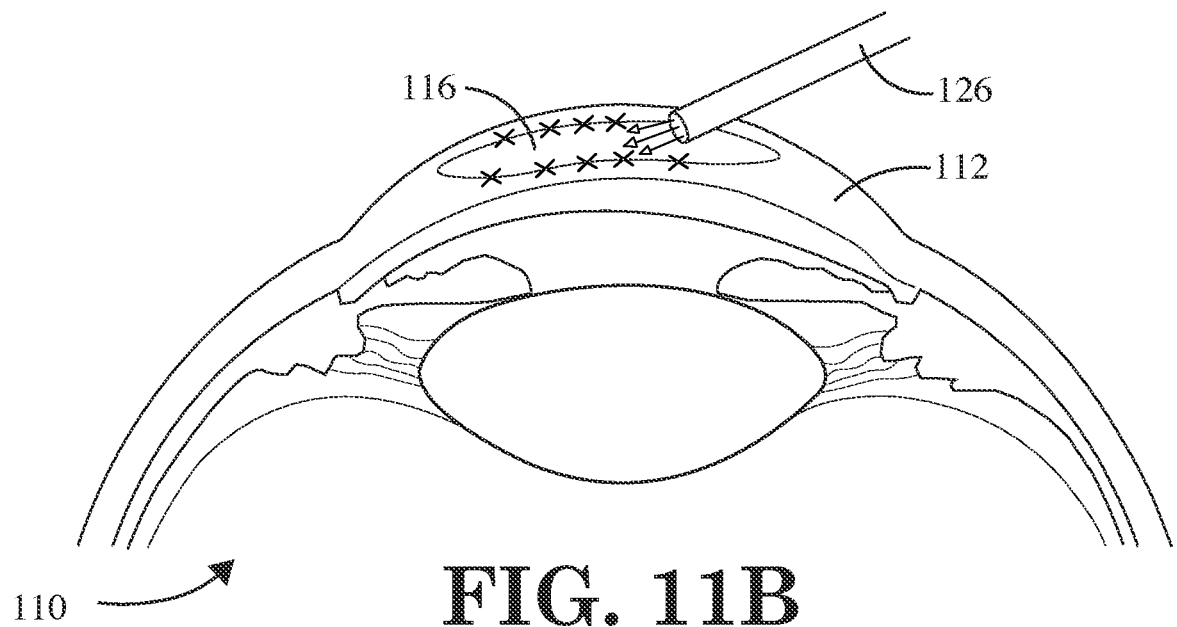
FIG. 11B is yet another partial side cross-sectional view of the eye of FIG. 8, which illustrates the irradiation of the stromal tissue surrounding the three-dimensional pocket of the eye using a fiber optic delivering ultraviolet radiation inside the three-dimensional pocket, according to an alternative embodiment of the invention.

Alternatively, as shown in FIG. 11B, a fiber optic 126 may be inserted into the corneal pocket 116 so as to apply the ultraviolet radiation and activate the photosensitizer in the wall of the corneal pocket 116. When the fiber optic 126 is used to irradiate the wall of the pocket 116, the ultraviolet radiation is applied internally, rather than externally as depicted in FIG. 11A.

Figure 12:
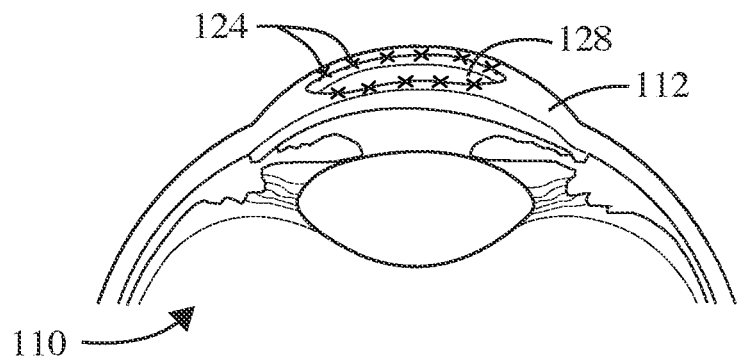
FIG. 12 is still another partial side cross-sectional view of the eye of FIG. 8, which illustrates a lens implant inserted into the pocket so as to change the refractive properties of the eye.

Now, with reference to FIG. 12, it can be seen that, after the wall of the corneal pocket 116 has been stiffened and is devoid of cellular elements by the activation of the cross-linkers, a lens implant 128 is inserted into the corneal pocket 116 in order to change the refractive properties of the eye. In particular, in the illustrated embodiment, the lens implant 128 is inserted through a small incision, and into the corneal pocket 116, using forceps or microforceps. In one or more embodiments, the lens implant 128 that is inserted inside the pocket 116 in the cornea 112 is flexible and porous. Also, in one or more embodiments, the lens implant 128 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymethacrylate, hydrogel, or a combination thereof. The surface of the lens implant 128 may have the appropriate shape to reshape the cornea 112 or the dioptric power to nullify the remaining spheric or astigmatic error of the eye. More particularly, in one or more embodiments, the lens implant 128 may have one of: (i) a concave surface to correct myopic refractive errors (i.e., a minus lens for correcting nearsightedness), (ii) a convex surface to correct hyperopic refractive errors (i.e., a plus lens for correcting farsightedness), or (iii) a toric shape to correct astigmatic refractive errors.

In the illustrative embodiment, the irradiation of the cornea 112 using the ultraviolet (UV) radiation 122 only activates cross-linkers in the portion of the stromal tissue surrounding the three-dimensional pocket 116, and only kills the cells in the portion of the tissue surrounding the pocket 116, so as to leave only a thin layer of cross-linked collagen to prevent an immune response and rejection of the lens implant 128 and/or encapsulation by fibrocytes, while preventing post-operative dry eye formation. In addition to preventing encapsulation of the lens implant 128 by fibrocytes, the cross-linking of the stromal tissue surrounding the pocket 116 also advantageously prevents corneal haze formation around the lens implant 128. That is, the cross-linking of the stromal tissue surrounding the lens implant 128 prevents formation of myofibroblast from surrounding keratocytes, which then convert gradually to fibrocytes that appear as a haze, and then white encapsulation inside the cornea, thereby causing light scattering in front of the patient's eye.

Figure 13:
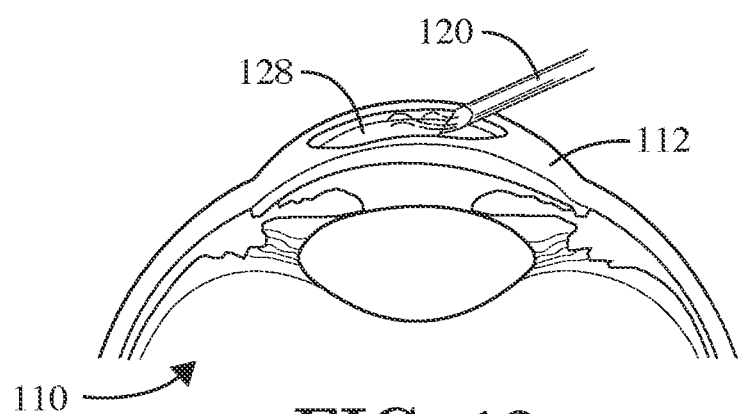
FIG. 13 is yet another partial side cross-sectional view of the eye of FIG. 8, which illustrates the reinjection of a photosensitizer into the three-dimensional pocket with the lens implant disposed therein so that the cross-linking procedure may be repeated.
Figure 14:
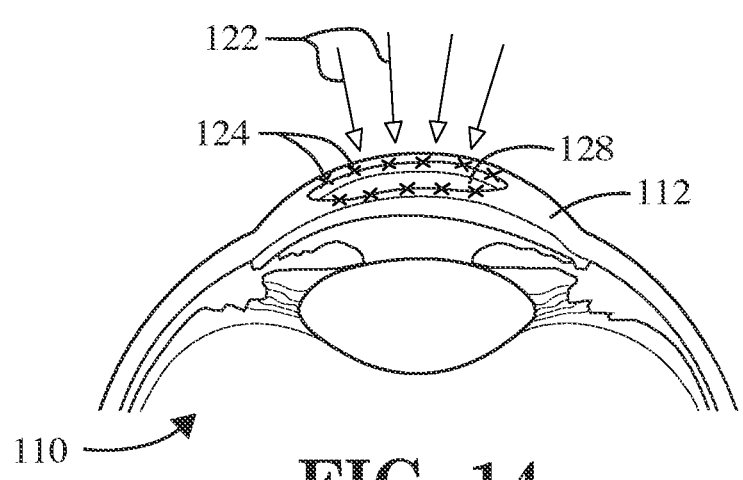
FIG. 14 is still another partial side cross-sectional view of the eye of FIG. 8, which illustrates the re-irradiation of the stromal tissue surrounding the three-dimensional pocket of the eye during the repetition of the cross-linking procedure.

As shown in FIGS. 13 and 14, the crosslinking procedure described above may be repeated after the lens implant 128 is implanted so as to prevent any cellular invasion in the area surrounding the implant 128. Initially, with reference to FIG. 13, the photosensitizer is reinjected inside the space between the lens implant 128 and the surrounding corneal tissue using a needle 120. In one or more embodiments, the needle 120 for injecting the photosensitizer may comprise a 30-32 gauge needle. Then, after the reinjection of the cross-linker, the cornea 112 is re-irradiated with ultraviolet radiation 122 to cross-link the tissue surrounding the lens implant 128 so as to prevent cellular migration towards the lens implant 128 (see FIG. 14).

In one or more embodiments, the lens implant or inlay 128 may be prepared ahead of time with known techniques, wherein the inlay 128 may be coated with a biocompatible material, such as collagen, elastin, polyethylene glycol, biotin, streptavidin, etc., or a combination thereof. The inlay 128 and the coating may be cross-linked with a photosensitizer or cross-linker, such as riboflavin, prior to being implanted into the pocket 116 in the cornea 112 of the eye.

In another embodiment, the lens implant or inlay 128 may be silicone, methacrylate, hydroxyethylmethacrylate (HEMA), or any other biocompatible transparent material, or a mixture thereof. The lens implant or inlay 128 also may be coated with materials, such as collagen or elastin, and may have a desired thickness of from 2 microns to 70 microns or more.

In yet another embodiment, the lens implant or inlay 128 is formed from an eye bank cornea, or a cross-linked eye bank cornea, etc. In general, there is a tremendous paucity of normal cadaver corneas for total or partial implants, such as for a corneal transplant of a corneal inlay. Because all the cellular elements are killed during the crosslinking of the corneal inlay, and because the corneal collagen is cross-linked and denatured, the remaining collagenous elements are not immunogenic when implanted inside the body or in the cornea of a patient. Advantageously, the prior cross-linking of the organic material, such as in the cadaver cornea, permits transplantation of the corneal inlay from an animal or human cornea or any species of animal to another animal or human for the first time without inciting a cellular or humoral response by the body, which rejects the inlay. Thus, cross-linking transparent cadaveric tissue for corneal transplantation, or as an inlay to modify of the refractive power of the eye, is highly beneficial to many patients who are on the waiting list for a corneal surgery. In addition, the surgery may be planned ahead of time without necessitating the urgency of the surgery when a fresh cadaver eye becomes available. In one or more embodiments, the collagens may be driven from the animal cornea, and cross-linked. Also, in one or more embodiments, the implant or inlay 128 may be made of cross-linked animal cornea or human cornea that is cut using a femtosecond laser to any desired shape and size, and then ablated with an excimer laser or cut with a femtosecond laser to a have a desired refractive power.

Figure 15:
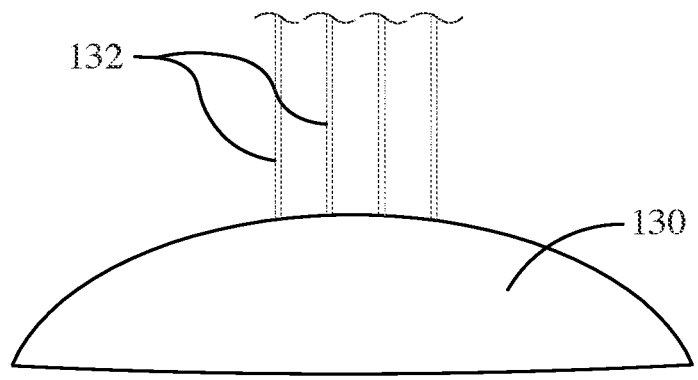
FIG. 15 is a side cross-sectional view illustrating the creation of a lens implant from an organic block of polymer using a excimer laser.
Figure 16:
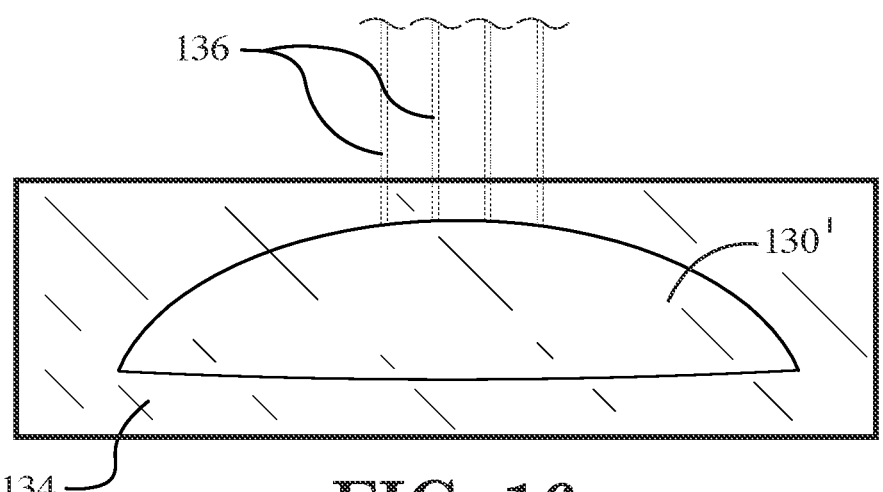
FIG. 16 is a side cross-sectional view illustrating the cutting of a lens implant from an organic block of polymer using a femtosecond laser.

For example, as shown in FIG. 15, the lens implant or inlay 130 may be formed from an organic block of a polymer (e.g., donor cornea) by cutting the lens implant 130 using an excimer laser (e.g., by using the laser beam(s) 132 emitted from the excimer laser). Alternatively, referring to FIG. 16, the lens implant or inlay 130' may be formed from an organic block 134 of a polymer (e.g., donor cornea) by cutting the lens implant 130' from the block 134 using a femtosecond laser or a computerized femto-system (e.g., by using the laser beam(s) 136 emitted from the femtosecond laser).

Figure 17:
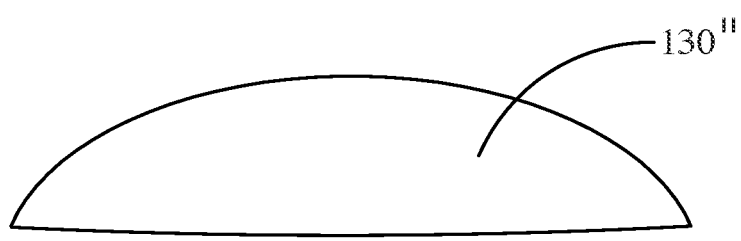
FIG. 17 is a side cross-sectional view illustrating a lens implant that has been formed using a three-dimensional printing technique or a molding technique.

In still another embodiment, as depicted in FIG. 17, the lens implant or inlay 130" is made using three-dimensional (3D) printing technology or a molding technique in order to form the lens implant or inlay 130" into the desired shape, size or thickness. The transparent material of the 3D-printed implant or inlay 130" may be coated with one or more biocompatible polymers and cross-linked prior to the implantation.

In yet another embodiment, after the implantation of an intraocular lens, the remaining refractive error of the eye may be corrected by the implantation of a lens implant or inlay 128 in the cross-linked pocket 116 of the cornea 112, thereby eliminating the need for entering the eye cavity to replace the original intraocular lens.

In still another embodiment, the remaining refractive error of the eye is corrected after an intraocular lens implantation by placing an inlay 128 on the surface of the cornea 112 of the patient while the shape of the cornea 112 is corrected with an excimer laser and wavefront optimized technology so that the patient is provided instant input on its effect on his or her vision. In this embodiment, an inlay similar to a contact lens is placed on the cornea 112 that, after correction, matches the desired refractive correction of the eye, and then, subsequently, the inlay 128 is implanted inside the cross-linked corneal pocket 116.

In yet another embodiment, the implant or inlay 128 may be ablated with an excimer laser for implantation in the cross-linked pocket 116, or after cross-linking the exposed corneal stroma in LASIK surgery.

In still another embodiment, a small amount of hyaluronic acid or a viscous fluid is injected into the pocket 116 prior to the implantation of the implant or inlay 128 so as to simplify the insertion of the implant or inlay 128 in the corneal pocket 116.

In yet another embodiment, the implant or inlay 128 is prepared having four marking holes of 0.1-2 millimeter (mm) in diameter in the inlay periphery at an equally sized distances so that the implant 128 may be rotated with a hook, if desired, after the implantation as needed to match the axis of an astigmatic error of the eye during the surgery as measured simultaneously with a wavefront technology system, such as an Optiwave Refractive Analysis (ORA) system or Holos® system, which are commercially available for measurement of astigmatism or its axis.

In still another embodiment, the implant or inlay 128 is located on the visual axis and may provide 1 to 3 times magnification for patients whose macula is affected by a disease process needing magnifying glasses for reading, such as in age-related macular degeneration, macular edema, degenerative diseases of the retina, etc. Because these eyes cannot be used normally for reading without external magnifier glasses, providing magnification by a corneal implant to one eye assists the patients in being able to read with one eye and navigate the familiar environment with their other eye.

In yet another embodiment, a part of the corneal stroma is removed from the eye of the patient, and its surface is corrected with an excimer laser to a desired refraction. Then, the removed part of the corneal stroma is cross-linked, and implanted back into the corneal pocket so as to correct the refractive power of the cornea.

In still another embodiment, the surface of the cornea 112 is treated after surgery in all cases daily with an anti-inflammatory agent, such as steroids, nonsteriodal anti-inflammatory drugs (NSAIDs), immune-suppressants, such as cyclosporine A or mycophenolic acid, anti-proliferative agents, antimetabolite agents, or anti-inflammatory agents (e.g., steroids, NSAIDS, or antibiotics etc.) to prevent inflammatory processes after the corneal surgery, inlay implantation or crosslinking, while stabilizing the integrity of the implant 128 and preventing future cell growth in the organic implant or the adjacent acellular corneal tissue. In this embodiment, the medication is injected in the corneal pocket 116 along with the implantation or the implant 128 is dipped in the medication first, and then implanted in the cross-linked corneal pocket 116.

In yet another embodiment, a cross-linked corneal inlay is placed over the cross-linked corneal stroma after a LASIK incision, and is abated to the desired size with an excimer laser using a topography guided ablation. By means of this procedure, the refractive power of the eye is corrected, while simultaneously providing stability to an eye prone to conceal ectasia postoperatively after a LASIK surgery. Then, the LASIK flap is placed back over the implant.

Figure 18:
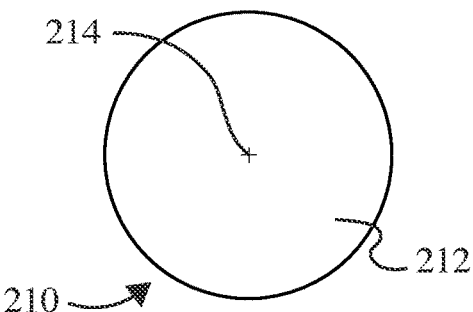
FIG. 18 is a front view of a cornea of an eye, according to yet another embodiment of the invention.

Yet another illustrative embodiment of a corneal lenslet implantation procedure with a cross-linked cornea is shown in FIGS. 18-23. In general, the procedure illustrated in these figures involves initially making an intrastromal square pocket surrounding the visual axis of the eye, and then, after forming the initial square pocket, a three-dimensional circular portion of diseased or weak stromal tissue is cut, removed, and replaced with a circular implant which fits into the circle that borders the four sides of the square. A front view of the cornea 212 of the eye 210 with the centrally-located visual axis 214 is illustrated in FIG. 18. Advantageously, in the illustrative embodiment of FIGS. 18-23, corneal tissue removal around the visual axis is greatly facilitated, and nearly perfect centration of the lens implant or inlay 220 about the visual axis is possible because the lens implant 220 fits within a depressed circular recess at the bottom of the pocket 216. As such, the undesirable decentering of the lens implant is prevented.

Figure 19:
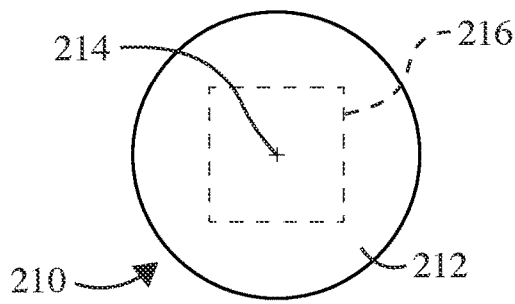
FIG. 19 is another front view of the cornea of the eye of FIG. 18, wherein a square-shaped intrastromal pocket has been formed in the cornea of the eye.

Initially, in FIG. 19, the forming of an intrastromal square-shaped pocket 216 surrounding the visual axis 214 (represented by a plus sign) in the cornea 212 of the eye 210 is diagrammatically illustrated. In particular, as shown in the illustrative embodiment of FIG. 19, the square-shaped pocket 216 is formed by making a two-dimensional intrastromal incision in the cornea 212 of the eye 210 using a femtosecond laser (i.e., the incision is cut in the cornea 212 using the laser beam(s) emitted from the femtosecond laser).

Figure 21:
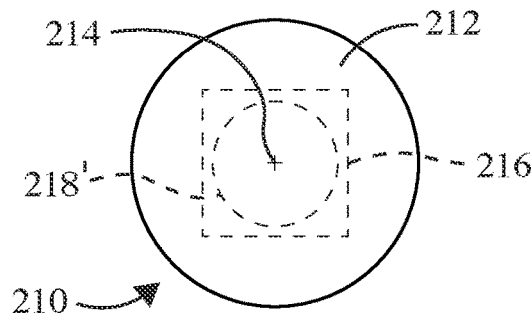
FIG. 21 is still another front view of the cornea of the eye of FIG. 18, wherein a circular three-dimensional portion of tissue having second diameter has been removed from the area within the square-shaped intrastromal pocket, the second diameter of the circular three-dimensional portion of tissue in FIG. 21 being larger than the first diameter of the circular three-dimensional portion of tissue in FIG. 20.
Figure 20:
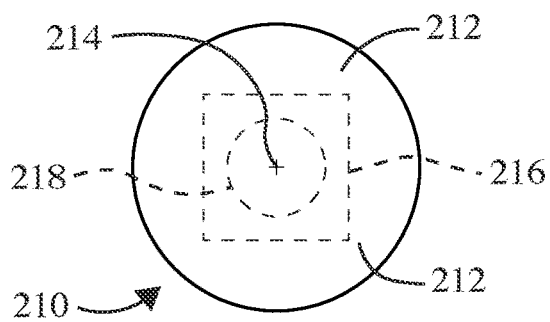
FIG. 20 is yet another front view of the cornea of the eye of FIG. 18, wherein a circular three-dimensional portion of tissue having a first diameter has been removed from the area within the square-shaped intrastromal pocket.

Then, in FIG. 20, the removal of a three-dimensional circular portion 218 of diseased or weak stromal tissue in the cornea 212 of the eye 210 is diagrammatically illustrated. In particular, as shown in the illustrative embodiment of FIG. 20, the three-dimensional circular stromal tissue portion 218 has a first diameter, which is less than a width of the square-shaped pocket 216 so that the three-dimensional circular stromal tissue portion 218 is disposed within the boundaries of the square-shaped pocket 216. The three-dimensional circular stromal tissue portion 218' depicted in FIG. 21 is generally similar to that illustrated in FIG. 20, except that the three-dimensional circular stromal tissue portion 218' depicted in FIG. 21 has a second diameter that is slightly larger than the first diameter of the three-dimensional circular stromal tissue portion 218 in FIG. 20. As such, the periphery of the three-dimensional circular stromal tissue portion 218' depicted in FIG. 21 is disposed closer to the square-shaped pocket 216, but still within the confines of the square-shaped pocket 216. In the illustrative embodiment, the three-dimensional circular stromal tissue portion 218, 218' may be removed using forceps or micro-forceps. In an exemplary embodiment, the diameter of the circular stromal tissue portion 218, 218' that is removed from the cornea 212 is between approximately 5 millimeters and approximately 8 millimeters, inclusive (or between 5 millimeters and 8 millimeters, inclusive).

In an alternative embodiment of the corneal lenslet implantation procedure, three (3) sequential cuts may be made in the stromal portion of the cornea 212 of the eye 210 using a femtosecond laser in order to form the pocket. First, a lower circular cut or incision centered about the visual axis (i.e., a lower incision with the patient in a supine position) is made using the femtosecond laser. Then, a second vertical cut is made above the lower incision using the femtosecond laser to form the side(s) of a circular cutout portion. Finally, a third square or circular cut (i.e., an upper incision) is made above the vertical cut using the femtosecond laser. In the illustrative embodiment, the lower incision is parallel to the upper incision, and the vertical cut extends between lower incision and the upper incision. In this alternative embodiment, the three-dimensional circular stromal tissue cutout portion bounded by the lower incision on the bottom thereof, the vertical cut on the side(s) thereof, and the upper incision on the top thereof is removed from the cornea 212 of the eye 210 using a pair of forceps. A cavity formed by the upper incision facilitates the removal of the three-dimensional circular stromal tissue cutout portion. As described above, the third cut or incision formed using the femtosecond laser may be an upper circular cut that is larger than the lower circular cut, rather than an upper square cut that is larger than the lower circular cut.

Figure 22:
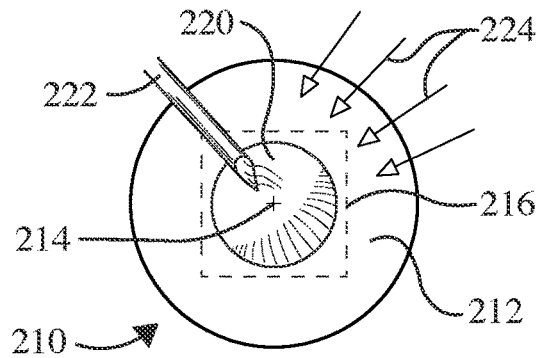
FIG. 22 is yet another front view of the cornea of the eye of FIG. 18, wherein a circular lens implant has been implanted in the area where the circular three-dimensional portion of tissue has been removed, and wherein a photosensitizer is being injected into the pocket in the cornea of the eye.

Turning to FIG. 22, after the three-dimensional circular stromal tissue portion 218, 218' is removed, a photosensitizer is applied inside the pocket 216 so that the photosensitizer permeates the tissue surrounding the pocket 216. The photosensitizer facilitates the cross-linking of the tissue surrounding the pocket 216. In the illustrative embodiment, the photosensitizer is injected with a needle 222 inside the stromal pocket 216. In one or more embodiments, the photosensitizer or cross-linker that is injected through the needle 222 inside the stromal pocket 216 comprises riboflavin, and/or a liquid suspension having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the pocket 216 may be aspirated through the needle 222 until all, or substantially all, of the excess portion of the photosensitizer is removed from the pocket 216 (i.e., the excess cross-linker may be aspirated through the same needle 222 so that the pocket 216 may be completely emptied or substantially emptied).

Next, turning again to the illustrative embodiment of FIG. 22, shortly after the photosensitizer is applied inside the pocket 216, the cornea 212 of the eye 210 is irradiated from the outside using ultraviolet (UV) radiation 224 so as to activate cross-linkers in the portion of the tissue surrounding the three-dimensional pocket 216, and thereby stiffen the cornea 212, prevent corneal ectasia of the cornea 212, and kill cells in the portion of the tissue surrounding the pocket 216. In the illustrative embodiment, the ultraviolet light used to irradiate the cornea 212 may have a wavelength between about 370 nanometers and about 380 nanometers (or between 370 nanometers and 380 nanometers). Also, in the illustrative embodiment, only a predetermined anterior stromal portion of the cornea 212 to which the photosensitizer was applied is cross-linked (i.e., the surrounding wall of the corneal pocket 216), thereby leaving an anterior portion of the cornea 212 and a posterior stromal portion of the cornea 212 uncross-linked. That is, in the illustrative embodiment, the entire corneal area inside the cornea 212 exposed to the cross-linker is selectively cross-linked, thereby leaving the anterior part of the cornea 212 and the posterior part of the stroma uncross-linked. The portion of the cornea 212 without the cross-linker is not cross-linked when exposed to the UV radiation. In an alternative embodiment, the cornea 212 may be irradiated using wavelengths of light other than UV light as an alternative to, or in addition to being irradiated using the ultraviolet (UV) radiation 224 depicted in FIG. 22. Also, microwave radiation may be used synergistically or additively to correct non-invasively the remaining refractive error(s) of the cornea. In addition, in an alternative embodiment, the ultraviolet (UV) radiation may be applied after the implantation of the lens implant 220 to perform the crosslinking, rather than before the implantation of the lens implant 220 as described above. Further, rather than applying the ultraviolet (UV) radiation from outside the cornea 212, the stromal tissue of the pocket 216 may be irradiated from inside by means of a fiber optic, before or after the implantation of the lens implant 220.

Figure 23:
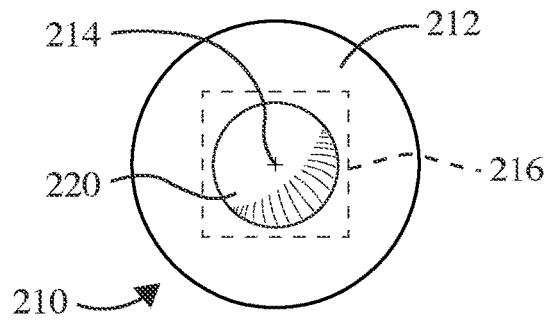
FIG. 23 is still another front view of the cornea of the eye of FIG. 18, wherein the circular lens implant is shown in the area where the circular three-dimensional portion of tissue was removed.

Now, with combined reference to FIGS. 22 and 23, it can be seen that, before or after the wall of the corneal pocket 216 has been stiffened and is devoid of cellular elements by the activation of the cross-linkers, a circular lens implant 220 is inserted into the circular recess at the bottom of the pocket 216 formed by the three-dimensional circular stromal tissue cutout portion 218, 218' that was removed. That is, the circular lens implant 220 fits within the periphery of the circular recess that borders the four sides of the squared-shaped pocket 216. In particular, in the illustrated embodiment, the circular lens implant 220 is inserted through a small incision, and into the circular recess at the bottom of the pocket 216 using forceps or microforceps. In the illustrative embodiment, the flexible lens implant 220 may be folded, inserted through the small incision, placed inside the circular recess at the bottom of the pocket 216, and finally unfolded through then small incision. In one or more embodiments, the lens implant 220 that is inserted inside the pocket 216 in the cornea 212 is flexible and porous. Also, in one or more embodiments, the lens implant 220 may comprise a hybrid lens implant with an organic outer portion and a synthetic inner portion. The organic outer portion of the hybrid lens implant may be made from a transparent, hydrophilic organic polymer, while the synthetic inner portion of the hybrid lens implant may be made from a transparent, gas permeable, porous flexible polymer. For example, the transparent, hydrophilic polymer forming the organic outer portion may be formed from collagen, chitosan, poloxamer, polyethylene glycol, or a combination thereof (or any other transparent hydrophilic coating which can be deposited over the entire lens surface), while the flexible polymer forming the synthetic inner portion of the hybrid lens implant may be formed from silicone, acrylic, polymethacrylate, hydrogel, or a combination thereof.

Advantageously, the lens implant 220 of the aforedescribed illustrative embodiment always remains perfectly centered around the visual axis 214 of the eye 210, and will not move because it is disposed within the circular recess at the bottom of the pocket 216. As explained above, the lens implant 220 may be formed from an organic material, synthetic material, polymeric material, and combinations thereof. The lens implant 220 may replace either a diseased tissue or create a new refractive power for the eye 210, as explained hereinafter.

In the illustrative embodiment, the lens implant 220 may correct the refractive errors of the eye 210. The refractive error correction may be done by the lens implant 220 having a curvature that changes the corneal surface of the cornea 212. Alternatively, the lens implant 220 may have a different index of refraction that corrects the refractive power of the cornea 212. In the illustrative embodiment, the lens implant 220 may have the appropriate shape to reshape the cornea 212 or the dioptric power to nullify the remaining spheric or astigmatic error of the eye. More particularly, in one or more embodiments, the lens implant 220 may have one of: (i) a concave anterior surface to correct myopic refractive errors (i.e., a minus lens for correcting nearsightedness), (ii) a convex anterior surface to correct hyperopic refractive errors (i.e., a plus lens for correcting farsightedness), or (iii) a toric shape to correct astigmatic refractive errors.

In the illustrative embodiment, the irradiation of the cornea 212 using the ultraviolet (UV) radiation 224 only activates cross-linkers in the portion of the stromal tissue surrounding the three-dimensional pocket 216, and only kills the cells in the portion of the tissue surrounding the pocket 216, so as to leave only a thin layer of cross-linked collagen to prevent an immune response and rejection of the lens implant 220 and/or encapsulation by fibrocytes, while preventing post-operative dry eye formation. In addition to preventing encapsulation of the lens implant 220 by fibrocytes, the cross-linking of the stromal tissue surrounding the pocket 216 also advantageously prevents corneal haze formation around the lens implant 220. That is, the cross-linking of the stromal tissue surrounding the lens implant 220 prevents formation of myofibroblast from surrounding keratocytes, which then convert gradually to fibrocytes that appear as a haze, and then white encapsulation inside the cornea, thereby causing light scattering in front of the patient's eye.

It is readily apparent that the aforedescribed corneal transplant procedures offer numerous advantages. First, the implementation of the aforedescribed corneal transplant procedures reduces the likelihood that the implanted cornea will be rejected by the patient. Secondly, the aforedescribed corneal transplant procedures enable the clarity of the transplanted cornea to be preserved. Finally, the aforedescribed corneal transplant procedures reduce the likelihood that the transplanted cornea will be invaded by migrating cells, such as migrating cells that might initiate an immune response such as macrophage, lymphocytes or leucocytes or vascular endothelial cells. These types of migrating cells are discouraged by the cross-linked corneal collagen which does not provide an easily accessible tissue to invade. In addition, the use of abovedescribed tissue adhesives reduces the surgical procedure significantly. Moreover, the aforedescribed corneal lenslet implantation procedures modify the cornea so as to better correct ametropic conditions. Furthermore, the corneal lenslet implantation procedures described above prevent the lens implant from moving around inside the cornea once implanted, thereby ensuring that the lens implant remains centered about the visual axis of the eye.

With reference to the illustrative embodiment of FIGS. 24-29, an exemplary method of preventing capsular opacification and fibrosis utilizing an accommodative intraocular lens implant will be explained. In general, the procedure illustrated in FIGS. 24-29 involves treating patients in need of cataract surgery and a replacement intraocular lens.

Figure 24:
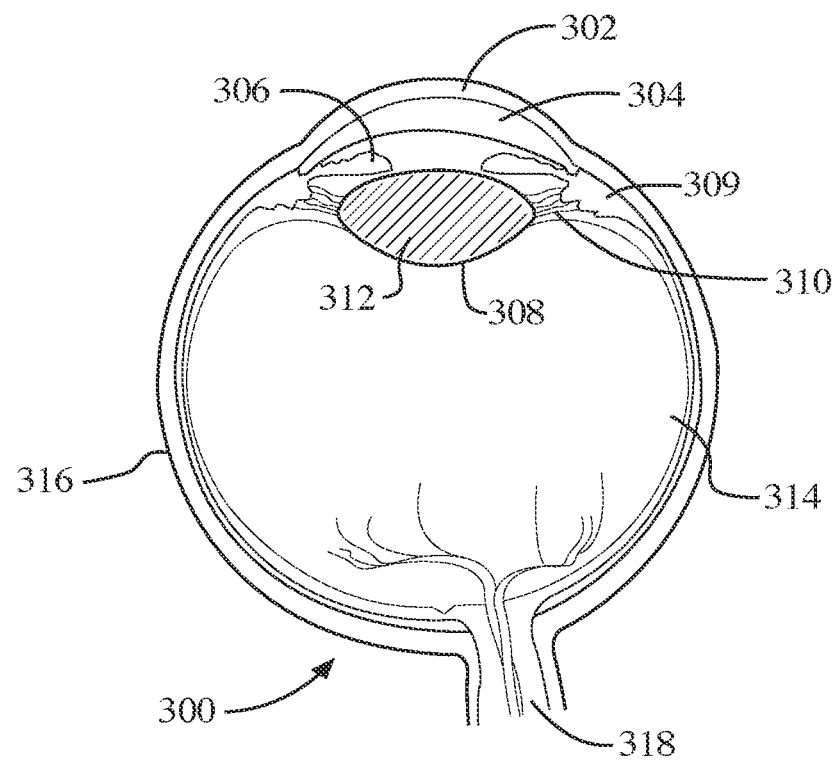
FIG. 24 is a side cross-sectional view illustrating an eye with a cataract, according to still another embodiment of the invention.

Initially, referring to FIG. 24, it can be seen that the eye 300 undergoing cataract surgery generally includes a cornea 302, an anterior chamber 304, an iris 306, a lens capsule or capsular bag 308, ciliary body 309, lens zonules 310, a vitreous cavity 314, a sclera 316, and an optic nerve 318. As shown in FIG. 24, the eye 300 has a cataract 312 (i.e., a cloudy lens), thereby requiring that cataract surgery be performed on the eye 300 of the patient.

Figure 25:
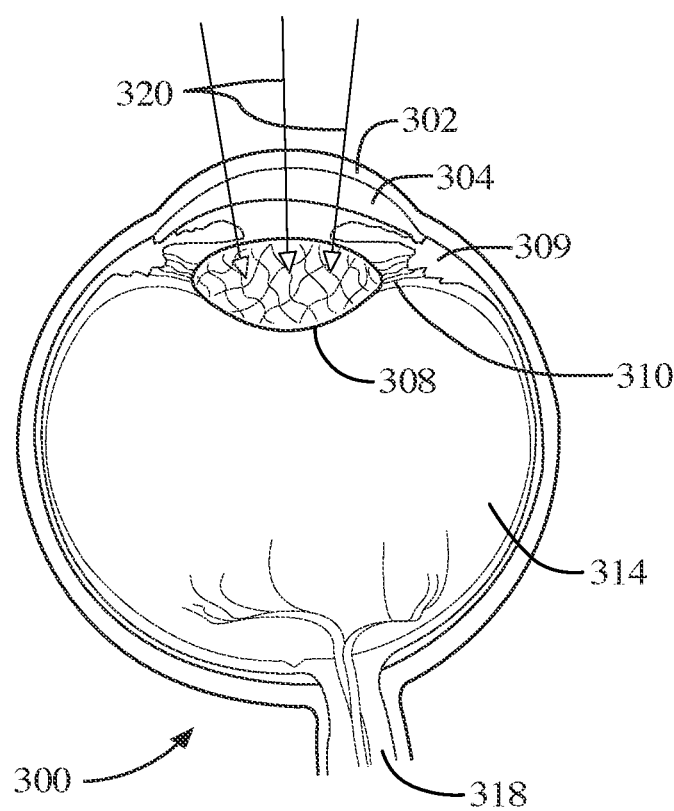
FIG. 25 is another side cross-sectional view of the eye of FIG. 24, which illustrates the breaking apart of the natural lens into lens fragments using a laser.

In FIG. 25, the first stage of the removal of the cortex and nucleus of the natural lens of the eye 300 containing the cataract 312 is diagrammatically illustrated. Specifically, in FIG. 25, the cloudy natural lens of the eye 300 is shown being broken apart into lens fragments by utilizing a femtosecond laser (i.e., the natural lens is broken apart by using the laser beam(s) 320 emitted from the femtosecond laser). The natural lens is initially broken apart into fragments so that it is capable of being more easily removed from the lens capsule 308 of the eye 300.

Figure 26:
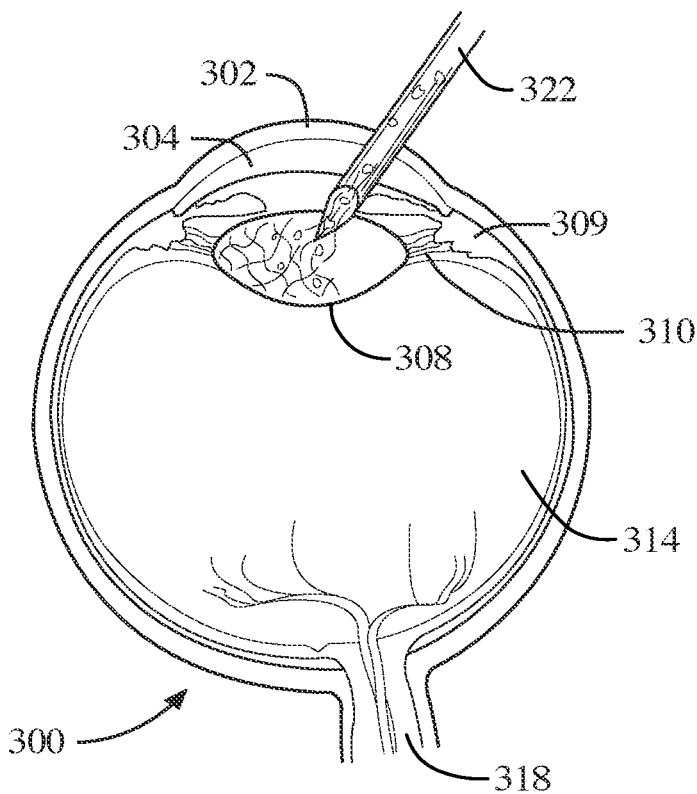
FIG. 26 is yet another side cross-sectional view of the eye of FIG. 24, which illustrates the irrigation and aspiration of the lens fragments of the natural lens using a probe.

Then, referring to FIG. 26, the second stage of the removal of the cortex and nucleus of the natural lens of the eye 300 containing the cataract 312 is diagrammatically shown. In particular, as depicted in FIG. 26, the lens fragments of the natural lens are being removed from the lens capsule 308 of the eye 300 using an ultrasonic probe 322. More particularly, the ultrasonic probe 322 irrigates and aspirates the lens fragments of the natural lens. In addition, the ultrasonic probe 322 may also be used to aspirate a substantial portion of the lens epithelium from the lens capsule 308 through an additional hole made in the lens capsule 308 and used as a bimanual system. That is, in the illustrative embodiment, the ultrasonic probe 322 may be used to aspirate as much of the lens epithelium as possible from the lens capsule 308 to prevent the undesirable propagation of lens epithelium cells following the cataract surgery.

Figure 27:
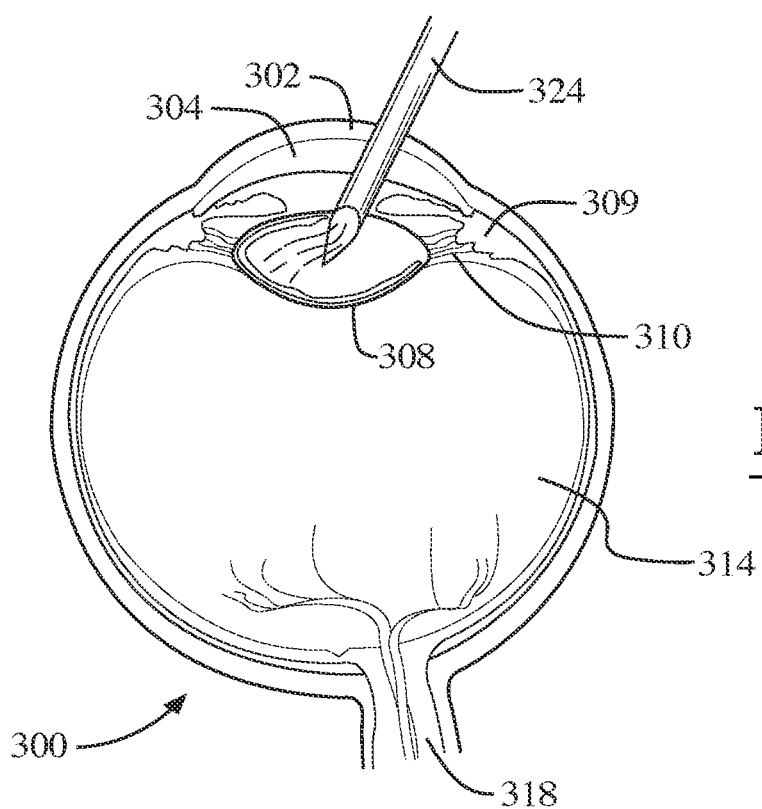
FIG. 27 is still another side cross-sectional view of the eye of FIG. 24, which illustrates the application of a photosensitizer to the capsular bag of the eye after the cataract has been removed.

Next, in FIG. 27, the injection of a cross-linker or photosensitizer (e.g., riboflavin) into the capsular bag 308 of the eye 300 is diagrammatically illustrated. In particular, as shown in the illustrative embodiment of FIG. 27, the cataract 312 has been removed from the capsular bag 308, which leaves the vast majority of the capsular bag 308 intact. Then, as shown in FIG. 27, a photosensitizer is applied inside the capsular bag 308 so that the photosensitizer permeates the tissue in both the anterior and posterior portions of the capsular bag 308. The photosensitizer facilitates the cross-linking of the tissue in the anterior and posterior portions of the capsular bag 308. In the illustrated embodiment of FIG.

27, the photosensitizer is injected with a needle 324 into the capsular bag 308 of the eye 300 by inserting the needle 324 through the anterior chamber 304 of the eye 300, and into the capsular bag 308 through the anterior wall of the capsular bag 308. In one or more embodiments, the photosensitizer or cross-linker that is injected through the needle 324 into the capsular bag 308 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the capsular bag 308 may be aspirated through the needle 324 until all, or substantially all, of the excess portion of the photosensitizer is removed from the capsular bag 308 (i.e., the excess cross-linker may be aspirated through the same needle 324 so that the capsular bag 308 may be completely emptied or substantially emptied). Also, in one or more embodiments, in order to kill the remaining lens epithelial cells that are generally attached to the rear side of the anterior portion of the lens capsule 308, the riboflavin may be in a relatively hypotonic solution that permits the lens cells to swell and makes them easier to remove or kill during the irradiation step described hereinafter.

Figure 28:
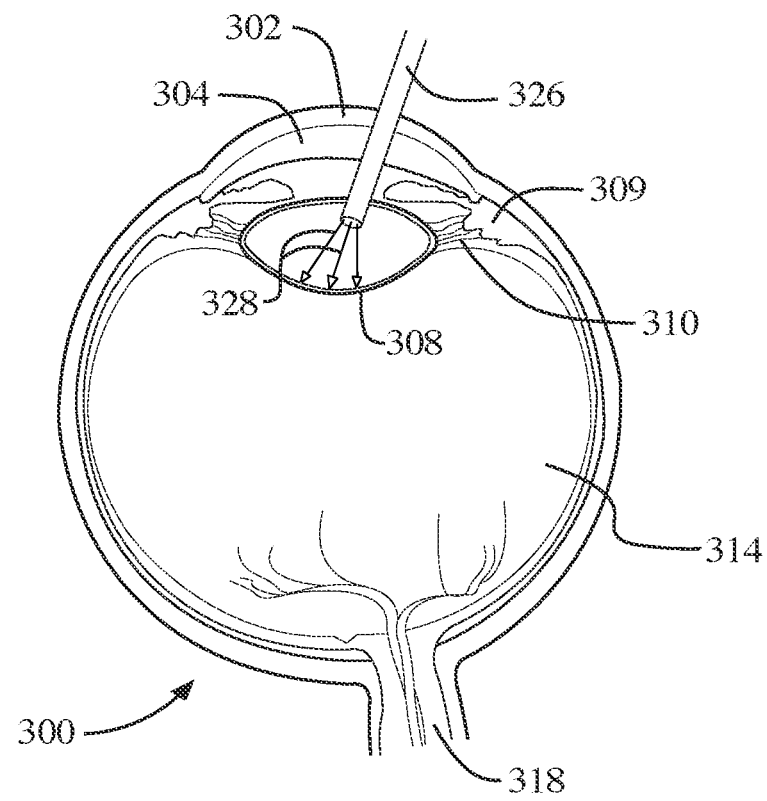
FIG. 28 is yet another side cross-sectional view of the eye of FIG. 24, which illustrates the irradiation of the capsular bag of the eye using a fiber optic so as to activate cross-linkers in the capsular bag.

Next, turning to FIG. 28, shortly after the photosensitizer is applied inside the capsular bag 308, the entire capsular bag 308 of the eye 300 (i.e., both the anterior portion and posterior portion of the lens capsule 308) is irradiated using a fiber optic 326 delivering ultraviolet (UV) radiation 328 so as to damage the remaining lens epithelial cells with UV laser light, thereby preventing capsular opacification and fibrosis. In the illustrative embodiment, the irradiation of the lens capsule 308 includes the anterior portion of the lens capsule 308 in order to prevent growth of the damaged lens epithelial cells and prevent cell migration and opacification because, in some cases, epithelial cells are still left in the lens capsule 308 after irrigation and aspiration of the lens fragments. Advantageously, the killing of the epithelial cells by irradiation prevents the further growth of the lens epithelial cells, and prevents their migration toward the posterior portion of the lens capsule 308 where they later become opaque. Also, in the illustrative embodiment, a painting technique may be utilized to deliver the ultraviolet light 328 to the capsular bag 308 of the eye 300 (i.e., the fiber optic 326 may be manipulated in such a manner by the surgeon so as to "paint" the ultraviolet light 328 on the capsular bag 308). Also, in the illustrative embodiment, ultraviolet (UV) radiation 328 may have a wavelength between about 370 nanometers and about 380 nanometers (or between 370 nanometers and 380 nanometers). In an alternative embodiment, the capsular bag 308 of the eye 300 may be irradiated using another wavelength of light as an alternative to, or in addition to being irradiated using ultraviolet (UV) radiation.

In an alternative embodiment, the anterior portion of the capsular bag 308 may be irradiated from outside the capsular bag 308 rather than from inside the capsular bag 308 as depicted in FIG. 28. In this embodiment, the fiber optic 326 may be disposed in the anterior chamber 304 of the eye 300 so that the ultraviolet (UV) light may be directed towards the anterior portion of the capsular bag 308. For example, the fiber optic 326 may be disposed at an acute angle relative to the capsular bag 308, but not perpendicular to the capsular bag 308 (so that the macula is protected and not damaged by the UV light emitted from the fiber optic 326).

Figure 29:
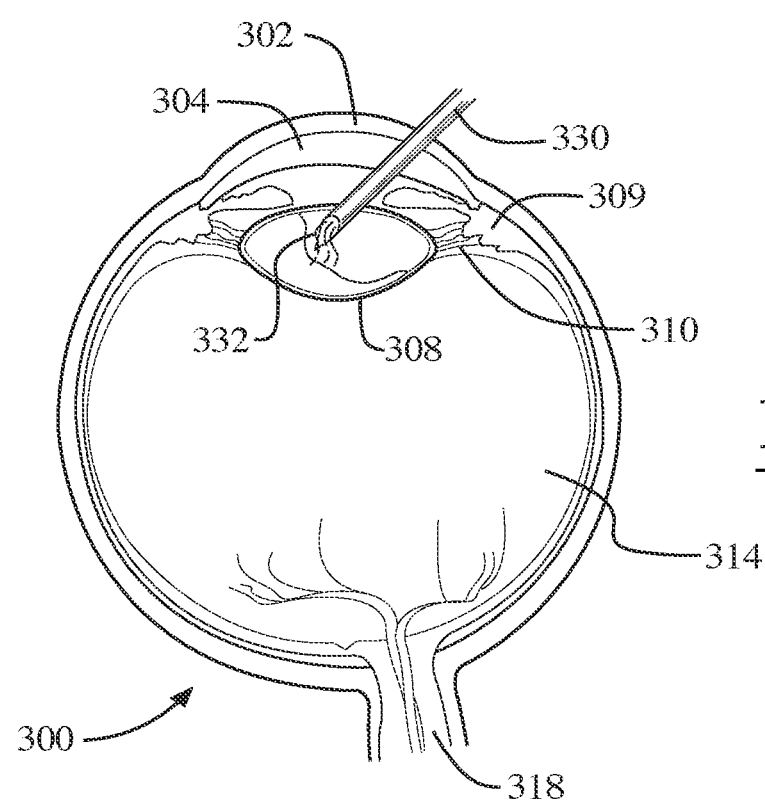
FIG. 29 is still another side cross-sectional view of the eye of FIG. 24, which illustrates the injection a transparent polymer into the lens capsule of the eye in order to form an accommodative intraocular lens for replacing the cortex and nucleus of the natural lens that was removed from the eye.

Finally, referring to FIG. 29, it can be seen that, after the tissue of the capsular bag 308 has been irradiated, a transparent polymer 332 is injected into the capsular bag 308 of the eye 300 using a needle 330 in order to form an accommodative intraocular lens implant for replacing the cortex and nucleus of the cloudy natural lens that was removed from the eye 300. In particular, in the illustrative embodiment, the needle 330 for injecting the transparent polymer 332 forming the accommodative intraocular lens is inserted into the capsular bag 308 of the eye 300 through an anterior hole or holes in the lens capsule 308. The hole or holes in the anterior chamber are plugged after the transparent polymer forming the accommodative intraocular lens hardens. In the illustrative embodiment, the transparent polymer that forms the accommodative intraocular lens remains flexible after the transparent polymer hardens or solidifies. Also, in the illustrative embodiment, after the transparent polymer that forms the accommodative intraocular lens is injected into the capsular bag 308 of the eye using the needle 330, the refractive power of the accommodative intraocular lens is adjusted using a wavefront technology unit intraoperatively so that the intraocular lens is able to be focused for a far distance without accommodation, and additionally is able to be focused for a near distance during accommodation by increasing the refractive power of the intraocular lens using the natural accommodative mechanism of the eye 300. Advantageously, intraoperative units utilizing wavefront technology are capable of indicating perfect refraction. During the injection process, both overfilling or under filling of the capsular bag 308 is not desirable because it does not provide proper refractive power for the lens and the eye 300.

In a further embodiment, the transparent polymer 332 that forms the accommodative intraocular lens implant is partially polymerized when injected into the capsular bag 308, and the transparent polymer becomes completely polymerized within a predetermined time period (e.g., within 5 to 20 minutes) after being injected into the capsular bag 308. In general, the polymerization time of the accommodative intraocular lens implant depends on the polymerization initiator that is used.

In one or more further embodiments, cataract surgery and glaucoma surgery with or without stent implantation may be done in a single session, wherein the photosensitizer is initially injected in the lens capsule after removal of the lens cortex and the nucleus. Then, a fiber optic is used to apply ultraviolet (UV) radiation so as to damage the lens epithelial cells and prevent their cellular proliferation. Immediately thereafter, the tissue around the surgical opening made in the eye wall during the glaucoma surgery with or without the shunt placement to drain the aqueous fluid outside the eye, is stained with the photosensitizer that was injected in the lens capsule. The photosensitizer migrates outside the eye through the surgical hole in the eye wall. The tissue, which is bathed by the photosensitizer (e.g., riboflavin), is then cross-linked with UV radiation applied through a fiber optic from the inside the eye or outside through the conjunctiva over the surgical hole or the shunt, regardless of the presence of a stent. The procedure achieves two goals simultaneously by preventing lens epithelial proliferation in the lens capsule, and by preventing fibroblast proliferation around the surgical hole of the tube.

Now, referring to the illustrative embodiment of FIGS. 30-41, an exemplary method for prevention of capsular opacification and fibrosis after cataract extraction, and for the prevention of fibrosis around a shunt or stent after glaucoma surgery will be explained. In general, the procedure illustrated in FIGS. 30-41 involves treating patients in need of both cataract surgery and glaucoma surgery. In the illustrative embodiment of FIGS. 30-41, the cataract and glaucoma surgeries are performed sequentially. However, as described hereinafter, the cataract and glaucoma surgeries may also be performed as two separate procedures. In these embodiments, the intraocular pressure (IOP) measurement is independent for a patient in need of cataract surgery and/or a glaucoma surgery.

Figure 30:
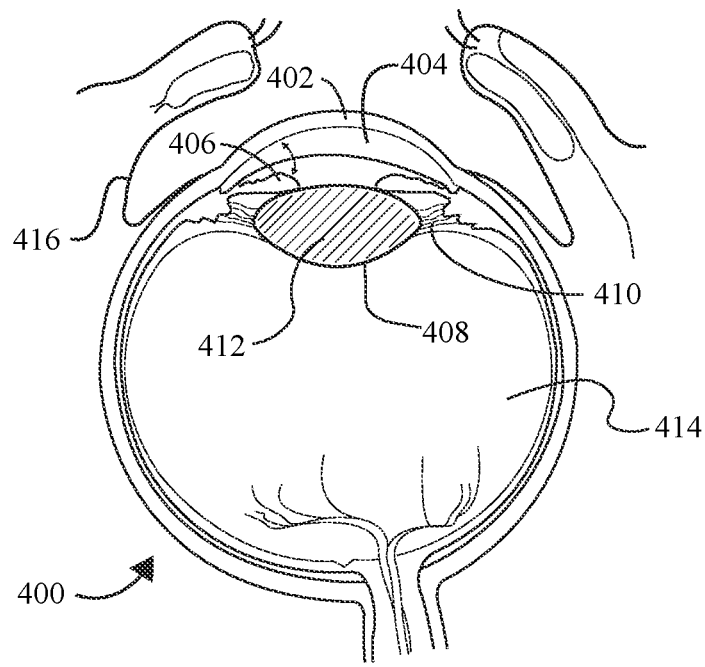
FIG. 30 is a side cross-sectional view illustrating an eye with a cataract, according to yet another embodiment of the invention.

Initially, referring to FIG. 30, it can be seen that the eye 400 undergoing cataract surgery generally includes a cornea 402, an anterior chamber 404, an iris 406, a lens capsule or capsular bag 408, lens zonules 410, a vitreous cavity 414, and a conjunctiva 416. As shown in FIG. 30, the eye 400 has a cataract 412 (i.e., a cloudy lens), thereby requiring that cataract surgery be performed on the eye 400 of the patient.

Figure 31:
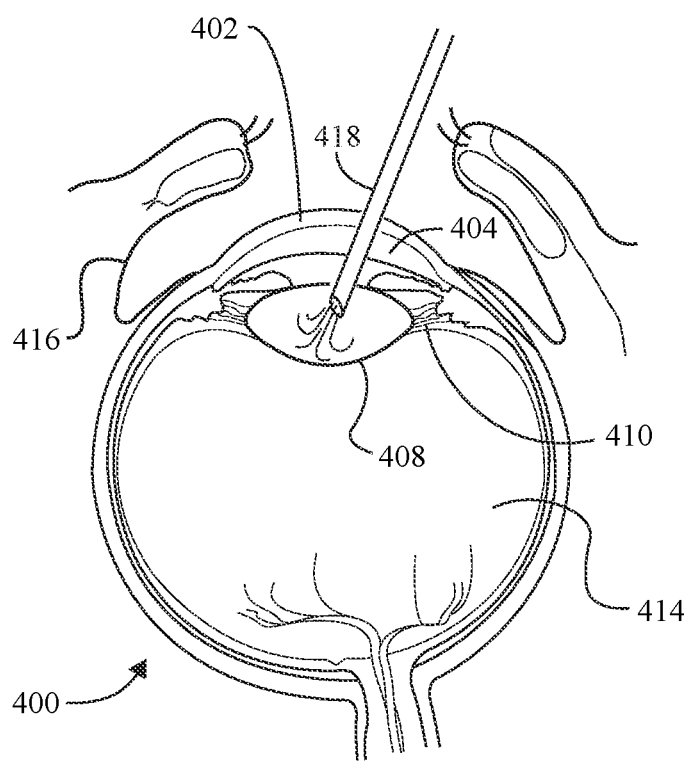
FIG. 31 is another side cross-sectional view of the eye of FIG. 30, which illustrates the application of a photosensitizer to a posterior portion of the capsular bag of the eye after the cataract has been removed.

In FIG. 31, the injection of a photosensitizer (e.g., riboflavin) into the posterior portion of the capsular bag 408 of the eye 400 is diagrammatically illustrated. In particular, as shown in the illustrative embodiment of FIG. 31, the cataract 412 has been removed from the capsular bag 408, which leaves the posterior portion of the capsular bag 408 intact. Then, as shown in FIG. 31, a photosensitizer is applied inside the capsular bag 408 so that the photosensitizer permeates the tissue in the posterior portion of the capsular bag 408. The photosensitizer facilitates the cross-linking of the tissue in the posterior portion of the capsular bag 408. In the illustrated embodiment of FIG. 31, the photosensitizer is injected with a needle 418 into the capsular bag 408 of the eye 400 by inserting the needle 418 through the anterior chamber 404 of the eye 400, and into the capsular bag 408. In one or more embodiments, the photosensitizer or cross-linker that is injected through the needle 418 into the capsular bag 408 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein). Also, in one or more embodiments, an excess portion of the photosensitizer in the capsular bag 408 may be aspirated through the needle 418 until all, or substantially all, of the excess portion of the photosensitizer is removed from the capsular bag 408 (i.e., the excess cross-linker may be aspirated through the same needle 418 so that the capsular bag 408 may be completely emptied or substantially emptied).

Figure 32:
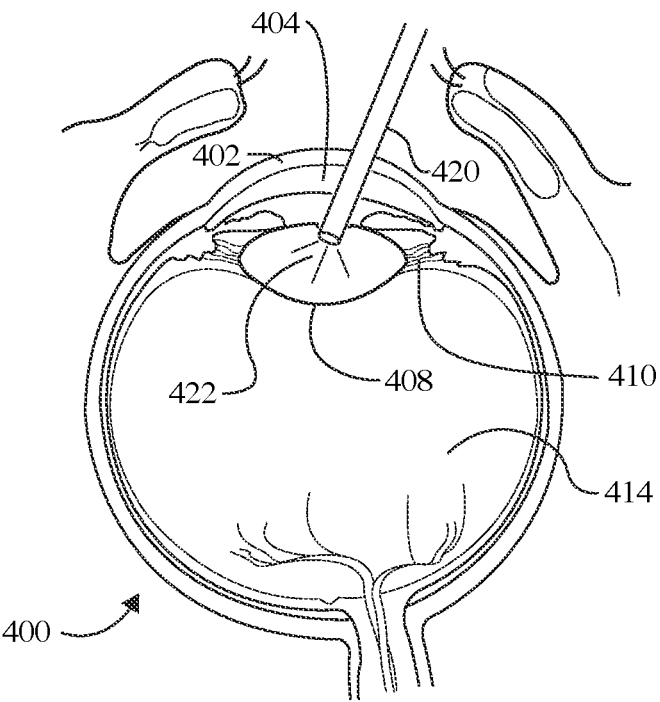
FIG. 32 is yet another side cross-sectional view of the eye of FIG. 30, which illustrates the irradiation of the posterior portion of the capsular bag of the eye so as to activate cross-linkers in the posterior portion of the capsular bag.

Next, turning to FIG. 32, shortly after the photosensitizer is applied inside the capsular bag 408, the remaining posterior portion of the capsular bag 408 of the eye 400 is irradiated using a fiber optic 420 delivering ultraviolet (UV) radiation 422 so as to damage the remaining lens epithelial cells with UV laser light, thereby preventing capsular opacification and fibrosis. In the illustrative embodiment, a painting technique may be utilized to deliver the ultraviolet light 422 to the posterior portion of the capsular bag 408 of the eye 400 (i.e., the fiber optic 420 may be manipulated in such a manner by the surgeon so as to "paint" the ultraviolet light 422 on the posterior portion of the capsular bag 408). Also, in the illustrative embodiment, ultraviolet (UV) radiation 422 may have a wavelength between about 370 nanometers and about 380 nanometers (or between 370 nanometers and 380 nanometers). In an alternative embodiment, the posterior portion of the capsular bag 408 of the eye 400 may be irradiated using another wavelength of light as an alternative to, or in addition to being irradiated using ultraviolet (UV) radiation.

Figure 33:
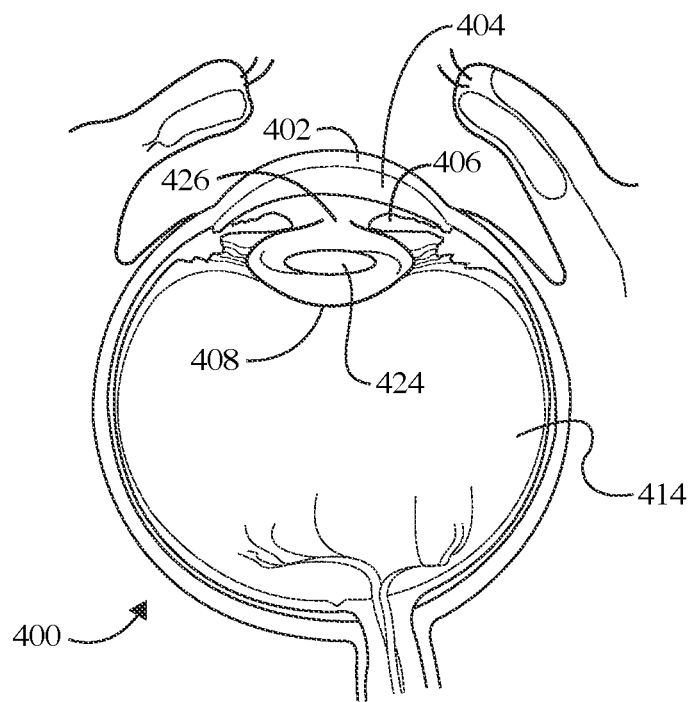
FIG. 33 is still another side cross-sectional view of the eye of FIG. 30, which illustrates the capsular bag of the eye after the removal of the cataract and the placement of an intraocular lens in the capsular bag.

Now, with reference to FIG. 33, it can be seen that, after the cataract 412 has been removed and the posterior portion of the capsular bag 408 has been irradiated, an intraocular lens 424 is implanted into the capsular bag 408 of the eye 400 in order to replace the cloudy natural lens that was removed. In particular, in the illustrative embodiment, the intraocular lens 424 is inserted into the capsular bag 408 of the eye 400 through the anterior opening 426 in the lens capsule 408.

Figure 34:
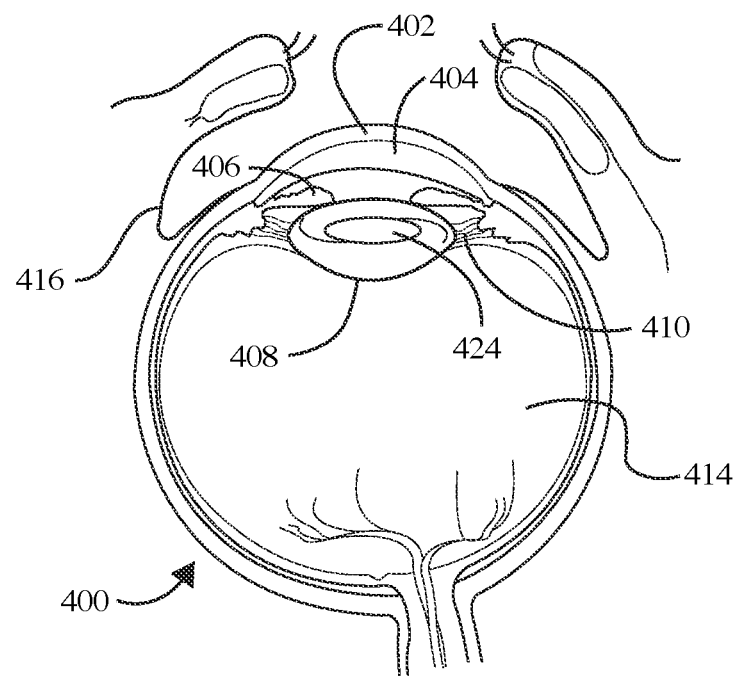
FIG. 34 is a yet another side cross-sectional view of the eye of FIG. 30, which illustrates the intraocular lens in the capsular bag of the eye prior to glaucoma surgery being performed on the eye.

Next, turning to FIGS. 34-38, the stent implantation and fibrosis prevention steps of the combined cataract extraction and glaucoma surgical procedure will be explained. Initially, the eye 400 with the implanted intraocular lens 424 therein is shown in FIG. 34.

Figure 35:
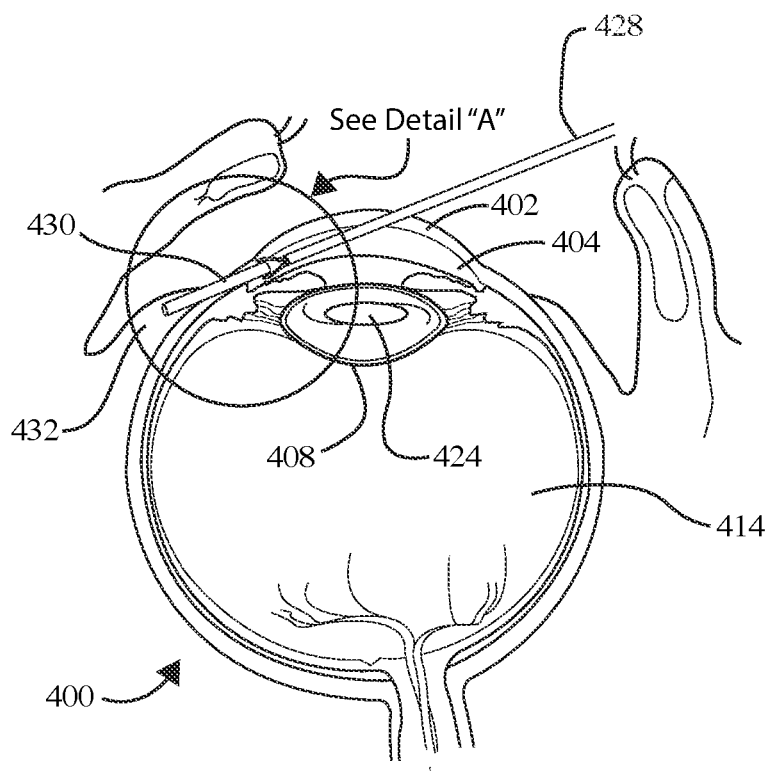
FIG. 35 is still another side cross-sectional view of the eye of FIG. 30, which illustrates the insertion of a stent through an anterior chamber of the eye and into the subconjunctival space.
Figure 36:
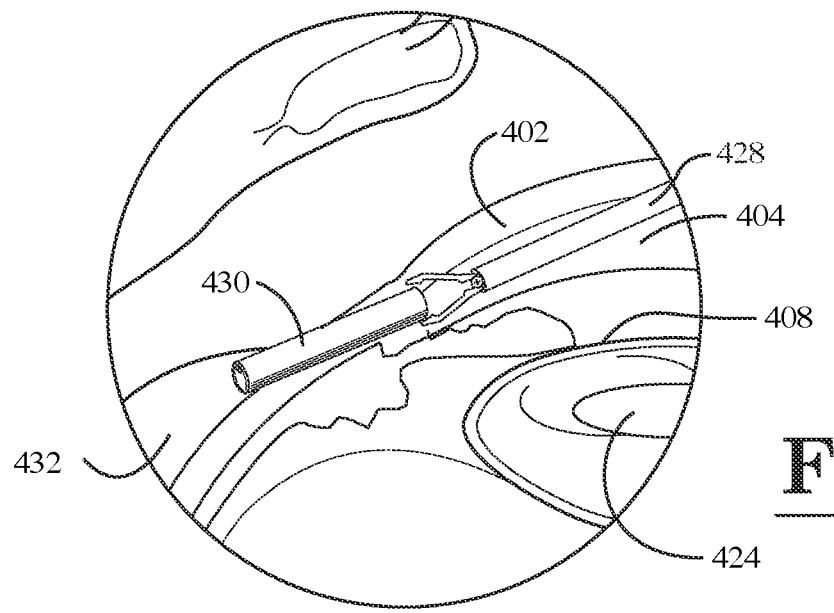
FIG. 36 is a partial, enlarged view illustrating the insertion of the stent in FIG. 35 (Detail "A")

In FIG. 35, the insertion of a glaucoma stent 430 through the anterior chamber 404, and into the subconjunctival space 432 of the eye 400 is diagrammatically illustrated. In particular, in the illustrated embodiment, the glaucoma stent 430 may be inserted into the subconjunctival space 432 of the eye 400 using a pair of forceps or microforceps 428. A detail view of the insertion of the glaucoma stent 430 is shown in FIG. 36. Once inserted, the glaucoma stent 430 extends from the anterior chamber 404 to the subconjunctival space 432.

Figure 37:
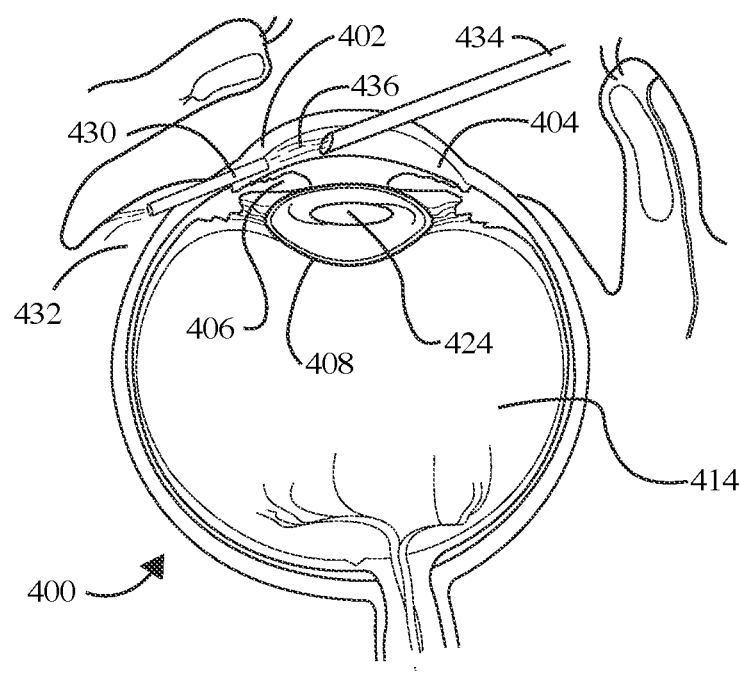
FIG. 37 is yet another side cross-sectional view of the eye of FIG. 30, which illustrates the application of a photo sensitizer to an anterior chamber of the eye so that the photosensitizer is capable of diffusing out of the stent and into the subconjunctival space.

Then, as shown in FIG. 37, the injection of a photosensitizer (e.g., riboflavin) into the anterior chamber 404 so that the photosensitizer diffuses into the tissue surrounding the glaucoma stent 430 is diagrammatically illustrated. In particular, as shown in the illustrative embodiment of FIG. 37, a photosensitizer is applied inside the anterior chamber 404 of the eye 400 and then a diffused stream 436 of the photo sensitizer travels through the central opening of the glaucoma stent 430, and into the subconjunctival space 432 so that the photosensitizer permeates the tissue surrounding the glaucoma stent 430. The photosensitizer facilitates the cross-linking of the tissue surrounding the glaucoma stent 430. In the illustrated embodiment of FIG. 37, the photosensitizer is injected with a needle 434 into the anterior chamber 404 of the eye 400 by inserting the needle 434 into the anterior chamber 404 of the eye 400, and letting the photosensitizer diffuse through the central opening in the glaucoma stent 430. In one or more embodiments, the photosensitizer or cross-linker that is injected through the needle 434 into the anterior chamber 404 comprises riboflavin, and/or a biocompatible fluid having nanoparticles of riboflavin disposed therein. Preferably, the cross-linker has between about 0.1% riboflavin to about 100% riboflavin therein (or between 0.1% and 100% riboflavin therein).

Figure 38:
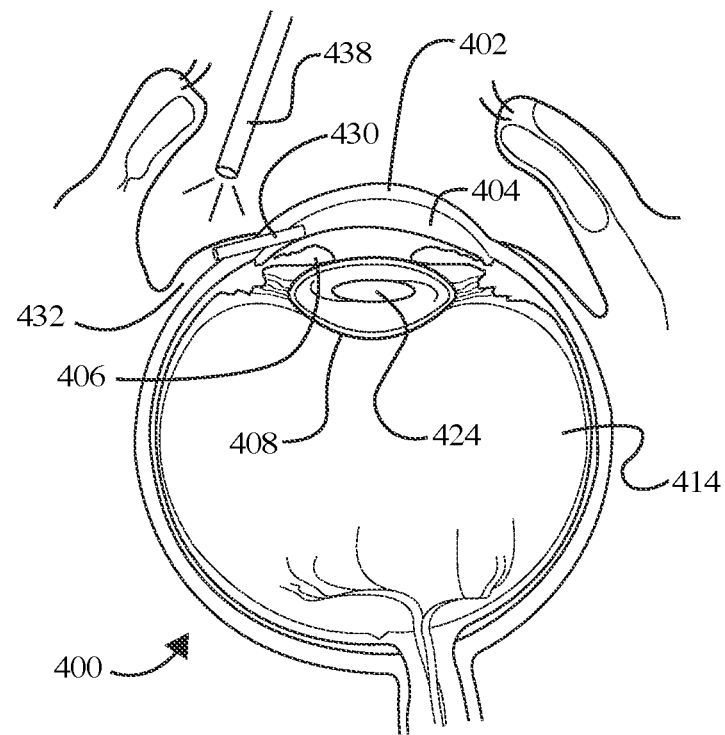
FIG. 38 is still another side cross-sectional view of the eye of FIG. 30, which illustrates the irradiation of the subconjunctival space so as to activate cross-linkers and prevent fibrosis around the stent outflow.

Next, turning to FIG. 38, shortly after the photosensitizer is applied inside the anterior chamber 404, the subconjunctival space 432 of the eye 400 is irradiated using a fiber optic 438 carrying ultraviolet (UV) light so as to cross-link the tissue surrounding the glaucoma stent 430, thereby preventing fibrosis around the stent 430 outflow. In the illustrative embodiment, a painting technique may be utilized to deliver the ultraviolet light to the subconjunctival space 432 of the eye 400 (i.e., the fiber optic 438 may be manipulated in such a manner by the surgeon so as to "paint" the subconjunctival space 432 with the ultraviolet light). Also, in the illustrative embodiment, ultraviolet (UV) radiation may have a wavelength between about 370 nanometers and about 380 nanometers (or between 370 nanometers and 380 nanometers). In an alternative embodiment, the subconjunctival space 432 of the eye 400 may be irradiated using another wavelength of light as an alternative to, or in addition to being irradiated using ultraviolet (UV) radiation.

Figure 39:
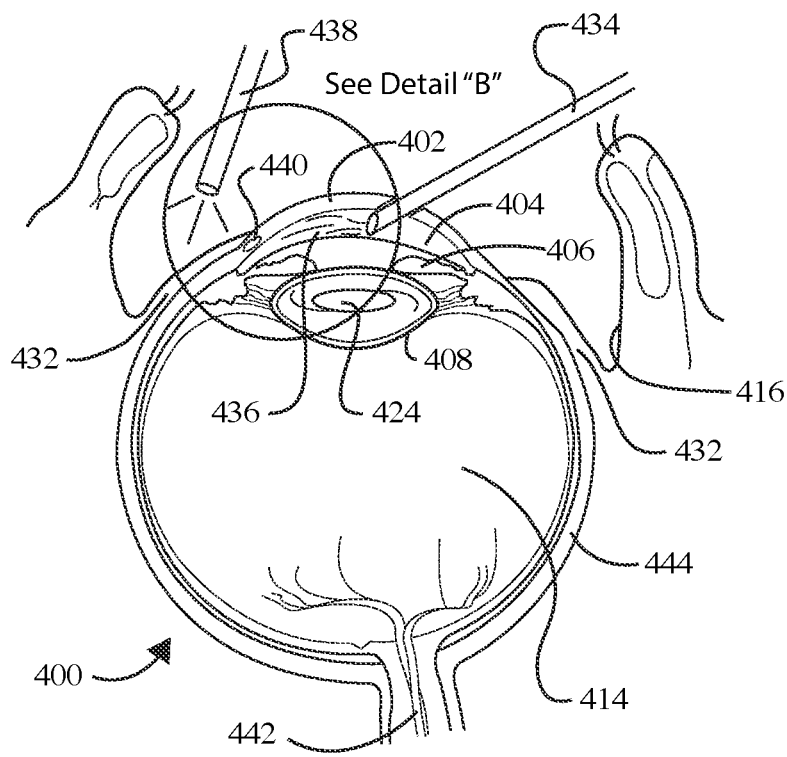
FIG. 39 is yet another side cross-sectional view of the eye of FIG. 30, which illustrates the application of a photo sensitizer to the anterior chamber of the eye and the irradiation of the subconjunctival space so as to activate cross-linkers and prevent fibrosis around a shunt or opening in the eye wall.
Figure 40:
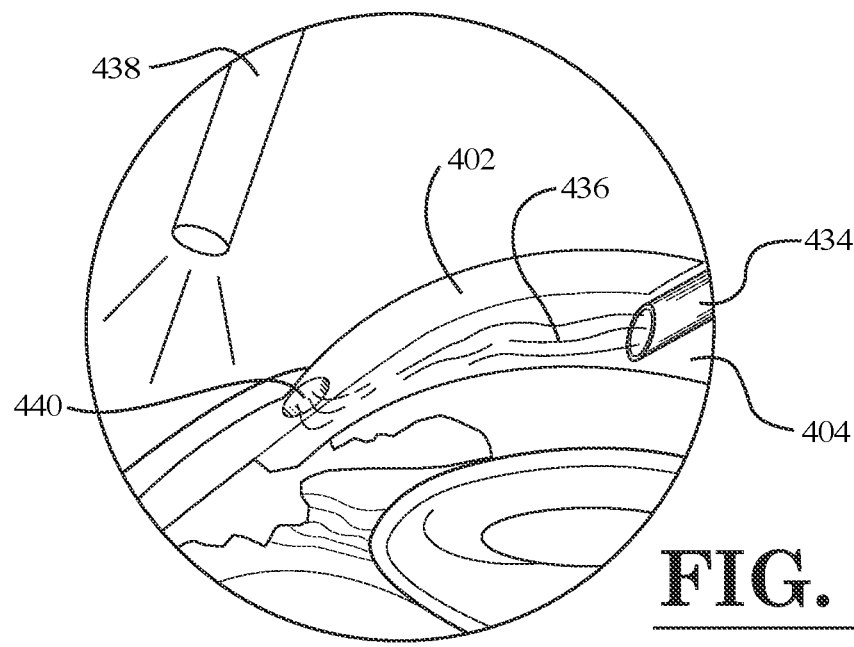
FIG. 40 is a partial, enlarged view illustrating the application of the photosensitizer and the irradiation of the space around the shunt or opening in the eye wall of FIG. 39 (Detail "B")

An alternative embodiment of the invention is depicted in FIG. 39. In particular, glaucoma drainage surgery is illustrated in FIG. 39. As shown in FIG. 39, the eye 400 undergoing glaucoma drainage surgery generally includes a cornea 402, an anterior chamber 404, an iris 406, a lens capsule or capsular bag 408 with an intraocular lens 424 disposed therein, a vitreous cavity 414, a conjunctiva 416, an optic nerve 442, and a sclera 444. Similar to the application of the photosensitizer described above with regard to FIG. 37, in the FIG. 39 embodiment, the photosensitizer (e.g., riboflavin in a biocompatible fluid) is injected into the anterior chamber 404 of the eye 400 using a needle 434. Then, a diffused stream 436 of the photosensitizer injected from the needle 434 travels through the opening or shunt 440 in the eye wall, and into the subconjunctival space 432 so that the photosensitizer permeates the tissue surrounding the opening or shunt 440. After which, with reference again to FIG. 39, the subconjunctival space 432 of the eye 400 is irradiated using a fiber optic 438 carrying ultraviolet (UV) light so as to cross-link the tissue surrounding the opening or shunt 440, thereby preventing fibrosis around the opening or shunt 440 outflow. A detail view of the application of the photosensitizer to the opening or shunt 440 is shown in FIG. 40. The opening or shunt 440 illustrated in FIGS. 39 and 40 is located in the angle of the eye between the iris 406 and the cornea 402. The opening or shunt 440 connects the anterior chamber 404 of the eye 400 to the subconjunctival space 432.

Figure 41:
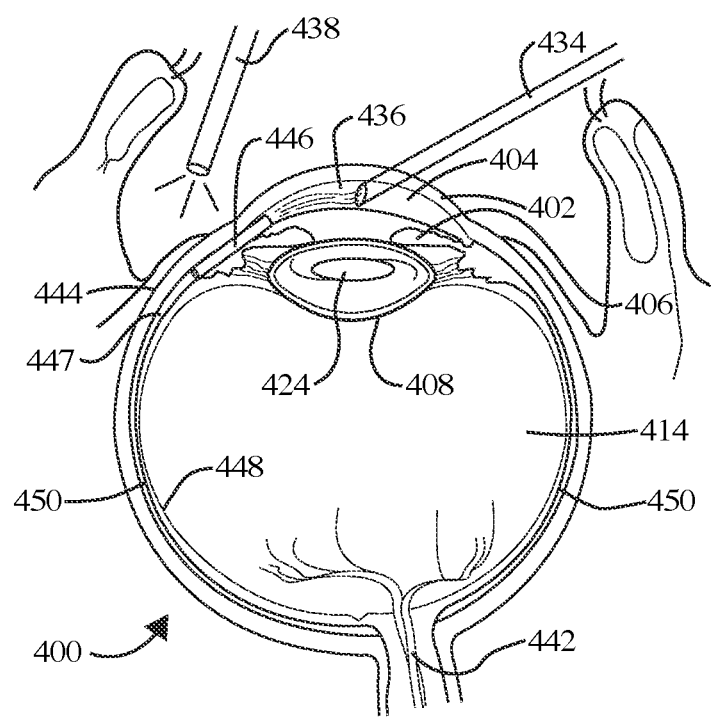
FIG. 41 is still another side cross-sectional view of the eye of FIG. 30, which illustrates the application of a photo sensitizer to the anterior chamber of the eye and the irradiation of the suprachoroidal space so as to activate cross-linkers and prevent fibrosis around a stent in the suprachoroidal space.
Figure 42:
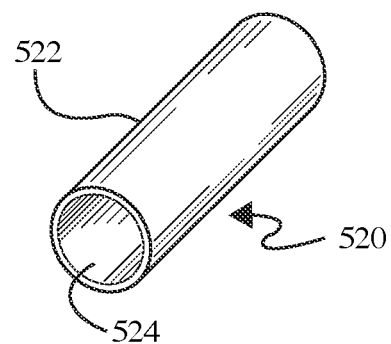
FIG. 42 is a perspective view illustrating a glaucoma stent having a coating provided thereon, according to an embodiment of the invention.

Another alternative embodiment of the invention is depicted in FIG. 41. In particular, a stent 446 positioned in the suprachoroidal space 447 of the eye 400 is illustrated in FIG. 41. More particularly, the glaucoma stent 446 in FIG. 41 extends from the angle of the anterior chamber 404 of the eye 400 to the suprachoroidal space 447. As shown in FIG. 41, the eye 400 undergoing glaucoma surgery generally includes a cornea 402, an anterior chamber 404, an iris 406, a lens capsule or capsular bag 408 with an intraocular lens 424 disposed therein, a vitreous cavity 414, an optic nerve 442, a sclera 444, a retina 448, and a choroid 450. Similar to the application of the photosensitizer described above with regard to FIG. 39, in the FIG. 41 embodiment, the photosensitizer (e.g., riboflavin in a biocompatible fluid) is injected into the anterior chamber 404 of the eye 400 using a needle 434. Then, a diffused stream 436 of the photosensitizer injected from the needle 434 travels through the glaucoma stent 446 in the suprachoroidal space 447 of the eye 400, and into the suprachoroidal space 447 so that the photosensitizer permeates the tissue surrounding the glaucoma stent 446. After which, with reference again to FIG. 41, the suprachoroidal space 447 of the eye 400 is irradiated using a fiber optic 438 carrying ultraviolet (UV) laser light so as to cross-link the tissue surrounding the glaucoma stent 446, thereby preventing fibrosis around the glaucoma stent 446 outflow.

In another embodiment, the application of the photosensitizer and the irradiation of the tissue surrounding the glaucoma stent 446 is repeated one or more additional times to cross-link the tissue surrounding the stent 446 again so as to prevent any cellular invasion in the area surrounding the stent 446.

In still another embodiment, the cataract surgery and the glaucoma surgery with or without stent implantation is done in two sessions. Initially, the photosensitizer is used to kill the lens epithelial cells using a fiber optic applying ultraviolet (UV) radiation, while in a subsequent glaucoma surgery with or without a stent, a photosensitizer (e.g., riboflavin) is injected in the anterior chamber after the glaucoma surgery with or without a stent and the wall of the outflow hole and the tissue in the subconjunctival space is then irradiated with ultraviolet (UV) light from the external side with a fiber optic in a painting fashion with the desired power to cross-link the collagenous tissue around the eye wall opening or around the stent to kill the cells, thereby preventing the cells from migrating in the surgical area and closing the outflow channel.

In yet another embodiment, in a previous glaucoma surgery involving a shunt or drainage tube, a minimal amount (e.g., 0.02 to 0.1 milliliters or less) of the photosensitizer (e.g., riboflavin) is injected in the anterior chamber of the eye so as to diffuse out of the surgically created hole or a shunt. Then, immediately thereafter, ultraviolet (UV) radiation is applied in an oscillatory painting fashion over the end of the drainage tube or stent, or over the surgically produced opening, at the desired power and duration in order to cross-link the tissue that comes into contact with the photosensitizer, etc.

In still another embodiment, the radiation is done shortly after injection of the photosensitizer (e.g., 5 to 60 seconds thereafter) or slightly longer after injection of the photosensitizer to prevent crosslinking or damage to the conjunctival superficial vessels or the conjunctival epithelial surface, so as to only crosslink the deeper laying tissue of the subtenon space or choroidal tissue immediately in contact with the photosensitizer over the pars plana. This process may be repeated to stabilize the tissue and further prevent tissue adhesion and encapsulation of the drainage shunt.

In one embodiment, the implant has a collagenous coating. The device may be in the form of a stent or a glaucoma drainage device connecting the fluid produced inside the eye to outside, either in the choroid or under the conjunctiva. The collagen coating can be conjugated with a photosensitizer that can be cross-linked after implantation with ultraviolet (UV) radiation or another wavelength of light that is applied to cross-link the collagen surrounding the implant, and to prevent cell growth or migration over the implant and encapsulation of the implant. Advantageously, by preventing cell growth or migration over the implant and the encapsulation of the implant, the aqueous fluid has unimpeded access to the subconjunctival space or the choroidal space.

In another embodiment, a collagen conjugated with a photosensitizer is injected surrounding the body of the implant after the stent or shunt implantation, and then the polymeric collagen and the surrounding tissue is cross-linked so as to provide an area for diffusion of fluid, and to kill the surrounding cells and prevent encapsulation of the implant or a part of it.

In yet another embodiment, the photosensitizer may be injected in the lens capsule after removal of the lens nucleus and the lens cortex so as to cross-link the remaining lens epithelial cells with ultraviolet (UV) light applied through a fiber optic in a painting fashion with an appropriate power to damage the epithelial cells prior to implantation of an intraocular lens (IOL), thereby preventing encapsulation and cell proliferation of the remaining epithelial lens cells in the lens capsule that create a fibrous-like encapsulation closing the space between the anterior and posterior leaflet of the remaining lens capsule or around an implanted intraocular lens. This cell proliferation causes a significant posterior capsular opacification about 3 to 12 months after cataract surgery in over 80% of the patients, or the implant may be tilted as a result of force applied to it, thus requiring laser surgery to cut the capsule open for the patient to have a clear view to the outside for uninterrupted light to reach the retina.

Now, referring to FIGS. 42-46, another embodiment of a glaucoma stent 520 and a surgical procedure using the stent 520 will be described. Initially, referring to the perspective view of the stent 520 in FIG. 42, it can be seen that the glaucoma stent 520 comprises a flexible tube with an external coating 522 disposed on the outside of the stent 520 and an internal coating 524 disposed on the inside of the stent 520. The external and internal stent coating 522, 524 is very important for the surgical procedure. Unless the external and internal stent coating 522, 524 is done with a substance, such as collagen, elastin, and/or polyethylene glycol (PEG), the stent 520 can irritate the surrounding tissue and excite cell migration and encapsulation. The coating may be applied to the stent 520 before or after the implantation of the stent 520. Preferably, the glaucoma stent 520 is formed from a solid, flexible, or semi-flexible material. For example, the stent material may be silicone-based or a mixture of polymers (e.g. acrylic and Hydroxyethyl methacrylate (HEMA), or HEMA alone, etc.) that preferably create a soft stent 520 for its placement under the conjunctiva of the eye. However, the stent 520 may also be implanted under the sclera of the eye. The glaucoma stent 520 may have a diameter between approximately 50 microns and approximately 700 microns (or between 50 microns and 700 microns), and the stent 520 may have a length between approximately 5 millimeters (mm) and approximately 15 millimeters (or between 5 millimeters and 15 millimeters). The diameter and the length of the stent 520 ultimately determine how much fluid is drained at a certain, desired intraocular pressure. This may also be decided by the doctor by him or her choosing a stent 520 that provides the desired pressure inside the patient's eye. In one embodiment, the glaucoma stent 520 may be three-dimensionally (3D) printed, and then coated as known in the art.

In one embodiment, the glaucoma stent 520 may be coated with a photosensitizer (e.g., riboflavin) before being implanted into the eye. Then, after the glaucoma stent 520 is implanted in the eye, the photosensitizer (e.g., riboflavin) may be released by the glaucoma stent 520 into the tissue surrounding the stent 520.

Figure 43:
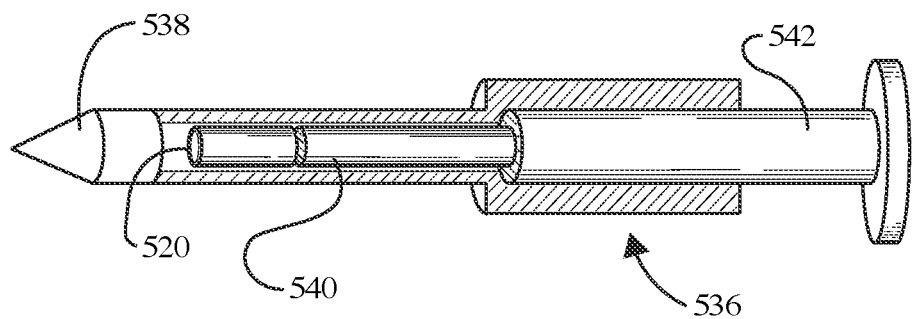
FIG. 43 is a side cross-sectional view illustrating a syringe used for the implantation of the stent of FIG. 42, according to an embodiment of the invention.

Next, turning to FIG. 43, a syringe 536 for implantation of the glaucoma stent 520 will be briefly described. As shown in FIG. 43, the syringe 536 comprises a sharp needle portion 538 for penetrating the tissue, a piston portion 540 for implanting the stent 520 into its desired location, and a plunger 542 for driving the piston 540, which in turn, drives the stent 520 into the tissue of the patient.

Now, referring to the illustrative embodiment of FIGS. 44-46, an exemplary surgical procedure using the stent 520 will be explained. Initially, referring to FIGS. 44-46, it can be seen that the eye 500 undergoing surgery generally includes a cornea 502, an anterior chamber 504, an iris 506, a lens capsule or capsular bag 508 with an intraocular lens 530 disposed therein, lens zonules 510, a vitreous cavity 512, a conjunctiva 514, a sclera 518, a retina 526, and an optic nerve 528.

Figure 44:
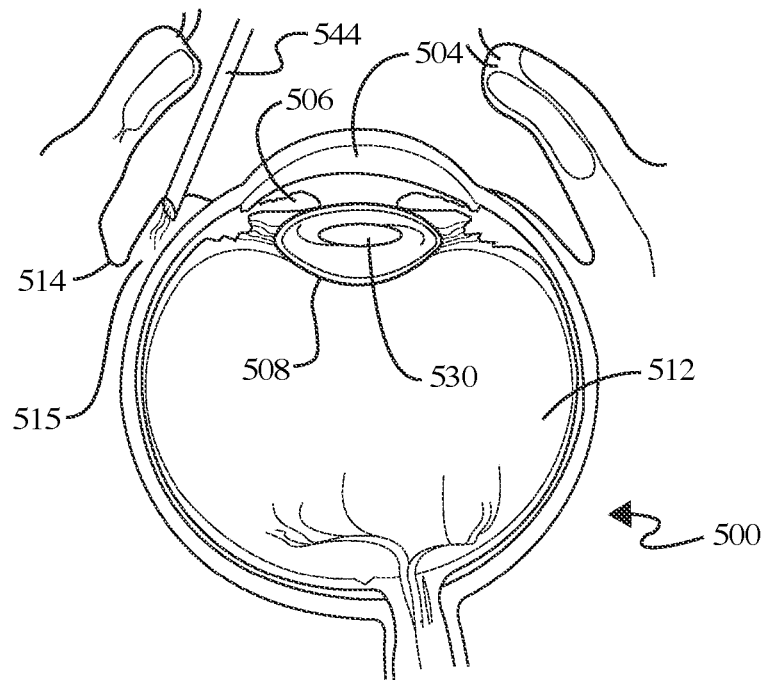
FIG. 44 is a side cross-sectional view of an eye, which illustrates the application of liquid collagen to the subconjunctival space, according to another embodiment of the invention.

In FIG. 44, liquid collagen and hyaluronic acid with or without a photosensitizer is initially injected in the subconjunctival space using a needle 544 so as to create a space (i.e., a bleb) for the stent 520. When the solution comprising the liquid collagen and the hyaluronic acid is subsequently cross-linked with ultraviolet light or another wavelength of light, a honeycomb structure is formed in the subconjunctival space around the stent outflow, thereby facilitating the draining of aqueous fluid from the stent. As such, when the stent 520 is subsequently positioned in liquid collagen that is cross-linked at the end of the surgery, the scar forming cells in the Tenon's capsule under the conjunctiva are killed, and the aqueous fluid is capable of diffusing through the stent 520.

Next, the glaucoma stent 520 is implanted into the conjunctiva 514 of the eye 500 using the syringe 536 described above. The syringe 536 is essentially loaded with the stent 520, and then the sharp needle portion 538 of the syringe 536 is used to penetrate the eye wall before the stent 520 is unloaded by the syringe 536. After the stent 520 is delivered into the tissue, the syringe 536 is withdrawn from the eye 500. Once inserted, the glaucoma stent 520 extends from the anterior chamber 504 to the subconjunctival space 515.

The cross-linked subconjunctival space or bleb may be created immediately before the implantation of the stent 520 during a single surgical procedure so as to prepare the space first so that the end of the stent 520 enters the cross-linked subconjunctival space during the surgery. Alternatively, the cross-linked subconjunctival space or bleb may be created during a first surgical procedure, and then the stent 520 may be implanted thereafter during a second, separate surgical procedure. In this alternative embodiment, the second surgical procedure may be performed a significant time after the first surgical procedure. The cross-linked subconjunctival space or bleb may be irradiated using either an external ultraviolet light or a handheld fiber optic connected to a laser that is placed close to the space or bleb and the tissue that will surround the stent 520 (i.e., the corneoscleral tissue). This tissue may be irradiated for 5 to 20 minutes so as to cross-link the tissue.

Figure 45:
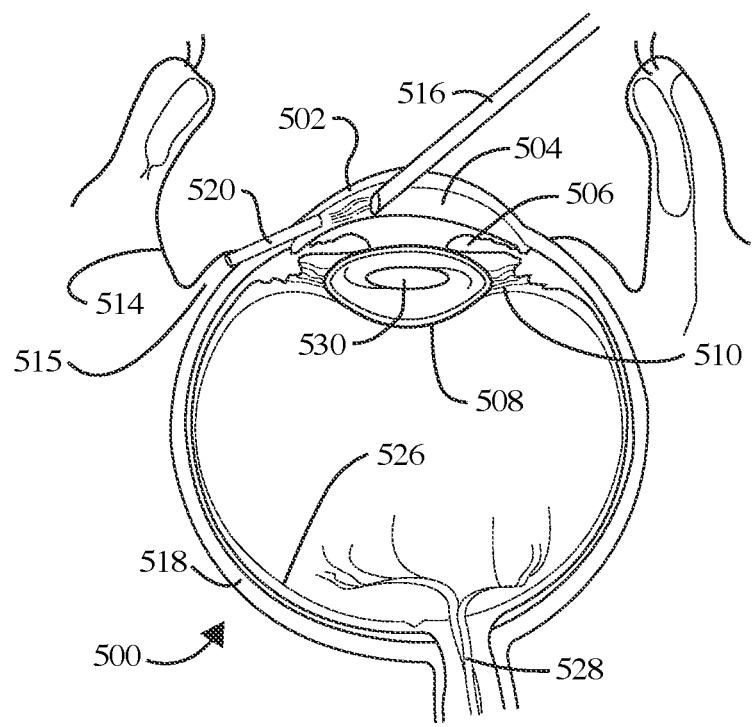
FIG. 45 is another side cross-sectional view of the eye of FIG. 44, which illustrates the application of a photosensitizer after the implantation of the glaucoma stent of FIG. 42 in the eye.
Figure 46:
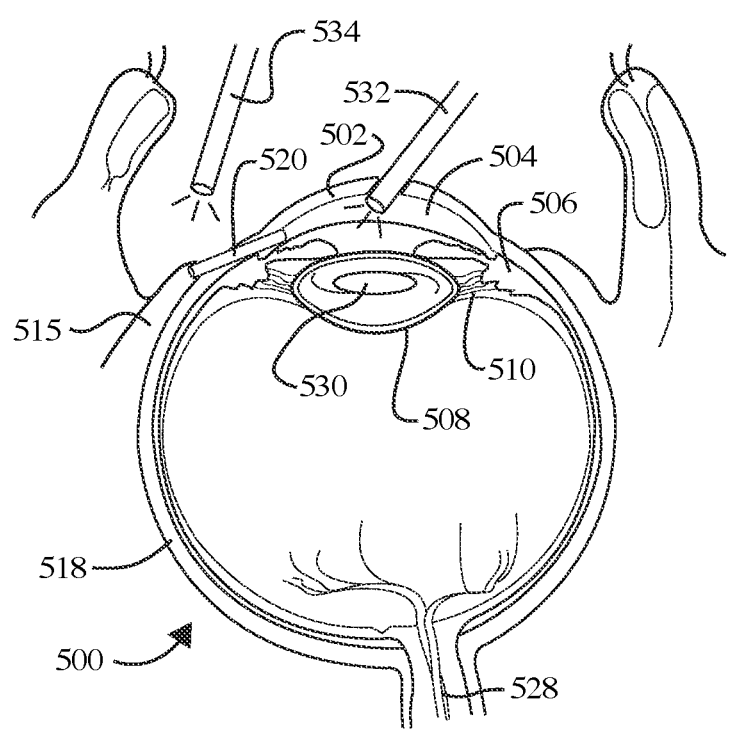
FIG. 46 is yet another side cross-sectional view of the eye of FIG. 44, which illustrates the irradiation of the glaucoma stent and the surrounding areas in the eye so as to activate cross-linkers and prevent fibrosis.
Figure 47:
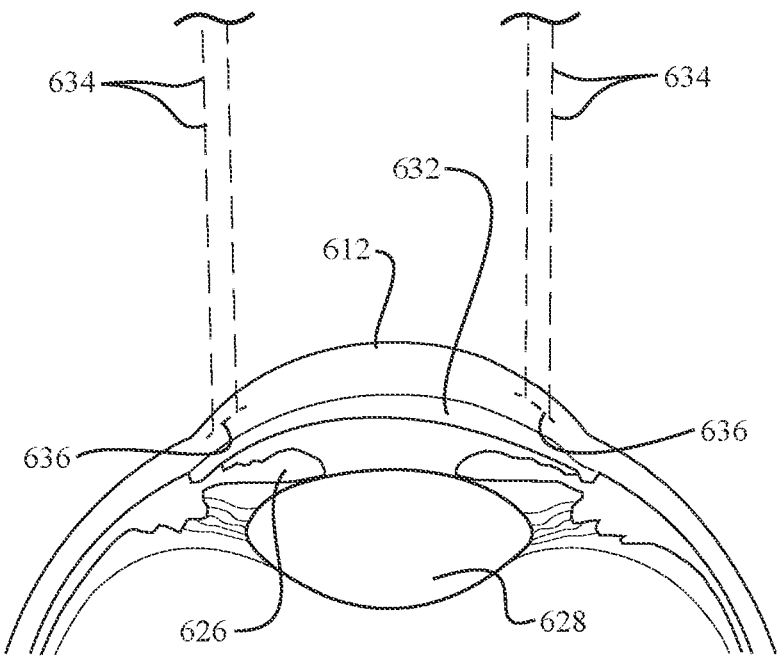
FIG. 47 is a partial side cross-sectional view illustrating the formation of an incision into a peripheral portion of a cornea of an eye so as to create a pocket for receiving a corneal intraocular pressure sensor, according to another embodiment of the invention.

Then, after the implantation of the stent 520 in the conjunctiva 514 of the eye, the photosensitizer (e.g., riboflavin in a biocompatible fluid) is injected into the eye 500 using a needle 516 (see FIG. 45). That is, similar to that described above, the photosensitizer or cross-linker is injected using the needle 516 into the anterior chamber 504 of the eye 500 after the implantation of the stent 520. The photosensitizer injected from the needle 516 travels through the glaucoma stent 520, and into the subconjunctival space 515 of the eye 500 so that the photosensitizer permeates the tissue surrounding the glaucoma stent 520. After which, at the end of the surgical procedure, the stent 520 and the areas surrounding the stent 520, both inside and outside, are cross-linked. In particular, with reference to FIG. 46, an inflow end of the glaucoma stent 520 proximate to the anterior chamber 504 of the eye 500 is irradiated using a fiber optic 532 carrying ultraviolet (UV) laser light so as to cross-link the tissue surrounding the glaucoma stent 520, thereby preventing fibrosis around the glaucoma stent 520. Also, as shown in FIG. 46, an outflow end of the glaucoma stent 520 in the subconjunctival space 515 of the eye 500 is irradiated using a fiber optic 534 carrying ultraviolet (UV) laser light so as to cross-link the tissue surrounding the glaucoma stent 520, thereby preventing fibrosis around the glaucoma stent 520 outflow.

Next, an illustrative embodiment of a method of implanting a corneal intraocular pressure sensor in an eye of a patient will be described below with reference to FIGS. 47-53. In general, the procedure involves the steps of forming a pocket in a cornea of an eye so as to gain access to tissue surrounding the pocket, applying a photosensitizer inside the pocket so that the photosensitizer permeates at least a portion of the tissue surrounding the pocket, irradiating the cornea so as to activate cross-linkers in the portion of the tissue surrounding the pocket, and inserting an intracorneal implant comprising a pressure sensor into the pocket after the tissue has been cross-linked. The pressure sensor of the intracorneal implant is configured to measure the intraocular pressure of the eye of the patient. As shown in FIGS. 47-53, the eye 610 undergoing the implantation of the pressure sensor generally includes a cornea 612, an iris 626, a lens 628, and an anterior chamber 632.

Initially, a pocket is formed in the cornea of the eye so as to gain access to tissue surrounding the pocket. In the illustrative embodiment, referring to FIG. 47, a two or three-dimensional portion of stromal tissue is first cut out from the cornea of the eye using a femtosecond laser (i.e., an incision 636 is first cut in the cornea 612 of the eye 610 using the laser beam(s) 634 emitted from the femtosecond laser). Then, the three-dimensional cut portion of the cornea 612 is removed using forceps so as to create a three-dimensional pocket for receiving the intracorneal implant. The formation of the three-dimensional pocket creates a cavity so that, when the intracorneal implant is placed in it, the implant will not exert any pressure on the stromal tissue of the cornea.

In one or more embodiments, an intrastromal corneal pocket is created in the peripheral part of the cornea involving 1 to 4 millimeter (mm) areas in width located between the cornea and the anterior sclera using a femtosecond laser. Prior to the laser application, if needed, the peripheral conjunctival capillaries are bleached out with a low dose of vasoconstrictive medication, such as 0.5% to 1% phenylephrine applied locally with a cotton swab applicator, and/or a low dose (0.1 to 2%) hyaluronic acid in a fluid is applied to make the corneal limbus area transparent.

In one or more embodiments, the three-dimensional pocket 624 formed in the peripheral portion of the cornea extends between 1 degree and 360 degrees around the corneal periphery (refer to the front view of FIG. 51), and the three-dimensional pocket is located at a predetermined distance from the Bowman's membrane in the corneal periphery of the eye.

In one or more embodiments, one or two incisions are used depending on the size of the pocket to access the intrastromal incision. Then, a curved probe is used to separate the remaining corneal adhesion between the walls of the incision, so as to create a pocket for the injection of a photosensitizer (i.e., a cross-linker).

Figure 48:
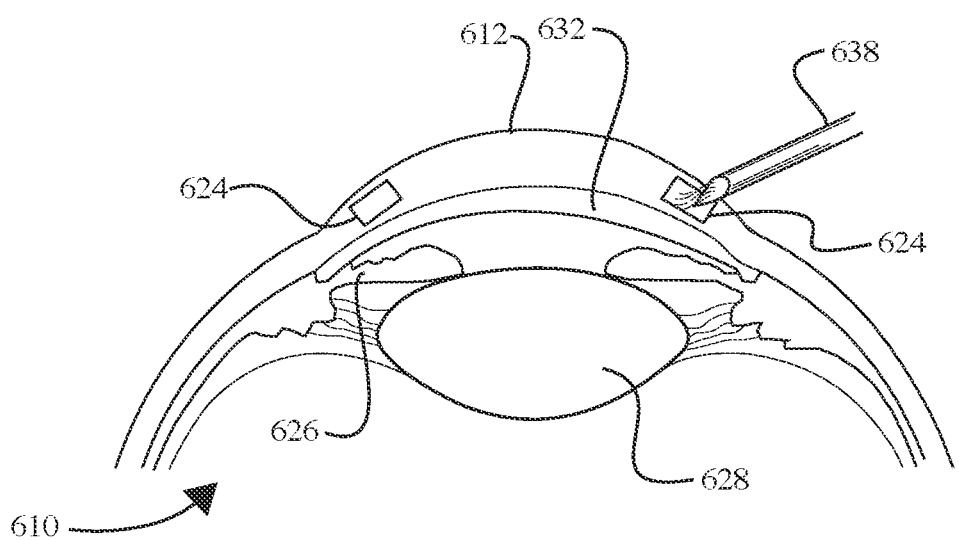
FIG. 48 is another partial side cross-sectional view of the eye of FIG. 47, which illustrates the injection of a photosensitizer into the pocket in the peripheral portion of the cornea of the eye.
Figure 49:
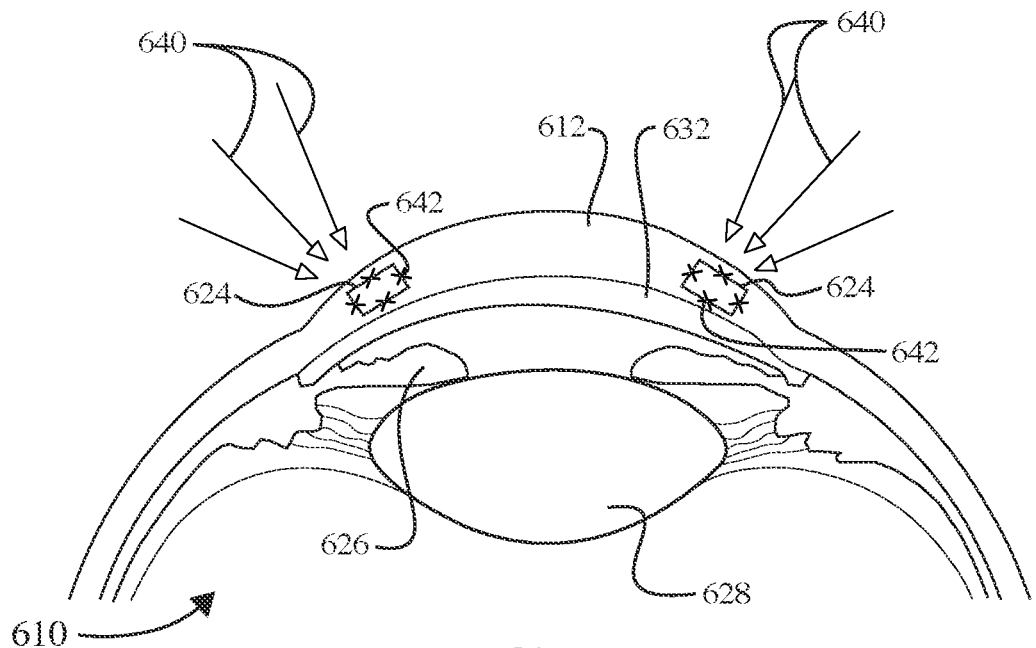
FIG. 49 is yet another partial side cross-sectional view of the eye of FIG. 47, which illustrates the irradiation of the stromal tissue surrounding the pocket in the peripheral portion of the cornea of the eye using ultraviolet radiation delivered from outside of the cornea.
Figure 50:
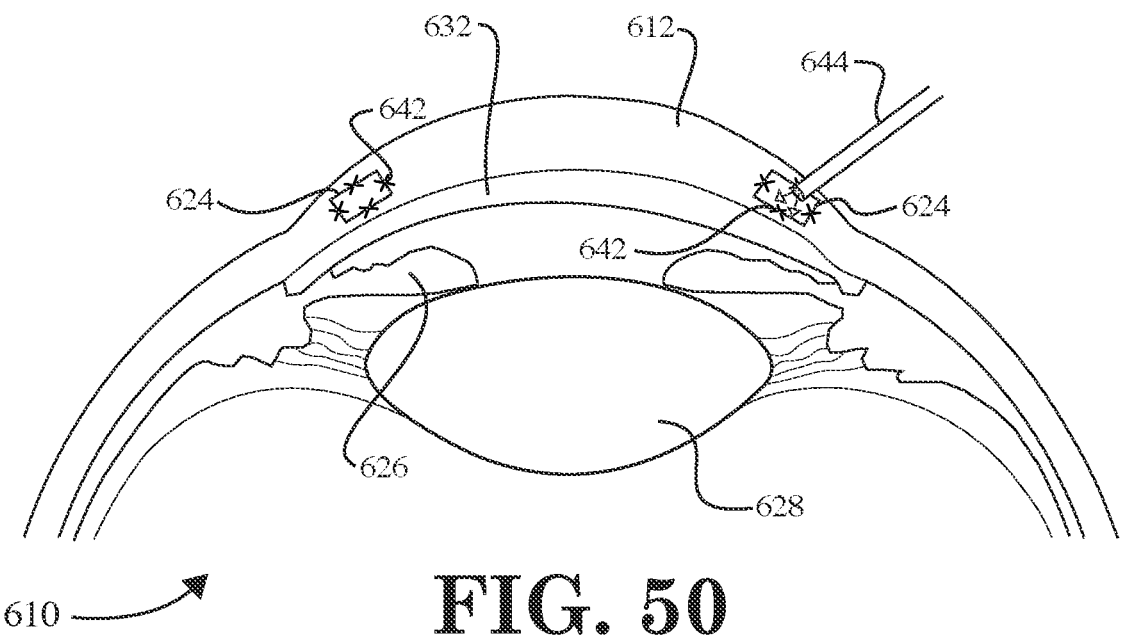
FIG. 50 is still another partial side cross-sectional view of the eye of FIG. 47, which illustrates the irradiation of the stromal tissue surrounding the pocket in the peripheral portion of the cornea of the eye using a fiber optic delivering ultraviolet radiation inside the pocket, according to an alternative embodiment of the invention.

After the three-dimensional pocket 624 is formed, a photosensitizer is applied inside the three-dimensional pocket 624 so that the photosensitizer permeates the tissue surrounding the pocket (refer to FIG. 48). The photosensitizer facilitates the cross-linking of the tissue surrounding the pocket 624. In the illustrative embodiment, a photosensitizer (i.e., a cross-linker), such as riboflavin, is injected with a needle 638 (see FIG. 48) at a concentration of about 0.5% to 4% in a biocompatible fluid, such as a physiological saline solution, etc., in a volume of 0.01 milliliters (ml) to 1 milliliters (ml) as needed for the extent of the pocket 624 to cover the internal walls of the corneal pocket 624 for a desired duration for the photo sensitizer to penetrate at least 20 microns beyond the corneal pocket 624 in the corneal stroma. This will take about a few seconds to about 30 seconds, while avoiding the crosslinking of the entire remaining wall of the cornea 612. In the illustrative embodiment, an effort is made to limit the corneal staining with the photosensitizer to the wall of the pocket 624 so that the photosensitizer never reaches the anterior or posterior full thickness of the cornea 612.

In one or more embodiments, 0.01 milliliters (ml) to 0.1 milliliters (ml) of 0.02 to 2% concentration lidocaine or bupivacaine solution may be injected alone or along with the photosensitizer in the corneal pocket 624 to anesthetize the cornea for a duration of 10 to 15 hours, thereby eliminating pain sensation or discomfort of the surgery.

In one or more embodiments, the width of the corneal pocket 624 may be 1 to 3 millimeters (mm), as needed. The pocket may be circular, semi-circular, C-shaped, doughnut-shaped, rectangular, or any other suitable shape.

Next, in the illustrative embodiment, shortly after the photosensitizer is applied inside the pocket 624, the cornea 612 of the eye 610 is irradiated from the outside using ultraviolet (UV) radiation 640 so as to activate cross-linkers in the portion of the tissue surrounding the three-dimensional pocket 624, and thereby stiffen a wall of the pocket and kill cells in the portion of the tissue surrounding the pocket.

In the illustrative embodiment, ultraviolet (UV) radiation 640 at a desired power of 0.5 to 50 mW/cm2 and a duration 1 to 15 minutes is applied to the cornea 612 of the eye 610 from outside in a stationary manner (see FIG. 49), or using a continuous painting or oscillatory technique with a focused small-sized spots of 1 to 4 millimeters (mm) and high energy to cover the width of the pocket, and to activate the photosensitizer in the corneal pocket 624, and thereby crosslink the collagen of the corneal stroma 642 surrounding the corneal pocket 624, kill all cells located within the cross-linked corneal area while providing a physical stability to the wall of the corneal pocket and preventing the wall from adhering to itself or to a future implant. In other embodiments, if a photosensitizer other than riboflavin is used, radiation with another wavelength of light may be applied to the cornea 612 of the eye 610 to cross-link the collagen of the corneal stroma 642 surrounding the corneal pocket 642.

In one or more embodiments, ultraviolet (UV) radiation at the desired power in a form of stationary or focused light for a duration of 1 to 5 minutes is applied, as needed, depending on the size of the pocket 624, and when using the painting method, the ultraviolet radiation is applied for 1 to 20 minutes depending on the size of the pocket 624. The power used for the UV radiation and the focal spot size of the laser that is used depends on the power of the radiation and the length of the pocket 624. The radiation may be applied externally, or via a fiber optic 644 inserted inside the pocket 624 in a painting fashion (see FIG. 50), so as to activate the photosensitizer and cross-link the collagen of the corneal stroma 642 surrounding the corneal pocket 624, thereby killing all cells located within the cross-linked cornea 642 while preventing encapsulation, cell migration, or rejection of the implant, and also providing an amorphous wall between the implant and the rest of the corneal stroma creating a vascular free zone only to the extent that the cross-linker has penetrated in the cornea surrounding the implant. The radiation is applied a short time after the cross-linker is injected in the pocket 624.

In one or alternative embodiments, the cornea is cross-linked from outside by dropping a cross-linker, such as riboflavin, at concentration of 1-2% in a physiological solution having dextran or hyaluronic acid or chondroitin sulfate over the corneal epithelium or denuded corneal epithelium for a period of time of 15 to 30 minutes. After which, the cornea 612 is cross-linked with the UV laser light for 10 to 50 minutes depending on the power of the UV laser applied, then waiting after cross-linking for a period of 3-4 weeks to implant the intraocular pressure sensor in the cross-linked cornea as described above.

Figure 51:
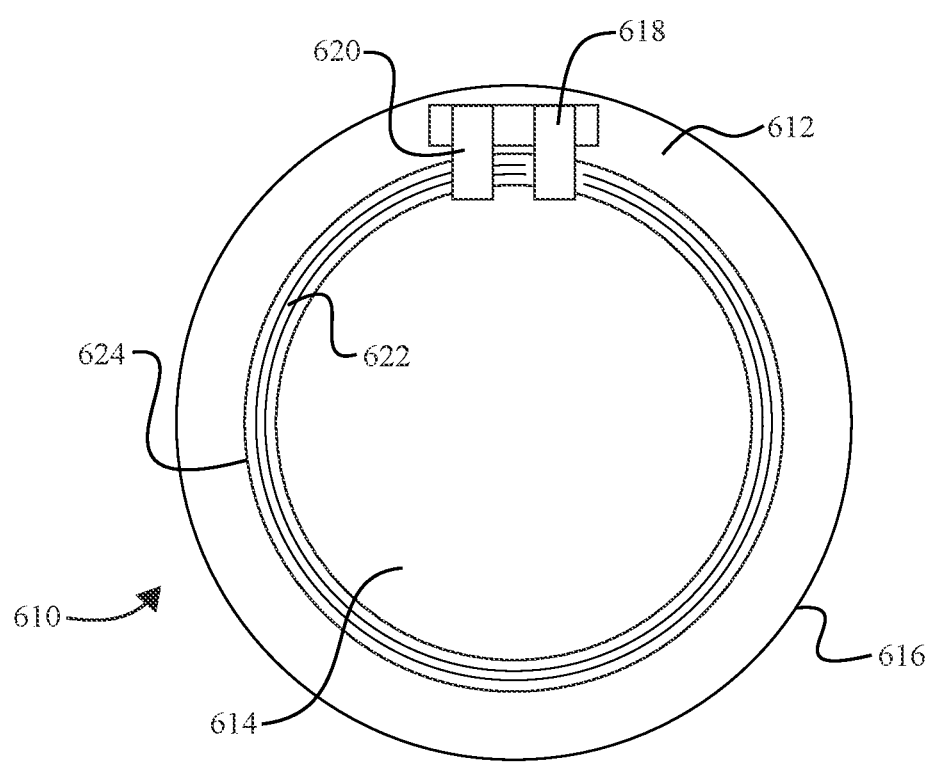
FIG. 51 is a front view of the eye of FIG. 47, which illustrates the components of a corneal intraocular pressure sensor disposed in the pocket in the peripheral portion of the cornea of the eye.
Figure 52:
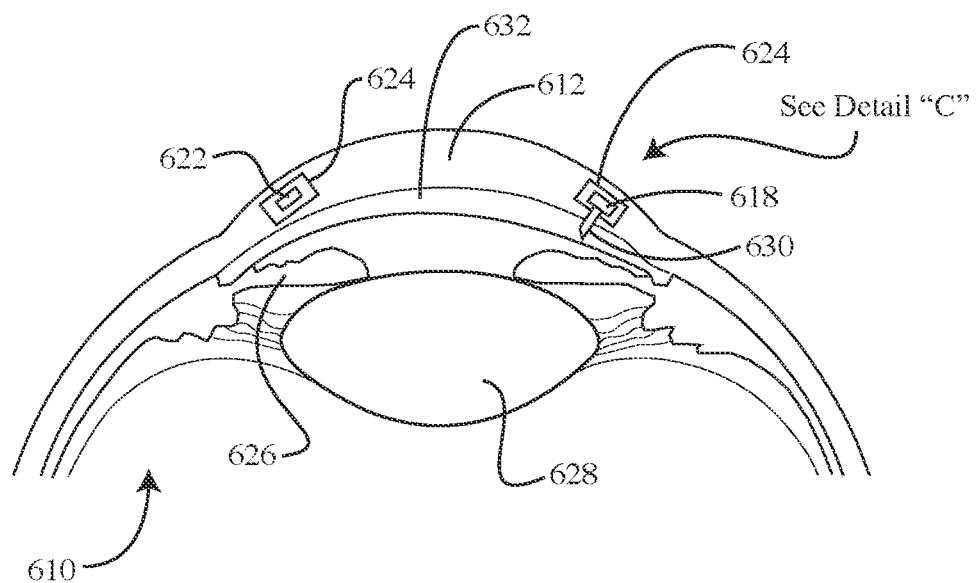
FIG. 52 is still another partial side cross-sectional view of the eye of FIG. 47, which illustrates the peripheral cross-linked corneal pocket with the components of the corneal intraocular pressure sensor disposed therein.
Figure 53:
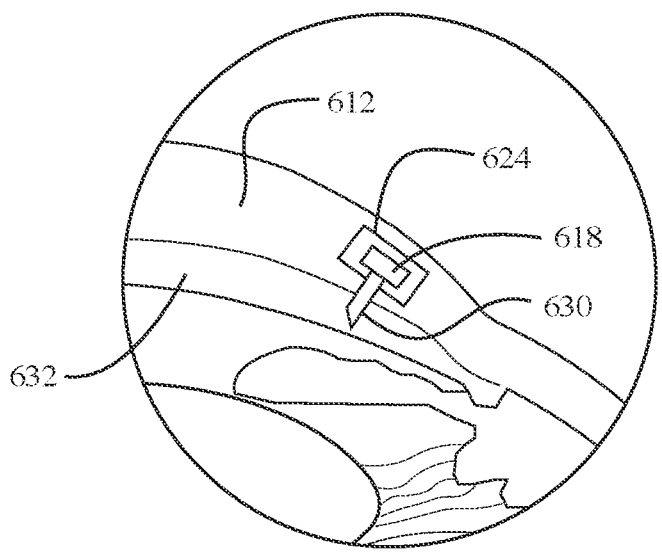
FIG. 53 is a partial, enlarged side cross-sectional view of the eye of FIG. 52 (Detail "C"), which illustrates the needle of the corneal intraocular pressure sensor extending into the anterior chamber of the eye.
Figure 54A:
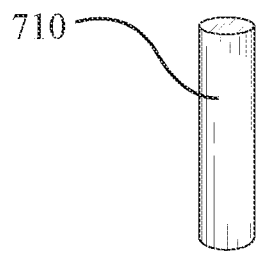
FIG. 54A illustrates a first exemplary shape for the drug delivery implant described herein, which is in the form of a rod-shaped implant.
Figure 54B:
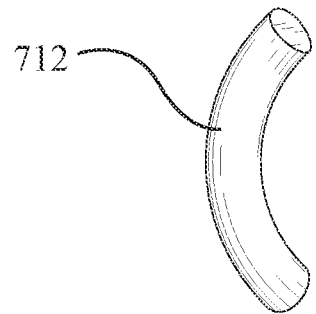
FIG. 54B illustrates a second exemplary shape for the drug delivery implant described herein, which is in the form of a curved implant.
Figure 54C:
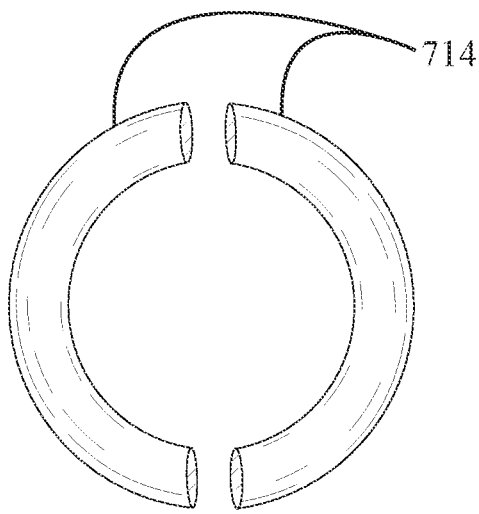
FIG. 54C illustrates a third exemplary shape for the drug delivery implant described herein, which is in the form of a two-part semi-circular implant.
Figure 54D:
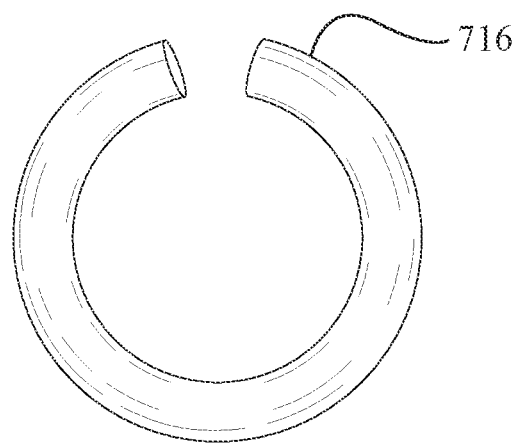
FIG. 54D illustrates a fourth exemplary shape for the drug delivery implant described herein, which is in the form of a one-part semi-circular implant.

Now, with reference to FIGS. 51-53, it can be seen that, after the portion of the tissue surrounding the pocket 624 has been stiffened and is devoid of cellular elements by the activation of the cross-linkers, an intracorneal implant comprising a pressure sensor 618 is inserted into the three-dimensional pocket 624 formed in the cornea 612 of the eye 610, which is in a location anteriorly disposed relative to the iris 626 and the lens 628. As shown in these figures, in the illustrative embodiment, the intracorneal implant is equipped with a pressure sensor 618, such as a capacitor, located in the corneal periphery of the eye 610. Also, as best shown in the sectional view of FIG. 53, the pressure sensor 618 of the intracorneal implant is equipped with a needle 630 that penetrates the rest of the cornea 612 and opens in the anterior chamber 632 of the eye 610 to measure the intraocular pressure directly by a portion of the sensor 618 being disposed inside the needle 630 without obstructing the central vision through the central cornea 614 (e.g., refer to FIG. 51). Turning to FIGS. 51 and 52, it can be seen that the sensor 618 is equipped with an antenna 622 that can transmit the information about the intraocular pressure for a duration of 24 hours and beyond while a receiver located outside of the eye 610 (e.g, a receiver on a regular eyeglass frame) receives the information and records and/or transmits the information to another remote device. The information is transmitted to a processor that transmits the information on the intraocular pressure uninterruptedly for years after implantation over a substantial distance to a doctor's computer or the patient's computer. The capabilities of the present invention are in stark contrast to the aforedescribed conventional contact lenses that can be carried only for 24 hours on the cornea to measure the intraocular pressure (IOP). If the conventional contact lenses are left on the cornea for a long time (i.e., greater than 24 hours), they can affect the integrity of the cornea, interfere with the oxygen and nutrition of the cornea, and ultimately lead to corneal abrasion or an infection.

In one or more embodiments, two-dimensional or three-dimensional stromal tissue is cut and/or removed with a femtosecond laser depending on the thickness of the sensor 618 and the antenna 622 and the location where the implant will be placed. As such, a pocket space 624 is created for the intracorneal implant to stay in place without exerting pressure on the remaining cornea 612 (see FIG. 52). As described above, after the pocket 624 is formed, it is followed by the cross-linking of the wall of the pocket so that the corneal pocket is cross-linked.

In one or more embodiments, the surface of the intraocular implant is coated with albumin or collagen, or another organic polymer, etc. that can absorb the photosensitizer after the implant is dipped in the photosensitizer and implanted in the corneal pocket. The photosensitizer leaks out of the polymeric coating of the implant into the corneal stroma, and then ultraviolet (UV) radiation at the desired power and duration is applied externally to activate the photosensitizer in the corneal pocket 624 and the implant coating to cross-link the collagen surrounding the implant, while killing all cells located within the cross-linked cornea, providing physical stability to the cornea, preventing the adhesion or gluing of the implant to the surrounding tissue, and preventing fibrous ingrowth or encapsulation, which can lead to an implant rejection. Also, advantageously, the cross-linking of the corneal pocket 624 makes it possible to exchange the implant when needed without the occurrence of much trauma to the cornea 612, because the prior cross-linking eliminates the cells that cause adhesion between the cornea 612 and the implant.

In one or more embodiments, if needed in the postoperative period, the cross-linking of the wall of the intraocular implant can be repeated by injection of riboflavin with a 33 gauge needle in the space between the implant and the wall of the cavity in which the implant resides, and then the cornea 612 with the implant may be subsequently cross-linked with ultraviolet (UV) radiation to prevent encapsulation of the implant that makes the inspection of the implant in the post-operative period difficult.

In one or more embodiments, the intraocular implant has a small diameter needle 630 (see FIG. 53) of 23 to 34 gauge with a capacitor sensor or a nanocomposite pressure sensor disposed in the inside thereof, positioned at a 90 degree angle relative to the body of the implant, and exposed to the aqueous fluid so as to measure the intraocular pressure (IOP) of the eye 610. The pressure sensor 618 of the intraocular implant is operatively connected to the processor of the implant, and to the antenna 622 and radio frequency (RF) generator 620 of the implant (see FIG. 51). The electrical energy for the radio frequency (RF) generator is provided by a small battery that can be charged from outside as it is done with inductive coupling using an electromagnetic field that transfers energy from a transmitter to a receiver, as known in the art. The needle 630 with the capacitor sensor inside it, penetrates the remaining corneal stroma located in the corneal periphery with minimal pressure, and is open to the inside of the anterior chamber 632 (see FIG. 53). In one or more embodiments, the needle 630 is less than 500 microns in length and less than 200 microns in diameter, and remains permanently in the anterior chamber 632 of the eye 610, without exciting a tissue response due to its cross-linked surface and its size, but can also be removed or replaced with ease. The intraocular pressure (IOP) values measured by the capacitor sensor are transmitted to a processor (e.g., a microprocessor), which is operatively coupled with the radio frequency (RF) generator 620, which transmits the information to remote devices by the means of the antenna 622. Because the wall of the corneal pocket 624 is cross-linked, it will not produce a scar around the implant and its sensor 618, radio frequency (RF) generator 620, and antenna 622, thus permitting direct visual inspection of the implant, which is capable of being removed and/or replaced if needed.

In one or more embodiments, the intraocular implant may be assembled during the surgery after the cross-linked pocket 624 is created. Initially, the antenna 622 is placed in the cross-linked pocket 624 that is disposed radially inward from the limbus 616 of the eye 610 (see FIG. 51), and then the sensor 618 and the radio frequency (RF) generator 620 are placed in the corneal pocket 624 and connected to the antenna 622 as a part of a minimally invasive surgery in the corneal periphery. The capacitor sensor is located inside the needle 630, and the tip of the needle 630 is pushed gently in the anterior chamber 632 of the eye 610 so as to measure the intraocular pressure (IOP) directly, continuously, and precisely from the inside of the eye 610. The sensor 618 with small needle 630 and the radio frequency (RF) generator 620 are located in the corneal periphery avoiding interfering with the patient's vision. In contrast to the other aforementioned conventional technologies, this implant does not need an intraocular surgery for its implantation and the natural crystalline lens 628 of the eye 610 does not need to be removed in order to obtain permanent intraocular pressure (IOP) information for the eye 610.

In one or more embodiments, prior to the insertion of the intracorneal implant into the pocket 624 of the eye 610, a predetermined amount of hyaluronic acid or a viscous biocompatible material is injected into the pocket 624 so as to simplify the insertion of the intracorneal implant in the cross-linked pocket 624.

In one or more embodiments, the pressure sensor and transmitter of the intraocular implant are located inside the peripheral cross-linked pocket 624 of the cornea 612 of the eye 610 that does not occupy the central corneal region 614 of the eye 610. Because the central corneal region 614 of the eye 610 remains open with the intracorneal implant, the intraocular pressure (IOP) may also be measured by a Goldmann applanation tonometer placed on the central part 614 of the cornea 612 that is exposed. Because the implant described herein is peripherally disposed, the central corneal region 614 of the eye 610 is not covered by a conventional contact lens pressure sensor, as described above. Therefore, the intraocular pressure (IOP) can be measured by an ophthalmologist in two ways using a Goldman applanation tonometer and by means of the pressure sensor of the intracorneal implant located in the anterior chamber 632 of the eye 610. Advantageously, the ability to take these dual intraocular pressure (IOP) measurements provides a means of comparison between the values obtained by the intraocular pressure sensor and the Goldmann applanation tonometer to correlate or properly adjust the values obtained from the corneal intraocular pressure (IOP) sensor so as to ensure that measurements by the corneal intraocular pressure (IOP) sensor represent the true intraocular pressure (IOP) of the eye 610, and so the corneal intraocular pressure (IOP) sensor is capable of being properly adjusted using the software of the processor of the corneal intraocular pressure (IOP) sensor. The information obtained with the corneal intraocular pressure (IOP) sensor is also capable of being transmitted remotely via the radio frequency (RF) generator 620, and recorded and forwarded to an ophthalmologist who, in turn, can control the intraocular pressure (IOP) by medication or surgery.

In one or more embodiments, the transmitter of the intracorneal implant may be implanted separately from the pressure sensor 618 during the surgery, but then reconnected during the implantation.

Advantageously, the surgical implantation method and the corneal intraocular pressure (IOP) sensor described herein is capable of measuring the intraocular pressure (IOP) all day and night for a long period of time (e.g., weeks, months, or years), and then recording the intraocular pressure data that is measured so that an ophthalmologist can control the intraocular pressure (IOP) of the patient's eye by medication or surgery.

Any of the procedures described herein can be used alone, or in conjunction with, simultaneously with, before or after any other procedure, method or device that would treat or monitor glaucoma, prevent capsular opacification and fibrosis after cataract extraction during cataract surgery and/or prevent fibrosis around a shunt or stent after glaucoma surgery.

Illustrative embodiments of a drug delivery implant and methods using the same will now be described hereinafter. In accordance with the various embodiments described herein, in order to provide the medication to the anterior and posterior part of the eye with a slow release drug system, it is required to create an immune privileged space inside the cornea to keep the cellular response away and prevent production of cytokine by them, and position the device outside the central visual axis so that the device would not interfere with the patient's vision.

In the embodiments described herein, the device is placed in the far corneal periphery so that it will not affect the vision or visual field of the patient, and so that it has created a so-called artificial "immune-privilege" which does not generate an immune response from the body while fluid, soluble medications or nano-particulates and micro-particulates can travel through it. See, for example, FIGS. 63A-70B.

Because of the location of the implant inside the cornea, the released medication bypasses the epithelial barrier of the cornea, while providing medication in a slow manner by diffusion to the anterior part of the cornea, to the sclera, to the conjunctival tissue, and to the posterior segment of the eye including the retina, choroid, and the optic nerve head. This technique can provide similar immune-privileged spaces in other part of the body so that devices implanted there are not encapsulated.

Figure 62:
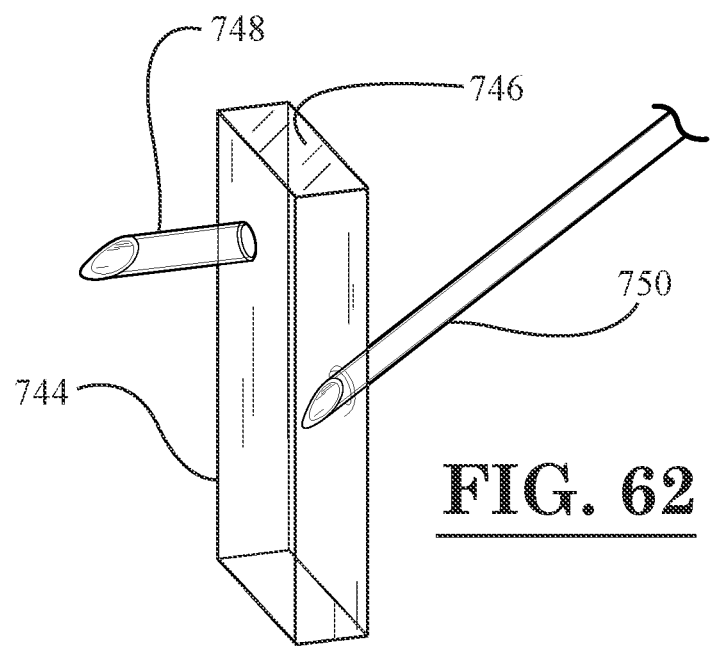
FIG. 62 illustrates yet another exemplary form of the drug delivery implant described herein, wherein the tubular implant comprises a needle for tissue penetration and the tubular implant is capable of being penetrating by a needle for taking liquid biopsies.

The drug delivery system of the embodiments described herein may be constructed so that it can have direct access to the anterior chamber, if needed, for both obtaining repeatedly a fluid biopsy from the eye or deliver medication(s) directly inside the eye in a fast or slow release manner, or for reducing the intraocular pressure of the eye by creating a minor flow through a porous implanted stent or tube through the corneal limbus without inducing a fibrous encapsulation of the stent. The stent can ameliorate also corneal dryness caused by dry eye syndrome. The stent can also be equipped with a pressure sensor indicating directly the intraocular pressure and communicating it with a radiofrequency device to outside the eye to a receiver or a processor. As one example, as shown in FIG. 62, the implant 744 may comprise a closed end 746 and a needle 748 for tissue penetration so that the implant 744 is capable of being used for taking liquid biopsies. In addition, stem cells or other cells can reside in, for example, a tubular implant, while having access to the oxygen and nutrients through the artificial barrier in an appropriately prepared corneal pocket. However the porous tubular implant permits these cells to migrate elsewhere in the eye or remain in place without being attacked by body's cellular response. Because the cellular body immune response is dependent on the production of the cells close to the implant or a foreign body to be taken up by the dendritic cells of the body at that location by creating a cell free space around the implant made of transparent amorphous cross-linked collagen. The invention of the embodiments described herein has eliminated the incentive for a Major Histocompatibility Complex (MHC) to occur. Because these MHC are present on the cell surface of the body cells to be activated in the production of an immune response. The release of theses cytokines activates the cellular immune system of the body to either eliminate the threat or isolate the device from the body completely by fibrocytes, thereby building a dense membrane (i.e., scar) around the implant. However, the cross-linked collagen permits the diffusion of water and small molecules permitting the needed growth factors from the incorporated stem cells placed inside the tubular implant needed for survival and the health of the cornea, retina etc.

Though this mechanism is very effective and useful, it affects the function of an implant that usually either releases a needed medication or measures or controls the release of a medication (e.g., measuring the blood glucose level and/or releasing insulin according to the glucose level found in the blood, etc.).

In order to isolate an implant in the body while preventing the immune cell to gain access to the device or build a membranous scar tissue around it, a method has been developed to isolate the implant in the body by killing all the cells adjacent to an implant, while maintaining a fluid-filled area around the implant or creating a barrier out of the surrounding tissue containing collagen and cross-linking the tissue in vivo. This barrier protects the implant from the antigen presenting dendritic cells in the tissue, while permitting the soluble medication or nano-sized particulate material to pass through the barrier so as to treat a pathological process in the body. One can also monitor the level of the analytes in the tissue fluid (e.g., aqueous fluid levels of glucose), which is a representative of the blood glucose level in the blood, from which it is originated. Aqueous level of most if not analytes found in the blood and could be used effectively to provide information on the health or disease processes affecting the eye or the body as a whole.

In the embodiments herein, implantation of a drug delivery device is described for the release or monitoring and controlling of a disease process in the eye, while crosslinking the tissue around the implant or implants (if more than one implant is provided). In any of the embodiments described herein, a plurality of drug delivery implants may be used (e.g., for delivering different medications), rather than a single drug delivery implant.

The technology described herein may be applied for any other device implantation in the body regardless of the location in the body. One of the benefits of the technology is that, if the device needs to be replaced, it can be done easily without dealing with the scar tissue formation that otherwise forms and makes the removal or replacement of the implant very complex because the tissue adhesions that usually forms between the tissue and the device.

One can use this concept described herein for diagnosis or therapy in diseases affecting the cornea, a metabolic disorder, genetic disorder, glaucoma, an infection affecting the eye or another portion of the body, a disease or disorder affecting the front or the back part of the eye or the conjunctiva or lens, an aging process, such as dry eye formation, retinal diseases including infective processes, genetic diseases requiring gene therapy (e.g., retinitis pigmentosa, etc. or metabolic disorders such as diabetes, etc.).

In one embodiment, if the media is clear, a two dimensional intrastromal corneal incision is created that is subsequently converted into a pocket in the corneal stroma using a femtosecond laser or a mechanical cutting system. The femtosecond laser passes through the clear media of the cornea. When the laser beam is focused inside the cornea, one can produce a two-dimensional cut or a three-dimensional cut around a thin part of the tissue that is removed to desired space, shape, depth, and location.

In another embodiment, in opaque elastic tissue (e.g., skin), one can use a knife or a syringe needle ending in a sharp cutting tip to cut a pocket in the tissue. If needed, the incision simultaneously involves removal of a three-dimensional tissue surrounding the surgical pocket to create some additional space for the implant using a similar cutting instrument, in the skin or soft tissue. In general, a cut creates a flexible three-dimensional space that can be filled with an implant. The implant is placed inside the needle and can be expelled from the needle by the syringe into the space created by knife.

In one or more embodiments, an injectable anesthetic (e.g., lidocaine or Bupivacaine) in a desired non-toxic preparation or concentration of 0.1-2% or more in a physiologic solution with, but preferably without, a preservatives, is injected in the corneal pocket to anesthetize the cornea postoperatively for a period up to 8-12 hours (e.g., if a PRK procedure is contemplated or after a corneal inlay implantation to prevent pain sensation completely in the postoperative period). This eliminates subjecting the entire corneal epithelium or the conjunctival epithelial cells to the damaging effect of topical anesthesia, which delays corneal re-epithelialization or conjunctival epithelial cells. Generally, the topical preservatives present in the topical anesthesia damages the cells that are bathed in them, and at times affects the regeneration of these cells (i.e., corneal epithelial or conjunctival cells) if applied frequently. Also, it may produce addiction to the topical anesthesia for eliminating the pain sensation caused by the loss of the corneal epithelial cells, whereas the injectable anesthetic does not damage the epithelial cells, including the nerve cells or their axons, except for blocking temporarily the neuronal transmission.

In one or more embodiments, the collagen cross-linker is mixed with the intracorneal locally injectable anesthetic, and injected simultaneously or sequentially in the corneal pocket.

In one or more embodiments, the pocket is filled with a biocompatible implant or implants (if more than one implant is provided) made of organic or non-organic material, or a mixture of it, and the implant is used for drug delivery. The implant may further be coated with a biocompatible material, such as collagen, elastin, polyethylene glycol, biotin and streptavidin, etc., as known in the art, or a composition thereof, to make the implant more biocompatible. The implant and/or the coating can be cross-linked with a cross-linker with the desired thickness and shape before or after implantation.

In one or more embodiments, the diameter of the corneal pocket can be 0.1 to 4 millimeters (mm), as needed. Only flat implants need a larger space with more than 0.2 mm. As shown in FIG. 63A-70B, the pocket can be circular, semi-circular, C-shaped, doughnut-shaped, rectangular, or any other shape.

In one or more embodiments, the implant or implants (if more than one implant is provided) can be located at a desired distance from the Bowman's membrane or from the corneal periphery, that is located away from the center of the visual axis (i.e., the implant may be off-centered, or ring-shaped in the peripheral cornea). See, for example, FIGS. 63A-70B.

In one or more embodiments, the implant or implants (if more than one implant is provided), is made to the desired shape, and size in diameter and length that fits with ease inside the corneal pocket without exerting pressure on the corneal tissue (i.e. without bulging it).

In one or more embodiments, a photosensitizer or cross-linker, such as riboflavin, is injected at the desired concentration in a biocompatible fluid or a viscous fluid prior to the implantation of the implant. However, it can be also administered simultaneously with the implant in the corneal pocket sufficiently to cover the internal wall of the pocket for a desired duration so that it penetrates at least 20 micron or wider, taking 5-30 seconds after injection prior to the cross-linking of the cornea, which prevents cell proliferation, encapsulation, or rejection of the implant while preserving an acellular barrier.

In one or more embodiments, ultraviolet (UV) radiation at the desired power (e.g., 1 to 4 mW/mm$^2$) and duration of 1-15 minutes, as needed, depending on the concentration of the photosensitizer or other radiation if another cross-linker is used (e.g., visible or infrared (IR) or another wave length) is applied externally to activate the photosensitizer in the corneal pocket, and to cross-link the collagen of the corneal stroma surrounding the corneal pocket, thereby killing only the cells located within the cross-linked cornea while preventing encapsulation of the drug implant while providing a physical stability to the cornea and preventing the wall of the pocket from adhering together or to the implant. This permits the implant to be replaced, if needed, with another implant with ease.

In one or more embodiments, the implant is coated with an organic material, such as collagen, dipped in a photosensitizer, or the implant can be coated with nanoparticles of the photosensitizer and implanted in the corneal pocket and ultraviolet (UV) radiation is applied with the desired power and duration using a painting technique using a small diameter fiber optic or other radiation with another wave length is applied if another cross-linker is used, externally or internally inside the pocket via a fiber optic to activate the photosensitizer in the corneal pocket and to cross-link the collagen of the corneal stroma surrounding the corneal pocket, thereby killing all cells located within the cross-linked cornea and cross-link the implant simultaneously. The corneal cross-linking prevents implant encapsulation with fibrous tissue, but provides a physical stability to the cornea without gluing the wall of the pocket together or to the implant.

In one or more embodiments, an injection of a small amount of hyaluronic acid in the pocket simplifies insertion of the drug implant in the corneal pocket.

In one or more embodiments, the drug implant has a tube-like structure with a size of 0.01 to 3 micron diameter holes in its wall, or having one micron or larger-sized holes for diffusion of fluid across it.

In one or more embodiments, the implant can be silicone, acrylic, methacrylate, hydroxyethyl methacrylate (HEMA), cross-linked organic or any other biocompatible transparent or non-transparent material, metallic or non-metallic, or a mixture thereof or coating other polymers, such as collagen or elastin with the desired thickness of 2 microns or more, as needed.

In one or more embodiments, the implant is made of various drug delivery polymers, such as polylactic acid or polyglycolic acid, or a combination thereof or polycaprolactone, or chitosan or other organic materials that can deliver the medication at a certain concentrations and dissolve within time ranging from 3-12 months or more.

In one or more embodiments, the biodegradable or non-biodegradable implant can be replaced with another one as before or a non-biodegradable material, but having biocompatible material or coating where the drug release occurs either through the small holes in the body of the implant at a certain rates depending on the size of the holes, or from one or both ends of the implant for drug delivery, as needed.

In one or more embodiments, the implant is a porous biodegradable polymer.

In one or more embodiments, the material inside the tubular implant is liquid, nanoparticles, suspension, powder, porous polymeric drug, etc.

In one or more embodiments, the implant is made using 3-D printing technology to the desired shape, size and/or coated with more biocompatible polymer(s) and cross-linked prior to the implantation, or it is implanted in a cross-linked pocket.

In one or more embodiments, the cross-linked corneal implant can be loaded with one or multiple medications needed for a short biocompatible drug delivery, or prophylactically to prevent an infection, or other used therapeutically medications to treat a disease process (e.g., inflammation, intraocular pressure (IOP), neovascularization, infection, or a cytokine, etc.).

In one or more embodiments, an organic cross-linked material can be used as above for a short term drug delivery of 1 to 4 weeks.

In one or more embodiments, an organic cross-linked material can be used as above for a short term drug delivery of 5 to 50 weeks or longer.

Figure 59:
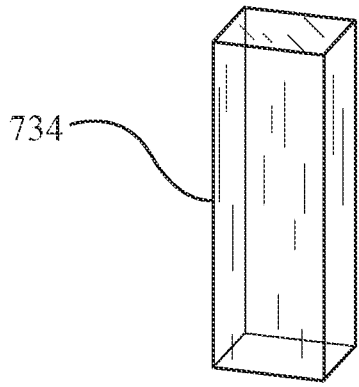
FIG. 59 illustrates still another exemplary form of the drug delivery implant described herein, wherein the implant is in the form of a rectangular flat tube.
Figure 63A:
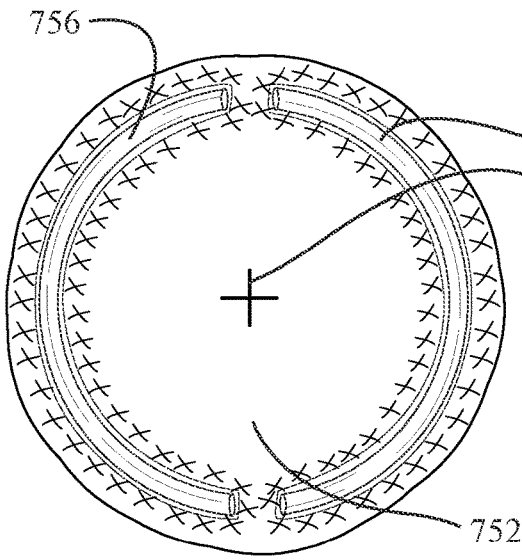
FIG. 63A is a front view of a cornea of an eye illustrating a two-part semi-circular drug delivery implant disposed in a cross-linked pocket in the peripheral portion of the cornea that is spaced apart from the central visual axis of the eye so as not to obstruct the central portion of the eye.
Figure 63B:
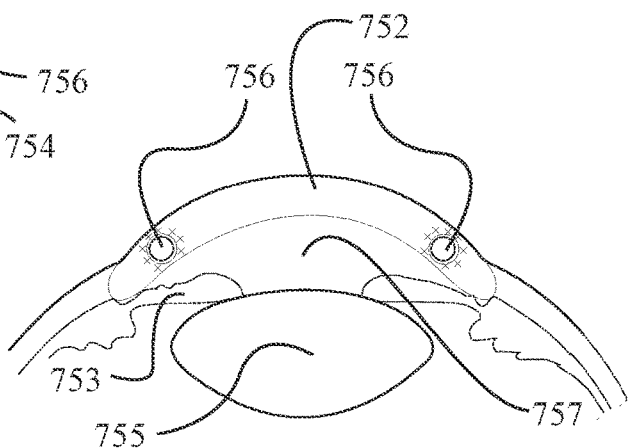
FIG. 63B is a partial side cross-sectional view of the eye of FIG. 63A illustrating the two-part semi-circular drug delivery implant disposed in the cross-linked pocket in the peripheral portion of the cornea.
Figure 64A:
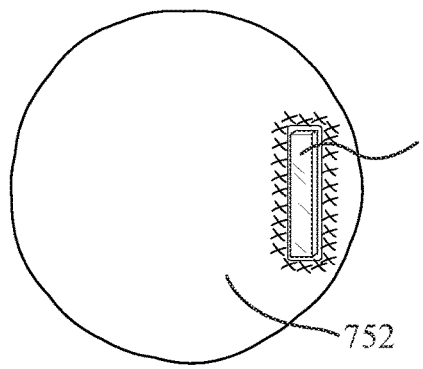
FIG. 64A is a front view of a cornea of an eye illustrating a generally linear drug delivery implant disposed in a cross-linked pocket in the peripheral portion of the cornea that is spaced apart from the central visual axis of the eye so as not to obstruct the central portion of the eye.
Figure 64B:
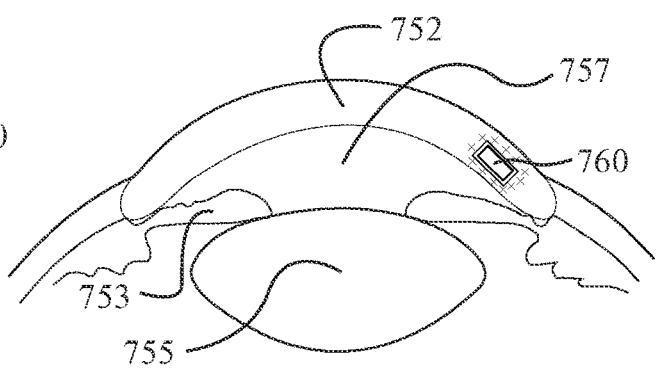
FIG. 64B is a partial side cross-sectional view of the eye of FIG. 64A illustrating the generally linear drug delivery implant disposed in the cross-linked pocket in the peripheral portion of the cornea.

In one or more embodiments, the implant is a C-shaped flexible or semi-flexible structure, and can be implanted in the prepared corneal pocket according to the size or the shape of the implant (e.g., centered around the visual axis having a string shape, rod-like shape, or flat shape), while removing a small 3-D tissue from the stroma for the pocket formation to provide space for the implant for drug delivery to the cornea or the anterior chamber, trabecular meshwork, conjunctiva, or diffusing toward the posterior segment, such as the retina, choroid or the optic nerve of the eye. As shown in FIGS. 54A-54D, the drug delivery implant may be rod-shaped 710, C-shaped 712, two-part semi-circular 714, or one-part semi-circular 716. Also, as illustrated in FIG. 59, the implant may also be in the form of a rectangular flat tube 734. In FIGS. 63A and 63B, a two-part semi-circular drug delivery implant 756 disposed in a cross-linked pocket in the peripheral portion of the cornea 752 that is spaced apart from the central visual axis 754 of the eye so as not to obstruct the central portion of the eye. As shown in FIG. 63B, the two-part semi-circular drug delivery implant 756 is disposed adjacent to the anterior chamber 757 of the eye, and anteriorly with respect to the iris 753 and lens 755 of the eye. In FIGS. 64A and 64B, a generally linear drug delivery implant 760 is disposed in a cross-linked pocket in the peripheral portion of the cornea 752.

Figure 66A:
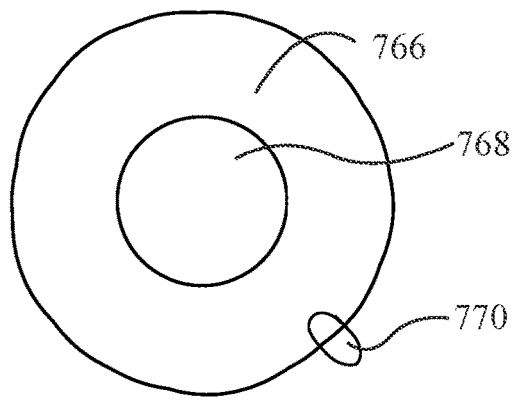
FIG. 66A is a front view of a cornea of an eye illustrating a pupil, cornea, sclera, and limbus of the eye.
Figure 66B:
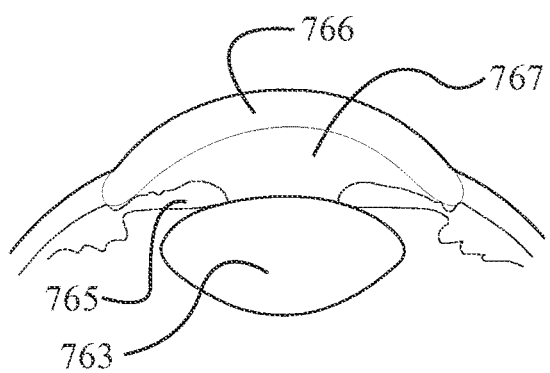
FIG. 66B is a partial side cross-sectional view of the eye of FIG. 66A illustrating an anterior chamber, iris, and lens of the eye.
Figure 67A:
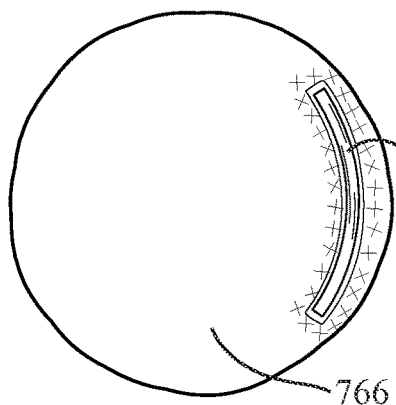
FIG. 67A is a front view of a cornea of an eye illustrating a one-part semi-circular drug delivery implant disposed in a cross-linked pocket in the peripheral portion of the cornea.
Figure 67B:
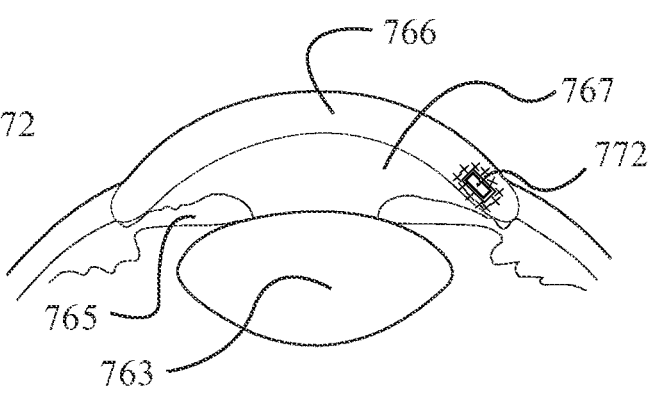
FIG. 67B is a partial side cross-sectional view of the eye of FIG. 67A illustrating the one-part semi-circular drug delivery implant disposed in the cross-linked pocket in the peripheral portion of the cornea.
Figure 68A:
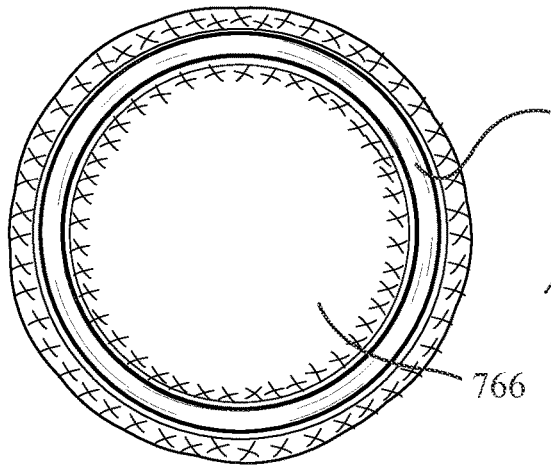
FIG. 68A is a front view of a cornea of an eye illustrating a doughnut-shaped drug delivery implant disposed in a cross-linked pocket in the peripheral portion of the cornea.
Figure 68B:
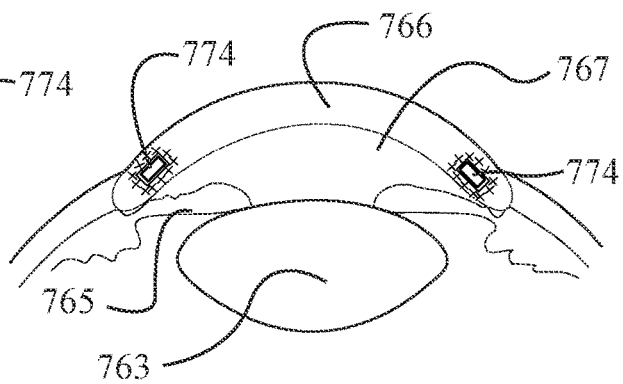
FIG. 68B is a partial side cross-sectional view of the eye of FIG. 68A illustrating the doughnut-shaped drug delivery implant disposed in the cross-linked pocket in the peripheral portion of the cornea.

Turning to FIGS. 66A and 66B, it can be seen that an eye generally includes a lens 763, an iris 765, cornea 766, an anterior chamber 767, a pupil 768, and a limbus 770. In FIGS. 67A and 67B, a one-part semi-circular drug delivery implant 772 is shown disposed in a cross-linked pocket in the peripheral portion of the cornea 766. In FIGS. 68A and 68B, a doughnut-shaped or ring-shaped drug delivery implant 774 is shown disposed in a cross-linked pocket in the peripheral portion of the cornea 766. In FIGS. 69A and 69B, a generally linear drug delivery implant 776 is shown disposed in a cross-linked pocket in the peripheral portion of the cornea 766.

In one or more embodiments, the implant is inserted in the corneal pocket through a small external incision made into the corneal pocket.

In one or more embodiments, the pocket itself can be filled with biodegradable nanoparticles for drug delivery to the entire ocular structures from the cornea to the optic nerve, and all tissues in between. The medication(s) can be anti-inflammatory, anti-infective, immune-suppressants, AntiVEGFs, biologics, Anti-PDGF, Anti IL-6, Rho kinase inhibitors, Wnt inhibitors, nerve growth factors, anti-glaucoma medications, gene(s) delivery in conjugation with viral or non-viral nanoparticles, such as nanoparticles, quantum dots, biodendrimers, etc. coated with polyethylene glycol (PEG) or cell penetrating agents along with an antibody to the specific tissue. This permits the genes or medications to be delivered after their migration out of the implant and the corneal pocket and to attach to the targeted cells in the cornea, conjunctiva, trabecular meshwork, retinal ganglion cells or photoreceptors, retinal and optic glial or nerve cells or their axons etc.

In one or more embodiments, the one or more medications in the drug implant may be anti-inflammatory agents, such as steroids, Dexamethasone, NSAIDS, Anti IL-17, Anti IL-6 and other Anti-ILs or antibiotics, fluoroquinolones, macrolides, cephalosporin A, vancomycin, aminoglycosides, penicillin and its derivatives or combination of antibiotics, etc., anti-virals, ganciclovir, valcyclovir, etc., anti-fungals, amphotericine B, etc., Anti-VEGFs, Avastin, lucentis, Aflilbercept, Anti-IL-6, anti-parasitic, etc., or other anti-inflammatory agents, such as NSAIDs or Rho kinase inhibitors, after any corneal surgery and act therapeutically to various diseases affecting the conjunctiva (e.g., dry eye), immune-suppressants, such as cyclosporine A, Mycophenolic acid, anti-proliferative agents, anti-metabolite agents, in uveitis, choroiditis or other medications, such as anti-glaucoma medication or combination of medications, gene delivery, DNA, RNA, siRNA etc. along with viral or non-viral delivery vehicles and CRISPR cas9 mediated homology-independent targeted integration (HITI) or homology directed repair (HDR) to modify the genetic components of various diseases of the eye.

In one or more embodiments, repeated crosslinking of the pocket can be performed as needed to prevent new cellular ingrowth and adhesion around the implant from the corneal tissue so that the implant's barrier is maintained, and the implant can be removed or replaced as needed (e.g., if the eye needs another or a combined medication to regulate disease process, such age related macular degeneration, glaucoma, uveitis, choroiditis or an infectious process of any origin).

In one or more embodiments, the peripheral cross-linked pocket is used to insert or inject medications needed to treat a corneal disease or glaucoma or a disease of the posterior segment. The medication can be in a form of nanoparticles, microspheres, lipid coating or PEG, streptavidin, biotin coating, etc., micelles, liposomes, thermosensitive chitosans, etc.

In one or more embodiments, one can inject or implant in the peripheral corneal pocket large-sized flexible, semi-solid or porous or solid rod, flat or tube or any shape and size polymeric material that can be absorbed with time and the medication is released slowly to the cornea or the anterior chamber of the eye or diffuses to the back of the choroid or retina and optic nerve.

In one or more embodiments, the diameter of these rod or flat-shaped shape implants can vary between 10 microns to 1 millimeter (mm) in diameter or larger with a length of 1 to 50 mm or longer.

Figure 61:
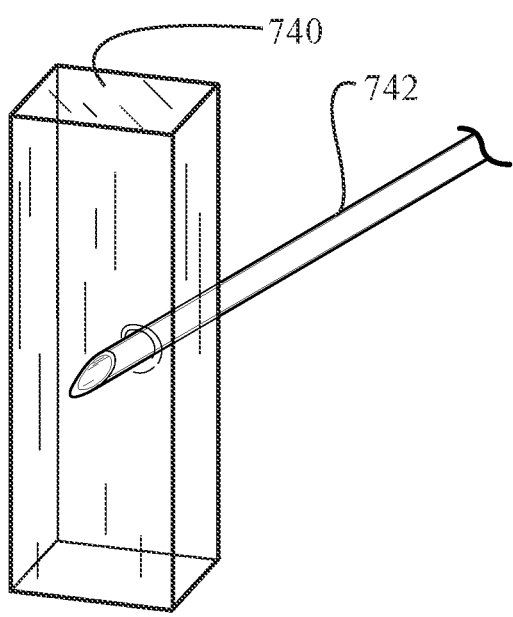
FIG. 61 illustrates still another exemplary form of the drug delivery implant described herein, wherein the implant is in the form of a rectangular tube that is refillable by injection.

In one or more embodiments, the porous tube can be made of semi-permeable non-biodegradable material that permits only the diffusion of the fluid/medication, etc. in and out of the tube, implanted in the peripheral cross-linked pocket. In these one or more embodiments, the tube can be refilled with medication as needed. For example, as shown in FIG. 61, the implant 740 in the form of a rectangular tube is refillable by injection with a needle 742.

In one or more embodiments, the drug implant tube contains stem cells, embryonic stem cells, ciliary hormone producing cells, or other hormone or factors producing stem cells, neuronal or glial stem cells, Mesnchymal stem cells, trabecular meshwork stem cells, limbal stem cells, modified skin stem cells, etc. in a biocompatible fluid that permits nutrition to reach the cells injected in the tube where the cells are immortalized to produce one or the other medication, growth factors, such as ciliary neurotrophic growth factor, RPE growth factor, nerve growth factors, anti-VEGFs, or other medications needed.

In one or more embodiments, the non-biodegradable tube with pores for drug and cell delivery is implanted in a cross-linked pocket with an implant in any part of the body for medication and cell delivery for various medications and functions.

Figure 57:
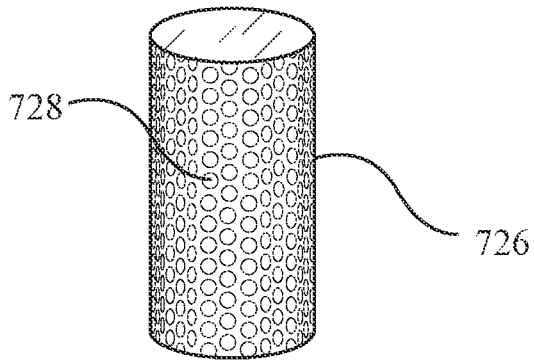
FIG. 57 illustrates another exemplary form of the drug delivery implant described herein, wherein the implant is tubular-shaped with holes formed in the side thereof.

In one or more embodiments, the implant is coated with biocompatible polymer(s) that is used for delivery of stem cells with medication in a corneal pocket. The implant has larger diameter holes of 5 microns and more in its wall permitting the cells to escape from the tubular implant into any tissue (e.g., corneal pocket containing stem cells, embryonic stem cells, ciliary body factor producing stem cells, neuronal or glial stem cells, Mesnchymal stem cells, trabecular meshwork stem cells, Limbal stem cells, modified skin stem cells, etc. in a biocompatible fluid) that permits nutrition to reach the cells injected in the tube where these cells can grow and pass through the holes of the implant and move toward a tissue. In FIG. 57, the tubular implant 726 has small holes 728 disposed in the circular peripheral side thereof, whereas the tubular implant 730 in FIG. 58 has large holes 732 disposed in the circular peripheral side thereof.

In one or more embodiments, the implant contains stem cells, embryonic stem cells, cilliary body hormone producing stem cells, neuronal or glial stem cells, Mesnchymal stem cells, trabecular meshwork stem cells, limbal stem cells, modified skin stem cells, etc. in a biocompatible fluid that permits nutrition to reach the cells injected in the tube along with Rho kinase inhibitors or Nerve growth factors to stimulate their regeneration and migration of theses cell and repair the pathology in the tissue.

In one or more embodiments, genetically modified cells are used to produce needed enzymes and medications. The combination of cross-linking of the cornea and killing the corneal cells and lack of vessels in the corneal makes it a suitable place for these cells in the tube implant to survive inside the tube without being attacked by the cellular body's response, thereby creating an immune privileged space for these cells to survive and produce medications needed locally or systemically (e.g. in many genetic diseases of the cornea such as Fuchs dystrophy, etc.).

In one or more embodiments, the pocket can be filled with a polymeric material that can become more semisolid, or becomes a gel, and contains medication for slow release of medication.

In one or more embodiments, the medication can be injected in the peripheral pocket along with corneal stem cells from the limbus or genetically modified skin stem cells, embryonic or pluripotential stem cells, or mesenchymal stem cells grown in the culture for implantation, in cases of cell loss of endothelium, or in genetically caused corneal opacification, such as macular dystrophy or trauma.

In one or more embodiments, the stem cells are mesenchymal stem cells injected in the corneal pocket along with ROCK inhibitors to replace or repair a cloudiness of the cornea.

In one or more embodiments, the stem cells are nerve cells to induce regeneration of the damaged corneal nerve (e.g., in diabetic patient) and after traumatic corneal injuries or after LASIK surgery.

In one or more embodiments, all tubular drug implants or devices are replaceable with ease.

In one or more embodiments, the tube can be refilled with medication to be used as slow release drug delivery that releases the drug in the cornea and anterior of the posterior segment of the eye.

In one or more embodiments, the tube is used for taking fluid samples from the eye.

In one or more embodiments, one creates an intrastromal corneal pocket in the peripheral cornea involving 2-4 mm 4-8 mm in width areas involving the cornea and the anterior sclera after bleaching out the peripheral conjunctival capillaries with a low dose of vasoconstrictive medication such as 0.5%-4% phenylephrine applied locally with a Q-tipped applicator using a femtosecond laser.

In one or more embodiments, a small knife can be used to create a pocket in the cornea or elsewhere under the skin etc. if needed.

In one or more embodiments, the pocket width is more toward the corneal side than the scleral side or vice versa. The circumferential extent of the pocket can be 1 degree to 360 degrees of the corneal periphery (see FIGS. 63A, 63B, 67A, 67B, 68A, and 68B).

In one or more embodiments, using a small incision to access the intrastromal incision, one uses a curved probe to separate the corneal adhesion for injection of a photosensitizer cross-linker, such as riboflavin, at the desired concentration of 0.5%-4% in a biocompatible fluid, such as a physiological saline solution, etc. or suspension of particulates in a volume of 0.01 milliliters (ml) to 1 milliliter (mm) as needed only for the extent of the corneal pocket to cover the internal walls of the pocket for a desired duration that the photosensitizer penetrates at least 20 microns and beyond the corneal pocket in the corneal stroma to isolate that localized area of the cornea from the rest so that it does not respond with cell migration into the surrounding implant and so that it avoids tissue bounding together or to the implant.

In one or more embodiments, 0.01 ml to 0.1 ml of 0.02-2% lidocaine or bupivacaine solution can be injected alone or along with the photosensitizer in the corneal pocket to anesthetize the cornea for the next 1-15 hours, thereby eliminating pain sensation or discomfort of the surgery, and dry eye after surgery.

In one or more embodiments, the width of the corneal pocket can be 1-3 mm as needed. The peripheral corneal pocket can be circular, semi-circular, C-shaped, doughnut-shaped, straight, curved, or any other shape.

In one or more embodiments, the cross-linked pocket can be located at a desired distance from the Bowman's membrane in the corneal periphery.

In one or more embodiments, the ultraviolet (UV) radiation or other appropriate wave length of light at the desired power 0.5-50 mW/Cm2 and duration of 1-15 minutes, or other radiation with another wave length is applied externally in a stationary pattern or as a continuous painting/oscillatory technique with a focused small sized spot of 1-4 mm and a high energy to cover the width of the pocket, or on a painting oscillatory fashion entering the corneal pocket with a small diameter fiber optic and to activate the photosensitizer in the corneal pocket and crosslink the collagen of the corneal stroma surrounding the corneal pocket, and preventing the wall from adhering to itself or to a future implant, while providing a physical stability to the wall of the corneal pocket and preventing cell migration and rejection of an implant.

In one or more embodiments, ultraviolet (UV) radiation at the desired power in a stationary or focused light for a duration of 10 seconds to 15 minutes for the stationary radiation, or for a duration of 10 seconds to 20 minutes for the painting approach, depending on the power of the radiation and the length of the pocket used (or other radiation with another photosensitizer and wave length) is applied externally or via a fiber optic inserted inside the pocket to activate the photosensitizer and cross-link the collagen of the corneal stroma surrounding the corneal pocket while preventing cell migration, encapsulation, or rejection of the implant and protecting the anterior corneal stroma and the stem cells.

In one or more embodiments, the corneal pocket is three-dimensionally cut in order to remove a part of the stroma and create a space for the implant.

In one or more embodiments, the wall of the corneal pocket can absorb the photosensitizer from the implant after it is dipped in a photosensitizer solution or the implant is coated with nanoparticles of the cross-linker and placed in the corneal pocket to leak out, which is then followed by UV radiation at the desired power and duration or other radiation with another wave length applied externally or internally via a fiber optic to activate the photosensitizer in the corneal pocket and cross-link the collagen surrounding the implant. This technique provides a physical stability to the cornea preventing adhesion or gluing the implant to the surrounding tissue and preventing fibrous ingrowth or encapsulation or rejection of the implant, which can lead to implant rejection. This makes it possible to exchange the implant when needed without much trauma to the cornea surrounding the implant.

In one or more embodiments, the photosensitizer is conjugated to the surface of the implant having a polymeric coating, such as collagen, that releases the photosensitizer (e.g., riboflavin) from the implant once it is exposed to the water content of the tissue in the corneal pocket surrounding it. The riboflavin is released and stains the wall of the implant which is subsequently cross-linked with UV light. This prevents tissue adhesion between the implant and the corneal tissue and maintains a potential space between the corneal wall and the implant, thereby preventing activation of an immunologic response or neovascular tissue response by releasing from the tissue vascular endothelial cell factors (VEGF) in response to a foreign implant. The cross-linking process can be repeated as needed every 6 months to a year or more as needed. The cross-linking of the collagen protects the implant containing particulate medication(s), which releases the drug for a long time, and prevents the pocket from being invaded by the immune cellular elements and keeps the lumen of the tube shaped implant open.

In one or more embodiments, during the cross-linking, the corneal pocket remains pristine not allowing cell traffic or access to the pocket surrounded by the cross-linked amorphous collagen or other cross-linked tissues located in that area.

In one or more embodiments, the crosslinking can be repeated again in the postoperative period after implantation by injecting a cross-linker in the corneal pocket through a needle inside the wall of the pocket, which diffuses readily through the potential space around the implant and the wall of the pocket, and then is irradiated with UV light from the outside.

In one or more embodiments, the implant can be made of silicone, acrylic, methacrylate, HEMA, metallic or non-metallic, synthetic, organic, polymeric biodegradable, etc., coated with another or a biocompatible polymeric materials or a mixture thereof or coated with, for example, collagen or elastin, formed with a desired thickness of 2 microns to 100 microns, and conjugated with a cross-linker or the cross-linker is injected in the potential pocket space in the tissue and is cross-linked.

In one or more embodiments, the implant is made by the use of 3-D printing technology with the desired material, shape, size or thickness, transparent or non-transparent organic or non-organic or a mixture of them, a material such as collagen elastin, synthetic polymers can be coated again with riboflavin nanoparticles with one or more biocompatible polymer(s), and cross-linked with UV light prior to or preferably after implantation.

Figure 55:
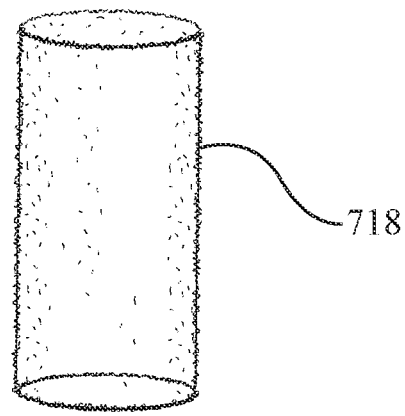
FIG. 55 illustrates an exemplary coated drug delivery implant, wherein the drug delivery implant is coated with a polymer and a photosensitizer.

In one or more embodiments, the implant is coated with a collagen polymer to a desired thickness or in combination with another polymer, such as polyvinyl alcohol, chitosan, polycaprolactone, etc., conjugated with riboflavin or another cross-linker and cross-linked before or after implantation in a preformed pocket with an appropriate wavelength of light or UV radiation to cross-link the polymeric coating inside the body allowing the cross-linker to be released in the tissue, and then cross-link the tissue surrounding the implant in order to, after implantation, release the incorporated medication from the implant slowly without inciting cellular attraction or encapsulation of the implant which inhibits a release of the medication(s) from the implant that is unpredictable. For example, as shown in FIG. 55, the implant 718 is coated with a polymer and/or a photosensitizer.

In one or more embodiments, the non-biodegradable flexible porous tube made of polymeric material or a non-organic compound in combination with cross-linked organic polymer coating is filled with microspheres, drug nanoparticles incorporated in a polymeric material, such as polylactic glycolic acid, chitosan, liposomes, polycaprolactone, or lipid-coated nanoparticles, etc. containing the medication so as to release the medication slowly from the tube implant.

In one or more embodiments, the implant can serve as a reservoir that releases the medications though the pores of 1 to 3 microns in diameter in its wall, and then can be refilled repeatedly by injecting in the tubular implant the medication through a 33-34 gauge needle through the cornea surrounding the tube.

In one or more embodiments, the implant releases immunosuppressive agents, such as cyclosporine, calcineurin inhibitors, mycophenolic acid, tacrolimus, siraliums, steroids, MPP inhibitors, NSAIDs, antimetabolytes, polycolonal antibodies, monocolonal antibodies, TNF inhibitors, Fingolimod, antibiotics, intraocular pressure (IOP) lowering agents, such as Rho kinase inhibitors, Fasudil, and other agents, pilocarpine, prostaglandin analogues, Brimonidine, etc., anti-virals, Anti-VEGFs, biologics, or neuroprotective releasing medication. The medications being released as needed at concentrations of nanograms or micrograms or mg/per hour depending on the polymeric material size of the holes, length of the polymer, etc.

In one or more embodiments, the implant can be positioned at any place in the body to control a function or release a medication without being encapsulated by the surrounding tissue, due to the cross-linking of the polymeric coating or the pocket being cross-linked prior to the implantation, while the medication can be an anti-VEGF, neuroprotective agents, such as nerve growth factors, Rho kinase inhibitor such as Fasudil, antibiotics, antiproliferative agents, anti-inflammatory agents, etc. at a non-toxic, beneficial concentration.

In one or more embodiments, the implant is made using 3-D printing technology to the desired shape, size or thickness from any material coated with collagen, elastin, or made of collagen, elastin, etc. or synthetic polymers which are further coated with more biocompatible polymer(s), such as acrylic, organic, etc., which are cross-linked prior to the implantation or coated with a cross-linker or the crosslinking nanoparticles are done subsequent to its release in the tissue prior to radiation with the UV light. In another embodiment, the implant is formed from glass using 3-D printing technology (i.e., the implant is 3-D printed glass).

In one or more embodiments, the implant is implanted in another part of the eye, such as under the conjunctiva, under the sclera, in the retina or sub-retinal space, under the skin using an implant containing medications such as Botox, or in other parts of the body using an implant which is coated with collagen to a desired thickness, dipped in a photosensitizer or has photosensitizer nanoparticles, such as riboflavin, etc. or the photosensitizer is injected surrounding the implant and implanted in desired location, such as under or over the sclera in the choroid, under the conjunctiva, etc. Then, ultraviolet (UV) radiation or another wavelength of light is used to cross-link the tissue at the desired power and duration depending on what technique is used. In these conditions, a focused UV or another wavelength of light is applied externally, in a painting oscillatory fashion only to the desired areas or internally through a fiber optic, etc. to activate the photosensitizer in the surrounding tissue where the implant is located. The cross-linked collagenous tissues surrounding the implant prevent creating an adhesion between the tissue and the implant or gluing the wall of the pocket together or to the implant. The cross-linked collagenous tissues surrounding the implant also have these additional benefits: (1) it is easier to replace the implant if needed, (2) fibrous ingrowth or encapsulation is prevented, (3) it permits injection of the cross-linker again to repeat the cross-linking process if needed, and (4) it prevents rejection of the implant and contributes to the slow release of the medication from the implant. Also, these implants can act as a shunt for glaucoma, or drainage shunt for cerebrospinal fluid, or other part of the body, such as a bladder neck for urine if the drainage system is provided with a unilateral valve that only opens when the bladder pressure increases to certain level, etc.

In one or more embodiments, the injection of a small amount of hyaluronic acid or other viscous fluid in the pocket simplifies the inserting of the implant in the peripheral corneal pocket or a pocket created in another tissue.

In one or more embodiments, the implant can be a biodegradable polymer carrying various medications and can be replaced.

In one or more embodiments, the implant is a tube-like structure having a thickness or diameter of 0.02 millimeters (mm) to 0.4 millimeters (mm) in one direction and up to 8 mm in another (flat) width, and being 1-60 mm long covering the entire corneal periphery without pressing the corneal tissue in any direction. The implant may be filled with a medication(s), a fluid, or a combination of them.

In one or more embodiments, the tube is not biodegradable having holes made in the wall of the tube with 0.2 to 3 microns in diameter, or 5 microns to 500 microns in diameter, to permit diffusion of the medications or cells placed in it to produce desired needed proteins, hormones, nerve growth factors, or other products needed for other body cell survival, such as cornea, retina, brain, etc.

In one or more embodiments, the tube has holes that are 5 to 15 microns in diameter so as to permit stem cells to exit the tube. The tube can be biodegradable implanted in a lightly cross-linked corneal pocket permitting, for example, stem cells to proliferate and/or migrate to the cornea. The stem cells can be obtained from limbal stem cells or mesenchymal stem or skin and cultured cells prior to the injection in the cornea or in another part of the body.

In one or more embodiments, the device is implanted in the wall of the vitreous cavity with one end closed and one end open to the vitreous cavity, or the implant can be under the retina or it can penetrate both the retina and the choroid and permit release of medication or the cells.

In one or more embodiments, the implant is implanted in the tissue surrounding the eye, on the face, etc. with one end closed and one end open to the tissue. The implant can be removed after the drug is released, and then replaced.

In one or more embodiments, the repeated crosslinking of the tissue surrounding the pocket can be performed as needed to prevent cellular ingrowth, and the implant can be removed and replaced as needed (e.g. in age related macular degeneration) to maintain delivery of the anti-glaucoma medication, anti-VEGFs, immunosuppressive or anti-inflammatory agents, or nerve growth factors, or Rho kinase inhibitors.

In one or more embodiments, the peripheral cross-linked pocket is used to insert or inject medications needed to treat a corneal disease, glaucoma, or a disease of the posterior segment. The medication can be in a form of nanoparticles, microparticles, micelles, liposomes, chitosans, polycaprolactone as nanoparticles, dendrimers, etc.

Figure 56A:
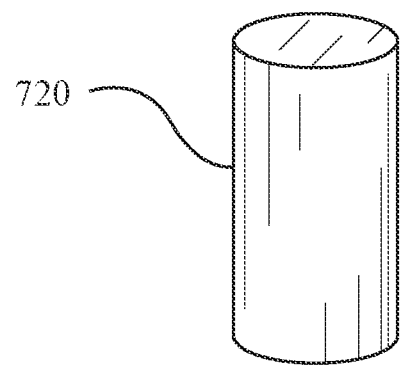
FIG. 56A illustrates a first exemplary form of the drug delivery implant described herein, which is in the form of a solid tubular implant.
Figure 56B:
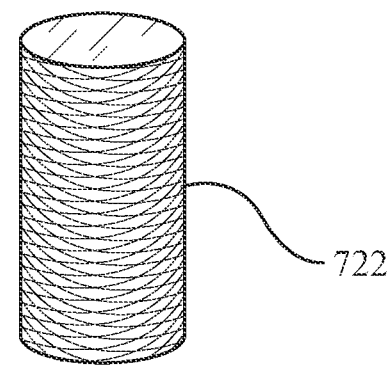
FIG. 56B illustrates a second exemplary form of the drug delivery implant described herein, which is in the form of a porous tubular implant.
Figure 56C:
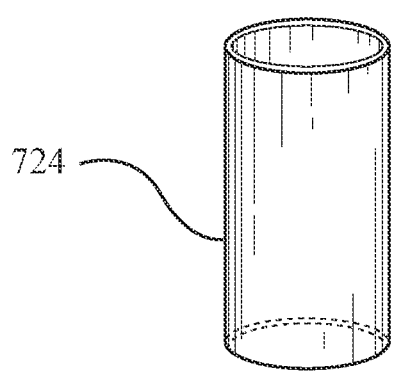
FIG. 56C illustrates a third exemplary form of the drug delivery implant described herein, which is in the form of a tubular implant with open ends.
Figure 60:
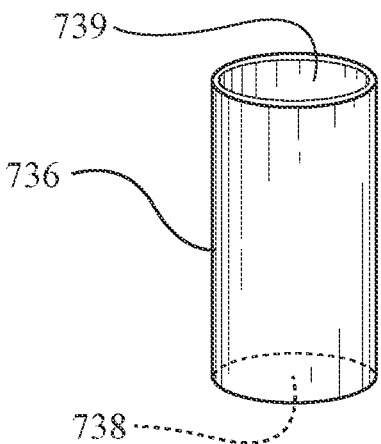
FIG. 60 illustrates yet another exemplary form of the drug delivery implant described herein, wherein the implant is in the form of a semi-solid or silicone tubular implant with one closed end and one open end.

In one or more embodiments, one can inject or insert an implant in the peripheral corneal pocket that is in the form of a large-sized flexible, semi-solid or solid, porous or solid rod-shaped implant, a flat implant, or tube-shaped implant that contains medication, or any shape and size polymeric material that can be absorbed with time and the medication is released slowly to the cornea or the anterior chamber of the eye or diffuses through the anterior chamber or through the sclera to the back of the eye, for treatment of the choroidal or retina and optic nerve diseases. As shown in FIGS. 56A-56C, the implant may be in the form of a solid implant 720, a porous implant 722, or a solid tubular implant 724 with an open end. Also, as shown in FIG. 60, the implant may be in the form of a semi-solid or silicone tubular implant 736 with one closed end 738 and one open end 739.

In one or more embodiments, the diameter of the rod or flat-shaped implant can have a length of 1 microns to a few millimeters (mm), or the length can be 1 to 40 millimeters (mm) or longer.

In one or more embodiments, the non-biodegradable tube is open-ended so that the medication exits only from one or both ends of the tube.

In one or more embodiments, the medication can be released for a duration of from 3 months to 3 or more years, such as when containing nanoparticles of fluoroquinolone dexamethasone, diclofenac, etc., and the implant can be replaced or removed if the desired effect has been achieved or reinjected in the corneal pocket.

In one or more embodiments, the tube is closed ended, but has pores for diffusion of the medication. For example, refer to the implants 726, 730 in FIGS. 57 and 58.

In one or more embodiments, the implant can be placed near any joint in the body and the cross-linking is done using ultraviolet (UV) radiation through the skin or through the fiber optic as described for localized drug delivery.

In one or more embodiments, the porous tube can be made of semipermeable non-biodegradable material that permits only the diffusion of fluid/medication, etc. in and out of the tube, and the tube is implanted in the peripheral cross-linked corneal pocket, wherein the tube can be refilled with medication as needed via an injection using a 33-34 gauge needle. For example, refer to FIG. 61.

In one or more embodiments, the tube contains cells in a biocompatible fluid that permits nutrition to reach the cells which are injected in the tube where the cells are immortalized to produce one or more medications, growth factors, such as a ciliary neurotrophic growth factor, RPE growth factor, nerve growth factors, anti-VEGFs, or other medications needed.

In one or more embodiments, the implant contains genetically modified cells producing other needed enzymes and medications. The combination of crosslinking of the cornea produces a wall of amorphous, acellular collagen and the corneal location that lacks vessels provides a suitable place for these cells in the tube implant to survive and produce medications as needed, which otherwise would have to be given repeatedly either locally or systemically, and in many genetic diseases of the cornea, such as Fuchs dystrophy, the cells have to be injected in the subconjunctival space where the cells could be attacked by the normal cellular body's immune response. The cross-linked pocket with the implant creates an immune-privileged space in the cornea or elsewhere for these cells to survive. For example, refer to FIGS. 63A-70B.

In one or more embodiments, the medication in the implant can be in any form or composition, such as antibiotics, anti-inflammatory, immune suppressants, anti-glaucoma medication, anti-vascular proliferation, stimulatory, such as Rho inhibitors. The polymers can be made of bio-degradable compounds, such as polylactic, polyglycolic acid or a combination of them, polycaprolactone, etc.

In one or more embodiments, the corneal cross-linked pocket contains a tubular implant filled with particulate immunosuppressive agents, such as cyclosporine etc., that release the medication at a constant, but low concentration of micrograms as needed. The medication diffuses in the cornea, sclera, and/or conjunctiva, thus eliminating the burning sensation of topical cyclosporine drops and the need for daily drop admiration in dry eye syndromes, or after refractive surgery or other diseases.

In one or more embodiments, the medication can be injected in the peripheral pocket along with corneal stem cells taken from the limbus or genetically modified stem cells and grown in the culture for implantation.

Figure 65A:
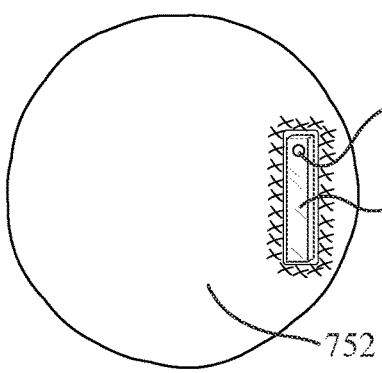
FIG. 65A is a front view of a cornea of an eye illustrating a tubular drug delivery implant disposed in a cross-linked pocket in the peripheral portion of the cornea, wherein the implant comprises a needle fluidly coupling the implant to the anterior chamber of the eye.
Figure 65B:
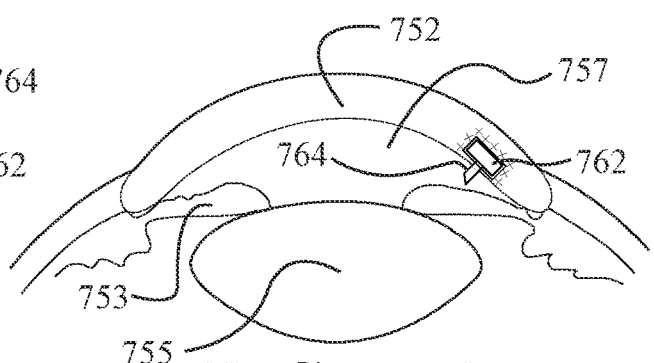
FIG. 65B is a partial side cross-sectional view of the eye of FIG. 65A illustrating the tubular drug delivery implant with the needle extending into the anterior chamber of the eye.

In one or more embodiments, as shown in FIGS. 65A and 65B, a non-biodegradable implant tube 762 as described herein is implanted in the cross-linked corneal pocket of the cornea 752 of the eye with iris 753 and lens 755, and the implant tube 762 is connected to the anterior chamber 757 with the aqueous fluid via a thin 23-34 gauge needle 764, where biomarkers such as VEGFs, glucose, and analytes, etc. are present both inside the aqueous and the tube system made of soft silicone. Similarly, as depicted in FIGS. 70A and 70B, an implant 778 is implanted in the cross-linked corneal pocket of the cornea 766 of the eye with iris 765, and the implant 778 is connected to the anterior chamber 767 with the aqueous fluid via a needle 780. The implants 762, 778 can be penetrated with a 30-34 gauge needle from outside and the aqueous can be aspirated in a volume of less than 0.50 microliters repeatedly over a long period of time without causing a collapse of the anterior chamber. The volume of the anterior chamber is 25 times more than the sample fluid taken. The minimal amount of aqueous fluid withdrawn will be replaced by the eye in less than 10 minutes. This provides a means of obtaining easily a fluid biopsy repeatedly from the eye without penetrating the entire cornea or the eye wall directly with the complication of iris or lens injury and retinal injury. The fluid sample can be examined in chronic disease processes, such as uveitis for biomarker of a disease, viral infection that persist in the eye long after the body has healed, such as Ebola, Zika, Herpes viruses or other viral diseases or non-viral infections that can be detected and treated appropriately. The biomarkers can be obtained from the implanted tube, and can provide valuable information on many metabolic diseases of the body or the eye, a systemic disease (e.g., Alzheimer disease), age related macular degeneration, glucose level, or other analytes (e.g., diabetes) in diabetic retinopathy and other slow progressive degenerative eye diseases, tumors, infection, uveitis, poisoning or drug overdose, etc.

In one or more embodiments, a plurality of implants are implanted in the cornea of the eye. In these one or more embodiments, each of the implants is used for a different purpose. For example, a first one of the implants may be in form of a corneal drug delivery implant used for delivering one or more medications to the eye, as described above. A second one of the implants may be used for taking liquid biopsies from a portion of the eye, as described herein (e.g., extracting a liquid biopsy of the aqueous fluid from the anterior chamber of the eye). A third one of the implants may be used for stem cell delivery and/or gene therapy in the manner described above. A fourth one of the implants may be used for measuring the intraocular pressure of the eye of the patient (e.g., intracorneal implant comprising a pressure sensor 618 illustrated in FIGS. 52 and 53). That is, the fourth implant may contain a pressure sensor configured to measure an intraocular pressure of an eye and to output a signal based on the measured intraocular pressure of the eye, the pressure sensor configured to be implanted in a cornea of the eye; a processor operatively coupled to the pressure sensor, the processor configured to generate intraocular pressure data based upon the signal outputted by the pressure sensor; and a transmitter device operatively coupled to the processor, the transmitter device configured to transmit the intraocular pressure data generated by the processor to a remote receiver located outside of the eye, the transmitter device configured to be implanted in the cornea of the eye. In addition to the pressure sensor, the third implant may further comprise a needle configured to penetrate a posterior portion of the cornea of the eye, the needle configured to open into the anterior chamber of the eye so as to measure the intraocular pressure of the eye without obstructing vision through the central cornea.

In one or more embodiments, one can measure the amount of VEGF present in the aqueous providing information on the disease progression requiring treatment (e.g., anti-VEGFs or no treatment). Anti-VEGFs or another medication can be administered directly in the tube to reach the posterior segment avoiding repeated intraocular injection through the sclera, without having the risk of retinal detachment or lens injury. As another example, liquid biopsy of aqueous in a patient with diabetic retinopathy, where the retina is in need of treatment with the laser coagulation, provides the information regarding whether the disease process is under the control or not.

In one or more embodiments, for the first time one can obtain from the aqueous biopsy, instant information needed for the doctor to diagnose a disease process at the bedside and be able to follow the process over a long period of time with ease.

In one or more embodiments, nanoparticles carrying other medications can be delivered as slow release nanoparticles from the tube in the anterior chamber to treat glaucoma for a long period of time, thereby eliminating the need for repeat therapy. These medications may include pilocarpine, prostaglandin analogues for treatment of glaucoma, Rho kinase inhibitors, or neuroprotective agents or Brimonidine, etc.

In one or more embodiments, the implanted tube is filled with desired medications, as described above, and is coated with collagen or albumin loaded with riboflavin particles that are diffused after implantation in the pocket. The ultraviolet (UV) radiation used for cross-linking permits the diffusing of the medication from the implant as a slow release device, and prevents vascular growth around the implant containing the medication.

In one or more embodiments, the implanted tube can be 100 microns to 1 millimeters (mm) in diameter and 4 mm to 40 mm long, or less than 100 micron in diameter and no longer than a few millimeters in length. The implanted tube may be filled with any desired medication to be implanted in any tissue and cross-linked after implantation.

In yet one or more further embodiments, methods are disclosed herein which include administering Wnt inhibitors either alone, or in combination with Rho kinase inhibitors (i.e., Rock inhibitors), that are useful for alleviating the effects of conditions that are caused by acute or chronic inflammatory processes, such as chronic inflammatory dry eye disease, lichen planus, arthritis, psoriasis, plantar fasciitis, pars planitis, papillitis, optic nerve neuritis, scleritis, keratitis, chronic Meibomian gland inflammation, and uveitis.

In one embodiment, Wnt inhibitors or Rho kinase inhibitors are used as topical drops, ointment, gel, non-toxic injectable formulation to treat the dry eye syndrome or mucosal inflammatory diseases, such as lichen planus, chronic joint disease, arthritis, chronic choroiditis, plantar fasciitis, pars planitis, scleritis, iritis, scleritis gingivitis, pars planitis and uveitis.

A method of treating dry eye with deficiency or aqueous production which is associated often with the Meibomian gland disease, affecting about 7% to 34% of all Americans, pathophysiology of chronic dry eye disease including a cycle of inflammation involving both innate and adaptive immune responses is also disclosed herein.

In one embodiment, dry eye syndrome (DES) or keratoconjunctivitis sicca, a disease affecting tear production leading to damage to the corneal surface, associated often with disturbance of Meibomian gland, lachrymal gland, conjunctival goblet cells, nasolacrimal duct and pain sensation is treated by Wnt inhibitors or Rho kinase inhibitors used as topical drops, ointment, gel, non-toxic injectable formulation.

In one embodiment, the method used for treatment of the eye utilizes over the counter physiological saline solutions with some other components to affect the inflammatory component of the dry eye or improve on the composing of the tear film, such as tear film osmolarity, or adding lipids, mucin, etc. Other topical medications include TheraTears® (Advanced Vision Research), Refresh® and Celluvisce® (Allergan), Tears Natural® and Bion Tears® (Alcon), GenTeal® and HypoTears® (CIBA Vision), each of which contain electrolytes and has varying pH levels, osmolarities, Restasis® (0.05% cyclosporine, Allergan), and Xiidra® (5% lifitegrast, Shire), which attacks the inflammatory process by a different mechanism than cyclosporine. Most of these medications are applied as a drop to maintain the conjunctival wetness as needed usually 1-3 drop during the day or ointment at night most of these medications may be used in combination with Rock inhibitors such as Fasudil, or Wnt inhibitors such as sulforaphane and vitamin D, etc.

In one embodiment, the administration of Rock inhibitors not only reestablishes the tear production by reducing the conjunctival inflammatory cytokines and inflammatory response, but also enhances the nerve fibers to grow and reestablish the function of conjunctival goblet cells to produce mucin, which is essential for tear film lubrication. Rho-associated protein Kinase (Rock) is a kinase belonging to the family of serine-threonine Kinase involved in regulating the shape and the cytoskeleton of the cells, it is an important regulator of cell migration, stimulates PTEN phosphatase activity, leading to uncontrolled cell division in cancer. Rock is active in inflammatory processes, cancer, Parkinson's disease, diabetes, and many neurodegenerative diseases and produces and stiffens collagen in tumors, such as pancreatic cancer. Therefore, Rock inhibitors inhibit inflammatory processes, blocking cell migration.

In one embodiment, Rock inhibitors may be used in combination with functionalized nanoparticles of polycaprolactone, polylactic or polyglycolic acid, etc. to reduce the inflammation during immune therapy or thermoimmune therapy. In one embodiment, a potent ROCK inhibitor, orally bioavailable Fasudil hydrochloride, inhibitor of cyclic nucleotide dependent- and Rho-kinases GSK 269962 is used. In one embodiment, potent and selective ROCK inhibitor GSK 429286, Selective Rho-kinase (ROCK) inhibitor H1152 dihydrochloride, or Botox is used.

In one embodiment, selective Rho-kinase (ROCK) inhibitor Glycyl H 1152 dihydrochloride, or another selective Rho-kinase (ROCK) inhibitor is administered as topical ointment, drop, or gel. Also, a more selective analogue of H1152, that is cell-permeable, a selective Rho-kinase inhibitor OXA 06 dihydrochloride, a potent ROCK inhibitor PKI1447 dihydrochloride, potent and selective ROCK inhibitor antitumor SB 772077B, a potent Rho-kinase inhibitor, vasodilator SR 3677 dihydrochloride, a potent, selective Rho-kinase (ROCK) inhibitor TC-S7001, a potent and highly selective ROCK inhibitor, orally active Y-27632 dihydrochloride or Botox also may be administered.

In one embodiment, aqueous tear-deficient dry eye, occurring as a result of not enough tears being produced due to a dysfunction of the lacrimal glands, is treated with Wnt inhibitors or Rho kinase inhibitors as topical drops, ointment, gel, or a non-toxic injectable formulation.

In one embodiment, the Wnt inhibitors compound that is used includes FH535, IWP-2, PNU-74654, IWR-Tendo, IWR-exo, demethoxycurcumin, sulforaphane and vitamin D, CCTO36477, KY02111, WAY-316606, SFRP, IWP, LGK974, C59, Ant1.4Br/Ant 1.4C1, ivermectin, niclosamide, apicularen and bafilomycin, XAV939, XAV939, G007-LK and G244-LM, NSC668036, SB-216763, gemtuzumab, and akinumab.

In one embodiment, patients with moderate-to-severe dry eye having both elements of evaporative dry eye and aqueous tear-deficient dry eye, and that are on topical medications for other diseases, such as glaucoma, drops, or antibiotics containing preservative that over time damage the conjunctival goblet cells and other cells and induce dry eye syndrome, are treated with Wnt inhibitors or Rho kinase inhibitors as topical drops, ointment, gel, or a non-toxic injectable formulation.

In one embodiment, administration of Wnt inhibitors, such demethoxycurcumin, sulforaphane and vitamin D, or Rho kinase inhibitors, such as Fasudil derivatives, is done as topical drops, a gel, a non-toxic injectable formulation, or injectable Botox, 1-100 units as needed, administered locally at multiple locations or Rock inhibitors molecules at doses of 1Pg-nanograms to a few micrograms as slow release delivery system.

In one embodiment, patients who are on topical medications for other diseases, such as glaucoma, drops or antibiotics containing preservatives and over time damage the conjunctival goblet cells and other cells and induce dry eye syndrome, or patients with dry eye and glaucoma are treated either by implanting matrices of polylactic acid or polyglycolic acid, polyanhydride, or chitosan polymers under the conjunctiva with slow release polymers containing either Wnt inhibitors or Rock inhibitors, such as Botox or Fasudil derivatives, releasing the medication over months or years locally at multiple locations to release the non-toxic doses of the medications from 1 picogram (pg) to 1 nanograms (ng) or more each day.

In one embodiment, patients who develop dry eye as a result of systemic medication, such as in cancer patients developing dry eye after administration of checkpoint inhibitors in cancer immune therapy, are treated either by Wnt inhibitors or Rock inhibitors with slow release polymers containing either Wnt inhibitors, such as demethoxycurcumin, CCTO36477, KY02111, WAY-316606, SFRP, IWP, LGK974, C59, Ant1.4Br/Ant 1.4C1, ivermectin, niclosamide, sulforaphane and vitamin D, or Rock inhibitors, such as Botox or Fasudil derivatives, etc., releasing the medication over months or years locally at multiple locations to release the non-toxic doses slow release medications from 1 pg to 10 ng each day or more.

In one embodiment, the Sjorgen syndrome is associated with low salivary flow, lymphocytic infiltration of the lacrimal gland and salivary gland auto antibodies in serum, rheumatoid factor, connective tissue diseases, such as Sjogren's syndrome, to the list of immune-related adverse events that can develop during cancer treatment with immune checkpoint inhibitors are treated with Rock inhibitors and Wnt inhibitors at non-toxic concentrations of sulforaphane and vitamin D, CCTO36477, KY02111, WAY-316606, SFRP, IWP, LGK974, C59, Ant1.4Br/Ant 1.4C1, ivermectin, niclosamide, or Rock inhibitors such as Botox or Fasudil etc., releasing the medication slowly over months or years locally at multiple locations to release the non-toxic doses slow release medications from 1 picogram (pg) to 10 nanogram (ng) each day locally.

In one embodiment, the patients being treated have a dry eye syndrome unassociated with Sjögren's syndrome (SS) (i.e., non-SS keratoconjunctivitis sicca (KCS)) with a sensation of foreign body in the eyes, photophobia, excessive tearing, ocular irritation and pain. Other symptoms are increased tear film osmolality, decrease in tear breakup time, increase in the conjunctival enzymes metalloproteinase 9 and 17, and changes in impression cytology of the conjunctival cells. These patients are treated with Rock inhibitors, such as injectable Botox, 1-10 units, or in combination with metalloproteinase inhibitors doxycycline, low molecular weight heparin, lovenox, and dexamethasone at concentration of 0.1%-5%.

In one embodiment, when inflammation is one of the mechanisms that causes damage to the ocular surface in dry eye disease seen in autoimmune diseases such as Sjögren's syndrome, and rheumatoid arthritis and neuropathic disorders, optic nerve neuritis, papillitis, scleritis, uveitis, inflammatory, infectious, chemical, traumatic diseases, etc., the patients are treated with injectable Rock inhibitors, such as Botox or Fasudil derivatives, conjugated with slow release polymers, etc. releasing the medication over months or years locally at multiple locations as the non-toxic doses release the medications slowly for months to a year at concentration of 1 pg to 10 ng each day.

In one embodiment, the pathological conditions resulting in dry eye include pemphigus and Sjogren's syndrome, which affect the eye by either damaging the conjunctival cells responsible for maintaining the wetness of the cornea and the conjunctiva, or by damaging the lacrimal glands of the eye and/or the meibomian glands of the eye lid or other pathological conditions resulting in dry eye include hypolacrimation, alacrima, Stevens-Johnson syndrome, marginal blepharitis pemphigus, ocular pemphigoid, scleritis, or diabetes are treated with the Rock inhibitor Fasudil, Botox, etc. at a picogram to nanogram concentration or in combination with metalloproteinase inhibitors, doxycycline 0.1%-5% solution, low molecular weight heparin 0.1%-5% solution, or dexamethasone 0.1-2% solution in combination with MTOR inhibitors at 0.1%-5% solution.

In one embodiment, the dry eye of patients occurring in post-corneal surgery (including but not limited to post-LASIK surgery) with surgical damage to the corneal nerves, other conditions resulting in dry eye including the aging process, environmental factors (e.g., dry home and/or work environments), and extended use of visual display terminals (e.g., employment, recreation) are treated with Rock inhibitors, or in combination with metalloproteinase inhibitors, low molecular with heparin, or Wnt inhibitors or Rock inhibitor, such as Botox, 1-100 units administered locally at multiple locations, small doses or Rock inhibitors molecule, Fasudil and its derivatives, etc., at doses of 1 nanogram (ng) to a few micrograms (μg) as a slow release polymer.

In one embodiment, the dry eye can also occur after cataract surgery and refractive surgery (i.e., the LASIK procedure) and photorefractive keratectomy, smile procedure, partial or complete corneal transplants, which are the majorities of present refractive surgery where these procedures are performed, but dry eye is more common with LASIK where the superficial nerves are cut, and where the eye dries out because the corneal reflex is affected and the eye subsequent to these surgeries becomes dry while many eyes experience regeneration of the nerves, but it takes about one year or more to achieve it all. Patients with these conditions are treated with Rock inhibitors, or in combination with metalloproteinase inhibitors, low molecular with heparin, or Wnt inhibitors or Rock inhibitors, such as Botox, 1-100 units administered locally over the cornea as drops 1-4 times daily or injectable preparation at multiple locations, small doses or Rock inhibitors molecule, such as Fasudil or its derivatives, etc., at doses of 1 nanogram or a few micrograms as a slow release non-toxic preparation.

In one embodiment, patients with paresis or paralysis of the fifth or seventh cranial nerves causing dry eye as a result of interfering with proper lid closure are treated with Rock inhibitors, such as Botox, 1-10 units administered topically over the cornea at multiple locations, and in small doses, or Rock inhibitors, such as the molecule Fasudil, or its derivatives, etc. at doses of 1 nanogram to a few micrograms as topical ointment, drop, gel, etc.

In one embodiment, the patient has lichen planus associated with a chronic inflammatory disease of the skin, mucous membranes, and nails presenting a burning sensation in the mouth, throat esophagus, vagina and the mucosa appears as a lattice-like network of white lines near sites of erosion. Lichen planus can also affect the skin accompanied with sensation of itching, reddish-purple polygon-shaped skin lesions on the lower back, wrists, and ankles. Lichen planus very rarely leads to oral cancer in about 5% of the patients. The cause of lichen planus is unknown, but it is thought to be the result of an autoimmune process with an unknown initial trigger. It is known that tobacco, alcohol, and stress aggravate the lesions. Thus far, there has not been a cure, but many different anti-inflammatory medications and procedures have been used in efforts to control at best the symptoms thereof. In one embodiment, the patients with lichen planus are treated either by Wnt inhibitors or Rock inhibitors as a topical solution drops, gel, non-toxic injectable formulation, ointment or oral, or if needed, systemic administration of these medications or Rock inhibitor, such as Botox, 1-100 units administered locally as ointment over the lesion or injectable preparation at multiple locations, small doses or Rock inhibitors as Botox or molecule Fasudil, and its derivatives etc. at doses of 1 nanogram to a few micrograms.

In one embodiment, the patients with lichen planus are treated locally, by topical or injection subcutaneously with either by Wnt inhibitors or Rock inhibitors, such as Botox, 10-100 units as needed administered locally at multiple locations or Rock inhibitors, such as Fasudil, etc. molecules at doses of 1 nanogram to a few micrograms.

In one embodiment, Wnt signaling is involved in the control of stem cell proliferation. Wnt mutation causes developmental defects in many disease processes including inflammation and cancer.

In one embodiment, the Wnt inhibitors compounds used are: FH535, IWP-2, PNU-74654, IWR-1endo. IWR-exo, demethoxycurcumin, sulforaphane and vitamin D, CCTO36477, KY02111, WAY-316606, SFRP, IWP, LGK974, C59, Ant1.4Br/Ant 1.4C1, Ivermectin, Niclosamide, apicularen and bafilomycin, XAV939, XAV939, G007-LK and G244-LM, NSC668036, SB-216763, gemtuzumab, akinumab Wnt inhibitors.

In one embodiment, the oral doses for the Wnt inhibitor niclosamide is 1 to 2 gram tablet once, or to repeat in 7 days, if needed.

In one embodiment, the small molecule Fasudil, a rock inhibitor Fasudil (HA-1077), a selective RhoA/Rho kinase (ROCK) inhibitor, or Y-27632, small molecule inhibitor of ROCK1 and ROCK2, Botulinum toxin a is rock inhibitor marketed under the brand names Botox, Dysport Myobloc. Xeomin, etc. Botulinum toxin, all having good penetration into the cornea, and do not increase intraocular pressure or cause cataracts and may be dissolved in an organic solvent such as DMSO or alcohol or sterol, lanosterol, squalene, and/or squalamine, or containing a polyanhydride, poly (glycolic) acid, poly(lactic) acid, or polycaprolactone polymer for the treatment of the lid, conjunctiva, lacrimal gland corneal diseases and glaucoma.

In one embodiment, Fasudil is used as a single, oral 40-80 milligram (mg) dose orally as two 40 mg Fasudil tablets are administered.

In one embodiment, the methods include administering Wnt inhibitors, either alone or in combination with Rho kinase inhibitors, orally, locally by injection or drops, spray or ointment for alleviating the effects of conditions that result in lack of moisture or wetness in the eye.

In one embodiment, Rho kinase inhibitors, may be administered orally, locally by injection or drops, spray or ointment for alleviating the effects of conditions that result in lack of moisture or wetness in the eye, such as the inflammatory conditions resulting in dry eye including pemphigus and Sjogren's syndrome, which affect the eye by either damaging the conjunctival cells, or by damaging the lacrimal glands of the eye and/or the meibomian glands of the eye lid.

In one embodiment, the required treatment of Rho kinase inhibitors, such as Botox in 1-2 units, may be administered locally by injection or drops, spray or ointment for other inflammatory processes resulting in dry eye include hypolacrimation, alacrima, xerophthalmia, Stevens-Johnson syndrome, pemphigus, ocular pemphigoid, marginal blepharitis, nerve pain, diabetes, and/or post-corneal surgery after cutting the corneal nerves (including but not limited to post-LASIK surgery). Other conditions resulting in dry eye include the aging process, environmental factors (e.g., dry home and/or work environments), and extended use of visual display terminals (e.g., employment, recreation, etc.).

In one embodiment, inhibition of Wnt signaling or ABC transporters by RNA interference may be a valuable therapeutic strategy in dry eye including hypolacrimation, alacrima, xerophthalmia, and Stevens-Johnson syndrome.

In one embodiment, a number of Rock inhibitors are used in non-toxic doses in combination with functionalized nanoparticles, conjugated with polymeric coatings, such as chitosan, polyanhydride, cyclodextrin as a potent ROCK inhibitor; bioavailable Fasudil hydrochloride, inhibitor of cyclic nucleotide dependent- and Rho-kinases GSK 269962, potent and selective ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor, more selective analogue of H1152, cell-permeable, selective Rho-kinase inhibitor OXA 06 dihydrochloride, potent ROCK inhibitor PKI1447 dihydrochloride, potent and selective ROCK inhibitor, antitumor SB 772077B, potent Rho-kinase inhibitor, vasodilator SR 3677 dihydrochloride, potent, selective Rho-kinase (ROCK) inhibitor TC-S7001, potent and highly selective ROCK inhibitor, orally active Y-27632 dihydrochloride and may be dissolved in an organic solvent such as DMSO or alcohol or sterol, lanosterol, squalene, and/or squalamine, or containing a polyanhydride, poly(glycolic) acid, poly(lactic) acid, or polycaprolactone polymer to reduce the inflammation processes in the eye, sclera, lid, conjunctiva, or other mucosal diseases, mouth, throat, skin, etc.

In one embodiment, Wnt inhibitors, such as canakinumab, ivermectin, or niclosamide may be dissolved in an organic solvent such as DMSO or alcohol or sterol, lanosterol, squalene, and/or squalamine, or containing a polyanhydride, poly(glycolic) acid, poly(lactic) acid, or polycaprolactone polymer prior to its application.

In one embodiment, small molecule Wnt inhibitor PKF118-310, the Wnt/β-catenin pathway inhibitor and Fasudil, a rock inhibitor Fasudil (HA-1077), a selective RhoA/Rho kinase (ROCK) inhibitor, or Y-27632, small molecule inhibitor of ROCK1 and ROCK2, etc. may be dissolved in an organic solvent such as DMSO or alcohol or sterol, lanosterol, squalene, and/or squalamine, or containing a polyanhydride, poly(glycolic) acid, poly(lactic) acid, or polycaprolactone polymer to release non-toxic medication slowly at a desired concentration.

In one embodiment, early management includes the use of lubricants, artificial tear substitutes, ointment, gel, or emulsion. Topical anti-inflammatory agents, topical Rock inhibitors, anti-interleukin (IL1) TNF-alfa TNF-α, hyaluronic acid, low molecular heparin 0.1-5% solution alone, or in combination with metalloproteinase inhibitors doxycycline 0.1-5% solution immunosuppressive agent or inhibitor, e.g., mycophenolic acid, as local or systemic therapy.

In one embodiment, topical Rock inhibitors are applied to the cornea as drops or spray or subconjunctval injection as a slow release compound combined with chitosans in 0.1 microgram/ml to 40 microgram/ml or more for topical application.

In another embodiment, the Rock inhibitors are coated with the slow release polymers, such as lactic acid, glycolic acid, etc. at a concentration of 200 nanograms to 1 micrograms/ml or more and administered topically, subconjunctival, or inside the eye subcutaneously inside the plantar fascial.

In another embodiment, the Rock inhibitors are released from a polymeric explant or implant (e.g., an implant as depicted in FIGS. 54A-58) either placed over or under the conjunctiva and sutured to the sclera to release, e.g., Fasudil, etc. at concentrations of 0.01 micrograms/ml to 40.0 micrograms/ml or more per day.

In one embodiment, the Rock inhibitors release, after placement in the upper or lower cul-de-sack of the conjunctiva or as a slow release punctal plaque or implanted subconjunctivally, at a rate of 1 picogram to a 10 nanograms/day of the medication.

In one embodiment, the Rock inhibitors release, after placement in the suprachoroidal space, inside the eye, behind the eye, inside the gingiva, subcutaneously in plantar fascia, or as a slow release polymeric plaque or implanted to release medication at a rate of 1 picogram to a 10 nanograms/day of the non-toxic medication.

In another embodiment, the nanoparticles or dendrimers are conjugated with Rock inhibitors and chitosan delivered as a slow release system that can be released from a temperature sensitive polymer that melts at 42-43 degrees C. and is used with a warm compressor over or under the lid, or light thermal application, or the use of a compressive focused ultrasound applied to lid, conjunctiva, cornea, or the lid releasing 1 picogram to a 10 nanograms/day of the medication.

In one embodiment, the Rock inhibitors or Wnt inhibitors are delivered with simultaneous application of amniotic membrane and slow release nanoparticles applied post corneal surgery, such as LASIK, cataract corneal transplant, or any other corneal surgical intervention at 10 picograms to 20 nanograms of medication per day.

In one embodiment, the Rock inhibitors or Wnt inhibitors are delivered with simultaneous application of amniotic membrane and low molecular weight heparin slow release nanoparticles applied post corneal surgery, such as LASIK, cataract, corneal transplant uveitis scleritis or chemical injury to the cornea or conjunctiva at concentrations of 0.001 micrograms/ml to 40 micrograms/ml or more or topical or subconjunctival Botox, at 1-100 units or topical at 1-5 units or more in a physiological solution of Botox, or similar preparations.

In one embodiment, the Rock inhibitors or Wnt inhibitors are delivered with simultaneous application of low molecular weight heparin (levonox) with other medications, such as tetracycline, Doxycycline or metalloproteinase inhibitors, dexamethasone 0.1%-1% concentration as slow release polymeric nanoparticles or liposomes applied post corneal surgery such as LASIK, cataract, corneal transplant, uveitis, scleritis or thermal or chemical injury to the cornea or conjunctiva, e.g., Fasudil derivatives, etc., at 0.1 micrograms/ml to 40 micrograms/ml or more, or Botox at 1-3 units.

In one embodiment, after LASIK or any refractive surgery or cataract surgery, Rock inhibitors at doses of 0.1 micrograms/ml to 40 micrograms/ml or more for topical application or Wnt inhibitor can be injected in the anterior chamber, or applied as drops in the post-operative period to replace prednisolone or other steroids, or NASIDs, and encourage regrowth of the cut neurons in the cornea.

In one embodiment, after LASIK or any refractive surgery or cataract surgery, Wnt inhibitors, or Rock inhibitors, such as botulinum toxin (Botox) can be injected under the conjunctiva or applied as drops in the post-operative period to encourage regrowth of the cut neurons in the cornea after LASIK or other corneal surgery at doses of 1 to 10 units of Botox injected under the conjunctiva or 1-2 drops daily at concentration of 10 picograms to 500 picograms of Botox in physiological solution or topical as drops.

In one embodiment, in dry eye syndrome, Rock inhibitors or Wnt inhibitor, such as botulinum toxin (Botox) can be applied as drops or injected subconjunctivally to eliminate the inflammatory component of the dry eye at doses of 1-10 units once a month or once every 2 to 3 months with slow release nanoparticle conjugates in biodegradable polymers.

In one embodiment, in dry eye syndrome, Rock inhibitors, such as botulinum toxin (Botox), Fasudil, etc. or Wnt inhibitors, such as niclosamide, ivermectin, FH535, IWP-2, PNU-74654, IWR-1endo. IWR-exo, demethoxycurcumin, sulforaphane and vitamin D can be given orally at the tolerated dose or 40 mg Fasudil or 1 gram niclosamide or 10-100 units of Botox to eliminate the inflammatory component of dry eye, sulforaphane at 400 micrograms and Vitamin D 3000-5000 IU.

In one embodiment, the Rock inhibitors, such as Fasudil derivatives at concentrations or 10 picograms to 10 nanograms to 1 microgram per drop Botox solution of 0.1 units of Botox can be administered with small molecule Wnt inhibitors at a low concentration 1-10 microgram.

In one embodiment, a topical or subconjunctival or intraocular administration of the Rock inhibitors, such as Fasudil derivatives, etc., at concentrations or 10 picograms to 100 nanograms/0.25 ml or Botox solution of 0.1-1 units can be administered with small molecule Wnt inhibitors or a low concentration of sulforaphane and vitamin D to inhibit the inflammatory processes or auto-immune response.

In one embodiment, Rock inhibitors are administered with antibody coated nanoparticles conjugated with thermosensitive nanoparticles and Adalimumab, a humanized antibody administered topically or subcutaneously at a non-toxic dose.

In one embodiment, Rock inhibitors are administered with antibody coated nanoparticles, dendrimers, liposomes, etc. to the conjunctiva as liposomes or ointment in Meibomian gland inflammation to release medication at a concentration of 1 picogram to 100 units or more picograms/0.25 ml to 0.5 ml along with an antibiotic.

In one embodiment, Wnt inhibitors or Rock inhibitors, such as Fasudil derivatives, etc. are administered with nanoparticles, dendrimers, thermosensitive polymers conjugated with polylactic or polyglycolic acid or chitosan, microspheres, liposomes, dendrimers, and combinations thereof, and they are administered as drops, or injected in the conjunctival or lacrimal glands along with immunosuppressive agents, such as mycophenolic acid, etc.

Figure 58:
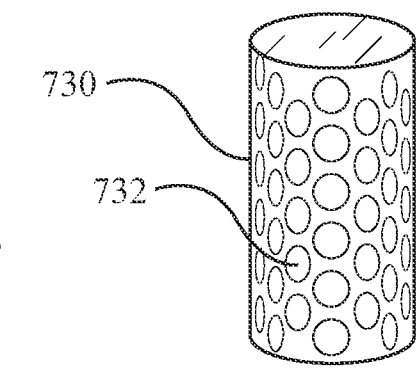
FIG. 58 illustrates yet another exemplary form of the drug delivery implant that is similar to that which is depicted in FIG. 57, except that the tubular-shaped implant of FIG. 58 has larger-sized holes formed in the side thereof.

In one embodiment, topical administrations, subconjunctival injections, sub-tenon injections, suprachoroidal injections, intravitreal injections can be combined with small molecule Wnt inhibitors or standard anti-inflammatory agents (e.g., steroids, dexamethasone, etc.), nanoparticle implants, biodegradable or non-biodegradable polymers, NASIDs, immunotherapy immunosuppressants, etc. to treat inflammatory processes of the lid conjunctiva or the cornea and the lid or throughout the day. For injection, a dose of about 50 picograms/ml to about 200 micrograms/ml may be used, or a surgical implant may be used, for example, in a diffusible walled reservoir (e.g., as shown in FIGS. 56B, 57, and 58) sutured to the wall of the sclera, or may be contained within an inert carrier, such as microspheres, dendrimers, or liposomes to provide a slow-release drug delivery system.

In one embodiment, a formulation of Wnt or Rock inhibitors is used from the group consisting of topical administration at a concentration of about 50 picograms/ml to less than 1 micrograms/ml, subconjunctival injection at a dose in the range of about 1 picogram/ml to about 200 micrograms/ml, intravitreal injection at a dose in the range of about 0.1 picogram/ml to about 20 micrograms/ml, or retrobulbar injection at a dose in the range of about 2 micrograms/ml to about 200 micrograms/ml in slow release microspheres or dendrimers. In one embodiment, a formulation of Wnt or Rock inhibitors is used comprising intraocularly administering to a patient after corneal surgery at picogram to nanogram concentrations.

In one embodiment, a formulation of Wnt or Rock inhibitors is used as a composition consisting essentially of Rock inhibitors in a pharmaceutically acceptable formulation and in an amount effective to enhance post-surgical to enhance ocular moisture, nerve regeneration in the patient wherein the composition is administered at a concentrations up to about 10 micrograms/ml by at least one of slow release polycaprolactone, polylactic, or polyglycolic acid, etc. over many months, intraocular administration of the composition, or is administered topically at a concentration in the range between about 10 picograms/ml to less than 1 microgram/ml depending on the composition of the medication.

In one embodiment, wherein the polymeric composition is administered by subconjunctival injection at a dose in the range of about 1 picogram/ml to about 20 micrograms/ml, intravitreal injection at a dose in the range of about 1 picogram/0.1 ml to about 20 nanograms/ml, or retrobulbar injection at a dose in the range of about 20 nanograms/ml to about 2 micrograms/ml.

In one embodiment, a formulation of Wnt or Rock inhibitors is used to enhance post-surgical ocular moisture or in papilitis, optic nerve neuritis, uveitis or scleritis in the patient wherein the composition is administered at a concentration up to about 50 picograms/ml by at least one of intraocular injection, or the composition is administered topically at a concentration in the range between about 50 picograms/ml to less than 1 micrograms/ml.

In one embodiment, a formulation of Wnt or Rock inhibitors is used wherein the composition is administered by subconjunctival injection at a dose in the range of about 1 picograms/ml to about 2 micrograms/ml, intravitreal injection at a dose in the range of about 1 nanogram/0.1 ml to about 20 nanograms/ml, or retrobulbar injection at a dose in the range of about 200 nanograms/ml to about 2 micrograms/ml.

In one embodiment, a method to treat an ocular condition in a patient comprises intraocularly administering to the patient a pharmaceutically acceptable formulation of a drug selected from the group consisting of Rock inhibitors, such as Fasudil or derivatives in nanogram to microgram concentrations in microspheres, dendrimers, physiological solution, botulinum toxin in picogram concentrations in polymeric microspheres or 0.3-5 units injectable, or Wnt inhibitors, such as niclosamide, ivermectin, nanogram to microgram concentration in microspheres, dendrimers, suspension or another polymer, sulforaphane 10-400 nanograms in microspheres, dendrimers, or another polymer and Vitamin D taken orally in 1000-5000 IU etc., Fasudil derivatives taken orally 1-40 mg, niclosamide orally in 10-500 mg tablets, sulforaphane in capsule 10-40 mg or more ivermectin taken orally 1-400 mg or more and topical formulation as drops, ointment, or gel in a non-toxic formulation for the patient undergo surgery in the eye for refractive errors, diabetic retinopathy, retinal detachment, or after cataract surgery or refractive surgery for the duration until the eye is free of inflammation and has recovered from the surgery.

In one embodiment, non-toxic doses of Rock inhibitors in an amount up to about 1-200 micrograms/ml effective to treat dry eye or another ocular condition selected from diabetic retinopathy, retinitis pigmentosa, or age related macular degeneration without substantial toxicity and at least one Wnt inhibitor or Rock inhibitor, wherein the composition is administered by at least one of intraocular injection at a concentration up to about 2 picograms/ml, or the composition is administered topically at a concentration in the range between about 1 picograms/ml to less than 10 nanograms/ml.

In one embodiment, a formulation of Wnt or Rock inhibitors is used as topical administration at a concentration between about 50 picograms/ml to 200 nanograms/ml, subconjunctival injection at a dose in the range of about 1 picograms/ml to about 20 micrograms/ml in a slow release polymer, intravitreal injection at a dose in the range of about 1 picogram/0.1 ml to about 2 micrograms/ml, or retrobulbar injection at a dose in the range of about 1 picograms/ml to about 200 nanograms/ml suspension in a slow release polymer depending on the composition of the medication.

In one embodiment, a method to treat an ocular condition in a patient by intraocularly administering a pharmaceutically acceptable formulation of Wnt inhibitors or rock inhibitors in an amount effective to treat the condition. The method provides treatment while avoiding systemic administration of systemic medication. In one embodiment, a sustained release pharmaceutically acceptable formulation is implanted intraocularly in a polymeric slow release compound having about 20 nanograms to 1 microgram or more of Fasudil to about 0.1 micrograms to 40 micrograms or 1 milligram of Fasudil or other Rock inhibitors implanted in or on the eye and may continuously deliver Fasudil for five or more years.

In another embodiment, a concentration up to about 10 or more micrograms of Rock inhibitors is administered intraocularly without substantial toxicity.

In another embodiment, Fasudil derivatives are taken orally 1-40 mg, niclosamide is taken orally in 10-500 mg tablets, sulforaphane is taken orally in capsule 10-40 mg or more, ivermectin is taken orally 1-400 mg or more, and topical formulations may be administered as drops, ointment, or gel in a non-toxic formulation.

In another embodiment, Rock inhibitors at a concentration in the range of about 1 picogram/ml (0.0000000001%) to less than 0.1 micrograms/ml (less than 0.001%) is administered topically. In other embodiments, Fasudil or another Rock inhibitor at a concentration in the range of about 1 nanogram/ml to about 200 micrograms/ml is injected under the conjunctiva, or a concentration in the range of about 1 picogram/0.1 ml to about 200 micrograms/ml is injected in the vitreous, or a concentration in the range of about 20 picograms/ml to about 200 nanograms/ml is injected behind the eyeball.

In one embodiment, the Rock inhibitors, such as Fasudil, etc., or Wnt inhibitors, such as niclosamide, are administered as topical or a spray at non-toxic concentrations of 1 picogram/ml to 20 nanograms/ml in a physiological pH balanced, with osmolarity of 310 to prevent and treat, decrease the time of onset, or lessen the severity of a wide variety of diseases such as lichen planus, ocular conditions, such as retinitis pigmentosa, ocular irritation following corneal surgery (e.g., LASIK surgery), age related macular degeneration, diabetic retinopathy, dry eye disease, scleritis, papillitis, and uveitis, scleritis pars planatis, vogt-koyanagii syndrome, psoriasis, Lichen Planus, etc.

In one embodiment, the Rock inhibitors, such as Fasudil, etc., or Wnt inhibitors, such as niclosamide, are administered as topical or a spray at non-toxic concentrations of 1 picogram/ml to 20 nanograms/m, or in an ointment or cream, or suspension of microspheres and dendrimers in meibomian gland disease.

In one embodiment, the Rock inhibitors, such as Botulinum toxins are administered as topical or a spray at non-toxic concentrations of 1 picogram/ml to 1 nanograms in a cream, ointment, suspension of microspheres or dendrimers, etc. for topical application in lichen planus, nerve damage after LASIK or refractive surgery procedures, or diabetes or wrinkle treatment.

In one embodiment, the Rock inhibitors, such as Fasudil 40-80 mg/kg, etc., or Wnt inhibitors, such as niclosamide, 100-500 mg or ivermectin, 250 mg to 2000 mg are administered orally to prevent and treat, decrease the time of onset, or lessen the severity of a wide variety of diseases, such as optic nerve neuritis, papillitis, variety of idiopathic uveitis, scleritis, or ocular conditions, such as retinitis pigmentosa, ocular irritation following corneal surgery (e.g., LASIK surgery), age related macular degeneration, diabetic retinopathy, dry eye disease, papillitis, uveitis, and lichen planus.

In one embodiment, the Rock inhibitors or Wnt inhibitors are administered as topical or a spray at non-toxic concentrations of 1 picogram/ml to 20 nanograms/ml in a physiological pH balanced solution with osmolality of 310 to treat the corneal nerve cuts after LASIK surgery to decrease inflammatory process and encourage fast regrowth of neurons from the cut end of the corneal nerves and enhance corneal sensation recovery time and prevent dry eye formation.

In one embodiment, the Rock inhibitors (40-80 mg/kg) or Wnt inhibitors are administered orally after LASIK surgery to decrease inflammatory process and to encourage fast regrowth of neurons from the cut end of the corneal nerves and enhance corneal sensation recovery time and prevent dry eye formation.

Another embodiment of the invention is a method to treat ocular conditions including ocular irritation following corneal surgery, conjunctivitis, canaliculitis or Schlemm's canal of the eye, iritis, lacrimal and Meibomian glands are treated with Rock inhibitors, such as Fasudil or its derivatives in nanogram to microgram concentrations in microspheres, dendrimers, physiological solution, Botulinum toxin in picogram concentrations in polymeric microspheres dendrimers, or 0.3-5 units injectable, or Wnt inhibitors, such as niclosamide, ivermectin, nanogram to microgram concentration in microspheres suspension or another polymer, sulforaphane 10-400 nanogram in microspheres, dendrimers, or another polymer and Vitamin D taken orally in 1000-5000 IU, etc.

In one embodiment, a sustained release pharmaceutically acceptable formulation is implanted intraocularly (e.g., using an implant as depicted in FIGS. 54A-58). For example, a matrix containing in the range of between about 0.4 to 1 mg Fasudil can last for ten or more years. In another embodiment, a concentration up to about 1 microgram Fasudil or others, or Rock inhibitors, is administered intraocularly, inside the joint in arthritis, or subcutaneously or subgingival injection in lichen planus without substantial toxicity.

In another embodiment, Rock inhibitors at a concentration in the range of about 1 nanogram/ml (0.0000001%) to less than 1 microgram/ml (less than 0.0001%) are administered topically. In other embodiments, Fasudil at a concentration in the range of about 1 nanogram/ml to about 20 microgram/ml is injected under the conjunctiva, or a concentration in the range of about 1 nanogram/0.1 ml to about 200 micrograms/ml is injected in the vitreous, or a concentration in the range of about 20 nanograms/ml to about 20 micrograms/ml is injected in a slow release polymer, such as polycaprolactone or polylactic or glycolic, in the vitreous cavity or behind the eyeball or other part of the body as needed.

In another embodiment, Rock inhibitors at a concentration in the range of about 1 nanogram/ml (0.0000001%) to less than 1 microgram/ml (less than 0.0001%) are administered topically. In other embodiments, Fasudil at a concentration in the range of about 1 nanogram/ml to about 20 micrograms/ml is injected under the conjunctiva, or a concentration in the range of about 1 nanogram/0.1 ml to about 200 micrograms/ml is injected in the vitreous, or a concentration in the range of about 20 nanograms/ml to about 20 micrograms/ml is injected in a slow release polymer, such as polycaprolactone or polylactic or glycolic, in the vitreous cavity or behind the eyeball in subconjunctival space, or subcutaneously as needed.

In another embodiment, a composition is formulated for intraocular administration and dosing with Fasudil derivatives in a pharmaceutically acceptable formulation (e.g., in a physiologically acceptable solvent, such as sterol, lanosterol, squalene, and/or squalamine, buffered to a physiological pH, etc.). The composition may be in a solution, a suspension, an emulsion, etc., and it may be administered in the form of eye drops, a cream, an ointment, a gel, an injectable, etc., to the eye and/or the eye lid. The composition contains niclosamide or Fasudil in an amount effective to treat an ocular condition without substantial toxicity or mucosal or joint inflammatory diseases.

In one embodiment, the non-toxic doses of Wnt inhibitors, Rock inhibitors, or Botox, act as an anti-inflammatory agent. The botulinum toxin or botox preparation may be administered topically to the eye or eye lid, forehead skin at 1 pictogram to 1 nanogram concentrations, 1 pictogram to 5 nanogram concentrations, for example, using drops, an ointment, a cream, a gel, a suspension of microspheres, dendrimers, etc. The agent(s) may be formulated with excipients such as methylcellulose, hydroxypropyl methylcellulose, hydroxypropyl cellulose, the LD50s of any naturally occurring botulinum toxin protein is at 1.3 nanograms per kilogram (abbreviated ng/kg). In a 75 kg (165 lbs.) subjects, the LD50 for botulinum toxin would be 97.5 nanograms if injected directly into a vein or artery. 100 unit vials contains 0.75 nanograms=750 picograms of botulinum toxin A in the entire vial.

In one embodiment, a dose of botulinum toxin in 100-2000 picograms will not be toxic if injected subcutaneously, or 750 picograms (100 units) 1-2 times a month will not be toxic. Higher doses can be used with caution and it would be desirable not to exceed these levels to prevent an immune response to the medication.

In one embodiment, a dose of botulinum toxin in 100-2000 picograms will not be toxic if injected subcutaneously, or 750 picograms (100 units) 1-2 times a month will not be toxic. Higher doses can be used with caution and it would be desirable not to exceed these levels to prevent an immune response to the medication.

In one embodiment, the concentrations 1-20 picograms of Botox in a physiological solution, or up to 30 picograms conjugated with antibody coated nanoparticles would be non-toxic to the body or when conjugated with thermosensitive polymeric coating of the nanoparticles in a physiologic solution or used as drops or injectable.

In one embodiment, the Wnt inhibitors or Rock inhibitors may be injected into the eye, for example, injection under the conjunctiva or tenon capsule, intravitreal injection, or retrobulbar injection. The agent(s) may be administered with a slow release drug delivery system, such as polymers, matrices, microcapsules, or other delivery systems formulated from, for example, glycolic acid, lactic acid, combinations of glycolic and lactic acid, liposomes, silicone, polyanhydride polyvinyl acetate alone or in combination with polyethylene glycol, etc. The delivery device can be implanted intraocularly, for example, implanted under the conjunctiva, implanted in the wall of the eye, sutured to the sclera, for long-term drug delivery or injected in the vitreous cavity (e.g., using an implant as depicted in FIGS. 54A-58).

In one embodiment, one uses a composition containing Rock inhibitors, such as Fasudil etc., at a concentration in the range of about 50 picogram/ml (0.000000005%) to about 50 micrograms/ml (0.005%), niclosamide at a concentration in the range of about 50 picograms/ml to about 50 micrograms/ml, or a combination of Fasudil or an immune suppressive agent, such as mycophenolic acid, to achieve a total concentration of both agents of about 50 picogram/ml to about 50 microgram/mw. Within this range, the agent(s) has wide safety and efficacy, permitting specific doses or administration protocols to be formulated for specific applications. For example, some patients may prefer once a day administration compared to administration more than once a day, so a higher concentration of agent(s) may be used for these patients.

In another embodiment, Rock inhibitors, such as Fasudil, may also be administered by injection. Intraocular injection may be desirable or necessary, for example, for conditions in which topical administration is either not advised or is inadequate, for patients who have difficulty self-administering medications, etc. In one embodiment, the volume injected is less than 0.3 ml. In another embodiment, the volume injected is in the range of about 0.01 ml to about 0.3 ml. For intravitreal administration (injection into the vitreous), Rock inhibitor concentrations in the range of about 1 nanogram/0.1 ml to about 20 microgram/ml (0.002%) may be used without toxicity or adverse side effects.

In another embodiment, niclosamide used in amounts ranging from about 1 nanogram to about 10 micrograms is contained in an aqueous-based cream excipient. In another embodiment, the amount of Fasudil, etc., or other Rock inhibitors ranges from about 1 nanogram to about 10 micrograms, and is contained in an aqueous-based cream excipient. In another embodiment, Fasudil and niclosamide or mycophenolic acid are present in an aqueous-based cream excipient in various proportions. In another embodiment, to achieve a total amount of combined agents of about 1 nanogram to about 10 micrograms, the drug(s) may be incorporated directly into the cream in solution, or may be contained in liposomes or microspheres, dendrimers, either in solution or in an anhydrous form. The cream formulation is usually applied to the eye at bedtime, but it may be applied any time throughout the day if the cream does not cause blurred vision. In another embodiment, the agent(s) is formulated as a solution or suspension and is applied topically in the form of eye drops.

In another embodiment, for long term delivery of a Rock inhibitor or a Wnt inhibitor, either alone or in combination, and/or for sustained release, a matrix housing containing the agent(s) may be implanted into the eye. For example, a reservoir containing in the range of about 1 milligram to about 5 milligrams of agent(s) is estimated to be able to release about 1 microgram agent(s) per day. At such a release rate, continuous, sustained dosing may occur over 1000 to 5000 days. If less than 1 microgram of agent(s) per day is released, sustained dosing may last up to or more than a decade. In one embodiment, less than 50 micrograms/day of agent(s) is released from the matrix. In another embodiment, agent(s) is released form the matrix at a rate in the range of about 50 picograms/day to about 50 micrograms/day. In another embodiment, agent(s) is released from the matrix at a rate in the range of about 1 microgram/day to about 5 micrograms/day.

In another embodiment, a surgically implanted intraocular device or matrix may be provided with a reservoir container (e.g., as shown in FIGS. 56B, 57, and 58) having a diffusible wall of polyvinyl alcohol or polyvinyl acetate or polycaprolactone and containing milligram quantities of a Rock inhibitor or Wnt inhibitor, or a combination of them may be implanted in the sclera. As another example, milligram quantities of agent(s) may be incorporated into a polymeric matrix having dimensions of about 1 millimeter (mm) by 2 millimeter (mm), and made of a polymer such as polycaprolactone, poly(glycolic) acid, poly(lactic) acid, or a polyanhydride, or a lipid such as sebacic acid, and may be implanted on the sclera or in the eye.

In another embodiment, as one example of an inert matrix, liposomes may be prepared from dipalmitoyl phosphatidylcholine (DPPC), preferably prepared from egg phosphatidylcholine (PC) since this lipid has a low heat transition. Liposomes are made using standard procedures as known to one skilled in the art. The agent(s), in amounts ranging from picogram to microgram quantities, is added to a solution of egg PC, and the lipophilic drug binds to the liposome.

In another embodiment, the implantable formation may be in the form of a capsule of any of the polymers previously disclosed (e.g., polycaprolactone, polyglycolic acid (PGA), polylactic acid (PLA), polyanhydride) or lipids that may be formulated as microspheres or dendrimers. As an illustrative example, Fasudil may be mixed with polyvinyl alcohol (PVA), the mixture then dried and coated with ethylene vinyl acetate, then cooled again with PVA. Niclosamide bound with liposomes may be applied topically, either in the form of drops or as an aqueous based cream, or may be injected intraocularly. In a formulation for topical application, the drug is slowly released over time as the liposome capsule degrades due to wear and tear from the eye surface. In a formulation for intraocular injection, the liposome capsule degrades due to cellular digestion, other slow release polymers, such as PLA, PGA, polycaprolactone, microspheres, dendrimers are also utilized.

In another embodiment, the time-release administration, however, is formulated so that the concentration released at any period of time does not exceed a toxic amount. This is accomplished, for example, through various formulations of the vehicle (coated or uncoated microspheres, coated or uncoated capsule, lipid, dendrimers, or polymer components, unilamellar or multilamellar structure, and combinations of the above, etc.). Other variables may include the patient's pharmacokinetic-pharmacodynamic parameters (e.g., body mass, gender, plasma clearance rate, hepatic function, etc.). The formation and loading of microspheres, dendrimers, microcapsules, liposomes, etc. and their ocular implantation are standard techniques known by one skilled in the art.

In another embodiment, a combination of Rock inhibitors or Wnt inhibitors may be dissolved in an organic solvent, such as DMSO or alcohol or sterol, lanosterol, squalene, and/or squalamine, or containing a polyanhydride, poly (glycolic) acid, poly(lactic) acid, or polycaprolactone polymer.

In one embodiment, Rock inhibitors, such as Fasudil or Botox, etc. or Wnt inhibitors, such as niclosamide, alone or in combination with low molecular weight heparin and metalloproteinase inhibitors, such as doxycycline, tetracycline, etc. can be used at non-toxic concentrations with or without dexamethasone, for dry eye or lichen planus lesions of the mucosa, or skin or other inflammatory diseases of the retina, cornea, conjunctival sclera or optic nerve neuritis, scleritis, uveitis in an appropriate physiological solution or ointment, etc.

In one embodiment, the intravenous solution form of Rock inhibitors or Wnt inhibitors may be diluted to achieve the indicated concentration using 0.9% NaCl or 5% dextrose, or an organic solvent such as dimethyl sulfoxide (DMSO) or sterol, lanosterol, squalene, and/or squalamine. Intraocular administration may be any of the routes and formulations previously described. For injection, either a solution, emulsion, suspension of a liquid, capsular formulation of microspheres, dendrimers, or liposomes, etc. may be used.

In one embodiment, Rock inhibitors or Wnt inhibitors or Botox may be injected subconjunctivally to treat uveitis at a dose in the range of about 1 picogram/ml to about 200 picograms/ml, or intravitreally at a dose of about 1 gram/0.1 ml to about 200 picograms/ml. In one embodiment, the dose is about 50 picograms/0.1 ml. To treat scleritis involving the anterior sclera, Rock inhibitors or Wnt inhibitors or Botox may be administered topically.

In one embodiment, Rock inhibitors or Wnt inhibitors or Botox may be injected to treat scleritis involving the posterior sclera, may be administered by retrobulbar injection at a dose in the range of about 20 picograms/ml to about 800 picograms/ml or more and dissolved in DMSO or a very low concentration of alcohol or sterol, lanosterol, squalene, and/or squalamine.

In one embodiment, to treat neuritis or papillitis, Rock inhibitors may be administered by retrobulbar injection at a dose in the range of about 200 picograms/ml to about 800 nanograms/ml of Fasudil and its derivatives, etc.

In one embodiment, to treat neuritis or papillitis, Rock inhibitors (e.g., Fasudil) may be administered orally at a dose in the range of about 40-80 milligrams of Fasudil tablets, etc. or one time niclosamide 1-2 grams orally.

In one embodiment, the ocular solutions contain at least one Rock inhibitor or Wnt inhibitor such as sulforaphane and provide anti-inflammatory, anti-cell proliferation, anti-cell migration effects if given orally with Vitamin D, topically as dendrimer or microsphere delivery or an injectable non-toxic preparation.

In one embodiment, the solution is administered intraocularly after cataract surgery before insertion of a replacement intraocular lens, resulting in reduced post-operative inflammation, which may eliminate the need for a steroid therapy.

In one embodiment, the solution may be one that is invasively administered, for example, an irrigation or volume replacement solution containing at least one Rock inhibitor, such as Botox, or Wnt inhibitor.

In one embodiment, the solution may be one that is non-invasively or topically administered in the form of drops, ointments, gels, creams, etc. and may include eye lubricants and contact lens solutions. The solution may contain a supratherapeutic concentration of agent(s), such as 40 micrograms/ml or to 80 micrograms/ml or more for topical application ranges, 40 nanograms/ml to 4 micrograms/ml Fasudil and its derivatives, etc. so that a therapeutic concentration of a topically administered solution accumulates in a diseased ocular structure sufficient to treat the disease.

In one embodiment, medications are administered with antibody coated nanoparticles, dendrimers, thermosensitive polymers, nanoparticles, dendrimers, lactic or glycolic acid, chitosan or combinations, etc. Immunosuppressives are all conjugated with the antibody coated nanoparticles for slow release as topical drops or an injectable preparation for dry eye after LASIK, meibomian gland inflammation, optic nerve neuritis, uveitis, scleritis, etc.

In one embodiment, Rock inhibitors or Wnt inhibitors are administered by topical drops, spray, subconjunctival injection, sub-tenon injection, suprachoroidal injection, intravitreal injection in combination with standard anti-inflammatory agents, etc. and steroids, dexamethasone, etc. as a nanoparticle implant formed from biodegradable or non-biodegradable polymers.

In one embodiment, a method of using Rock inhibitors or Wnt inhibitors is disclosed where Rock inhibitors or Wnt inhibitors are administered at non-toxic doses to lichen planus of the skin or mucosa. Lichen which is associated with is a chronic inflammatory disease of the skin, mucous membranes and nails, presents a burning sensation in the mouth, throat esophagus, vagina, pharynx, stomach, anus, bladder, conjunctiva, and the mucosa appears as a lattice-like network of white lines near sites of erosion can also affect the skin accompanied with sensation of itching, reddish-purple polygon-shaped skin lesions on the lower back, wrists, and ankle thought to be the result of an autoimmune process with an unknown initial trigger.

In one embodiment, a formulation of Wnt or Rock inhibitors is used to treat the lesion of Lichen planus conditions using Rock inhibitors and Wnt inhibitors as topical drop spray application or injection into the subcutaneous tissue around or inside the lesion, or implantation in multiple sites close to the lesion releasing, e.g., Fasudil, etc., at doses or 1-500 picograms or injection of Botox around the lesion or inside the lesion at 10-100 units once a month or once every 2-3 months.

In one embodiment, a formulation of Wnt and/or Rock inhibitors is used to treat the lesion of lichen planus conditions using Rock inhibitors and/or Wnt inhibitors used as topical or drop spray application, mouth wash preparation of Fasudil derivatives at 1 nanogram to 1 microgram or more preparation or Wnt inhibitors, such as niclosamide, ivermectin, nanogram to microgram concentration in microspheres, dendrimer suspension or, sulforaphane 10-400 nanograms in microspheres, dendrimers, or in another polymer in addition to Vitamin D taken orally in 1000-5000 IU, etc. or injection into the subcutaneous tissue around or inside the lesion, or implantation in in multiple sites close to the lesion releasing, e.g., Fasudil, etc., at doses or 1-500 picograms or injection of Botox around the lesion or inside the lesion at 10-100 units once a month, or once every 2-3 months.

In one embodiment, in treating lichen planus, for example, a topical administration may contain between about 10 picograms/ml drug to about 50 micrograms/ml of Fasudil, etc. or other Rock inhibitors in a formulation which may be applied at bedtime or throughout the day or as an injection, a dose of about 50 picograms/ml to about 200 micrograms/ml around or inside the lesion. In one embodiment, the medication may be used as a surgical implant, for example, in a diffusible walled reservoir (e.g., as shown in FIGS. 56B, 57, and 58) sutured to the surrounding tissue, or may be contained within an inert carrier, such as microspheres, dendrimers, or liposomes, to provide a slow-release drug delivery system to release the medication at 1 picogram to 100 picograms (e.g., Fasudil, etc.) per day.

In one embodiment, a formulation of Wnt or Rock inhibitors is used to treat ocular conditions, such as dry eye disease, as well as other conditions, is disclosed. Rock inhibitors and Wnt inhibitors are used as s topical drop spray application or injection into the eye, or implantation in or on the eye (e.g., using an implant as depicted in FIGS. 54A-58). For example, a topical administration may contain between about 10 picograms/ml drug to about 50 micrograms/ml drug in a formulation which may be applied at bedtime.

In one embodiment, the patient is administered with Rock inhibitors or Wnt inhibitors alone or in combination with NSAIDs or to treat plantar fasciitis associated with chronic pain in the bottom of the foot and heal it, which is caused by being overweight, with more less inflammatory processes as seen also in other conditions such as osteoarthritis, spondylitis, reactive arthritis due to over use of immune response.

In one embodiment, non-toxic doses of Rock inhibitors, such as Fasudil, etc., 200 picograms to 2 nanograms or as Botox (10-100 units) is administered locally at multiple locations in treatment of plantar fasciitis or diabetic neuronal pain.

In one further embodiment, the pathway of inflammation and scarring in the cornea after refractive surgery is blocked by inactivation of Rho Kinase, GSK and Wnt pathway by using either a polymeric implant, or biodegradable polymeric nanoparticles or microparticles that release Rock inhibitors, such as fasudil, netarsudil, or a Wnt combination with Rock inhibitors, such as fasudil, netarsudil, botox, SAR407899, etc. and/or Wnt inhibitors, such as FH535, IWP-2, PNU-74654, IWR-1endo, IWR-exo, or GSK inhibitors SB-216763 without having the side effects of steroid in the eye that can produce an increased intraocular pressure or can reduce the immune defense activation that combats infection.

In one embodiment, after refractive surgery or cataract surgery, the corneal nerves are cut or ablated by administration of a laser, thus producing loss of corneal sensitivity, epithelial erosion and inflammation/infection, due to the loss of the corneal reflex and lid reflex that normally keeps the corneal surface moist and prevents dry eye formation. These complications can be prevented by topical application of Rock inhibitors, Wnt inhibitors, integrin inhibitors, or GSK inhibitors to encourage the nerve growth while inhibiting TGF beta production and scarring.

Example 1

A 26 year old patient had undergone a LASIK procedure for a −5.00 D correction of myopia 3 month ago. The patient developed a dry eye condition with loss of cornel reflex and low tear film production as measured with Schirmer's test and slightly reduced visual acuity. The ocular examination demonstrated loss of corneal sensation and reduced tear film production and presence of debris in the conjunctiva and the lid margin with a mild inflammation of the conjunctiva. The patient was treated with topical application of a Rock inhibitor, such as rhopressa solution applied one or twice daily in a physiological solution. The patient felt relieved of the discomfort within two (2) weeks, and the tear production increased from the previous exam. In three months, the patient was symptom free, the visual acuity improved, and the treatment was reduced to once a day drops.

In one embodiment, one uses Rock inhibitor alone or in combination with GSK 3 inhibitors SB-216763, etc. to encourage the corneal nerve growth and faster recovery of the corneal sensation and rehydration that maintains the health of the mucin producing cells of the conjunctiva and meibomian gland.

In one embodiment, a topical application or polymeric slow release delivery of Rock inhibitors, Wnt inhibitors, integrin inhibitors, or GSK inhibitors are used to treat dry eye.

The following anti-inflammatory Rock inhibitors are administered to the external adnexa and conjunctiva as drops in the form of polymeric nanoparticles or microparticles, or are implanted under the conjunctiva or skin affecting the inflammatory cell pathway, and are readily available. The Rock inhibitors are administered at non-toxic concentrations of 0.01 ng to 30 ng or more microgram/ml release for a short time or a long duration. The Rock inhibitors may be potent ROCK inhibitors, such as Ropresa, netarsudil, Fasudil hydrochloride, inhibitor of cyclic nucleotide dependent- and Rho-kinases GSK 269962, Potent and selective ROCK inhibitors GSK 429286, Selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor or Botulinum toxin, such as Botox in 1-100 international units or very slow release with porous silicon implant; orally active Y-27632 dihydrochloride and SAR407899 as a topical solution, polymeric nanoparticles or microparticles with or without cell penetrating peptides or implant.

In one embodiment, after corneal surgery or cataract extraction, a preparation of Rock inhibitors, Wnt inhibitors, integrin inhibitors, or GSK-3 inhibitors alone, or in combination can be used to reduce the inflammatory side effects of inflammation and scarring or loss of corneal sensation.

In one embodiment, one uses a bioerodible implant comprising a non-anti-inflammatory agent acting on cell pathways of inflammation including Wnt inhibitors, Rho inhibitors, integrin inhibitors, GSK inhibitors SB-216763, or lithium chloride at micro to millimolar (mM) concentrations or in combinations, wherein the inflammation is mediated by various conditions.

Example 2

A 67-year female patient with a history of dry eye and cataract extraction in both eyes is complaining of discomfort, with the sensation of foreign body and dryness, hyperemia, mucoid discharge photophobia, and reduced visual acuity, which is not relieved by over-the-counter eye drops. The patient had typical symptoms of dry eye disease with meibomian gland dysfunction, with reduced Schirmer's test results for tear film production, blepharitis, and redness of the lid margins and crusting of the lashes. The patient was initially treated with over-the-counter artificial tear preparation, hyaluronic acid and gel, and ointment at night, and absorbable punctal plug, which did not improve the symptoms significantly, and subsequently topical anti-inflammatory topical agent, such as a steroid and cyclosporine that moderately improved the condition. Since her inflammation was not significantly reduced, she was treated with an off label use of a Rock inhibitor at concentration of 2 micrograms/ml twice daily drops combined with topical tetracycline along with application, low molecular weight heparin, 1% solution (Lovenox), a light shampooing of the lashes at night, and an ointment at night. The symptoms were relieved significantly after a month of therapy.

In one embodiment, after laser surgery, a preparation of a bioerodible implant comprising of Rock inhibitors, Wnt inhibitors, or integrin inhibitors alone or in combination can be used to reduce the inflammatory and side effects, such as scarring on the external eye or inside the eye, or on the skin or mucosa.

In one embodiment, after refractive surgery, and/or in a case of dry eye, integrin inhibitors, are administered with cell penetrating peptides (CPP) or activatable cell penetrating peptide (ACPP) coated dendrimers or nanoparticles or macrolides, such as cyclosporine A, mycophenolic acid, tacrolimus or ascomycin as nanoparticles or conjugated with the dendrimers, or in a preparation in the early stage of glaucoma as a topical medication at concentrations of Rock inhibitors of 1-5 microgram/ml once or twice per day and macrolides at concentrations of 0.000000001% to 1% in a physiological solution.

In one embodiment, lasers are used to cut and/or coagulate the tissue (e.g., exam or infrared (IR) lasers). In this embodiment, lasers may be used for refractive surgery, cosmetic surgery, excision, or ablation of the tumors, etc.

In one embodiment, after refractive surgery or cataract extraction, one administers a polymeric implant or nanoparticles of dendrimers containing inhibitors of the Glycogen Synthase Kinase-3 (GSK-3) which is a serine/threonine protein kinase that plays a key role in Wnt/β-catenin signaling during embryonic development, inflammation, and cancer. Inhibition of GSK-3 by SB-216763 inhibits the Wnt pathway in inflammation and cell proliferation and encourages the nerve growth.

Other lasers are used to treat diabetic retinopathy, macular edema, etc. to reduce the ischemic retina and VEGF production or externally, such as skin or mucosa. However any laser application, including when used as cosmetic skin or mucosal resurfacing and skin tightening, is associated with minor or major thermal release with damage to the cells exposed to it and causes cytokine release, activation of inflammatory cell pathways with leakage of the fluid from the capillaries. In one or more embodiments, Rock inhibitors, Wnt inhibitors, integrin inhibitors and/or inhibition of GSK-3 by SB-216368 are applied to the laser treated areas, before or after treatment, thereby reducing the unwanted side effects of laser application, such as inflammation and activation of TGF-beta and scarring.

In one embodiment, the Rock inhibitors, Wnt inhibitors, integrin inhibitors, and GSK-3 inhibitors are used in combination with cosmetic fillers as slow release polymeric implants, or nano- or micro-particulates or liposomes or micelles to reduce the inflammatory process, the available fillers include Juvederm and Juvederm Voluma (hyaluronic acid filler, Allergan); Belotero (hyaluronic acid, Merz Pharmaceuticals); Sculptra (poly-L-lactic acid, Sanofi); and Artefill/Bellafill (polymethylmethacrylate, Suneva).

In one embodiment, Rock inhibitors, Wnt inhibitors, GSK-3 inhibitors, and/or Integrin inhibitors can be added to any solution, ointment, cream with antibiotics, antifungals, antivirals after cosmetic laser application or after the application of focused ultrasound for tissue tightening.

In one embodiment, in laser cosmetic resurfacing, e.g., application of laser, visible or infrared, $CO_2$, or Erbium laser or radiofrequency or focused ultrasound can be associated with excessive inflammation, fluid release from the skin and subdermal tissue, or from the mucosal tissue in mouth or after vaginal laser resurfacing causing pain and unforeseen scaring. The use of Rock inhibitors, e.g., netarsudil, Fasudil hydrochloride, or topical solution, inhibitor of cyclic nucleotide dependent- and Rho-kinases GSK 269962, potent and selective Rock inhibitor GSK 429286, or Lithium chloride selective Rho-kinase (ROCK) inhibitor H1152 dihydrochloride, at non-toxic concentration when released alone, or with integrin inhibitors, or Wnt inhibitors alone or in combination with a preparation of lanosterol, squalene or squalamine as a topical preparation, or polymeric slow release nano-microparticles reduces the inflammatory process and enhances the healing process, while squalamine has the advantage of acting as anti-bacterial, anti-fungi, antiviral etc., thus preventing infection of the superficial wound created after laser surgery of the skin or mucosa. The anti-inflammatory agents such as squalene, lanosterol or squalamine can contribute to the health of these cells and assist in dissolving the debris from the skin or mucosa, and in combination, e.g. rock inhibitors act as anti-inflammatory without producing side effects of steroids or NSAIDs, such as coronary disease, gastric ulcer, infection, bacterial, fungi or viral infection.

Example 3

A fifty year old female patient had undergone a $CO_2$ laser facial resurfacing for skin rejuvenation for photo-damaged skin, rhytides, and wrinkles. The per pulse power used for the laser ablation had been below that which is normal, and the beam had reached deeper tissue rather than causing superficial skin surface evaporation. She developed an excessive erythema, swelling of the treated area which was initially treated with complete closed dressing, and application of antibiotic Bactroban ointment and later the face was treated with Cetaphil, which did not decrease the inflammatory response. Topical steroidal ointment was avoided out of fear of infection, since the edema swelling lasted more than ten days the patient was, in addition to the standard therapy, administered a physiological solution having 1 microgram/ml Rock inhibitor and at night with a cream having similar concentration of Rock inhibitor. The patient was advised to return if the swelling did not decrease and increased exudate was noted. Seven days after final examination the erythema and swelling was reduced and the face regained its normal appearance.

The cosmetic facial or mucosa surgery utilizes laser thermal energy to damage superficial skin or mucosal layer end encourage their rejuvenation. The depth of and size of the laser application is decided upon by the need of the condition. The pulsed carbon dioxide ($CO_2$) and erbium: yttrium-aluminum-garnet (Er:YAG) or other infrared lasers are the most common laser used in skin/mucosal resurfacing though radio frequency wave and focused ultrasound also are used for one or the other indication. The absorption of (Er:YAG) laser is more by subcutaneous tissue whereas the ($CO_2$) is by the water molecules producing deeper skin lesion of 50-100 μm, creating a thermal necrosis. In general, skin evaporation requires a fluence about 5-7 $J/cm^2$, whereas the Er:YAG laser requires fluence of 0.5 and 1.7 $J/cm^2$.

The advantage of the Er:YAG laser is reduction of leakage of fluid from the tissue; however, the applications of these lasers depend on the location and degree of tissue tightening that is needed. The contra indications are active inflammatory lesions of the skin, or viral, bacterial, fungal infections, etc.

Though erythema after laser skin or mucosa resurfacing takes about 5-7 days to heal. During which time, the skin and mucosa are vulnerable to infection, continuation or excessive inflammation, and the use of steroids, etc.

In general, the skin is treated postoperatively with topically applied anti-bacterial ointment, cream such as mupirocin 2% (Bactroban), or other antibiotics or antiviral medications such as valcyclovir taken orally and skin treatment with topical Silver sulfadiazine. The complications are sever erythema, edema that might last for weeks that requires application of steroidal cream with hydrocortisone 2.5% cream etc. addition to Retin-A 0.05% that might lead to dermatitis or in combination with hydroquinone 5%, for a month or more. Hyperpigmentation is also another side effect of the laser surgery that might require micropeels with 30-50% glycolic acid, etc.

The major complication of the procedure is infection caused by bacteria, viruses or fungi, often associated with the use of steroids in the cream.

In one embodiment, after cosmetic skin or mucosal laser surgery, one uses Rock inhibitors, Wnt inhibitors, integrin inhibitors and/or GSK inhibitors, such as SB-216763 in a physiological solution, cream or polymeric slow release nano- or micro-particles, liposomes or micelles to reduce the inflammatory process without being in need of steroidal medications.

In one embodiment, after cosmetic skin or mucosal laser surgery, one uses Rock inhibitors, Wnt inhibitors, integrin inhibitors, and/or GSK inhibitors or lithium chloride at a non-toxic concentrations, to reduce the inflammatory process without being in need of steroidal medications, but in the presence of the bacteria, viruses, or fungi infection, one can add anti-bacterial medication of anti-viral or anti-fungal medication as known in the art to the above mentioned cell pathway inhibitors without having the side effects of the steroid that is known to encourage the growth of bacteria, viral, and specifically fungal infections.

Example 4

A 55-year patient underwent a routine $CO_2$ laser facial resurfacing and was treated initially with the routine post-operative therapy including complete closed dressing, and application of antibiotic Bactroban ointment and skin treatment with topical Silversulfadiazine and later the patient's face was washed with Cetaphil, in addition to application of steroidal ointment, to reduce postoperative inflammation and systemic ciprofloxacin to prevent infection. Two days post-operative, the patient noticed pain and sever exudation from the treated areas with associated red exudate. The patient was given additional antibiotics to cover *pseudomonas* infection, but because of the worsening of the condition, the patient was given systemic penecilin and carbapenem to treat a potential *propionibacterium* infection. A laboratory examination revealed presence of therapy resistant *propionibacterium* which cannot respond to the standard medication, because of the side effects of systemic clindamycin, the wound area was treated with a 1% riboflavin solution for a period or ten minutes, then radiated with UV radiation of 10 miliW/cm2 as a oscillatory or painting technique for 30 minutes to cover the entire wound area and kill the bacteria. Subsequently the laser-treated area was cleansed and washed with a physiological solution having 500 microg clindamycin/ml and 1 microgram Rock inhibitor per day and dressed with a cream containing the same medications without riboflavin daily. The systemic medication was continued with carbapenem, the healing process continued for another week as gradually the wound healing took place in an additional 10 days and the skin gradually gained its normal appearance.

In one embodiment, after cosmetic surgical resurfacing, the infection might be caused by antibiotic resistant bacteria, one can administer a solution of riboflavin at concentrations of 0.1-4% or more and followed with the UV radiation to the exposed surfaces without producing any skin burn but crosslinking the proteins of the bacteria, viruses, or fungi, and oozing vessel along with antibiotic antibody-coated nanoparticles with cell penetrating peptides (CPP) or ACPP, to enhance penetration of the medication inside the pathogens and damage them while combining the medications with non-toxic does of Rock inhibitors, Wnt inhibitors, integrin inhibitors and/or GSK inhibitors SB-216368 to reduce post-surgical inflammation, prevent release of TGF beta and other cytokines to prevent sever scarring, the treatment can be repeated daily as needed until a complete wound healing is achieved. In one embodiment, one can administer any other photosensitizer with a different wavelength of light to initiate a photodynamic effect in the skin and treat the skin as described above subsequently.

In another embodiment, the disease is Acne vulgaris, one of the most common skin diseases in the United States characterized by chronic skin disease of the hair follicles and their accompanying sebaceous gland. The disease initiates without inflammation in the mild early stages but it is accompanied by inflammatory processes associated with infection caused by the *Propionibacterium acnes*, an anaerobic bacteria leading to severe nodulocystic acne.

At present, the blockages of the glands were treated by mechanical extraction, injection of steroid in the lesion, or light or laser application to the lesion.

In one embodiment, Acne vulgaris is treated initially with topical tretinoin, clindamycin and benzoyl peroxide, isotretinoin topical Retinoi; however, retinoid can induce dermatitis, and should be used with topical and systemic antibiotics, such as doxycycline, tetracycline, minocycline, in combination with topical or intradermal injection of Rock inhibitors, Wnt inhibitors, integrin inhibitors, GSK inhibitors and/or oral medication, such as a combination of ethinyl estradiol, drospirenone.

In one embodiment, one administers the Rock inhibitors and Wnt inhibitors, integrin inhibitors, and/or GSK-3 inhibitors, such as SB-216368, at non-toxic doses to reduce the vascular leakage after laser surgery for acne or debridement in this disease process and eliminate the side effects of infection or delayed wound healing specifically in diabetic patients.

In one embodiment, in patients having facial acne, the Retinoids are comedolytic and reduces desquamation when given along with antibacterial benzoyl peroxide applied topically twice daily. However, the patients can develop dermatitis after application within 2 weeks.

In one embodiment, in patients with acne one administers Rock inhibitors, Wnt inhibitors, GSK-3 inhibitors and/or integrin inhibitors, as a solution at a non-toxic dose of nanograms to micrograms/ml administered for skin debridement or as ointment, cream or polymeric slow release nanoparticles, microparticles, liposomes, micelles, etc. with squalene or squalamine, or lanosterol, and its derivatives used to reduce the inflammatory processes while eliminating the need for steroid therapy, thereby eliminating steroid associated complications, such bacterial or viral infections, or often fungal infections.

The frequent use of topical and oral antibiotics to treat C. acne bacteria or other bacteria produces often antibiotic resistance bacterial infection.

In one embodiment, one administers a combination topically or by injection of riboflavin at 0.1-2% or more concentrations in combinations with Rock inhibitors as a topical or injectable preparation to crosslink the collagen of the subdermal or submucosal tissue using the UV laser radiation at 360-400 nm wavelength or another wavelength with another photosensitizer and 1 milliwatt to 10 milliwatt or more of power as needed along with anti-bacterial, antifungal, antivirals, etc. to damage the bacteria, fungi, viruses, or parasitic infections.

Example 5

An 18 year male patient was referred because of prior therapy of an acne infection. The patient was initially treated with by mechanical extraction, injection of steroid in the lesion and light application to the area. Despite the therapy with topical tretinoin, and benzoyl peroxide, isotretinoin and topical Retinoid and clindamycin, the bacterium found by laboratory examination revealed to be *propionibacterium* resistant to the antibiotics including clindamycin. The clinical examination showed about 10 mm swollen lesion with deep red hollow around a central exudate. The lesion was treated administration of a 2% solution of riboflavin containing 20 microgram/ml Rock inhibitor Fasudil nanoparticles conjugated with CPP in addition GSK inhibitor SB-216368 in millimolar concentrations for 1-2 hours, followed by UV radiation of 5 mW/cm2 for a period of ten minutes, followed by daily administration of a cream dressing having squalamine in addition to polymeric nanoparticles of Rock inhibitors and GSK inhibitors for daily application, and oral carbapenem. The lesion gradually decreased indicating that the local therapy of antibiotic resistant bacteria is possible with the riboflavin crosslinking combined with an antibiotic to which a bacterium might be resistant.

In one embodiment, any therapy resistant acne is treated with application of solution or mixture of riboflavin, antibody-coated nanoparticles in addition to Rock inhibitors, conjugated with cell penetrating agents (CPP) to penetrate the skin and attached to the C. acne bacteria, and they are damaged by UV radiation which crosslinks the protein of the bacteria and the collagenous tissue around the gland and also simultaneously damages the comedone producing cells of the gland and reduce inflammation.

In one embodiment, the polymeric implant or polymeric nano- or micro-particles with CPP can be combined with antibiotics, antifungals, antivirals, antineoplastic, macrolides, etc. as needed.

In one embodiment, the biodegradable polymeric compositions orthoesters, anhydrides, amides, calcium alginate polysaccharides functionalized celluloses, carboxymethylcellulose polycaprolactone copolymers of glycolic and lactic acid, polymers of D-lactic acid, L-lactic acid, racemic lactic acid, glycolic acid, preferably about 2-150 micrometers in diameter and 20 microns to 4 mm in length, porous silicon implant or nano- or micro-particles are used to deliver the Rock inhibitors, Wnt inhibitors, GSK inhibitors, and integrin inhibitors.

In one embodiment, after crosslinking, the skin glands of the skin are treated with a solution of viscous gel, or ointment containing Rock inhibitors, Wnt inhibitors, integrin inhibitors and/or GSK-3 inhibitors at non-toxic doses to inhibit inflammatory response in the tissue.

One procedure involves topical administration of a 1-10% or more solution of riboflavin in a physiological solution having the osmolarity of 200-400 or more mOSm and the pH of 5-8, with or without low molecular weight heparin in 0.1-1% or combined with cell penetrating peptides (CPP) or activatable cell penetrating peptides (ACPP) for enhance cell penetration, with or without dextran, or cyclodexterin or metallic nanoparticle or organic nanoparticles conjugated with riboflavin that are also UV light absorbing to simultaneously heat up the nanoparticle and damage the cell wall of the bacteria, fungi, or the viral proteins, and the prions.

In one embodiment, the crosslinking solution also contains an antibiotic to which the C. acne is generally sensitive, such as doxycycline tetracycline, minocycline, and/or clindamycin, and is used with Rock inhibitors, Wnt inhibitors, integrin inhibitors, and/or GSK-3 inhibitors individually or in combination.

In one embodiment, the crosslinking solution can contain riboflavin and/or retinoids along with another medication and riboflavin, and Rock inhibitors, Wnt inhibitors, integrin inhibitors and/or GSK-3 inhibitors, where the UV radiation does not affect these medications except for activating the photosensitizer riboflavin, which after UV exposure, creates singlet oxygen and reactive spices that crosslinks the protein, damaging or killing the bacteria, fungi, or viruses including prions and comedone producing sebaceous glands or sweat glands or the skin debris preventing recurrent of infection in these areas or undesirable odor.

In one embodiment, one uses the riboflavin alone or in combination with Rock inhibitors, for topical application, or if needed micro-puncture with radiofrequency needle of the area, and crosslinking the superficial skin glands with UV radiation and eliminating the sweat glands and sebaceous glands in the areas needed to eliminate undesirable odor from the secretion of these glands along with microbiota the accumulate and grow in that area.

In one embodiment, the crosslinking solution can contain squalamine, squalene or lanosterol to encourage with or without CPP or ACPP for dissolving the comedone and debris that accumulate in the outflow channels and seal and sebaceous gland, or along with another medication, such as riboflavin or psoralens, in nanoparticles or microparticles or in combination of both, with UV radiation by two different mechanisms, riboflavin crosslinks the proteins of the bacteria, while psoralens damages their DNA.

In one embodiment, the UV radiation can be applied with 1-30 mW or more for a short period of 1 minute to 60 minutes depending on the surface areas that are treated to eliminate the bacteria, microbiota, and eliminate the sebaceous glands and sweat glands, or the infected skin areas as needed.

In one embodiment, the crosslinking solution, in addition to riboflavin has a Rock inhibitor, such as Fasudil and its derivatives, netarsudil or SAR407899, and is coated with slow release polymers, such as lactic acid and/or glycolic acid at a concentration of 200 nanograms to 1 micrograms/ml or more and is administered topically, or subcutaneously inside the acne lesion using nano- or microparticles with (alpha)-cyclodextrin, or (beta)-cyclodextrin, or (gamma)-cyclodextrin, hydroxypropyl-b-cyclodextrin (bHPCD) for slow release and tissue penetration with or without cell penetrating agents.

In one embodiment, Botulinum toxin botox can be used as a Rock inhibitor in solution, or in polymeric nanoparticles, to release the medication at a slow rate of 1 picogram or more a day to 1 nanogram or 1-100 international units along with a cream with or without squalene in addition, or as solution with polymeric nanoparticles for administration on the skin, mucosa, or cornea as solution of suspension, etc.

In one embodiment, one implants or injects bioerodible polymeric nano- or microparticles for slow release having Wnt inhibitors or Rock inhibitors, integrin inhibitors, or GSK-3 inhibitors alone or in combination with or without ACPP, whereby an agent is released from the polymeric component, such as PLA, PGLA, or combination thereof by erosion of the polymer, and the medication is delivered topically or injected in the subdermal tissue at a release rate of 0.01 nanograms to 1 microgram/ml or more to achieve a constant release concentration of 1 nanogram or more a day for 3 weeks to 6 month or more than a year after laser surgical procedure.

In one embodiment, in patient with acne, Rock inhibitors, such as Fasudil derivatives, Netarsudil C28H27N3O3 (Rhopressa), or SAR407899, netarsudil etc. at concentrations of 10 picograms to 100 micrograms/0.25 ml or Botox solution of 0.1-1 to 25-100 international units can be administered as a slow release implant or injectable as nano- or microparticles with CPP or (alpha)-cyclodextrin, or (beta)-cyclodextrin, or (gamma)-cyclodextrin, hydroxypropyl-b-cyclodextrin (bHPCD) in the dermis or subdermal tissue or inside the acne lesion as a slow release polymeric plaque or implanted to release medication at a rate of 1 picogram to 10 nanograms/day or more of the non-toxic medication along with a nontoxic dose of a macrolide such as cyclosporine, mycophenolic acid, tacrolimus, or ascomycin etc. at concentrations of 0 00000001-1% w.v or applied to the skin or conjunctiva or mucosa of the mouth or genitalia as non-toxic doses to treat inflammatory diseases of the eye, skin, or mucosa.

In one embodiment, the nanoparticles or dendrimers are conjugated with Rock inhibitors, CPP and integrin inhibitors such as abciximab, Eptifibatide, Tirofiban, $\alpha IIb\beta 3$ antagonists, Natalizumab, 3 mg to ±52 µg/mL, MLN-00002, Firategrast, IVL745, antagonists of $\alpha v\beta 3$ and/or $\alpha v\beta 5$ integrins, LM609, Vitaxin, Abegrin, CNTO95, Cilengitide. MLD-based disintegrins, L000845704, SB273005, or risuteganib, Volociximab, JSM6427, or GSK inhibitors and chitosan or PEG delivered as a slow release system that can be released as a temperature sensitive polymer that melts at 42-43 degrees C. using a warm compressor over or under the lid, or thermal application with light, low level laser light, or the use of a compressive focused ultrasound applied to lid, conjunctiva or cornea or the lid releasing 1 picogram to 10 nanograms/day or more of the medication.

In one embodiment, Rock inhibitors or integrin inhibitors are injected after crosslinking in the acne lesion at non-toxic concentrations in the lesion to reduce inflammatory processes and reduce cellular proliferation, blocking TGF beta, and scar formation.

In one embodiment, the Rock inhibitors, such as Fasudil derivatives at concentrations or 10 picograms to 10 nanograms to 1 microgram per drop Botox solution of 0.1 units of Botox can be administered with small molecule Wnt inhibitors, such as FH535, IWP-2, PNU-74654, IWR-1endo, IWR-exo, Demethoxycurcumin, CCTO36477, KY02111, WAY-316606, SFRP or integrin inhibitors, such as abegrin cilengitide, abciximab, tirofiban, natalizumab eptifibatide or at a low concentration of 1 microgram to 10 micrograms as a solution, or in an ointment containing squalene or lanosterol or squalamine to combat bacterial, viral, and fungal infections, while reducing simultaneously the inflammatory processes without steroidal medication that creates the side effect of encouraging bacterial, viral, or fungal infections or parasitic infection of a lesion.

In one embodiment, before or after crosslinking of the acne using topical riboflavin or Psoralens in nano- or microparticles with or without CPP or ACPP solution and UV radiation, one can apply topically an ointment or cream containing squalene, lanosterol, or squalamine to dissolve the comedone of the acne alone or in combination with Rock inhibitors, such as fasudil netarsudil, botox, SAR407899, etc. and/or Wnt inhibitors, such as FH535, IWP-2, PNU-74654, IWR-1endo, IWR-exo, Demethoxycurcumin, CCTO36477, KY02111, WAY-316606, SFRP or integrin inhibitors such as abegrin cilengitide, abciximab, tirofiban, natalizumab eptifibatide.

In one embodiment, the Rock inhibitors are selected from the group consisting of Fasudil, Ripasudil, RKI-1447, Y-27632, GSK429286A, Y-30141, Botox and combinations thereof where the device such as porous silicon or polylactic acid or polycaprolactone releases the Rock inhibitor for 1 year to 3 years at a rate of about 1 micrograms/day to 5 micrograms/day, and botox as a concentration of 1-100 international unit or more released at 1 units or more per day.

In one embodiment, one administers to the eye surface or under the conjunctiva, in the choroid, in the anterior chamber, or in the vitreous cavity, the Rock inhibitor for reducing TGF-β production after therapy and the subsequent scar formation in form of drops or combined with polymeric nanoparticles for slow release delivery after any ocular surgery such as retinal detachment, or complicated retinal detachment traumatic retinal detachment, as proliferative vitreoretinopathy, vitrectomy with or without air or silicone oil tamponade, refractive surgery LASIK, smile surgery, or intracorneal implantion or corneal crosslinking, small molecule PRK or transepithelial PRK, smile procedure, corneal inlay, etc., glaucoma surgery, trans-scleral laser application, for glaucoma, or retinal tear, or application to the ciliary body or from inside the eye to the ciliary processes in glaucoma, cataract surgery laser trabeculoplasty, as polymeric, dendrimers, PGA, PLA or combination or polycaprolactone or chitosan or as liposomal or micelle form.

In one embodiment, Rock inhibitors, such as Fasudil (HA-1077 a selective RhoA/Rho kinase (ROCK) inhibitor), Y-27632, small molecule inhibitor of ROCK1 and ROCK2 which acts as an anti-inflammatory agent and Ripasudil, netarsudil etc. in form of drops or combined with polymeric nanoparticles or implants for slow release delivery are administered at non-toxic concentrations for daily use or slow release after laser cosmetic, ocular, laser facial, mucosal resurfacing, or after transurethral resection of benign prostate, vaginal laser resurfacing, the ablation of cervical localized tumors or precancerous lesions on the skin or mucosa.

in one embodiment, Wnt inhibitors are compounds, such as FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1 or oral ivermectin, niclosamide, or apicularen and bafilomycin, XAV939, XAV939, G007-LK and G244-LM, NSC668036, SB-216763, gemtuzumab, etc. are used in form of drops at pico and nM concentrations, or integrin inhibitors, as solution, or combined with polymeric nanoparticles for slow release delivery of polymeric implants or injectable, or as an ointment.

The conventional signaling receptors and integrins serves as linkers between the actin cytoskeleton and extracellular intracellular signaling matrix, stimulating the cell survival, growth, and cell proliferation.

In one embodiment, the anti-integrins are used as a solution of polymeric erodible nanoparticles, microparticles, and are administered to inhibit cell proliferation and migration and scar formation where the integrin inhibitors are selected from the group consisting of abegrin cilengitide, abciximab, tirofiban, natalizumab, and eptifibatide, and the drug delivery system includes dendrimers, PGLA, PLA or combination of them to treat skin or mucosal inflammation after surgical laser surgery, or in acne vulgaris, etc.

In one embodiment, the cell penetrating peptides extend the agent penetration to at least one of the posterior segment of the eye or anterior segment of the eye or from the cornea to the retina using Rock inhibitors.

In one embodiment, the mucophilic preparation comprises a compound selected from the group consisting of chitosan, a dendrimer, cell penetrating peptide (CPP), activatable cell penetrating peptide (ACPP), hyaluronic acid, low molecular weight heparin, squalene and its derivatives and combinations thereof.

In one embodiment, the Rock inhibitors are administered with macrolides, such as cyclosporine A, mycophenolic acid, tacrolimus, or ascomycin in the early stages of glaucoma as a topical medication at concentrations of Rock inhibitors 1-5 micrograms/ml once or twice per day and macrolides at concentrations of 0.000000001% to 1% in a physiological solution. In one embodiment, to reduce inflammatory processes, one administers polymeric nanoparticles or dendrimers of Wnt inhibitors compounds, such as FH535, IWP-2, PNU-74654, IWR-1endo, IWR-exo, Demethoxycurcumin.

In one embodiment, Rock is active in inflammatory processes, and activates TGF-β formation, that creates scar formation specifically after any surgery, such as skin, intraocular surgery such as retinal detachment, vitrectomy with or without air or silicone oil, tamponade, leading to cell proliferation and redetachment of the retina and Rock inhibitors prevent side effects of excessive scar formation, such as proliferative retinopathy and keloids in cosmetic surgery.

In another embodiment, Rock and other enzymes are activated by inflammatory processes that can be prevented prophylactically before or after the surgery, to reduce TGF-β formation, that creates undesirable scar formation specifically after any surgery, such as skin, mucosa, intraocular surgery such as retinal detachment, vitrectomy with or without air or silicone oil, tamponade, leading to cell proliferation and re-detachment of the retina and Rock inhibitors prevent side effects of excessive scar formation such as proliferative retinopathy and keloids in cosmetic surgery or laser surgery for acne and/or in psoriasis using Rock inhibitors, such as fasudil, rhopressa, netarsudil, and in nano- to microgram concentrations in 1 ml or more or Botulinum toxin as Botox etc. at 1-100 international units depending on the location of application and if used in a slow release filler's absorbable polymers, such as lactic acid or hyaluronic acid or in slow absorbable implant, such as porous silicon, or one administers Wnt inhibitors, such as FH535, IWP-2, PNU-74654, IWR-1endo, IWR-exo, Demethoxycurcumin, CCTO36477, KY02111, WAY-316606, SFRP or integrin inhibitor such as abegrin, cilengitide, abciximab, tirofiban, natalizumab, eptifibatide, GSK inhibitors or integrin inhibitors at non-toxic doses and applied in a physiological solution or as slow release polymeric nanoparticles, microparticles, or as biodegradable implant or inside the space provided in a non-biodegradable implant that can be removed and replaced as needed.

In one embodiment, rock inhibitors are used in hair transplantation to reduce inflammatory responses of the transplanted cells at concentrations of 1 nanogram to 30 microgram/ml.

In one embodiment, Rock inhibitors with GSK inhibitors are used after corneal transplantation to reduce corneal transplant rejection as polymeric nano- or microparticles, etc.

In one embodiment, the Rock inhibitor in tissue or hair transplantation is Botox used at picogram concentrations or as international units 1/0.1 ml to 20 IU or more/0.1 ml in the post-operative period to prevent rejection and inflammation.

In another embodiment, the Botox or similar compound, such as Fasudil, botulinum toxin, (Botox), rhopressa, netasudil, etc. or Wnt inhibitor such as FH535, IWP-2, or integrin inhibitors, are used with squalamine to prevent inflammation and rejection after tissue transplantation.

In one embodiment, Rock inhibitors are used with GSK inhibitors and/or integrin inhibitors in sub-chronic inflammation of hair follicles leading to hair loss, the preparation can be used as a solution, polymeric nanoparticles or microparticles for slow release of picogram release/day.

In one embodiment, Rock inhibitors and a macrolide, such as cyclosporine, mycophenolic acid, or tacrolimus, etc. is used with Rock inhibitors as in a solution, cream, ointment or slow release polymeric nanoparticles or microparticles with biodegradable polymers for treatment of chronic inflammatory processes, such as glaucoma, male hair loss, or alopecia areata, acne vulgaris, in the form of a solution, cream etc. to slow down the loss of hair or prevent it, or in psoriasis to reduce the inflammatory component of the disease without the use of steroidal ointment, or after cosmetic surgery to reduce thermal damage and inflammation.

One of the most common causes of hair loss is male alopecia, which is hormonal and genetic. It occurs during the puberty and continues thereafter. This process though is not considered inflammatory, it is hard to not expect that a very slow progressive inflammation might cause the apoptotic loss of hair stem cells and the hair bulb. However inflammatory processes cause more rapid loss of the hair, such as alopecia areata, psoriasis, or other skin diseases.

The standard therapy for the hair loss is the use of topical minoxidil a blood pressure lowering medication applied twice daily. Minoxidil (Rogaine) is available at 2% to 5% concentrations preparations where it slows down the loss of hair, the mechanism of its action are local vasodilatation and/or nonspecific replacement of dihydrotestosterone (DHT)-binding sites in the hair bulb and nonspecific occupation of dihydrotestosterone (DHT)-binding sites in the hair. The alternative medication is finistride, a 5-alpha reductase inhibitor that blocks conversion of testosterone to DHT. Finasteride is taken orally and is more effective than minoxidil. The other method that may help with the maintaining the hairs longer in women's hair loss, and potentially in men, is the use of laser light radiation to heat up the skin and potentially open the skin capillaries. In progressed stages at present the only manner to cover the loss of hair is by transplantation of some of the remaining hair to new area. The surgical techniques is done as strip transplantation or mini-grafts and micrografts. Minigrafts and micrografts are removed with the size of 1-3 mm in diameter using a knife and a fine forceps or trephine and implanting them in the slit or holes in the recipient skull. Postoperatively, the skin is treated locally with oral prednisone to reduce the swelling of the tissue, and the pain is controlled with ibuprofen, acetaminophen, or codeine etc.

The postoperative side effects are bleeding, tissue swelling, edema, potentially infection, scar or keloid as a result of cytokine release activation of Wnt pathway rho enzymes producing TGF beta that induces excessive scar and keloids.

In one embodiment, after hair transplantation, one administers the standard medication, such as anti-infective solution and dressing to the area to prevent infection with simultaneous administration of oral proscar (finastride) and topical Rock inhibitors, Wnt inhibitors, and/or GSK-3 inhibitors or integrin inhibitors as slow release polymeric nanoparticles or microparticles with or without CPP or ACPP to inhibit the inflammatory component of hair transplantation after the surgery, or in combination with other anti-inflammatory medications, such as squalamine or lanosterols to combat infection as a solution or cream.

In one embodiment of early stage of male alopecia, or alopecia areata that is localized to one or more areas of the skull, one may administer a therapy, such as oral finasteride or topical application of a solution or cream having Rock inhibitors, such as fasudil, Netarsudi, or SAR407899 as a lotion with or without polymeric slow release nanoparticles or microparticles with or without CPP or ACPP, with or without squalamine to inhibit the inflammatory component at non-toxic concentrations or picogram to 100 nanograms or more, or in case of Botulinum toxin at 1-10 international units or more per milliliter applied using a Q-tipped applicator followed with femtosecond, nanosecond, micropulses, millipuses or pulses of less than one second to two second duration or more of laser with wavelength of green to infrared, preferably yellow or red wavelength with an energy length that does not produce any injury or scratches to the skin, but has the effect of tissue rejuvenation and stimulating the stem cells of the hair follicles using a thin laser probe with transparent smooth surface with no sharp edges that can pass through the hair to reach the skull directly, running it over the skull's skin covering all areas to be treated with one or multiple fibers optics ending at the probe's end can fire simultaneously or individually and the power supply has a battery or the hand piece can be disposable.

In one embodiment, the Rock inhibitor is one of Botulinum toxin at 1-10 international units or more per milliliter applied to the skin of the scalp with a Q-tipped applicator as polymeric nanoparticles or microparticles of polylactic or glycolic acid or orthoesters with or without CPP or ACPP, with or without squalamine to release the medication slowly over time to prevent inflammatory processes of the hair bulbs.

Example 6

A 24 year old male patient having symptoms of male inherited androgenic pattern baldness which started 2 years earlier with the loss of hair and thinning of the central and the top of the skull, had used the usual medication to reduce the testosterone hormone, but has not been effective in preventing the hair loss. He chose to be treated with the standard oral finistride medication and laser pulses to the skull treated with topical Rock inhibitors in polymeric nanoparticles or microparticles releasing the medication at concentrations of 100-1000 nanograms/ml applied daily with a Q-tipped applicator daily and the laser pulses once to three times per week to rejuvenate the hair cells and stimulate the stem cells to multiply by laser pulses, 1-3 times a week; the patient returned for the follow-up of 2 month and felt that the hair loss has been diminished by the daily use of the topical application of Rock inhibitors and the laser application sessions.

In one embodiment of early stage male alopecia, or alopecia areata that is localized to one or more areas of the skull, one can administer oral finasteride or topical application of a solution having Rock inhibitors, such as fasudil, Netarsudi, or SAR 407899 as a solution with or without polymeric slow release nanoparticles or microparticles with or without CPP or ACPP but no Botox to inhibit inflammatory component at non-toxic concentrations or picogram to 100 nanogram concentrations applied using a Q-tipped applicator followed with femtosecond, nanosecond micropulses or millipulses or pulses of less than one second to two second pulse duration or more of a laser with the wavelength of green to infrared preferably yellow or red wavelength with an energy length that produces no or minimal injury or scratches to the skin to stimulate the stem cells of the hair follicles, using a thin laser probe with a transparent smooth surface and no sharp edges that can pass through the hair to reach the skull directly, rubbing it over the skull's skin covering all areas to be treated without stopping in one place to prevent excessive injury to the skin having one or multiple fibers optics ending at the probe's end that is connected to a diode laser and can fire individually or multiple pulses as the probe moves over the skin and the power supply has a battery or the hand piece can be disposable.

In one embodiment, after cosmetic surgery, the topical administration of Rock inhibitors, anti-integrin inhibitors or other anti-inflammatory medications, such as squalamine or lanosterols alone or in combination with a macrolide as drops, polymeric nanoparticles or implants for slow release over a long period of time to reduce the inflammation and scarring.

Psoriasis is a genetic disease associate with an autoimmune response with elevated tumor necrosis factor (TNF), release of cytokines, interleukin IL-12, IL-17, IL-23 inflammation and cell proliferation and manifested as plaques demonstrating dry, itchy, swollen, scaly areas of the skin found around the joints (e.g., elbow and knee) with or without joint involvement, and the skin around the plaques are red and inflamed. The lesions may affect any part of the body and may be associated with exfoliation and inflammation which is in general treated with systemic and, in addition to phototherapy, systemic cyclosporine, injectable secukinumab, Adalimumab, etanercept, with their systemic side effects including lymphoma and topical application cooking oil, sea salt, topical steroids and Vitamin D as Calcipotriol with some limited beneficial effect.

In one embodiment, a patient suffering from skin psoriasis which is treated with the standard topical medications and steroid, causes thinning of the skin, bruising and bleeding.

In one embodiment, the psoriasis lesions of a patient are treated with a combination of Rock inhibitors such as Fasudil, botulinum toxin, (Botox), rhopressa, netasudil, etc. and/or Wnt inhibitor compounds, such as FH535, IWP-2, PNU-74654, IWR-1endo, IWR-exo, Demethoxycurcumin, CCTO36477, KY02111, WAY-316606, SFRP or integrin inhibitor such as abegrin cilengitide, abciximab, tirofiban, natalizumab eptifibatide, risuteganib alone or in combination locally used in non-toxic concentrations or picogram to 1-30 or more micrograms as nanoparticles or dendrimers with ACPP or CPP for better tissue penetration, microparticles, PLA, PGLA, or combination, or polycaprolactone, or as liposomes, or micelles to reduce the inflammation processes locally alone or in combination with systemic immune therapy.

In another embodiment psoriasis lesions of a patient are treated with a combination of Rock inhibitors such as Fasudil, botulinum toxin, (Botox), rhopressa, netasudil, etc. or Wnt inhibitor compounds, such as FH535, IWP-2, PNU-74654, IWR-1endo, IWR-exo, Demethoxycurcumin, CCTO36477, KY02111, WAY-316606, SFRP or integrin inhibitors such as abegrin, cilengitide, or Wnt inhibitor with ACPP or CPP for better tissue penetration or integrin inhibitors alone or in combination locally used in non-toxic concentrations or picogram to 1-30 or more micrograms as nanoparticles or dendrimers in combination with Calcipotriol in treatment of psoriasis as lotion, ointment, or cream with 0.001-0.008% of calcipotriol to reduce the inflammatory response.

Example 7

A 15 year old female patient was suffering from early stage psoriasis around the elbows and neck that did not improve despite the topical therapy, steroids, Vitamin D analogues, Calcipotriene (Dovonex calcineurin inhibitors, Salicylic acid, topical retinoids, coal tar and moisturizers in an ointment, light and UVB radiation, the patient refused to have systemic immune suppressants such as methotrexate, cyclosporine or biologics such as secukinumab (Cosentyx) and ixekizumab (Taltz)etanercept (Enbrel), infliximab (Remicade), adalimumab (Humira), ustekinumab (Stelara), golimumab (Simponi), apremilast (Otezla), the patient was treated with therapies without steroids but administering Rock inhibitors, such as nanoparticles, or microparticles conjugated with CPPs or slow release implant of Fasudil etc. or Wnt inhibitors or integrin inhibitors alone or in combination with other topical therapies such as squalene as ointment or cream which improved her condition without having the side effects of steroids, biologics.

In one embodiment, the psoriasis lesions of a patient are treated with a combination of Rock inhibitors such as Fasudil, botulinum toxin, (Botox), rhopressa, netasudil, etc. or Wnt inhibitors such as FH535, IWP-2, PNU-74654, IWR-1endo, IWR-exo, Demethoxycurcumin, CCTO36477, KY02111, WAY-316606, SFRP or integrin inhibitors such as abegrin cilengitide, abciximab, tirofiban, natalizumab eptifibatide, risuteganib alone or in combination locally used in non-toxic concentrations of picogram to 1-3 or more micrograms as nanoparticles, dendrimers, microparticles, PLA, PGLA, or combination or polycaprolactone or as liposomes, or micelles or implantable along with fillers such as Juvederm and Juvederm Voluma (hyaluronic acid filler; Allergan), Belotero (hyaluronic acid; Merz Pharmaceuticals), Sculptra (poly-L-lactic acid), Sanofi or combination or as porous implantable porous silicon injected under the skin to release the medication over 1-3 years, and gradually reduce the inflammation processes locally alone or in combination with systemic immune therapy.

In one embodiment, the joint psoriasis is treated with injection inside the joint of preparation of Rock inhibitors such as Fasudil, botulinum toxin, (Botox), rhopressa, netasudil, etc. or Wnt inhibitors such as FH535, IWP-2, PNU-74654, IWR-1endo, IWR-exo, Demethoxycurcumin, CCTO36477, KY02111, WAY-316606, SFRP or integrin inhibitors such as abegrin cilengitide, abciximab, tirofiban, natalizumab eptifibatide alone or in combination locally used in non-toxic concentrations or picogram to 1-3 or more micrograms as nanoparticles dendrimers, microparticles, PLA, PGLA, or combination or polycaprolactone or as liposomes, or micelles or implantable erodible polymers with the size of 0.1-3 mm and diameter of 10-100 or more microns.

In one embodiment, one administers the combination of Rock inhibitors in nano and picogram concentrations such as fasudil, Netarsudil and macrolides such as cyclosporine, mycophenolic acid, tacrolimus, or ascomycin etc. at concentrations of 0 00000001-1% w.v or applied as non-toxic doses in the treatment of open angle glaucoma or in conjunction with alpha adrenergic anti-glaucoma medications as topical drops or polymeric nanoparticles or implants under the conjunctiva, to the cornea, and Rho-kinases GSK 269962, potent and selective Rock inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent Rock inhibitor PKI1447 dihydrochloride, potent and selective Rock inhibitor; antitumor SB 772077B, potent Rho-kinase inhibitor; vasodilator SR 3677 dihydrochloride, potent, selective Rho-kinase (ROCK) inhibitor TC-S7001, potent and highly selective Rock inhibitor; orally active Y-27632 dihydrochloride or SAR407899.

In one embodiment, the integrins are transmembrane receptors that act as mechanosensors and signal transduction platforms, adhesion molecules in many diseases processes, and their inhibition can prevent or treat the development of the inflammatory diseases and their sequelae.

In one embodiment, one administers polymeric nanoparticles or dendrimers with the anti-integrins such as Risuteganib, vedolizumab, integrin-targeted therapeutics, abegrin cilengitide, abciximab, tirofiban, natalizumab eptifibatide are used alone or in combination with Rho-kinase inhibitors or Wnt inhibitors among others, or anti-VEGFs, GSK-3 inhibitors, or GSK 429286 to reduce the inflammation and reduce cell proliferation, and can be used simultaneously for drug delivery purposes in cutaneous inflammatory diseases.

In one embodiment, one administers polymeric nanoparticles or dendrimers with Rock inhibitors, Wnt inhibitors, integrin inhibitors, or GSK inhibitors that are used in a slow release form as polymeric nanoparticles such as biodegradable polylactic acid, polyglycolic acid, (PLGA) copolymer, PLGA copolymer, about 10% to 90% by weight of the implant, or a 50/50 PLGA copolymer for about 3-months to a year, or in porous silicon for 1-3 years in concentrations of 0.01 microgram/day to 5 micrograms/day as needed.

In one embodiment, the GSK-3 inhibitor lithium chloride at mM concentrations or SB-216763, a GSK-3β cell-permeable inhibitor can be added to the solution of Rock inhibitors or the ointments to interrupt the Wnt pathway and reduce localized skin inflammation and enhance the nerve growth after the skin surgery or inflammatory skin or mucosa diseases preventing severe fibrosis of the tissue.

In one embodiment, the Rock inhibitors, Wnt inhibitors, integrin inhibitors, or GSK inhibitors are used along with antiproliferative medications after removal of cutaneous precancerous lesion or after skin or tumor resection or with antibiotics in infection caused by bacteria using nanoparticles, dendrimers, and microparticles of PLA, PGLA, with crosslinking the tissue using riboflavin and UV radiation.

In one embodiment, the Rock inhibitors, Wnt inhibitors, integrin inhibitors, Fasudil, botulinum toxin, (Botox), rhopressa, netasudil, etc. or Wnt inhibitors such as FH535, IWP-2, or GSK inhibitors are used along with macrolides, anti-infective medication with or without squalamine are administered in a physiological preparation with polymeric nanoparticles, microparticles, or cream for surface application after thermal or chemical burns of the skin or mucosa such as conjunctiva, mouth, accidental ingestion of hot fluid or chemical, etc. face, hand, legs or skull etc. as a solution, cream, etc. to reduce inflammation and scarring.

In one embodiment, nanoparticles deliver Rock inhibitors, Wnt inhibitors, integrin inhibitors, Fasudil, rhopressa, netasudil, etc. or Wnt inhibitors such as FH535, IWP-2, or GSK inhibitors are used along with macrolides, anti-infective medication with or without squalamine are administered in a physiological preparation with polymeric nanoparticles, microparticles, or cream with or without squalamine/antibiotics or with semifluorinated alkane/siloxane for surface application after thermal or chemical burns of the skin or mucosa such as conjunctiva, mouth, accidental ingestion of hot fluid or chemical etc. face, hand, legs or skull etc. as solution, cream, etc. to reduce activation of TGF-beta and scarring.

In one embodiment, nanoparticles deliver rock inhibitors, Wnt inhibitors, integrin inhibitors, Fasudil, rhopressa, netasudil, etc. or Wnt inhibitors such as FH535, IWP-2, or GSK inhibitors are used along with macrolides, anti-infective medication with polymeric nanoparticles, microparticles, surface application after thermal or chemical burns of the skin or mucosa such as conjunctiva, mouth, accidental ingestion of hot fluid or chemical etc. face, hand, legs or skull to the respiratory tract to reduce activation of TGF-beta and scarring, and fibrosis after inflammatory diseases of the lung.

Inhalation has been used for long time for delivery of medication not only to the lung but also for systemic therapy bypassing intravenous administration. However, it seems to be most attractive for the diseases affecting the lungs and the cardiovascular system which is closely related to the arterial oxygenated blood returning to the heart, left ventricle, aorta and coronary arteries etc.

The distribution of the medication through inhalation is fast and can be also localized to specific lobes of the lung if delivered through a nasal tube under bronchoscopy visualization of the catheter or a tube, after local spray anesthesia of the surfaces of the nasal, throat and trachea. The respiratory tract include nose pharynx followed by trachea, bronchi and lung alveoli. The right lung has three lobes whereas the left lung has two lobes. Both have alveoli, blood that are covered with a layer of mucin and fluid and function as gas exchange, in addition to its vessels and lymph nodes. The clearance of the medication from the lung occurs mostly by systemic absorption, mucociliary or macrophage enzymatic activity.

Liquid nebulizers or pressure metered doses are used to deliver aerosolized medications in the respiratory system, however, the use of standard methodology has suffered from short half life time necessitating repeated applications.

Small lipophilic and hydrophobic drugs are comprehensively absorbed within 1-2 minutes from the lung into the systemic circulation via passive diffusion, while small hydrophilic drugs are absorbed within 65 minutes, factors that contribute to enhance drug bioavailability are slowing down the enzymatic degradation, targeting the site of the lung, or the diseases process, reduce the frequency of the application of the medication and reducing local or systemic side effects. Among these factors are the size of the particles delivered.

In general, the particles of 2-3 microns are deposited in the upper respiratory tract, whereas the smaller than 2 micron particles reach the lung alveoli and the particles smaller than 0.5 micron can also be exhaled. Therefore, the size of the particles determines where the particles travel and also the length of the duration of the drug delivery. The majority of deposited particles are cleared by mucociliary clearance that is increased by inflammatory diseases of the lung. The aerosolized particles have a size of 0.001 to about 100 microns. One successful example of particulate-based drug delivery system includes the use of large porous microparticles (LPPs) with size greater than 5 μm, but with a density of less than 0.1 g/L or less. The LPPs showed an appealing ability to escape macrophage uptake and deposit homogeneously in the lung.

In one embodiment, the nanoparticles or microparticles can be can be the size of 0.1-5 microns, can be swellable after administration, crosslinked or noncrosslinked chitosan, or pegulated poly chitosans, micelles, hyaluronic acid, HA-conjugated medication, PEG-microspheres of lactic acid or glycolic acid or combination liposomes filled with medication, solid lipid nanoparticles or PEG-SLN, chitosan, poly (lactic-co-glycolic) acid, poly(lactic) acid, poly(butylcyanoacrylate), and poly(lactic-co-lysine, poly butylcyanoacrylate (PCL) or Polymeric micelles, amphiphilic macromolecules self-assemble to core-shell nanostructure or Cyclodextrins (CDs) are cyclic polymers of α-D-glycopyranose composed of cyclic oligosaccharides, CDs; α-, β- and γ-CDs, etc.

In one embodiment, the antibody-coated polymeric nanoparticles can carry antibiotics, antifungals, antiviral medication, macrolides, antiproliferative agents in addition to Rock inhibitors, or Wnt inhibitors or GSK inhibitors or integrin inhibitors to reduce inflammatory components of the lung disease, prevent pulmonary fibrosis, in patients with tumors of the lung along with antiproliferative agents, multiple checkpoint inhibitors, or immune stimulators such as IL-2, Tumor Necrotic Factors, Toll-like receptors, etc.

In one embodiment, the antibody coated polymeric nanoparticles are delivered with nebulizers, or pressure metered dose devices.

In one embodiment, the antibodies are coated to deliver the medications etc.

In one embodiment, the nanoparticles are delivered locally in the lung under the control of a bronchoscope in aerosolized polymeric nanoparticles.

In one embodiment, the polymeric nano- or microparticles are delivered in semifluorinated alkane that evaporates fast while leaving the medication at the desired location locally or diffusely in the lung carrying Rock inhibitors, or Wnt inhibitors, or GSK inhibitors or anti-integrins in conjunction with antibiotics, antifungal, antivirals, anti-neoplastic medication to control the inflammatory process in the lung and eliminating the side effects of steroids or NSAIDS.

In one embodiment, the polymeric nano or microparticles are delivered in semifluorinated alkane that evaporates fast while leaving the medication at the desired location locally or diffusely in the lung carrying Rock inhibitors, or Wnt inhibitors, or GSK inhibitors or ant-integrins in conjunction with medications that stabilize heart rhythm, or treat atherosclerotic disease of the coronary vessels, aorta, lung vessels or acrotic artery and the entire circulatory diseases.

Although semifluorinated alkane (SFA) compounds have been described for the transport of various medications, and to deliver various medications, the maximal expected duration of medication after the SFA evaporation is about 4-6 hours. They have not been described to transport slow release medications from polymeric compounds such as polymeric compositions orthoesters, Anhydrides, amides, calcium alginate polysaccharides functionalized celluloses, carboxymethylcellulose, polycaprolactone, copolymers of glycolic and lactic acid, polymers of D-lactic acid, L-lactic acid, racemic lactic acid, glycolic acid, or porous silicon (not silicone oil), etc. The SAF delivery of medication using nanoparticles of 1-100 nm limits the duration of the medication release, which occurs fast. However, polymeric nanoparticles can be made from preferably about 1 nm-150 micron in diameter and 20 micron-1 mm or more in length depending if it is used for inhalation or on the surface of the skin or mucosa and use the SAF for their carrier while the polymeric compound remains on or inside the tissue for days or even months if desired for the release of the medication depending on the percentage of the drug per volume of the polymer such as 10% w/v to 50% w/v or more is selected and the polymeric compound. This combination of SAF with polymeric slow release compound(s) delivers the medication longer than described previously for the semifluorinated alkane/medication alone and eliminates the need for daily multiple applications. One can also choose the previously described composition of SFA with a straight chain or branched perfluoro alkyl group or a composition depending on the number of carbon molecules, etc. that can evaporate faster or slower at room temperature or when it reaches 37 C, or the body temperature. The active component of the SFA/Polymer for use in the present preparation are compounds that inhibit or stimulate one or the other cellular activity such as Wnt inhibitors, Rock inhibitors, GSK inhibitors, or integrin inhibitors; though practically any other medications can be delivered with this system such as antibacterials, antifungals, anti-virals anti-parasitics, anti-inflammatory agents, including prostaglandin analogues, antihistaminic, growth hormones, or biologics, anti-VEGFs, macrolides, anti-proliferative, vasoconstrictive or vasodilatators.

In one embodiment, perfluorocarbon liquids or semifluorinated alkane such as F4H5, F4H6, F4H8, F6H6 F6H8 etc. alone or in combination with one siloxane can be used as a carrier formulation to carry slow release polymeric nano- to microparticles of polylactic, micelles, or polycaprolactone, copolymers of glycolic and lactic acid of Rock inhibitors, such as fasudil netarsudil, SAR407899, etc. and/or Wnt inhibitors such as FH535, IWP-2, PNU-74654, IWR-1endo, IWR-exo, or GSK inhibitors SB-216763 etc. at non-toxic concentrations releasing 1 picogram to nanogram/ml or higher concentrations or integrin inhibitors such as abciximab, Eptifibatide, Tirofiban, αIIbβ3 antagonists, Natalizumab, 3 microgam/ml as topical applications after refractive surgery of the cornea, cataract, LASIK or smile procedure or glaucoma surgery or glaucoma laser surgery or after cosmetic facial laser surgery or skin resurfacing, or after laser surgery, etc. for laser and non-laser treatment of acne vulgaris or as topical application, lotion, cream in dry eye, psoriasis, skin or mucosa burn, or after laser surgery for hair regrowth or hair transplantation along with an antibiotic to prevent infection while discouraging keloid formation, in oral, nasal, or respiratory system diseases, for asthma, pulmonary hypertension, or in treatment of pneumonia to inhibit TGF-beta activation and to prevent pulmonary fibrosis.

Example 8

A 40 year old patient had undergone a LASIK procedure one month ago for a −7.00 D correction of myopia developed reduced visual acuity in an irritated eye with presence of debris at the lid margin and low tear film production. The corneal sensation was reduced as measured with Cochet Bonnet aesthesiometer, loss of cornel reflex, the conjunctiva and the lid margin were inflamed. The patient was treated with topical application of a Rock inhibitor as polymeric PGLA nanoparticle and in semifluorinated alkane and polymeric PGLA nanoparticle of cyclosporine, once a day for one week then as needed once or twice a week. The treatment was continued for another three months, the discomfort disappeared and tear production increased and visual acuity returned to normal.

In one embodiment, perfluorocarbon liquids or semifluorinated alkane such as F4H5, F4H6, F4H8, F6H6 F6H8 etc. alone with or without siloxane with polymeric slow release nano-microparticles of polylactic, polyglycolic acid, or polycaprolactone or porous silicon dispersed in the semifluorinated alkane formulation, conjugated with or without an additional amphiphilic cationic polymer such as such as CPP or ACPP, poly{N—[N-(2-aminoethyl)-2-aminoethyl] aspartamide} (PEG-pAsp(DET)/semifluorinated alkane complex etc. as a lotion or suspension, cream to carry Rock inhibitors such as fasudil, netarsudil, SAR407899, etc. and/or Wnt inhibitors such as FH535, IWP-2, PNU-74654, IWR-1endo, IWR-exo, etc. or integrin inhibitors such as abciximab, Eptifibatide, Tirofiban, αIIbβ3 antagonists, Natalizumab, 3 microgam/ml or GSK inhibitors at non-toxic concentrations of 1 picogram to nanograms or more daily release from the nanoparticles at a concentration as needed with or without squalamine, lanosterol, squalene preparation for topical application after refractive surgery of the cornea, cataract, LASIK or smile procedure or glaucoma surgery or after cosmetic facial laser surgery or skin resurfacing, vaginal laser surgery, or after acne laser surgery or without surgery etc. to prevent cellular proliferation, scar formation and keloid and for treatment of acne vulgaris encouraging wound healing, without the use of steroid and NSAIDs or as topical application or injected under the skin in psoriasis, or after laser surgery for hair regrowth with or without laser application or hair transplantation to encourage hair growth and prevent keloid formation.

Intraocular inflammation affects the trabecular meshwork of the eye, blocking the outflow channel of the intraocular fluid. In addition, inflammation incites production of cell adhesion molecules, cell adhesion, cell proliferation, cell migration and production of the fibrous membrane leading to damage to the trabecular meshwork and outflow channels of the aqueous.

Rock inhibitors block the activity of the Rho enzyme which is a part of the serine-threonine family that acts when the Wnt signaling is activated during the inflammation and cell proliferation, and scar formation. Its inhibition reduces the inflammation and cell proliferation, and in addition, it enhances the vascular blood flow and prevents vasoconstriction and ischemia. Polymeric delivery of Rock inhibitors for a long therapeutic effect after ocular surgery that prevents inflammation and scarring of the tissue specifically where the clear media is important, such as the cornea, has not been reported.

In one embodiment, an exemplary dosing of netarsudil 0.02% (0.2 mg per ml)=200 microgram/ml or 20 microgram/ 0.1 ml.

In one embodiment, one administers topically, at doses of 1-200-microgram per milliliter or more, or injects intraocularly, subconjunctivally, in the choroid, or the vitreous at doses of 1-20 micrograms per 0.1 milliliter or more, as implants a bio-erodible implant or polymeric nanoparticle or microparticles to release the medication at a non-toxic dose of nanogram to microgram concentrations or more per day for a long time at 1-6 or 12 months comprising an anti-inflammatory agent acting on cell pathways of inflammation including Wnt inhibitors, Rho inhibitors such as fasudil, netasudil, or ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, botulinum toxin (Botox) potent, selective Rho-kinase (ROCK) inhibitor TC-57001, potent and highly selective ROCK inhibitor; orally active Y-27632 dihydrochloride, where the inflammation is mediated by various conditions of the eye, such as post ocular surgery procedures such as refractive surgery, LASIK, smile, PRK, trauma, cataract surgery, glaucoma surgery, complicated or recurrent vitreoretinal surgery, and/ or laser surgery.

In one embodiment, one administers the Rock inhibitors with a slow release drug delivery system, such as polymers, matrices, microcapsules, nanoparticles or microspheres, microparticles of porous silicon or other delivery systems formulated from, polyglycolic acid, lactic acid, combinations of glycolic and lactic acid, liposomes, silicon, as nano- or microparticles with (alpha)-cyclodextrin, or (beta)-cyclodextrin, or (gamma)-cyclodextrin, hydroxypropyl-b-cyclodextrin (bHPCD) or polyanhydride polyvinyl acetate alone or in combination with polyethylene glycol, etc. The delivery of the polymeric implant for slow release of medication such as porous silicon implant, polycaprolactone can be implanted intraocularly where the inflammation is mediated by various conditions of the eye such as post ocular surgery procedures such as refractive surgery, such as LASIK, smile procedure, trauma, cataract surgery, glaucoma surgery, or glaucoma selective laser trabeculoplast (SLT) for glaucoma, vitreoretinal surgery, vitrectomy, sub-retinal surgery, recurrence of retinal detachment, and laser surgery of the retina in diabetic retinopathy or diabetic macular edema.

Integrins are transmembrane proteins which are active in cell proliferation and cell-to-cell adhesion in many disease processes and scarring.

In one embodiment, one administers integrin inhibitors as a slow release drug delivery system, such as polymers, matrices, microcapsules, nanoparticles or microspheres, microparticles of porous silicon or other delivery systems formulated from polyglycolic acid, lactic acid, combinations of glycolic and lactic acid, liposomes, silicone, as nano- or microparticles with (alpha)-cyclodextrin, or (beta)-cyclodextrin, or (gamma)-cyclodextrin, hydroxypropyl-b-cyclodextrin (bHPCD) or polyanhydride polyvinyl acetate alone or in combination with polyethylene glycol, etc. The delivery of polymeric implant for slow release of medication such as porous silicon implant, polycaprolactone can be implanted intraocularly such as abegrin cilengitide, abciximab, tirofiban, natalizumab eptifibatide or a low concentration 1 micrograms to 10 micrograms as a solution or polymeric nano- or microparticles or suspension, topically, at doses of 1-200-micrograms per milliliter or more or injecting intraocularly, subconjunctivally, in the choroid, or the vitreous at doses of 1-20 micrograms per 0.1 milliliter or more, or as implants as a bio-erodible implant or polymeric nanoparticles or microparticles to release the medication at a non-toxic dose of a nanogram to microgram concentration or more per day for a long time at 1-6 or 12 or more months comprising integrin inhibitors or in combination with GSK inhibitors, wherein the chronic inflammation-mediated by various conditions of the eye such as in diabetes retinopathy, immune response, optic neuritis, retinitis, uveitis, or caused by pathogens or post-ocular surgery procedures such as refractive surgery, trauma, cataract surgery, glaucoma surgery, vitreoretinal surgery, laser surgery regenerative procedures such as stem cell transplantation and gene therapy, clinically the inflammatory process is associated with low grade to frank serum leakage from the vascular structure of the retina or the choroid causing bleeding, damage to the vascular endothelial cell, vascular occlusion and ischemia, or macular edema.

Wnt signaling pathways are activated by the cell surface receptors initiating cell division, cell proliferation, and inflammation and cancer cell metastatic process.

In one embodiment, the Wnt inhibitors such as Dickkopf (Dkk) proteins, Wnt Inhibitory Factor-1 (WIF-1) in a non-toxic nano- to microgram concentration, Rock inhibitors or integrin inhibitors such as abegrin cilengitide, abciximab, tirofiban, natalizumab eptifibatide or a low concentration 1 microgram to 10 micrograms as a solution or GSK-3 inhibitors with or without ACPP may be injected into the eye, for example, injection under the conjunctiva or tenon capsule, intravitreal injection, or retrobulbar injection as a slow release nanoparticle. The agent(s) may be administered with a slow release drug delivery system, such as polymers, matrices, microcapsules, nanoparticles or microspheres, microparticles of porous silicon or other delivery systems formulated from, polyglycolic acid, lactic acid, combinations of glycolic and lactic acid, liposomes, porous silicon, as nano- or microparticles with (alpha)-cyclodextrin, or (beta)-cyclodextrin, or (gamma)-cyclodextrin, hydroxypropyl-b-cyclodextrin (bHPCD) or polyanhydride polyvinyl acetate alone or in combination with polyethylene glycol, etc. The delivery of a polymeric implant for slow release of medication such as porous silicon implant, polycaprolactone can be implanted intraocularly, in the peripheral lens capsule after cataract surgery, as a circle, C-shaped, rod, wire or nanoparticle, over the lens in the choroid for example, implanted under the conjunctiva, implanted in the wall of the eye, sutured to the sclera, for long-term drug delivery or injected in the vitreous cavity for a short term drug administration where the inflammation is mediated by various conditions of the eye such as post ocular surgery procedures such as corneal refractive surgery, LASIK, smile, photorefractive keratectomy, trauma, cataract surgery, glaucoma surgery, vitreoretinal surgery, laser surgery, or infection.

In one embodiment, the topical application of Rock inhibitors, integrin inhibitors, GSK-3 inhibitors, Wnt inhibitors are applied to the cornea and conjunctiva as a solution or polymeric nanoparticles or an implant under the conjunctiva to release medication for 3-6 months delivering nanogram to microgram concentrations or in case of Botulinum toxin (Botox) <1-10 international unit as an injection in 0.1-3 milliliters or topical application or spray or evaporative solution or in a evaporative semifluorinated alkane to enhance corneal nerve growth and corneal sensation to prevent dry eye or pain and scarring after the corneal surgery including corneal transplant, and cataract extraction.

In one embodiment, biodegradable polymeric compositions are orthoesters, anhydrides, amides, calcium alginate, polysaccharides, functionalized celluloses, carboxymethylcellulose, polycaprolactone, copolymers of glycolic and lactic acid, polymers of D-lactic acid, L-lactic acid, racemic lactic acid, glycolic acid, porous silicon implant or nano- or microparticles. The polymer can be of any size, but preferably for injectable compounds, it can be about 2-150 micrometers or larger in diameter and 20 microns to 4 millimeters in length or longer.

In one embodiment, the polymeric implant or nano- or microparticles can be combined with antibiotics, antifungals, antivirals, antineoplastic macrolides, etc. as needed.

In one embodiment, the device contains a ROCK inhibitor such as Fasudil, netarsudil, etc. or ROCK inhibitor selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitor TC-57001, potent and highly selective ROCK inhibitor; orally active Y-27632 dihydrochloride.

In one embodiment, the device may also contain at least one of an anti-vascular endothelial growth factor (VEGF), such as avastin, ranizumab, afibercept, an anti-platelet derived growth factor (PDGF), an integrin inhibitor such as abegrin cilengitide, abciximab, tirofiban, natalizumab eptifibatide or a low concentration 1 microgram to 10 micrograms as a solution, a beta-blocker, an adrenergic agonist, a carbonic anhydrase inhibitor, a cholinergic agent, a prostaglandin analog, a derivative of cannabinoid receptors, and combinations thereof working synergistically as needed or GSK inhibitor 429286.

In another embodiment, Rock inhibitors or integrin inhibitors such as abciximab, Eptifibatide, Tirofiban, αIIbβ3 antagonists, Natalizumab, 3 mg to ±52 μg/mL, MLN-00002, Firategrast, IVL745, antagonists of αvβ3 and/or αvβ5 integrins, LM609, Vitaxin, Abegrin, CNTO95, Cilengitide. MLD-based disintegrins, L000845704, SB273005, Volociximab, JSM6427, are administered intraocularly or topically to a patient suffering from ocular inflammatory processes caused by viral or non-viral infection or after eye surgery, such as glaucoma, retinal detachment, or cataract extraction at a concentration in the range of about 1 nanogram/ml (0.0000001%) to less than 1 microgram/ml (less than 0.0001%).

In one embodiment, injectable or polymeric nanoparticle or microparticles of the Wnt inhibitors such as FH535, IWP-2, PNU-74654, IWR-1endo, IWR-exo, niclosamide or Rock inhibitors or integrin inhibitor such as abegrin cilengitide, abciximab, tirofiban, natalizumab eptifibatide or a low concentration 1 microgram to 10 micrograms as a solution or polymeric nanoparticles, GSK-3 inhibitors 429286, alone or in combination with or without ACPP may be injected into the vitreous cavity as an implant or nano- or microparticles at concentration of 1 nanogram to few microgram release per day for 1-6 months in chronic inflammatory diseases, such as diabetic retinopathy, uveitis, macular edema, dry and wet macular degeneration, with or without anti VEGFs, retinal detachment, ocular tumors, multifocal choroiditis, uveitis, proliferative vitreoretinopathy (PVR), fungal or viral infections, sympathetic opthalmia, histoplasmosis, and uveal diffusion.

In another preferred embodiment, proliferative vitreoretinopathy (PVR) caused by recurrent retinal detachment and formation of traction bands and membrane over and under the retina, nanoparticles, e.g., dendrimer or microparticles of the Wnt inhibitors such as FH535, IWP-2, PNU-74654, IWR-1endo, IWR-exo, niclosamide or Rock inhibitors or integrin inhibitors such as abegrin cilengitide, abciximab, tirofiban, natalizumab eptifibatide or a low concentration 1 microgram to 10 micrograms as a solution or polymeric nanoparticles with CPP, or GSK-3 inhibitor 429286, alone or in combination with or without ACPP may be injected in the vitreous cavity, subconjunctivally, or inside the choroid to prevent the side effects of the surgery.

Laser trabeculoplasty is a procedure in which argon laser is applied to the trabecular meshwork of the eyes outflow channels. ALT is applied to reduce the intraocular pressure in about 20-30% of cases after the one year. The disadvantages have been potential scar formation in the trabecular meshwork. Subsequent studies using selected laser trabeculoplasty (SLT) demonstrated that the thermal or coagulative energy may not have been needed for many of the patients.

Though various laser pulses have been used for SLT, no report describes the use of femtosecond to nanosecond pulses.

In one embodiment, SLT laser application using femtosecond, nanopulse or micropulse application encourages the renewal of the remaining cells, and to treat glaucoma. In one embodiment, therefore it would be desirable to eliminate the inflammatory process using Rock inhibitors such as fasudil hydrochloride (inhibitor of cyclic nucleotide dependent- and rho kinases); netarsudil rhpressa, GSK 429286 (a selective ROCK inhibitors); H 1152 dihydrochloride (a selective ROCK inhibitor); glycyl-H 1152 dihydrochloride (a more selective analog of H 1152 dihydrochloride); HA 1100 hydrochloride (a cell-permeable, selective ROCK inhibitor); SR 3677 hydrochloride (a potent, selective ROCK inhibitor); Y 39983 dihydrochloride (a selective ROCK inhibitor); and Y 27632 dihydrochloride a selective p160 ROCK inhibitor or Wnt inhibitors, such as FH535, IWP-2, PNU-74654, IWR-1endo, IWR-exo, niclosamide or integrin inhibitor such as abegrin cilengitide, abciximab, tirofiban, natalizumab, eptifibatide or a low concentration 1 micrograms to 10 micrograms as a solution or polymeric nanoparticles with CPP or GSK3 inhibitors 429286 have a beneficial effect and assists in reduction of the intraocular inflammation at the trabecular meshwork, thus reducing the intraocular pressure while increasing the inflow and outflow of the aqueous and simultaneously having a neuroprotective effect on the retinal ganglion cells.

In one embodiment, in addition to abegrin cilengitide, abciximab, tirofiban, natalizumab, or eptifibatide, the integrin inhibitor may also be in the form of R-G-Cysteic Acid (i.e., linear form of R-G-NH—CH(CH.sub.2-SO.sub.3H) COOH or cyclic form of R-G-NH—CH(CH.sub.2-SO.sub.3H)COOH) and their a derivatives as a solution or slow release compound such as PLGA or micelles or other polymeric nanoparticle.

In one embodiment, one implants or injects a bioerodible polymer having a Wnt inhibitor such as FH535, IWP-2, PNU-74654, IWR-1endo, IWR-exo, niclosamide inhibitors or Rock inhibitors or integrin inhibitor or GSK-3 inhibitors 429286, alone or in combination with or without ACPP, whereby an agent is released from the polymeric body by erosion of the polymer, and the medication is delivered in the vitreous cavity or in the anterior chamber at the rate of 0.1 nanograms to 1 micrograms per milliliter or more to achieve a constant concentration of 1 nanogram to microgram or more per day for 3 weeks to 6 months after SLT or any other surgical procedure.

The increased intraocular pressure over time damages the retinal ganglion cells through various pathways, specifically activation of transient receptor potential vanillod isoform4 (TRPV4) ion channels, pannexin-1 (Panx1), and p2x7 receptors that ultimately lead to the retinal ganglion cell degeneration. In one embodiment, with the rise in the intraocular pressure, Rock inhibitors are administered simultaneously with probenecid to inhibit pannexin-1 (Panx1), and p2x7 receptors.

In one embodiment, one uses Rock inhibitors, with Wnt inhibitors or Anti-integrins or GSK inhibitors given topically subconjunctivally or intravitreally as a slow release polymer that reduces the signal for cellular adhesion and proliferation to eliminate the side effects of the rise in the intraocular pressure and damage to the retinal ganglion cells.

In one embodiment, the Wnt inhibitors or Rock inhibitors or integrin inhibitors such as abegrin cilengitide, abciximab, tirofiban, natalizumab eptifibatide or a low concentration 1 microgram to 10 micrograms as a solution or polymeric nanoparticles or GSK inhibitors 429286 can be in polymeric nanoparticles, micelles, solution as a topical application, delivering the medication from one nanogram to one microgram to 20 micrograms per day or more. The medication can be implanted or injected in the eye as an implant in a micro-nanoparticle format in dendrimers, or polylactic or polyglycolic acid or a combination or as slow drug delivery polymers using chitosan or polycaprolactone, porous silicon or coated with CPP or ACPP to reduce the inflammatory process, etc.

In one embodiment, small molecule Wnt inhibitor PKF118-310, the Wnt/β-catenin pathway inhibitor and Fasudil, a Rock inhibitor Fasudil (HA-1077), a selective RhoA/Rho kinase (ROCK) inhibitor, or Y-27632, small molecule inhibitor of ROCK1 and ROCK2, with CPP or ACPP, etc. may be dissolved in an organic solvent such as DMSO or alcohol or sterol, lanosterol, squalene, and/or squalamine, with CPP or ACCPP or containing a polyanhydride, poly(glycolic) acid, poly(lactic) acid, or as nano- or microparticles with (alpha)-cyclodextrin, or (beta)-cyclodextrin, or (gamma)-cyclodextrin, hydroxypropyl-b-cyclodextrin (bHPCD) or polycaprolactone polymer or dendrimers to release a non-toxic dose of medication slowly at desired concentration to the external or internal eye at a non-toxic concentration or along with a macrolide, cyclosporine A, mycophenolic acid, ascomycin, tacrolimus or anti-integrin or GSK-3 inhibitors 429286, or such as a topical lithium or zinc preparation, bis-indole, indirubin, aminopyrimidines, arylindolemaleimides SB-216763, Paullones, pyrazolo [3,4-b] quinoxalines, human kinome, tideglusib, β-carboline alkaloids β-carboline alkaloids Palinurin and tricantin, peptide L803-mts, Axin GID-25 residues, NP-Tideglusib (Noscira).

Other lasers are used to treat diabetic retinopathy, macular edema, to reduce the ischemic retina and VEGF production. However, any laser application, including when used to treat the retinal tear, or open a hole in the iris for passage of aqueous, is associated with minor or major thermal release and damage to the cells exposed to it and causes activation of inflammatory cell pathways leakage of the fluid from the capillaries and cytokine release. The Rock inhibitors, Wnt inhibitor and integrin inhibitors or GSK inhibitors 429286, application to the laser treated areas reduces the unwanted side effects of laser application such as inflammation, cell migration and severe scar formation.

In one embodiment, after laser surgery, a preparation of Rock inhibitors, Wnt inhibitors, or integrin inhibitors alone or in combination can be used to reduce the inflammatory side effects and severe scar formation.

In one embodiment, the Rock inhibitor is used to reduce TGF-β production after therapy and the subsequent scar formation in form of drops or combined with polymeric nanoparticles for slow release delivery after any ocular surgery such as retinal detachment, vitrectomy, retinotomy, glaucoma surgery, cataract surgery, laser trabeculoplasty by intraocular injection or as slow release nanoparticles, dendrimers, polyglycolic acid (PGA) or polylactic acid PLA or a combination or polycaprolactone or chitosan or as liposomal preparation or micelles.

In one embodiment, the Rock inhibitors are selected from the group consisting of Fasudil, Ripasudil, RKI-1447, Y-27632, GSK429286A, Y-30141, and combinations thereof where the device releases the ROCK inhibitor for 3 months to 3 years.

In one embodiment, the Rock inhibitors are selected from the group consisting of Fasudil (HA-1077 a selective RhoA/Rho kinase (ROCK) inhibitor), Y-27632, small molecule inhibitor of ROCK1 and ROCK2 which act as an anti-inflammatory agent and Ripasudil, Netarsudil etc.

In one embodiment, the Rock inhibitors, such as Fasudil (HA-1077 a selective RhoA/Rho kinase (ROCK) inhibitor), Y-27632, small molecule inhibitor of ROCK1 and ROCK2 which acts as an anti-inflammatory agent and Ripasudi, netarsudil, etc. in form of drops or combined with polymeric nanoparticles, dendrimers, or microparticles for slow release delivery after any ocular surgery such as retinal detachment, glaucoma, cataract and after trauma.

In one embodiment, the Rock inhibitor Fasudil (HA-1077) a selective RhoA/Rho kinase (ROCK) inhibitor), a selective ROCK inhibitor such as SAR407899, Y-27632, small molecule inhibitor of ROCK1 and ROCK2 or Ripasudi, netarsudil are administered and released at nanogram to microgram concentrations in a polymeric drug delivery or Botulinum toxin such as Botox as picogram to nanogram concentrations or 1-10 units or more concentration per day which act as an TGF beta inhibitor and as anti-inflammatory agent after retinal surgery, glaucoma surgery preventing cell proliferation and adhesion.

The conventional signaling receptors and integrins serve as linkers between the actin cytoskeleton and extracellular intracellular signaling matrix, stimulating the cell survival, growth, and cell proliferation.

In one embodiment, the anti-integrin are used to inhibit cell proliferation and migration and scar formation in microgram concentrations, e.g., in retinal detachment surgery, vitrectomy to prevent development of proliferative vitreoretinopthy that leads to fixed fold and re-detachment of the retina or after cataract surgery or laser surgery of the retina and trabecular meshwork or laser surgery of the iris or ciliary body or laser of ciliary processes to reduce the intraocular pressure where the integrin inhibitors are selected from the group abegrin, cilengitide, abciximab, tirofiban, natalizumab eptifibatide at non-toxic doses of nanogram to microgram concentrations per milliliter or more.

In one embodiment, the Rock inhibitors such as fasudil, netarsudil, etc. or anti-integrins such as abciximab, Eptifibatide, Tirofiban, αIIbβ3 antagonists, Natalizumab at microgram per milliliter, MLN-00002, Firategrast, IVL745, antagonists of αvβ3 and/or αvβ5 integrins, LM609, Vitaxin, Abegrin, CNTO95, Cilengitide. MLD-based disintegrins, L000845704, SB273005, Volociximab, JSM6427, can be administered as prophylaxis of scar formation after laser surgery, in refractive surgery, post cataract complication or macular edema, or post glaucoma surgery to prevent encapsulating of a stent or closing the drainage channel by a scar, or after retinal surgery or vitrectomy to prevent postoperative cell proliferation in the vitreous cavity over and under the retina and inhibiting cell proliferative vitroretinopathy, or after refractive surgery.

In one embodiment, the non-toxic doses of Wnt inhibitors, integrin inhibitors and/or Rock inhibitors, or Botox, act as an anti-inflammatory agent. The botulinum toxin or botox preparation may be administered topically to the eye or eye lid, forehead skin at 1 picogram to 1 nanogram concentrations, 1 pictogram to 5 nanogram or higher concentrations of microgram concentrations, for example, using drops, an ointment, a cream, a gel, a suspension of microspheres, dendrimers, micelles, etc. The agent(s) may be formulated with excipients such as methylcellulose, hydroxypropyl methylcellulose, hydroxypropyl cellulose, the LD50s of any naturally occurring botulinum toxin protein is at 1.3 nanograms per kilogram (abbreviated ng/kg). In a 75 kg (165 lbs.) subjects, the LD50 for botulinum toxin would be 97.5 nanograms if injected directly into a vein or artery. 100 unit vials contains 0.75 nanograms=750 picograms of botulinum toxin A in the entire vial and the amount of non-toxic doses are 1-50 or more international units.

In one embodiment, one administers polymeric nanoparticles or dendrimers to inhibit the Glycogen Synthase Kinase-3 (GSK-3) which is a serine/threonine protein kinase, and plays a key role in Wnt/β-catenin.

In one embodiment, the (GSK-3) inhibitor 269962, is administered in a slow release polymeric form or lithium or zinc preparation, bis-indole indirubin, aminopyrimidines, arylindolemaleimides SB-216763, Paullones, pyrazolo [3,4-b] quinoxalines, human kinome, tideglusib, β-carboline alkaloids β-carboline alkaloids Palinurin and tricantin, peptide L803-mts, Axin GID-25 residues, NP-12/Tideglusib at non-toxic concentrations.

In one embodiment, when nanoparticles are coated with cell penetrating peptides (CPPs), the agent penetration is extended to at least one of the posterior segment of the eye or anterior segment of the eye or from the cornea to the retina.

In one embodiment, a mucophilic preparation such as chitosan or micelles, of Rock inhibitors, integrin inhibitors, or Wnt inhibitors is administered comprising a compound selected from the group consisting of chitosan, dendrimer, coated or linked with cell penetrating peptides (CPPs), activated cell penetrating peptides (ACPPs), hyaluronic acid, and combinations thereof.

In one embodiment, the integrin inhibitors are administered with cell penetrating peptide or ACPP coated dendrimers or nanoparticles, macrolides such as cyclosporine A, mycophenolic acid, tactolimus or ascomycin as nanoparticles or conjugated with the dendrimers or in a solution in the early stage of glaucoma as a topical medication at a concentration of Rock inhibitors of 1-5 micrograms per milliliter once or twice per day and macrolides at concentration of 0.000000001% to 0.1% in a physiological solution.

In one embodiment, a porous tubular implant further contains stem cells, or genetically modified stem cells, for slow release where the stem cells are selected from the group consisting of cultured stem cells, genetically modified stem cells, embryonic stem cells, mesenchymal stem cells, neuronal stem cells, pluripotent stem cells, glial stem cells, stem cells or genetically modified stem cells having complement receptor 35, and combinations thereof to treat loss of cells in the retina, retinal pigment epithelium, corneal genetic diseases or loss of ganglion cells or choroid or cells in trabecular meshwork.

In one embodiment, the Rock inhibitors are administered with macrolides such as cyclosporine A, mycophenolic acid, tacrolimus or ascomycin in the early stage of glaucoma as topical medication at a concentration of Rock inhibitors 1-5 microgram/ml once or twice per day and macrolides at concentration of 0.000000001% to 0.1% in a physiological solution for topical application or injection in the eye.

In one embodiment, the slow release preparation of Rock inhibitors or integrin inhibitors or combination thereof are administered inside the eye as a polymeric implant in the lens capsule after cataract surgery, or implanted in the vitreous or in the anterior chamber or in the suprachoroidal space or under the conjunctiva to deliver medication for 3-6 months to release medication at microgram concentrations in a non-toxic dose daily after cataract surgery, glaucoma surgery, to prevent encapsulation of a glaucoma stent or bleb scarring or membrane formation after retinal surgery, or cell proliferation after retinal surgery, or retinal laser surgery.

In an embodiment, where a patient's eye shows increased intraocular pressure or glaucoma, activation of transient receptor potential vanillod isoform4 (TRPV4) ion channels, pannexin-1 (Panx1), and p2x7 receptors are activated leading to glial cell activation and inflammatory response involving Toll-like receptors, complement molecules, tumor necrosis factor-α (TNFα), and interleukin-1.beta, leading to degeneration of the ganglion cells, retina, systemic or topical or local administration of probenecid, nanoparticle-coated probenecid, mefloquine, alone or preferably with ROCK inhibitors inhibit the panx1 pathway preventing release of ATP and ganglion cell degeneration.

In one embodiment, one uses laser pulses to heat up the tissue and create a scar around a retinal tear preventing a retinal detachment or cryosurgery by freezing the retinal tissue around the retinal tear that is not seldom is associated with heavy scars and traction formation. The laser surgery is also often associated with inflammation that causes cell proliferation on the retina, producing traction on the retina or pre-retinal and sub-retinal scar formation, inducing re-detachment of the retina due to cell proliferation in proliferative vitreoretinopathy. In one embodiment, one administers a slow release preparation of Rock inhibitors or integrin inhibitors or combination thereof inside the eye as a polymeric implant, or nano- or microparticles in the lens capsule after cataract extraction, or after laser or retinal surgery, or the polymeric implant placed as described in U.S. application Ser. No. 15/269,444, which is expressly incorporated by reference herein in its entirety, in the vitreous or in the anterior chamber or in the suprachoroidal space or under the conjunctiva to deliver medication for 3-6 months and release medication at microgram concentrations in a non-toxic dose daily and prevent the side effects of the surgery.

In one embodiment, one administers polymeric nanoparticles or dendrimers to inhibit the Glycogen Synthase Kinase-3 (GSK-3) which is a serine/threonine protein kinase, and plays a key role in Wnt/β-catenin pathway.

In one embodiment, the GSK-3 inhibitor such as 429286, are administered with cell penetrating peptides ((CPP) or ACPP coated-dendrimers or nanoparticles, or macrolides such as cyclosporine A, mycophenolic acid, tacrolimus or ascomycin as nanoparticles or conjugated with the dendrimers or in a solution in the early stage of glaucoma as a topical medication at concentration of Rock inhibitors of 1-5 micrograms per milliliter once or twice per day and macrolides at concentration of 0.000000001% to 0.1% or more in a physiological solution.

In one embodiment, in a dry form of age related macular degeneration, one administers laser applications around the degenerative areas to induce a minor inflammation that acts as a beacon for the stem cells and simultaneously one injects 1000-100,000 genetically modified stem cells along with Rock inhibitors to induce retinal pigment growth within the areas where these cells are lost and to enhance regeneration of the sensory retina.

In one embodiment, in a dry form of age related macular degeneration, one administers laser spots around the degenerative areas to induce a minor inflammation that acts as a beacon for the stem cells or genetically modified stem cells and simultaneously injects 1000-100,000 modified stem cells along with Rock inhibitors under the retina close to the degenerative areas to stimulate regrowth and survival or the survival of the stem cells, while the slow release polymer releases Rock inhibitors in the vitreous cavity for 1-3 years using porous silicon implant, polylactic acid or injectable porous nano- or microparticles carrying Rock inhibitors with GSK-3 inhibitors.

In one embodiment, when the stem cells of a patient also carry the genetic defect that they have inherited, the stems cells of the patient are modified in cell culture prior to the administration to the eye. The stem cells may be cultured stem cells, genetically modified stem cells, embryonic stem cells, mesenchymal stem cells, neuronal stem cells, pluripotent stem cells, glial stem cells, etc. These stem cells can be genetically modified using the technology known as non-homologous end joining (NHEJ) or homologous directed repair (HDR) in which the gene modification is done along with CRISPR cas9 or Cpf1 using nanoparticles as a vector to deliver the gene(s) inside the cells, or to cut out the mutated gene, eliminating the side effects of immune activation, as observed with the viral vector gene delivery. The functionality of this technology is described in the U.S. Pat. No. 10,022,457, which is expressly incorporated by reference herein in its entirety.

In one embodiment, for gene transfer, one uses CRISPR-conjugated to the desired nanoparticles via thiol to create a strong electrostatic bound. CRISPR-NP are then conjugated with Cas 9 and gRNA to be used in non-homologous end joining NHEJ or the NP-DNA conjugate is hybridized with the donor DNA, thus creating NP-donor DNA suspended in sodium silicate, generating NP-Donor-Cas9 RNP-silicate, which is re-suspended in a cationic polymer such as cyclodextrin or calixarene-based polycationic amphiphiles polymer as gene delivery systems or PAsp(DET) to be used in Homology Directed repair (HDR) after administration to the stem cells with appropriate gene(s).

In one embodiment, the nanoparticles, can be metallic, such as gold or ferric oxide, combination of silica/gold, QDs, polymeric organic, cationic polymeric NP, PAsp(DET), piezoelectric, such as perovskites, quartz, or other vectors such as Naked DNA, etc. with the size of 5-50 nanometers.

In one embodiment, the nanoparticle is gold or ferromagnetic covered with gold before conjugated with the CRISPR 'gRNA-cationic polymer and or gold NP-Donor DNA and suspended in silicate and a cationic polymer.

In one embodiment, one can attach multiple genes to the nanoparticles via thiol or amine, amide, before suspending in silicate and cationic polymer to encourage cell penetration and escape from the endosome after their administration to the tissue culture.

In one embodiment, the nanoparticle is PAsp(DET) or gold to which CRISPR or donor DNA is attached via thiol, before suspending the complex in sodium silicate to be followed by another cationic polymer to enhance cell penetration and endosomal escape and gene(s) delivery to the nucleus after their administration to the stem cell culture.

In one embodiment, the device further contains stem cells, where the stem cells are selected from the group consisting of cultured stem cells or modified genetically modified stem cells, genetically modified stem cells, embryonic stem cells, or modified genetically modified embryonic stem cells, mesenchymal stem cells, or genetically modified mesenchymal stem cells, neuronal stem cells, or genetically modified stem cells, neuronal pluripotent stem cells, glial stem cells, or genetically modified stem cells, neuronal stem cells having complement receptor 35, and combinations thereof.

In one embodiment, the method comprising injecting stem cells or genetically modified stem cells to replace the loss of endothelial cells and normalize the function of the perifoveal capillaries in patients with diabetic macular edema associated with vascular leakage, demonstrable deep retinal vascular deformation or loss, age related macular degeneration, glaucoma, and retinal ischemia either centrally or peripherally.

In one embodiment, the stem cells or genetically modified stem cell are administered at a concentration of about 5,000 to 100,000 stem cells or genetically modified stem cells having complement receptor 35 (CD 35) in combination with ROCK inhibitors.

In one embodiment, the method comprising injecting stem cells or genetically modified stem cells to replace the loss of endothelial cells and normalize the function of the perifoveal capillaries in patients with diabetic macular edema associated with vascular leakage, demonstrable deep retinal vascular deformation or loss, age related macular degeneration, glaucoma, and retinal ischemia either centrally or peripherally.

In one embodiment, the stem cells or genetically modified stem cell are administered at a concentration of about 5,000 to 100,000 stem cells or genetically modified stem cells having complement receptor 35 (CD 35) in combination with Rock inhibitors.

In accordance with one or more further embodiments, there is provided a method of treating, reducing, or alleviating a medical condition in a patient. The method includes administering to a patient in need thereof a biocompatible drug comprising one or more antiviral medications together with one or more cell pathway inhibitors dissolved in a non-toxic semifluorinated alkane or other liquids, the patient having one or more respiratory tract inflammatory diseases, the one or more cell pathway inhibitors blocking an inflammatory response of inflamed tissue without inhibiting an immune response of the patient, and the semifluorinated alkane evaporating quickly upon administration to the patient so as to leave the biocompatible drug at a desired treatment location. The administration of the biocompatible drug to the patient treats the one or more respiratory tract inflammatory diseases, reduces the symptoms associated with the one or more respiratory tract inflammatory diseases, and/or alleviates the one or more respiratory tract inflammatory diseases.

In a further embodiment, the one or more respiratory tract inflammatory diseases are selected from the group consisting of influenza, parainfluenza, severe acute respiratory syndrome, a coronavirus, an Epstein-bar virus, a herpes virus, an infection, and combinations thereof.

In yet a further embodiment, the one or more respiratory tract inflammatory diseases comprise a coronavirus, the coronavirus selected from the group consisting of COVID-2, COVID-19, or their mutations, and combinations thereof.

In still a further embodiment, the biocompatible drug further comprises nanoparticles or microparticles used as a carrier of the biocompatible drug; and the biocompatible drug with the semifluorinated alkane and the nanoparticles or microparticles is administered by inhalation to the patient to treat one or more respiratory tract inflammatory diseases.

In yet a further embodiment, wherein the nanoparticle or microparticle carriers comprise slow release polymeric nanoparticles or microparticles; and the semifluorinated alkane is used to transport the biocompatible drug with the slow release polymeric nanoparticles or microparticles.

In still a further embodiment, the slow release polymeric nanoparticles or microparticles are conjugated with a viral specific antibody while carrying at least two antiviral medications for intranasal inhalation to specifically target one or more viruses, the viral specific antibody being obtained from plasma/serum of patients who have recovered from a viral infection or the viral specific antibody being produced in a tissue culture using dead viruses cultured with T-cell lymphocytes or natural killers that produce the viral specific antibody in addition to producing exosomes or extracellular vesicles (ECV) that are both able to be harvested.

In yet a further embodiment, the one or more antiviral medications are selected from the group consisting of amantadine, Lopinavir, linebacker and equivir, Arbidol, a nanoviricide, remdesivir, oseltamivir, ribavirin, and combinations thereof In still a further embodiment, the one or more cell pathway inhibitors are selected from the group consisting of Rock inhibitors, Wnt inhibitors, glycogen synthesis kinase 3 (GSK-3) inhibitors, integrin inhibitors, IL-1 inhibitors, IL-6 inhibitors, and combinations thereof.

In yet a further embodiment, the biocompatible drug further comprises one or more protease inhibitors in combination with the one or more antiviral medications and the one or more cell pathway inhibitors.

In still a further embodiment, the method further comprises the step of, after treatment with the biocompatible drug, removing cytokines, enzymes, dead cells, from the circulation of the patient by plasmapheresis so as to prevent a cytokine storm.

In yet a further embodiment, the biocompatible drug is administered to the patient by inhalation, orally, intravenously, or combinations thereof.

In still a further embodiment, the biocompatible drug is administered through the nasal mucosa to reach branches of the trigeminal nerve or olfactory nerve for delivery of the biocompatible drug to the brain, brain vasculature, and the cerebrospinal fluid where the semifluorinated alkane rapidly evaporates at body temperature in the tissue leaving the biocompatible drug at the desired treatment location.

In yet a further embodiment, the method further comprises administering a stabilized hypochlorous acid, hypobromous acid (HOBr), bromamine, or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] or Benzalkonium chloride and slow release polymeric nanoparticles carrying at least two of the antiviral medications together with one or more cell pathway inhibitors and heparin or low molecular weight heparin, or with poly phenols, such as catechin, found in fruit and vegetables, in a semifluorinated alkane or a suitable medium, the administration being in the nose as inhalation, in spray or nebulized form to treat viral encephalitis or lung inflammation to kill one or more viruses and prevent the side effects of inflammation or as prophylaxis of viral infection in the respiratory tract, encephalitis, vasculitis, dementia.

In still a further embodiment, the method further comprises administering tocilizumab in combination with at least one antiviral medication to treat a viral infection of the lung, viral brain encephalitis, and/or brain vasculitis; and administering at least one cell pathway inhibitor, Wnt inhibitor, GSK inhibitor, or integrin inhibitor with or without complement pathway inhibitors such as C3 inhibitors—AMY-101 (NCT04395456) and APL-9 (NCT04402060); C5 inhibitors—eculizumab (NCT04346797 and NCT04355494), C1 esterase inhibitors, which block the classical complement pathway, through nose inhalation by spraying, aerosolization, or nebulization to reach both brain and lung tissue, and to reduce the inflammatory process and eliminate the side effects of the infection.

In yet a further embodiment, the method further comprises administering interferon or pegylated interferon and another antiviral medication in combination with the one or more cell pathway inhibitors, where the interferon or pegylated interferon acts as an antiviral in the upper and lower respiratory tract, thereby blocking the replication of the RNA and DNA of the viruses at an early stage of viral infection.

In still a further embodiment, the method further comprises administering a TMPRSS2 inhibitor and an ACE-2 inhibitor in combination with the one or more cell pathway inhibitors, where the TMPRSS2 inhibitor inhibits entry of the virus into the cell.

In accordance with one or more other embodiments of the present invention, there is provided a method of preventing a medical condition in a patient. The method includes administering prophylactically a treatment compound or substance to prevent the occurrence of a viral infection, the treatment compound or substance being selected from the group consisting of one or more antiviral medications, one or more cell pathway inhibitors, a type of mouthwash, hydrogen peroxide, povidone-iodine, ethanol, chlorhexidine, cetylpyridinium chloride, an IL-1 inhibitor, an IL-6 inhibitor, an IL-8 inhibitor, and combinations thereof. The treatment compound or substance is administered topically, intranasally, or as a mouthwash.

In a further embodiment of the present invention, the viral infection is SARS-CoV-2, COVID-19, or a mutation thereof, and the treatment compound or substance disrupts the SARS-CoV-2, COVID-19 or their mutations' lipid envelope.

In yet a further embodiment, the method further comprises administering a stabilized hypochlorous solution, or in chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT], or Benzalkonium chloride in a semifluorinated alkane or liquid with slow release chitosan encapsulated nanoparticles in a saline solution or in oral form to pass through the stomach to release a medication in the intestine to locally prevent the intestinal side effect of the viral infection.

In still a further embodiment, the method further comprises administering prophylactically one or two antiviral medications as a nasal spray, in aerosolized or nebulized form, or spray together with zinc in a saline solution orally in aliginate or chitosan encapsulated beads or nasally in polycaprolactone in a saline solution to damage the invading viruses before entering the nasal mucosa.

In yet a further embodiment, the method further comprises administering tamoxifen in combination with at least one antiviral medication to treat a viral infection of the lung, viral brain encephalitis, and/or brain vasculitis; and administering at least one cell pathway inhibitor, Wnt inhibitor, GSK inhibitor, and/or integrin inhibitor through the nose inhalation by spraying, aerosolization, or nebulization to reach both brain and lung tissue, and to reduce the inflammatory process and eliminate the side effects of the infection.

In accordance with yet one or more other embodiments of the present invention, there is provided a method of preventing a medical condition in a patient. The method includes administering to a patient, experiencing a medical condition, one or more antiviral medications together with one or more additional medications selected from the group consisting of one or more Wnt inhibitors, one or more Rock inhibitors, one or more GSK inhibitors, one or more integrin inhibitors, one or more IL-6 inhibitors, one or more TGF beta inhibitors, one or more macrolides, low molecular weight heparin, or with catechin in a semifluorinated alkane or a suitable medium and combinations thereof. The one or more antiviral medications and the one or more additional medications are administered orally, intranasally, intravenously, subcutaneously, topically, intraperitoneally, and/or by inhalation in a simultaneous, sequential, or separate manner.

In a further embodiment of the present invention, the medical condition is selected from the group consisting of a lung viral infection, a brain viral infection, an intestinal viral infection, vasculitis, COVID-2, COVID-19, or their mutations, Alzheimer's disease, dementia, neuralgia, kidney disease, cardiac disease, encephalitis, and combinations thereof.

In yet a further embodiment, the medical condition is in a form of an end stage medical condition selected from the group consisting of an end stage lung infection, an end stage brain infection, encephalitis, and combinations thereof; and wherein the one or more antiviral medications comprise a plurality of different antiviral medications to treat the end stage lung infection, the end stage brain infection, and/or encephalitis.

In still a further embodiment, the one or more additional medications administered to the patient comprise low molecular weight heparin to enhance nerve repair and prevent blood coagulation so as to combat an overactive immune response.

In yet a further embodiment, the one or more antiviral medications and/or the one or more additional medications are administered in a physiological solution or semifluorinated alkane or a physiological liquid using polymeric slow release nanoparticles or microparticles, micelles, liposomes, and/or dendrimers as a drug carrier, the polymeric slow release nanoparticles or microparticles comprising at least one of polylactic acid, polyglycolic acid, polycaprolactone, porous silicon, chitosan, and a polyethylene glycol-polylactic acid (PEG-PLA) block copolymer.

In still a further embodiment, the slow release polymeric nanoparticles or microparticles, micelles, liposomes, and/or dendrimers are conjugated with a viral specific antibody so as to form antibody-coated slow release polymeric nanoparticles or microparticles, antibody-coated micelles, antibody-coated liposomes, and/or antibody-coated dendrimers.

In yet a further embodiment, the one or more antiviral medications are selected from the group consisting of amantadine, Lopinavir, linebacker and equivir, Arbidol, a nanoviricide, remdesivir, oseltamivir, ribavirin, and combinations thereof.

In still a further embodiment, the one or more additional medications administered in a physiological solution or semifluorinated alkane or a physiological liquid or any other suitable medium to the patient comprise one or more Rock inhibitors in a form of botulinum toxin at a picogram concentration level.

In one embodiment, the semifluorinated alkane and medications are administered preferably by nasal inhalation mouth inhalation, inhaler, as a spray, nanoparticles or microparticles, in a solution, or powder, or subcutaneous, or intramuscular, or intravenously, combined as a cocktail or sequentially, orally etc.

In one embodiment to produce a vaccine, various methodologies can be employed, such as a weakened virus is administered to the patient to produce lasting antibodies, such as the use of polio vaccine developed initially by Sabin and improved by Salk by using killed or inactivated viruses.

In another embodiment, one can use a subunit of the virus, such as one of a protein of the virus, such as in the hepatitis B vaccination made by Novavax and similar vaccines used in Russia.

In one embodiment, the gene is implanted to a harmless virus, such as the chimpanzee adenovirus producing flu-like symptoms, such as in Sars-COVID-2, or engineered spike-protein. When the human adenovirus is used to carry a part of the gene that makes the spike-protein, it potentially has the side effect of inflammation against the adenoprotein if the patient has been previously exposed to adenovirus.

In one embodiment, one can inject the genetic code with human RNA or DNA if needed by electroporation which is not very effective, but using messenger RNA or mRNA to carry the code letters that make a part of the virus (S-Protein) can be administered to instruct the cell to make, e.g., the S-protein of the virus where the cell produces it and initiates an immune response to the virus in the body. In order to bring mRNA inside the cells they are encapsulated in lipid nanoparticles, which penetrate the body's cell membrane, into its cytoplasm not in the nucleus and use the cells machinery to build the appropriate antigenic protein. This technology permits the immune cells to recognize the antigen and attack the viruses or other organism.

In yet a further embodiment, despite the technological advances there are some shortcomings that one does not know how long the mRNA vaccines provides an immune response to the patients, therefore there is still a need for alternative technologies or improving the standard technologies, by further administering viral-like particles to induce humoral and cellular immune response and interferon production for therapy and/or for vaccination of the patient.

In one embodiment, the method comprises administering one to two or more vaccines such as, dead organisms, or their proteins or mRNA such as Moderna vaccine and Pfizer vaccine, or AstraZeneca vaccine and with viral like particles (VLP) conjugated with the viral antigen at a lower concentration of vaccine than normally is given and if needed an adjuvant in a semifluorinated alkane or in a solution with or without a pathway inhibitor or complement C1-C3-C5 inhibitor either nasally by inhalation or intramuscularly or intravenously separately or sequentially, or combined as a cocktail to reduce the side effects of the vaccines and increase the efficacy of the vaccination or to be repeated multiple times in an intervals of 3, 6, 9, or 12 months, etc. as needed, while the intranasal or inhalation simplifies for the people storing the vaccine at a low temperature using a home refrigerator for self-administration in different intervals as prescribed by a doctor.

In one embodiment, a vaccine is prepared from viruses or bacteria, fungi, etc. in a semifluorinated alkane and a saline, etc. solution containing riboflavin or another photosensitizer, with an adjuvant or viral like particles (VLP), etc., with or without pathway inhibitors or another anti-inflammatory compound or antiviral or antibiotic, antifungal where the organism is killed with radiation exposure, such as x-ray or cobalt radiation etc. or preferably UV radiation such as UVA, UVB, or UVC wavelength or another wavelength of a LED, diode or laser, etc., applied to the entire pathogen in the container, Petri dish for a period of one second to 5 minutes or more and stored in a refrigerator with or without Benzalkonium chloride (BAC) at a low temperature and can be used for repeated vaccination as needed by nasal or intramuscular administration, or as adjuvant to another vaccine prepared by other means or used after initial use of another vaccine for the same organism, eliminating the need for the use of formalin, thimerosal, formaldehyde, glutaraldehyde, etc. which are toxic and produce excessive and lasting inflammation at the site of the administration or because of unpleasant smell cannot be used for nasal spray or inhalation.

In one embodiment, a vaccine cocktail is prepared from viruses or bacteria, fungi, etc. in a semifluorinated alkane and a saline etc. solution containing riboflavin or another photosensitizer, with an adjuvant with or without viral like particles (VLP), etc., with or without pathway inhibitors or another anti-inflammatory compound or antivirals or antibiotics, antifungals where the organism is killed with radiation exposure such as x-ray or cobalt radiation, etc. or preferably UV radiation, such as UVA, UVB or UVC wavelength or another wavelength of an LED, diode or laser, etc., applied to the entire pathogen in the container, Petri dish for a period of one second to 5 minutes or more and the solution, etc. is collected, filtered, and stored in a refrigerator with or without Benzalkonium chloride (BAk) less than 0.01% at a low temperature and can be used for repeated self-vaccination/administration as needed by nasal or intramuscular administration, or as adjuvant to another vaccine prepared by other means, such as mRNA vaccines etc. or used after initial use of another vaccine for the same organism, but self-administered preferably by inhalation or orally, weekly for 1-2 months or more intranasally as a spray or nebulization to eliminate all potential pathogens, such as viruses that might remain in the nasal cavity, throat, pharynx, trachea, or in the alveoli and potentially reactivate and induce an epidemic or pandemic infection.

In one embodiment, the vaccines are distributed as a single dosage to be stored in refrigerator and administrated intranasally, orally, or subcutaneously by people for 1 to 3 months, up to 5 months or longer, etc. as needed.

In one embodiment, the vaccines are distributed in older patients as a single dosage with spermidine to enhance their immune response, to be stored in refrigerator and administrated intranasally, orally, or subcutaneously by people for 1 to 3 months, up to 5 months or longer, etc. as needed.

In another embodiment, one or more anti-inflammatory agents, such as NSAIDs, combined with one or more vaccines along one or more pathway inhibitors are administered to reduce a severe immune response to vaccines in patients with allergic history.

In one embodiment, vaccine is administered in a semifluorinated alkane combined with pathway inhibitors as a spray simultaneously or sequentially, with or without antibody-coated nanoparticles, etc., the combination therapy can include a vaccine such as dead viruses or mRNA or antibodies against viral proteins such as spike proteins, etc., the vaccination also include medications such as low molecular weight heparin, Ebselen, catechin, mycophenolic acid or pathway inhibitors or complement inhibitors that modify the severe immune response such as bone ache, fever, malaise, headache, etc. or side effect after a second challenge with repeated vaccinations, or observed immediately after administration of the vaccine combination preferably through the nose by inhalation though it can be given intramuscularly or subcutaneously by an injector, etc. as known in the art.

In still a further embodiment, the method further comprises administering one or more serum antibodies conjugated with the viral-like particles to induce an enhanced cellular immune response and interferon production in the patient.

In yet a further embodiment, during treatment or after treatment with the one or more antiviral medications and/or the one or more additional medications, the method further comprises the step of removing cytokines, enzymes, and/or dead cells from the circulation of the patient by kidney dialysis, blood dialysis, and/or plasmapheresis so as to suppress a cytokine storm.

In still a further embodiment, methylene Blue solution, a derivative of phenothiazine, is prepared at a concentration of 0.25-2 mg/liter in semifluorinated alkanes or in a fluid for nasal inhalation, oral, topical or intravenous administration alone to act as an antioxidant, or with one or two antivirals such as Ebselen or remdesivir, valacyclovir, etc. and one or more Wnt inhibitors or anti-integrins, etc. or LMWH to treat viral respiratory tract infections and/or CNS viral involvement prophylactically or therapeutically.

In yet a further embodiment, when a patient has a severe viral kidney or liver disease, or viral respiratory disease, or viral brain encephalitis, an intravenous administration or oral or inhalation or topical application of methylene Blue, which acts as antioxidant and converts methemoglobin to hemoglobin and acts as an antiviral at a concentration of 0.25-2 mg/liter or less than 1 nM concentration, with one or two antivirals, such as Ebselen or remdesivir, Favipiravir, doxycycline, valacyclovir for inhalation or oral administration, etc. with one or more Wnt inhibitors or an anti-integrin, Rock inhibitor or GSK inhibitor, etc. and LMWH in a semifluorinated alkane or in a fluid containing bile salt to kill the viruses including influenza, SARS-CoV-2, COVID-19, or their mutations and reduce severe inflammatory processes followed with dialysis, hemodialysis, serum electrophoresis to remove unwanted toxins and creatinine, etc. and simultaneously act to prevent blood clothing after methylene Blue administration.

In still a further embodiment, a vaccine is prepared from viruses or bacteria, fungi, etc. or an adjuvant or a synthetic adjuvant such as toll-like receptor 4 agonist in a semifluorinated alkane and a saline, such as a bile salt, etc. solution containing riboflavin or methylene Blue or another photosensitizer, with or without viral-like particles (VLP), etc., with or without pathway inhibitors or another anti-inflammatory compound or antiviral, such as remdesivir, Favipiravir, valacyclovir, administered by inhalation or orally, and with or without an antibiotic, such as tetracycline derivatives and/or an antifungal where the organism is killed with radiation exposure to UV radiation such as UVA, UVB, or UVC wavelengths or another wavelength (670 nm) produced by an LED, diode or laser, etc., or the viruses' RNA or DNA are damaged with methylene blue while the s antigen remains undamaged to induce a strong immune response to the virus applied to the pathogens in a container, Petri dish to damage the viral DNA and/or viral RNA and parts of the capsular protein, etc. for a period of one second to 5 minutes or more and then the remaining dead components of the virus is stored in a refrigerator with or without Benzalkonium chloride (BAC) at a low temperature to be used for repeated vaccination as needed, e.g., by nasal self-administration or intramuscular administration, or as an adjuvant to another vaccine, such as mRNA vaccines, etc. or after initial administration of another vaccine of the same organism, to stimulate an immune response to the pathogen, thereby eliminating the need for the standard use of formalin, thimerosal, formaldehyde, glutaraldehyde, etc. for the production of vaccines, but are toxic and produce excessive and lasting inflammation at the site of the administration.

In one embodiment, the RNA or DNA of the viruses are damaged with methylene blue while the S-antigen remains undamaged, and are administered along with antivirals or benzalkonium chloride or another adjuvant to induce a strong immune response to the virus in the body kept with the pathogens that has grown in a container, Petri dish to damage the viral DNA and/or viral RNA and parts of the capsular protein, of the virus etc. for a period of few hours or more and then the remaining dead components of the dead virus can be irradiated once more with a light of 670 nm wavelength for a few more minutes, stored in a refrigerator with or without Benzalkonium chloride (BAC) at a low temperature to be used for repeated vaccination with pathway inhibitors such as Wnt, Rock, or GSK inhibitors or GSK beta inhibitors or another adjuvant such as toll-like receptor agonists etc. as needed, e.g., by nasal self-administration or intramuscular or subcutaneous, etc. administration, or as an adjuvant to another vaccine, such as mRNA vaccines, etc. or after initial administration of another vaccine of the same organism, to stimulate an immune response to the pathogen, thereby eliminating the need for the standard use of formalin, thimerosal, formaldehyde, glutaraldehyde, etc. for the production of vaccines, that are toxic and produce excessive and lasting inflammation at the site of the administration.

In one embodiment, antivirals can be combined with Methylene blue, a phenothiazine dye, a cationic compound to enhance damage to the viruses, bacteria's anionic RNA or DNA, and simultaneously acting as anti-oxidant and anti-depressant when given in combination with of one of the pathway inhibitors, such as GSK inhibitors or GSK beta inhibitors and/or Wnt inhibitors, such as Ivermectin or Niclosamide, in a solution or as polymeric slow release nanoparticles or in semifluorinated alkanes to be administered systemically, or preferentially by inhalation, one or multiple times daily at below the toxic dose of methylene blue at 1-2 mg/L to reach both the lung and the brain preventing or treating viral inflammatory disease of the lung or the brain, etc. and preventing subsequent chronic Alzheimer's or Parkinson diseases and nerve damage and preventing or treating the tangled tau neurofibriles and preventing Tau protein's toxicity by activating plasma membrane calcium ATPase, thus preventing endoplasmic reticulum (ER) stress response and unfolding the protein (UPR).

In yet a further embodiment, the vaccine production uses a simple easy to produce methodology to be used anywhere, but specially in developing countries, for any known or unknown viruses or bacteria where the incubation of the methylene blue with viruses or bacteria, or fungi, etc., after the organism has grown on a cell culture media, etc. with or without a semifluorinated alkane or in culture media, a physiological saline solution, etc., one adds a solution containing methylene Blue alone at a <5 microMolar or 0.25%-1% or more concentration in sodium phosphate buffer of pH 7.4 at 50 mM concentration or preferably more, for less than 2 hours to days, etc. with or without another adjuvant, with or without pathway inhibitors or another anti-inflammatory compound, such as Baricitinib or antivirals including valacyclovir, etc. or an antibiotic if available, where the RNA or DNA of the organism is damaged without damaging the viral or bacterial membrane containing the S-protein (antigen), etc. for vaccine production using the remaining dead viruses or proteins without crosslinking the viral or bacterial proteins, stored in a refrigerator with or without Benzalkonium chloride (BAC) at a low temperature and used for repeated vaccination as needed by nasal inhalation, at a low volume that can be subsequently be increased until neutrazing antibodies are discovered in the body or oral, or intramuscular administration, or as adjuvant to another vaccine prepared by other means, such as mRNA vaccines for nasal inhalation or after the initial use of another vaccine from the same organism, thereby eliminating the need for the standard use of formalin, thimerosal, formaldehyde, glutaraldehyde, etc. which are toxic and produce excessive and lasting inflammation at the site of the administration.

In still a further embodiment, methylene Blue at a 1 mg/L concentration is administered intravenously with LMWH or heparin mimetics or complement inhibitors or pathway inhibitors and at least one or more antivirals, such as remdesivir and valacyclovir, and with or without polyclonal antibodies cocktails and/or anti-inflammatory agents such as Baricitinib, etc. to kill the viral pathogens with or without simultaneous light/laser radiation of the blood inflow tubing, for a period or 4, 8, 16, or 30 minutes followed by dialysis, hemodialysis, serum electrophoresis to remove dead viruses and unwanted toxins and methylene Blue from the blood that is reinfused to the patient.

In yet a further embodiment, one administers a vaccine as a cocktail, etc. to boost the immune response of a person to specific viral, bacterial or fungal pathogens by administering a low dose of a vaccine that is presently used for vaccination, the amount of this booster vaccine can be from 5%-99% of the original volume and its contents, or preferably 10% or 20% or 40% or 60% volume, etc. with or without pathway inhibitors such as Rock, Wnt, GSK or integrin inhibitors, or complement C1, C3, C5 inhibitors, etc. along with or without antivirals, antibiotics or antifungals or with or without an-anti-inflammatory agent, such as a IL-7 inhibitor, DMF or Baricitinib, etc. or an immune enhancer such as spermidine, etc. for inhalation or injected intramuscularly, subcutaneously, or orally or intravenously or preferably by nasal inhalation, as drops or spray, or by an inhaler etc. so the patients can either self-administer the vaccine in different doses at described intervals either before the regular standard vaccination, during the sickness, shortly thereafter, or beyond the original vaccination or sickness to either recognize an allergic response to the vaccine and/or to boost gradually the immune response of the patient who is old or has cancer or is an immunosuppressed patient, where the vaccine can be prepared the standard way of killing the bacteria, or render them defenseless, or using a specific protein part of the virus, or using mRNA, etc. of the virus.

In still a further embodiment, the method further comprises the step of: delivery of oxygen to the patient by extracorporeal membrane oxygenation when the blood oxygenation level of the patient is low.

In another further embodiment, the treatment does not apply any means that provides 100% oxygen to the patient, since 100% oxygen is toxic to the tissue and increases the inflammatory response that is not desirable in patients with COVID-19.

In one embodiment, the amount of oxygen for inhalation is 20-30% or 30-40% or 40-50% or 50-80% best with standard C-Pap used for sleep apnea coupled with an oxygen tube supplying a certain amount of oxygen or with glutathione peroxidase to the air through the nose or mask.

In one embodiment, the treatment is divided into two or three stages, depending on the severity of the lung inflammation, at least one or two antivirals, one to two Rock inhibitors or one to two Wnt inhibitors, one or two GSK inhibitors, or one or two integrin inhibitors, at least one or two protease inhibitors alone or at least one or two IL-1 or IL inhibitors or one to two known antivirals, such as amantadine, nucleoside analogs such as AZT, aciclovir, ganciclovir, and vidarabine in combinations are used as inhalation where the medication is dissolved in semifluorinated alkanes or combined as polymeric release nanoparticles or one to two known antivirals such as amantadine, nucleoside analogs such as AZT, aciclovir, ganciclovir, and vidarabine, or again depending on the severity of the disease, e.g., in end-stage disease, one can administer these combination of medications, orally, intravenously, semifluorinated alkanes with alkyl chains are harmless in the examined range from $C_6$ to $C_{10}$ but preferably $C_6$, in addition to inhalation with simultaneous administration of macrolide immune-suppressants, such as cyclosporine A, mycophenolic acid and with heparin or low molecular weight heparin (Lovenox) with or without catechin in a semifluorinated alkane or a suitable medium, such as low carbon perfluorocarbon liquid C4-C6, to block viral receptors, heparan sulfate and Sialic acid, and to enhance nerve repair and prevent blood coagulation, etc. to prevent overactive immune response and blood clot formation and to prevent vascular infarct, a side effect of the COVID-19 infection. Furthermore plasmapheresis, kidney dialysis can be done to remove cytokines with or without extra-corporal oxygenation if blood oxygenation remains low with the ventilator, or along with Glutathione peroxidase, catalase, etc.

In the abovedescribed treatment with two or three stages, the antiviral agents prevent either the attachment of viruses to the cell wall or block their cell penetration or inhibit the virus replication by damaging the nucleic acid (DNA or RNA) of the virus, etc. The anti-inflammatory compounds affect the cell pathway of cell inflammation in response to various agents affecting the cells in a tissue or in an organ. Among the most important anti-inflammatory compounds are Wnt inhibitors that prevent early stage inflammation, Rock inhibitors that prevent rock proteins activation, which blocks TGF beta that stimulates scar formation after the inflammation is controlled. Similarly, integrin inhibitors contribute to healing of the inflamed tissue preventing it from becoming overactive producing over active scarring, and GSK-3 are active in intracellular signaling pathways, involved in cellular proliferation, migration, and apoptosis. Inhibition of GSK-3 contributes to the healing process. GSK-3 inhibitors increases the CD8(+) OT-I CTL function and the clearance of viral infections. Interleukins (ILs) are a group of cytokines produced by cells and participate in a number of inflammatory processes. There are a number of interleukins from IL-1 to IL-17, inhibition of these cytokines significantly reduces an inflammatory response in the tissue produced after a number of diseases, such as bacterial and viral infections, etc. Azidothymidine (AZT) or Zidovudine (ZDV) is an antiretroviral used to prevent and treat HIV/AIDS infection along with Acyclovir, ganciclovir and Vidarabine are active against a broad spectrum of viral infection in patients with AIDS or acquired immunodeficiency syndrome, etc. Semifluorinated alkanes are non-toxic and do not cause irritation, and can carry oxygen used previously as a blood substitute. However, no one has used this characteristic to deliver simultaneously oxygen in the lung simultaneously with other medications by loading them also with oxygen prior to its administration as aerosolized nanodrops or microdrops in the spray system. Semifluorinated alkanes dissolve numerous hydrophilic or hydrophobic compounds. Their temperature transition from liquid to vapor is low, so they can evaporate easily. They can be formed as a liquid compound or can be aerosolized for inhalation through the nose or mouth along with various medications. Their applications are best for surfaces of the skin or mucosa or aerosolized for inhalation to reach the alveoli of the lung, etc. They may not be approved yet for intravenous application. For the latter application, one can use a physiologic solution with a pH of 7-7.5 and osmolality of about 300 mosmol having 0.9% or more saline, to administer the medications intravenously or as spray for inhalation. The anti-inflammatory agents described above, including the anti-virals can be taken orally, such as Zidovudine and Acyclovir, ganciclovir and Vidarabine, etc. However, a formulation of these and others antivirals can be given intravenously or intramuscularly in solution or can be dissolved in semifluorinated alkanes for inhalation.

In one embodiment, a method of drug delivery is described for treatment of respiratory tract inflammatory diseases or encephalitis caused by various viruses, such as influenza, parainfluenza, SAR or coronaviruses, COVID-2 or COVID-19, or their mutations, etc., EBV, Herpes virus, etc., or a bacterial infection, etc., where the anti-viral medications are administered along with cell pathway inhibitors to block an inflammatory response of the tissue which does not inhibit an immune response, such as a Rock inhibitor, Wnt inhibitor, GSK inhibitor, integrin inhibitors, with or without complement pathway inhibitors such as C3 inhibitors—AMY-101 (NCT04395456) and APL-9 (NCT04402060); C5 inhibitors—eculizumab (NCT04346797 and NCT04355494), eculizumab, Ultomiris, and C1 esterase inhibitors, which block the classical complement pathway or in combination, dissolved in a non-toxic or non-irritative semifluorinated alkanes liquid, or other liquids, which are amphiphilic liquids dissolving both hydrophilic and hydrophobic drugs, or as polymeric slow release nanoparticles carrying the medication applied as a spray or evaporative solution or in a evaporative aerosolized drops during the inhalation passing through the nose or mouth or olfactory or trigeminal nerves, etc. to the brain or the lung alveoli, while on the way the nano- or micro-droplets attach to the nerve receptors, fibers of olfactory nerve reaching the olfactory bulb and the brain or attach to the mucosa, epithelia or endothelial cells of the nose pharynx, larynx, epiglottis, trachea, bronchi and lung alveoli. The semifluorinated alkanes rapidly evaporates at body temperature leaving the medication(s) or slow release nanoparticle on the surface of the tissue in the brain or the lung, thus releasing the medication over a time period of one day to one week to 3 weeks or months depending on the composite of the polymer.

In one embodiment, the semifluorinated alkanes or perfluorocarbon liquid which are non-toxic fluidics, and serve as solvents alone or in combination with other solvents, such as polyethylene glycol (PEG) or ethanol, etc., dissolve hydrophobic and hydrophilic medications with ease and thereby enhancing the penetration of the medication in the tissue therefore are best suitable for inhalation, spray or nebulization delivery of medications both to the lung and brain through the respiratory pathway or through the olfactory and trigeminal nerves to the brain.

In one embodiment, the semifluorinated alkanes or perfluorocarbon liquid with low carbon chains evaporate faster in one day to a week, and higher carbon chain forms evaporate in a few weeks to months.

In one embodiment, the low density semifluorinated alkane or perfluorocarbon liquid or another solution are used by mixing them with viral or bacterial or fungi antigens or modified mRNA, for vaccination, or combined with antibodies or other medications, etc. to be administered by injection intramuscular or inside a body cavity or preferably to be applied locally or topically or as an ointment or as an spray or nebulized as micro-droplets or nano-droplets or the vaccination is combined with therapeutic medications such as pathway inhibitors, Rock, Wnt, GSK, or integrin inhibitors or complement inhibitors C1, C3, C5 inhibitors alone or as slow release polymeric nanoparticles for nasal spray or inhaler where the nanodroplets or microdroplets after inhalation locate themselves over the mucosal surfaces of the nose, pharynx, and deliver medication to the mucosal cells or to the blood, etc. and the nanoparticles continue releasing the medications for weeks, or months depending on their compositions to prevent excessive inflammatory or anaphylactic response to the vaccination.

In one embodiment, a low density semifluorinated alkane or perfluorocarbon liquids or another solution are used by mixing them with combinations with various slow release PEGylated polymeric slow release polymeric nanoparticles or microparticles, such as lactic acid, glycolic acid, or in combination or polycaprolactone, porous silicon, anhydride, micelles, liposomes, solid lipids, etc. conjugated with antibodies or other medications, such as antivirals, antibacterials, antifungals, or anti-parasites, etc. to be administered by injection intravenously or inside a body cavity as an emulsion or to be applied locally or topically or injectable emulsion or ointment or as spray or nebulized as microdroplets or nano-droplets for therapeutic medication for nasal inhalation as a spray or inhaler where the nano-drops or micro-drops after inhalation locate themselves over the mucosal surfaces of the nose, pharynx, larynx, bronchi, and alveoli to be positioned between the fluid on the surface of the mucosal cells and the air and prevent dryness of the alveoli mucosa and deliver medication to the cells or to the blood, etc. and the nanoparticles continue releasing the medications for weeks, months or years depending on the compositions.

In one embodiment, oxygenated or non-oxygenated semifluorinated alkanes or perfluorocarbon liquid with carbon chain of 3-10 C with antibody-coated viral-like particles and/or viral-like particles are conjugated with viral antigens administered nasally as a spray or inhalation or repeated in another time interval from one month to one year, etc. as needed to create an immune response to the viral antigen or viral protein or proteins or to the combination of VLP and antigens enhancing the immune response and, since the spray or the inhaler can be stored in the refrigerator, the patient can be instructed to perform repeated self-vaccination as prescribed by the doctor depending on the presence or absence of the neutralizing antibody in the blood of the patient.

In another embodiment, oxygenated or non-oxygenated low density semifluorinated alkanes or a perfluorocarbon liquid with antibody-coated viral-like particles in combination with complement inhibitors administered nasally as a spray or inhalation and repeated in another time of one month to one year as needed to create an immune response to the viral antigens or viral proteins while complement inhibitors reduce the allergic response to the antigens or VLPs, the spray or the inhaler can be stored in the refrigerator, and the patient can be instructed to perform repeated self-vaccination as prescribed by the doctor depending on the presence or absence of neutralizing antibody in the blood of the patient.

In one embodiment, the antibody-coated PEGylated polymeric slow release nanoparticles with desired medications are mixed with a low density oxygenated or non-oxygenated semifluorinated alkanes (SFA) having 4-8 carbons and 100% oxygen in the container that is capable of delivering a puff of oxygen and nebulized SFA or perfluorocarbon liquids at a low carbon chain of 4-8 carbons that evaporate within one week to a month or longer depending on the carbon chain.

In one embodiment, the oxygenated semifluorinated alkanes (SFA) carries PEGylated nanoparticles that carry the needed gene(s) along with CRISPR with a cationic compound and thiol where the gene delivery is done through the nasal delivery or with an inhaler to the lung to modify genetic defect of the alveolar cells, etc. such as pulmonary fibrosis, the nanoparticles are conjugated with thiol or cell penetrating peptides to enhance their penetration in the cells.

In one embodiment, the oxygenated or non-oxygenated semifluorinated alkanes/nanoparticle emulsions evaporate and leave the slow release polymeric nanoparticles on the cell surface to release the medication for a long time to the lung, or brain, or in the circulation.

In one embodiment, the oxygenated or non-oxygenated semifluorinated alkanes or perfluorocarbon liquids are administered by spraying, nebulization or an inhaler along with medications where the droplets of SFA or PFCL pass through the nasal pathways to the lung alveoli where they can pick up oxygen from the air or blood and release them when the blood oxygen concentration drops below 94%.

In another embodiment, the semifluorinated alkane with an emulsion of polymeric release nanoparticles and genes penetrate or are picked up through the cell membrane where the medication is released or they may picked up by the endothelial cells and enter the circulation to continue being active and release the medication elsewhere in the body such as lung, heart, and brain, etc.

In one embodiment, a low density semifluorinated emulsion with antibody-coated particles carrying the medication are picked up by the neuronal cells in the mucosal cells of the nose and elsewhere, and travel to the brain through the olfactory nerve and bulb or through the trigeminal nerves brought to the brain and are released to treat viral bacterial, or fungal encephalitis.

In one embodiment, the semifluorinated emulsion with antibody-coated slow release polymeric nanoparticles carrying the medication such as antivirals, antibiotics, or antifungals alone or in combination with pathway inhibitors or complement inhibitors where the nanoparticles are picked up by the neuronal cells, in the mucosal lining of the nose and elsewhere and travel to the brain through the olfactory nerve and bulb or through the trigeminal nerves brought to the brain and are released to treat viral bacterial, or fungal encephalitis, or chronic inflammatory diseases, such as Alzheimer's disease or Parkinson's disease.

In one embodiment, the inhaled semifluorinated alkanes with nano-droplets and/or micro-droplets work as lubricants in the respiratory tract after their inhalation by nasal spray or nebulization or through an inhaler reducing the dryness of the respiratory pathways.

In one embodiment, the oxygenated semifluorinated alkanes and polymeric slow release nanoparticles can enhance medication penetration in the tissue such as antiviral, protease inhibitors, or polymerase inhibitors and since they are not nutrients will prevent bacterial growth on them and the oxygen damages the bacteria and viruses enhancing the effect of antivirals and antibiotics or antifungal medication on these organisms.

In one embodiment, a method of drug delivery is described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medication is administered in a physiological solution or semifluorinated alkane or a physiological liquid or a suitable medium along with cell pathway inhibitors to block an inflammatory response of the tissue which does not inhibit immune response, such as Rock inhibitors such as Fasudil hydrochloride, or ROCK2, Fasudil1-(5-Isoquinolinesulfonyl)-2 Methylpiperazine Calcium Channel Blockers, or as SAR407899, or Inhibitor of cyclic nucleotide dependent- and Rho-kinases GSK 269962, potent and selective ROCK inhibitor GSK 429286, selective Rho-kinase (ROCK) inhibitor H1152 dihydrochloride, selective Rho-kinase (ROCK) inhibitor Glycyl H 1152 dihydrochloride, selective Rho-kinase (ROCK) inhibitor; more selective analogue of H1152, cell-permeable, selective Rho-kinase inhibitor OXA 06 dihydrochloride, potent ROCK inhibitor PKI1447 dihydrochloride, potent and selective ROCK inhibitor; antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor Y-27632 dihydrochloride, Botox or botulinum toxin in conjunction with at least two antivirals, such as Glidesivir, Favipiravir, Remdesivir, nanoviricides, GS-6207 (Lenacapavir/Gilead) in picomolar concentration, or GS-CA1, Oya1, umifenovir, tamivir ribavirin dissolved in a liquid semifluorinated alkanes, or other liquids, or as polymeric slow release nanoparticles applied as drops or spray or evaporative solution or in a evaporative aerosolized nano- to micro-drops that travels through the nasal mucosa to reach the lung alveoli, while on the way, attaches to the mucosa, epithelia or endothelial cells or nose pharynx, larynx, epiglottis, trachea, bronchi and lung alveoli. The semifluorinated alkanes rapidly evaporate at body temperature leaving the medication(s) or slow release nanoparticles of polylactic, polyglycolic acid or combination thereof, or combination of polycaprolactone, anhydrides, porous silicone, micelles, and/or liposomes on the surface of the tissue or slow release nanoparticles on the surface of the tissue, releasing the medication over a time period of one day to one week to 3 weeks or months depending on the composite of the polymer.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medications are administered in a physiological solution or semifluorinated alkane or a physiological liquid or a suitable medium with a cell pathway inhibitor to block an inflammatory response of the tissue which does not inhibit an immune response, such as in a physiologic pH adjusted to 7-7.5 pH and osmolarity of 280-300 mOsm or slow release polymeric nanoparticles from the Wnt compound, such as FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, Ivermectin, Niclosamide, apicularen and bafilomycin, XAV939, XAV939, G007-LK and G244-LM, NSC668036, SB-216763, gemtuzumab, etc., small molecule Wnt inhibitor PKF118-310, the Wnt/β-catenin pathway inhibitor dissolved in a liquid semifluorinated alkane, or other liquids, or as polymeric slow release nanoparticles applied as a spray or evaporative solution or in evaporative aerosolized drops that travel through the nasal mucosa to reach the lung alveoli while on the way attaches to the mucosal, epithelial, or endothelial cells of nose pharynx, larynx, epiglottis, trachea, bronchi and lung alveoli. The semifluorinated alkane rapidly evaporates at body temperature, thereby leaving the medication(s) or slow release nanoparticles on the surface of the tissue, releasing the medication over a time period of one day to one week to 3 weeks or months depending on the composite of the polymer.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medication is administered in a physiological solution or semifluorinated alkane or a physiological liquid or a suitable medium with a cell pathway inhibitor to block an inflammatory response of the tissue which does not inhibit an immune response like steroids, the cell pathway inhibitor being, for example, a GSK 269962 inhibitor or GSK inhibitors, such as synthetic small-molecule ATP-competitive inhibitors, and substrate-competitive inhibitors, non-ATP-competitive inhibitors, where FRAT/GBP competes with Axin inhibiting GSK-3 activity or anti-integrins such as Risuteganib, vedolizumab, anti-integrins, such as abciximab, Eptifibatide, Tirofiban, αIIbβ3 antagonists, Natalizumab, 3 mg to ±52 µg/mL, MLN-00002, Firategrast, IVL745, antagonists of αvβ3 and/or αvβ5 integrins, LM609, Vitaxin, Abegrin, CNTO95, Cilengitide. MLD-based disintegrins, L000845704, SB273005, Volociximab, JSM6427 or dissolved in a liquid semifluorinated alkanes or other liquids with other medications or as polymeric slow release nanoparticles applied as a spray or evaporative solution or in evaporative aerosolized drops that travels through the nasal mucosa to reach the lung alveoli while on the way attaching to the mucosal, epithelial or endothelial cells or nose pharynx, larynx, epiglottis, trachea, bronchi and lung alveoli where the semifluorinated alkane/medication(s) rapidly evaporates leaving the medication(s) or slow release nanoparticles on the surface of these organs after inhaling one time to 10 times as needed, thereby releasing the medication over a time from one day to 2 weeks or more. However, the dose applied through this methodology is <30 times in concentration compared to systemic medication given intravenously, etc. and it is more effective locally, to combat the viruses and their complications.

In one embodiment, a method of drug delivery described for treatment of respiratory tract inflammatory diseases caused by various viruses, such as influenza, parainfluenza, SAR or coronaviruses, COVID-2 or COVID-19 or their mutations, etc., EBV, Herpes virus, etc., or bacterial infections, etc. where the anti-viral medications are administered in a physiological solution or semifluorinated alkane or a physiological liquid or a suitable medium with IL-1 and/or IL-6 inhibitors, such as Kevzara (sarilumab) or nitric oxide (NO) donor (NONOate), interleukin antagonists, or in combination with Rock inhibitors, etc. to block inflammatory response IL-6 of the tissue which does not inhibit immune response (as steroids do), dissolved in liquid semifluorinated alkanes or other liquids with other medications or as polymeric slow release nanoparticles applied as a spray or an evaporative solution or in evaporative aerosolized drops that travel through the nasal mucosa to reach the lung alveoli while on the way attaching to the mucosal, epithelial or endothelial cells or nose pharynx, larynx, epiglottis, trachea, bronchi and lung alveoli where dissolved medication in the semifluorinated alkanes rapidly evaporates from the lung leaving the medication(s) and/or slow release nanoparticles on the surface of these organs after inhaling, one time to 10 times or more as needed releasing the medication over a time period from one day to 2 weeks or more.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medication is administered in a physiological solution or semifluorinated alkane or a physiological liquid or a suitable medium with a protease inhibitor, such as Ebselen, an inhibitor to target (SARS-CoV-2), COVID-19, or their mutations, Mpro or Ganovo to block the entry of the virus in the cell dissolved in a liquid semifluorinated alkane or other liquids which does not cause irritation, with other medications, or as polymeric slow release nanoparticles applied as a spray or evaporative solution or in a evaporative aerosolized drops that travel through the nasal mucosa to reach the lung alveoli while on the way attaching to the mucosal, epithelial or endothelial cells or nose pharynx, larynx, epiglottis, trachea, bronchi and lung alveoli where the semifluorinated alkane rapidly evaporates leaving the medication(s) or slow release nanoparticles on the surface of these organs after inhaling one time to 10 times as needed, thereby releasing the medication over a time from one day to 2 weeks to months or years.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus etc., or bacterial infections, etc. where the anti-viral medication such as Lopinavir, or linebacker and equivir, or HIV protease inhibitor darunavir, is administered in a physiological solution or semifluorinated alkane or a physiological liquid or a suitable medium with a protease inhibitor such as Ganovo or INO-4800 to block the entry of the virus into the cell and APNO1 an angiotensin converting enzyme 2 to block the virus adhesion to the cells, or in combination with a Rock inhibitor, Wnt inhibitor, GSK inhibitor, or integrin inhibitor or IL-1 or IL-6 inhibitor Kevzara or nitric oxide (NO) donor (NONOate) or interleukin antagonists, such as anakinra, dissolved in a liquid semifluorinated alkane or other liquids with other medications as a nanoparticle compound or as polymeric slow release nanoparticles applied as spray or evaporative solution or in evaporative aerosolized drops that travel through the nasal mucosa to reach the lung alveoli while on the way attaching to the mucosal, epithelial or endothelial cells or nose pharynx, larynx, epiglottis, trachea, bronchi and lung alveoli where the semifluorinated alkane rapidly evaporates because of high body temperature, leaving the medication(s) or slow release nanoparticles on the surface of these organs after inhaling one time to 10 times or more as needed, releasing the medication over a time from one day to 2 weeks to months or years in the chronic disease of the lung.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial or fungal infections, etc. where the anti-viral medication such as Lopinavir, or linebacker and equivir, Arbidol, NanoViricide and/or an HIV protease inhibitor darunavir, is administered in a physiological solution or semifluorinated alkane or a physiological liquid or a suitable medium with a protease inhibitor such as Ganovo or INO-4800 to block the entry of the virus to the cell and APNO1 an angiotensin converting enzyme 2 to block the virus adhesion to the cells, or in combination with PolyTop mAb therapy or cocktail of antibody therapy by Regeneron Velochimmune or Vir's antibody platform or VAAST platform human monoclonal antibody or TZLS-501 an IL 6 inhibitor or Kevzara or Actems Tocilizumab with Rock inhibitors, Wnt inhibitors, GSK inhibitors or integrin inhibitors or anti-bacteria or antifungal or IL-1 inhibitors dissolved in a liquid semifluorinated alkane or other liquids and other medications and polymeric slow release nanoparticles are applied as a spray or evaporative solution or in evaporative aerosolized drops that travel through the nasal mucosa or mouth to reach the lung alveoli while on the way attaching to the mucosal, epithelial or endothelial cells or nose pharynx, larynx, epiglottis, trachea, bronchi and lung alveoli where the semifluorinated alkane/medication(s) rapidly evaporates leaving the medication(s) or slow release nanoparticles on the surface of these organs after inhaling one time to 10 times or more as needed releasing the medication over a time from one day to 2 weeks, months, or years.

In one embodiment, after inhalation or systemic treatment of viral inflammation with antivirals, a severe inflammatory response is treated with Rock, Wnt, GSK, or integrin inhibitors alone or in conjunction with other therapeutic immunosuppressant agents dissolved in the semifluorinated alkanes or other liquids with other medications, such as a macrolide, cyclosporine A, mycophenolic acid, ascomycin Immunomycin, FR-900520, FK520, is an ethyl analog of tacrolimus (FK506) for inhalation, can reduce the overt inflammatory response of the disease process; while MPA inhibits inosine monophosphate dehydrogenase. Mycophenolic mophetil alone or in combination with reverse transcriptase inhibitor abacavir, prevents most viral replications by depletion of Guanine, depletion of guanosine in substrate guanine triphosphate (GTP), while simultaneously preventing endoplasmic stress induced by viral infections in the neuronal cells, thereby preventing neurofibrillary and misfolding of proteins such as amyloid, however, in a later stage of the disease, steroids can be used even though steroids have their unwanted side effects and also can be replaced with NSAIDs that are more desirable, however, inhalation, or by an inhaler would be preferable to systemic therapy, except in desperate end stage cases where systemic steroids, such as prednisone, dexamethasone, fluoroquinolone, etc. might be useful in combination with antivirals and antibacterials, such as Tetracycline derivative medications, a metalloproteinase inhibitor, demeclocycline, doxycycline, Adoxa, Vibramycin, Minocycline, Minocin, etc. to treat inflammatory viral lung or brain infections through the nasal inhalation, etc.

In one embodiment, in an immunosuppressed individual after organ transplantation, for viral infection prophylaxis or therapeutically in addition to inhalation therapy, systemic administration of natural killer cells or modified killer T-cells systemically along with Wnt, Rock, GSK inhibitors and integrin inhibitors, antibiotics such as, Tetracycline derivative medications a metalloproteinase inhibitor, include Demeclocycline, Doxycycline, Adoxa, Vibramycin, Minocycline, Minocin, antifungals, both as inhalation dissolved in semifluorinated alkanes or other liquids, or systemically can be given to combat an inflammation or any superinfection with bacteria and fungi which require additional antibacterial and/or antifungal medications can be administered in a physiological solution or semifluorinated alkane or a physiological liquid or a suitable medium both systemically, inside a body cavity, or by inhalation dissolved in semifluorinated alkanes or other liquids as needed.

In one embodiment, a method of drug delivery described for treatment of respiratory tract inflammatory diseases caused by various viruses, such as influenza, parainfluenza, SAR or coronaviruses, COVID-2 or COVID-19, or their mutations, etc., EBV, Herpes virus, etc., or bacterial infections, etc. where the anti-viral medication such as Lopinavir, favipiravir or linebacker and equivir, unifenovir and a vaccine, such as lipid-encapsulated mRNA 1273, COVID-19 S-Timer, or SARS-COVID-2, viral-like particles (VLP) or an adjuvant or viral Lily vaccine etc. with antibody-coated nanoparticles administered simultaneously or sequentially with a Rock inhibitor, Wnt inhibitor, GSK inhibitor, or integrin inhibitor in a solution or dissolved in a liquid semifluorinated alkane or other liquids with other medications or as polymeric slow release nanoparticles applied as a spray or evaporative solution or in evaporative aerosolized drops that travel through the nasal mucosa to reach the lung alveoli while on the way attaching to the mucosal, epithelial, or endothelial cells or nose, pharynx, larynx, epiglottis, trachea, bronchi and lung alveoli where the semifluorinated alkane rapidly evaporates leaving the medication(s) or slow release nanoparticles on the surface of these organs after one or more times of inhalation as needed.

In one embodiment, a vaccine prepared as described with methylene blue is administered in a physiological solution or semifluorinated alkane or a physiological liquid or a suitable medium by inhalation, or intranasally to a patient every 3-6 months or at a lower quantity to prevent re-infection by a coronavirus that causes COVID-19.

In one embodiment, the described medications can be supported by frequent inhalation and oral administration of Glutathione peroxidase, catalase, flavonoid, containing polyphenyls, epigallocatechin gallate catechins (EGCG) having antioxidants compounds found in black tea, coffee, oolong, white tea, Pu-reh, Chamomile tea, the vegetable, such as fruits or coco, Mpro enzyme inhibitors and antioxidant, antimicrobial, antidiabetic, antiallergic, anticancer, hypocholesterolemic, statins and immunomodulatory mangiferin, genistein, estradiol, berberine and baicalein, sulforaphane, vitamin D and high doses of vitamin C, vitamin E, D, or quercetin, curcumin, resveratrol, Alpha-lipoic acid, tocopherols and tocotrienols, carotenoids, glutathione tocopherols, carotenoids, and other plant based Wnt inhibitors, ivermectin, niclosamide, etc. reducing excessive glutamate that can cause neuronal death, and Alzheimer's disease.

Example 9

The patient was a 60 year old female patient with no history of heart disease, and had a running nose and cough of 2 days duration, fever and chills, and a productive cough. The patient was somewhat weak and had loss of appetite and sense of the smell recently, no history of heart disease or smoking. Her EKG was normal, the influenza virus culture became positive and she was treated with a combination of remdesivir, a Wnt inhibitor (e.g., Ivermectin), and a protease inhibitor dissolved in a semifluorinated alkane or other liquids used for inhalation 4 times along with supportive therapy for 3 weeks through which she gradually recovered.

In one embodiment, in early coronavirus infection, it is treated with a combination of an antiviral medication such as Remdesivir, oseltamivir ribavirin at non-toxic concentrations or Rock inhibitor or Wnt inhibitor, or GSK inhibitor or integrin inhibitor at non-toxic concentrations in a liquid of semifluorinated alkanes or other liquids which does not cause irritation, sprayed in the nose or through the mouth or nebulized for deep breathing through the mouth 1-10 times or more as needed.

Example 10

A 50 year-old man felt that he might have come in contact with someone who had been sneezing in the bus on his was to home 3 days ago. He complained of cold-like symptoms, but had a significant elevated temperature of 101 degrees F. and muscle weakness, sore throat, some coughing, the chest x-ray showed normal lung image with no difficulty in breathing. His influenza virus test became positive. He was treated with a combination of fasudil, a Rock inhibitor and oseltamivir (Tamiflu) in a semifluorinated alkane for inhalation 4 times daily dissolved in semifluorinated alkane or other liquids and oral Tylenol, and baby aspirin 2-3 times daily as needed, his symptoms improved gradually within 3 days while he was on therapy and followed for 5 weeks when the symptoms completely recovered and he returned to work.

In one embodiment, in early coronavirus infection without history of hypertension or known cardiac disease, QTC prolongation or failure, stent or infarct, it is treated with a combination of an antiviral medication such as Remdesivir, tamivir, ribavirin at non-toxic concentrations and/or Rock inhibitor or Wnt inhibitor, or GSK inhibitor or integrin inhibitor, TGF beta inhibitors or in combinations, at nontoxic low concentration of Hydroxychloroquine/chloroquine which has shown some efficacy against viruses such as HIV, Zika virus, even SARS-CoV, by oral administration high doses of 400 mg to 600 mg with the side effect of heart and kidney disease, but low concentrations of 6 mg or less were used in a liquid semifluorinated alkane which does not cause irritation, sprayed in the nose, or through the mouth, or nebulized for inhalation, deep breathing through the mouth 1-4 times or more as needed to block intracellular penetration of the virus. Of note is that previously high oral doses of 600 mg Hydroxychloroquine/chloroquine had been given orally and not by inhalation at 1/100 of the oral dose. The oral daily administration can have serious systemic complications.

In one embodiment, antivirals alone or combined with protease inhibitors, or with convalescent plasma, antibody against COVID-19, Baricitinib, etc. can be administered when dissolved in semifluorinated alkanes or other liquids which does not cause irritation, sprayed in the nose or through the mouth or nebulized for inhalation, with C-Puff for deep breathing through the mouth 1-4 times daily or as slow release polymeric nanoparticles once for prophylactic viral upper respiratory tract prior to the start of the infection or in situations that one suspects that he or she might come or have come in contact with a person carrying viral diseases wherein the antiviral can be chosen depending on the expectation of specific viruses and the treatment can continue for a period of time until the danger passes, e.g., in traveling by plane to certain areas with reported cases.

Example 11

A 44 year-old male executive had to travel to Italy by plane to an area which was considered a hot zone for coronavirus. The person was not complaining or having any symptoms of influenza his blood pressure was normal, no fever or running nose, etc. His temperature was 97 degrees F. and his examination was otherwise normal. He was advised of the option of doing nothing or not traveling or treating himself prophylactically with daily application of combination therapy with oseltamivir (Tamiflu) and Baricitinib, and a GSK inhibitor, intra-nasally followed with deep breathing 3-4 times daily in a semifluorinated alkane for 3 days until he returned, he was then examined for signs of COVID-19 disease. He felt that the medication was well tolerated and no side effects were produced, his repeat examination showed he was normal with no fever, cough, or running nose, etc.

In one embodiment, a method of drug delivery described for treatment of respiratory tract inflammatory diseases caused by various viruses, bacteria, etc. or chronic smoking or exposure to toxic aerosolized nanoparticles and air pollution or asthma and allergens and pathogens, where the inflammation or its consequences are treated with an inflammatory cell pathway inhibitor to block the inflammatory response of the tissue while it does not inhibit an immune response, such as a Rock inhibitor, Wnt inhibitor, GSK inhibitor, or integrin inhibitors IL-1 and IL-6 inhibitors dissolved in liquid semifluorinated alkanes or other liquids as the drug, or in polymeric slow release nanoparticles applied locally as a spray or evaporative solution or in evaporative aerosolized drops that travels through the nasal cavity or mouth to reach the lung alveoli and while on the way attaching to the mucosa, epithelial or endothelial cells of the mouth, nose throat, pharynx, larynx, epiglottis, trachea, bronchi and lung alveoli where the semifluorinated alkanes which is non-toxic or causes irritation to the tissue, rapidly evaporates leaving the medication(s) or slow release nanoparticles, such as polymeric lactic, glycolic acid, or in combination, or porous silicon or polycaprolactone, etc. on the surface of these tissues, releasing the medications over a time of daily inhalation, daily for one week to 3 weeks, then the release of the medication from the nanoparticles continues for months or years to inhibit chronic inflammatory lung diseases.

In one embodiment, the disease process affects many other organs and creates an inflammatory response that can damage these organs, such as in bacterial or viral infections or immune or autoimmune response, chronic inflammation of the prostate, gastro-intestinal tract, joints, one applies a similar strategy for treatment combining anti-bacterial and antiviral with Rock inhibitors, Wnt inhibitors, GSK inhibitors, and integrin inhibitors, IL-6 inhibitors, Baricitinib interleukin antagonists (anakinra), in a known non-toxic dose administered locally, systematically, or orally either with semifluorinated alkane or the standard way in a physiological solution, or in the form of polymeric functionalized nanoparticles for slow release of the medication.

In one embodiment, the patient having a cytokine storm as a result of a viral infection and body's cellular immune/humoral response receiving the inventive therapy, undergoes plasmapheresis to remove, e.g., such cytokines, enzymes, dead cells, etc. from the circulation. Plasmapheresis is a known method to remove unwanted toxic components from blood plasma. Because the patient's plasma is treated extracorporeal, then reinfused, in contrast to reinfusing only cellular components of the patient's blood, plasmapheresis also beneficially detoxifies the patient's plasma without compromising blood volume and with minimal or no fluid loss. This technique avoids the serious complications and side effects of simply returning the cellular components of the blood to the patient. Additionally, all precautions are observed to avoid hypotension and loss of calcium ions in the process of citrate anticoagulation that this procedure requires. The patient can be treated initially with presently available anticoagulants such as heparin, or low molecular weight heparin, polyphenols, such as catechins, coumadin, etc., which can be immediately neutralized post-procedure. Neutralization uses standard techniques known in the art, such as calcium, etc. Hemofiltration treatment is performed with activated carbon, treatment on non-ionic exchange resins, etc. for removing free toxins and also toxin bound with plasma proteins, etc. as in renal dialysis methods. The process may be instituted or repeated as needed. The addition of Rock inhibitors or Wnt inhibitors, GSK inhibitors, integrin inhibitors, IL-1 inhibitors, or IL-6 inhibitors along with other therapeutic agents, such as disulfiram, anakinra, or macrolide immune suppressants such as cyclosporine, Tacrolimus, mycophenolic acid, Ascomycin, Immunomycin, FR-900520, FK520, is an ethyl analog of tacrolimus (FK506) which can be administered in a physiological solution or semifluorinated alkane or a physiological liquid or a suitable medium, systemically or for inhalation dissolved in semifluorinated alkanes or a suitable medium can reduce the overt inflammatory response seen in immune therapy or an autoimmune disease. In some cases with kidney involvement or its protection, kidney dialysis, hemodialysis and or serum electrophoresis is done to remove unwanted toxins and creatinine, etc.

The viral and microbial pathogens can gain access to the brain passing through the damaged endothelial cells of the brain or spinal cord vessels through the circulation or alternatively through the olfactory or trigeminal nerves directly bypassing all barriers of the brain. In one embodiment, a similar route through the nasal mucosa can be utilized to deliver medications to fight the pathogens or provide medications needed to enhance brain nerve survival such as in Alzheimer's disease or Parkinson's disease, etc.

In one embodiment, the viruses are transmitted to brain via circulation using transcellular penetration of the brain capillaries with infected leukocytes.

In one embodiment, the virus gains access to the tissue by using the ACE2 cell receptors of the nasal epithelial cells with the assistance of TMPRSS2 and Purine protein that are found in the mucosa lining of the nose where they reside and multiply before moving toward the respiratory airways and the lung or use the existing channels that lead to the brain through the olfactory nerve or trigeminal nerves. In one embodiment, one can block these enzymes using Rock inhibitors or other protease inhibitors at microgram to milligram concentrations of Rock inhibitors, Wnt inhibitors, GSK inhibitors, or integrin inhibitors, or low concentrations of hydroxychloroquine at 1-6 milligrams in solubilized or aerosolized formulation for inhalation, etc. or blocks the viruses by at least two antivirals such as Tamiflu, Baricitinib, Glidesivir, Tonofovir Disproxil fumarate, lamivudine, efavirenz, Delutegravir and maraviroc, or in combinations, Favipiravir, Xofluza, Remdesivir, nanoviricides, Oya1, umifenovir, tamivir ribavirin dissolved in liquid semifluorinated alkanes or other physiological liquids in combination or sequentially.

In one embodiment, one or at least two antivirals are used with Rock inhibitors, Wnt inhibitors, GSK inhibitors, or integrin inhibitors as polymeric slow release nanoparticles applied as drops or spray or an evaporative solution or dissolved in liquid semifluorinated alkanes or other physiological liquids, in an evaporative aerosolized nano- to micro-drops that travels through the nasal mucosa to reach the branches of trigeminal nerve or olfactory nerve to the brain, brain vasculature, and cerebrospinal fluid where the semifluorinated alkanes rapidly evaporate at body temperature in the tissue leaving the medication(s) or slow release nanoparticles of polylactic, polyglycolic acid, polycaprolactone, porous silicon, micelles or liposomes combination thereof, or the medications move in the respiratory tract, through the nose, throat, and bronchi to the lung alveoli, and release slowly the medications from the nanoparticles over a time period of one day or one week to 3 weeks or months depending on the composition of the nanoparticles.

In one embodiment, the slow release polymeric pluralities of nanoparticles are conjugated with a viral specific antibody while carrying at least one or two antivirals to specifically target the viruses.

In one embodiment, the viral antibody can be obtained from plasma/serum of the patients who have recovered from the infection or the antibody can be produced in the tissue culture against the dead viruses which is cultured with T-cell lymphocytes or natural killers that produce the antibody in addition to producing exosomes or extracellular vesicles (ECV) that can both be harvested to be conjugated with the slow release polymeric nanoparticles or alone to be used for intranasal administration to travel to the brain and lung and kill viruses and the ECV contribute to recovery of the brain and its vasculature by their anti-inflammatory effect.

In one embodiment, the viral antibody coated polymeric nanoparticles are conjugated with antivirals and pluralities of antibodies coated nanoparticles combined with cellular pathway inhibitors or IL-1 and/or IL-6 inhibitors, such as kevzara or nitric oxide (NO) donor (NONOate), interleukin antagonists or rituximab, tocilizumab, etc. administered intra-nasally by inhalation and the same delivery system of semifluorinated alkane or a physiological saline solution with slow release polymeric nanoparticles to seek the viruses, release the medication and block their entry to the endothelial cells, brain, etc. or kill the viruses while releasing the medications and protecting the nose, lung, or brain tissue from further invasion of viruses and reducing the inflammation of the brain and the nerves involved that cause neuralgia and pain.

In one embodiment, pluralities of viral or a fragment of the viral S protein antibody(s) coated polymeric nanoparticles are conjugated with CPP, or ACPP and one or two antivirals with semifluorinated alkanes or a solution is administered intra-nasally, intravenously intramuscularly, topically to enhance cell penetration of the nanoparticle inside the cells to damage the viruses outside the cells and those which have penetrated the cells In one embodiment, pluralities of ACE-2 or neuropilin receptors antibody(s) coated polymeric nanoparticles are conjugated with CPP, or ACPP, or heparin or catechins or linoleic acid and one or two antivirals to block the viruses to enter the cells via ACE-receptors or neuropilin receptors inside the cells by nasal or topical, or systemic administration.

In one embodiment, after inhalation of antivirals, and cellular pathway inhibitors or IL-1 and/or IL 6 inhibitors, such as kevzara of rituximab, tocilizumab, etc. are absorbed through the lung capillaries in the blood and travel to the heart and brain via circulation first, before they are diluted as is the case with intravenous administration, since in brain vasculitis, the blood brain barrier (BBB) is broken, the medication and nanoparticles gain access rapidly to the inflamed areas of the brain where the medication is released over a long time protecting the brain substance and preventing fibrin induced beta amyloid oligomers production and microglial proliferation that encourages a chronic inflammation leading to Alzheimer disease, dementia or neuralgia, etc.

In one embodiment, the intranasal administration and inhalation reduces the side effects or systemic administration of medications, such as cellular pathway inhibitors or IL-1 and/or IL 6 inhibitors such as kevzara of rituximab, tocilizumab, or antivirals, etc. because the medication reaches directly to the source of inflammation and it is applied at a significantly lower dose than the systemic administration of these medications.

In one embodiment, the medications can be simultaneously administered in a physiological solution or semifluorinated alkane or a physiological liquid or a suitable medium orally, intravenously and nasally as needed for therapy and/or as prophylaxis of the viral infection when traveling, or flying by airplane, etc.

In one embodiment, Hypochlorous acid (HOCL) is produced by myeloid cells such as neutrophils, immune cells, eosinophils, mononuclear phagocytes, and B lymphocytes. The non-myeloid cells such as fibrocytes, etc. can also generate Hypochlorous acid (HOCl) in the presence of a solution of sodium chloride (NaCl) in the tissue.

In one embodiment, the stabilized Hypochlorous acid is in general prepared in a physiological saline solution of 0.9%-1.5%, preferably 1%, with Hypochlorous acid at 0.01%, 0.03%, and 0.1% w/v at pH of 3.0-5.0 and the concentration of 0.1 to 2.8 µg/ml. In the cell, the primary enzyme responsible for production of the Hypochlorous acid in presence of NaCl is myeloperoxidase found in phagosomes. In one embodiment, hypochlorous acid is conjugated with taurine that is an antioxidant reducing to toxicity of Hypochlorous acid when it is used in combination of other medications to treat respiratory disease or medication is intended to reach brain through the nasal administration.

In one embodiment, stabilized Hypochlorous acid or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] and slow release polymeric nanoparticles carrying at least two antivirals and Rock inhibitors or GSK inhibitors or Wnt inhibitors and IL-6 inhibitors, interleukin antagonists, etc. are administered in a physiological solution of or Benzalkonium chloride or semifluorinated alkane or a physiological liquid or a suitable solution in the nose as inhalation in spray or nebulized form in viral encephalitis or lung inflammation in (SARS-CoV-2), COVID-19 or their mutations to kill the viruses and prevent the side effects of inflammation in the brain and lung.

In one embodiment, stabilized Hypochlorous acid or chloramines, the stable N-chloro derivatives and slow release polymeric nanoparticles carrying at least two antivirals and Rock inhibitors or GSK inhibitors and IL-6 inhibitors, etc. are administered in a physiological solution or semifluorinated alkane or a physiological liquid along with heparin or low molecular weight heparin, or heparin mimetics or synthetic heparin, such as PG500 and PG545, or polyphenols such as catechins or Ebselen and/or glutathione peroxidase, and superoxide dismutase (SOD)—metabolize oxidative toxic intermediates requiring zinc, selenium, manganese iron, copper, and for ideal catalytic activity applied in the nose as inhalation, in spray or nebulized form to treat viral encephalitis or lung inflammation in (SARS-CoV-2), COVID-19 or their mutations to kill the viruses, etc., such as coronaviruses and prevent the side effects of inflammation or as prophylaxis of viral infection in the respiratory tract, encephalitis, vasculitis, dementia, and neuralgia, etc.

In one embodiment, one can administer prophylactically, one or two antivirals as nasal spray, aerosolized or nebulized form, or oral zinc lozenges, or zinc orally at about 15 mg/day, vitamin D<than 4000 IU/day, atrovastatin or other statins oral 10-50 mg/day more and/or gargle with salt and lukewarm water at a salt concentration of >0.9% to 1.5% or more Na Cl or spray it as aerosolized or nebulized for nasal inhalation, etc. to damage the invading viruses before entering the nasal mucosa, etc.

In one embodiment, increasing the salt concentration enhances the action of the myeloperoxidase to create Hypochlorous acid or chloramines, the stable N-chloro derivatives to fight viruses.

In one embodiment, one can administer prophylactically, antiviral nasal spray, aerosolized or nebulized form of zinc or oral zinc lozenges, or zinc at about 15 mg, vitamin D<than 4000 IU/day and/or with salt and lukewarm water or as spray it as aerosolized or nebulized for nasal inhalation, or hydrogen peroxide at <3% concentration mouthwash or gargle in a short time.

In one embodiment, the mouthwash Listerine in low concentrations or diluted form can be applied to the nose, mouth, or throat mucosa to eliminate viruses.

In one embodiment, povidone iodine toxicity to the eye was tested after injection in the eye 0.1 mL of 50, 100, 200, or 400 micrograms (microg) of PVP-I in 1 eye without toxic effect; higher concentrations of 100 milligrams to 1000 milligrams or more has been used routinely to sterilize the skin prior to surgery.

In one embodiment, povidone iodine at 400 micrograms to 10 milligrams or more can be used as inhalation/day, inhalation through both nostrils for 1-14 days or using Q-tipped applicator with a mixture of 1-20% ethanol and 0.1-1% or more povidone iodide or other iodine preparations, such as cadexomer, Inadine, tincture of iodine iodophor, lugol iodine, etc. can be administered with or without Ebselen and/or glutathione peroxidase, and superoxide dismutase (SOD)—metabolize oxidative toxic intermediates requiring zinc, selenium, manganese iron, copper, and for ideal catalytic activity applied in the nose in a physiological solution or semifluorinated alkane or a physiological liquid or another medium to eliminate viruses and bacteria in the nose respiratory tract.

In one embodiment, Povidone iodine 0.1% is combined with zinc <15 mg in a solution or ointment, etc. applied to the skin of the upper lip, nasal skin, and nose mucosa entrance to damage the invading viruses/bacteria before entering the nasal mucosal cells, etc. reducing the chance of the infection during traveling by plane, etc.

In one embodiment, squalene nanoparticles combined with riboflavin applied to the nose and exposed to a low level of UV radiation of 3 mW/cm2 for one minute damage the viral particles in the nose without crosslinking the nasal proteins.

In one embodiment, the hypochlorous acid (HOCL) is stabilized at PH 5 and less can be applied as drops or spray or nebulized form locally or by inhalation to the nose and its surrounding tissue to eliminate viruses.

In one embodiment, the stabilized hypochlorous solution is acid at a pH 3 to pH 9 and the concentration of 0.01% to about 0.05% or in a semifluorinated alkane or liquid as a slow release nanoparticles of lactic acid, polyglycolic acid, polycaprolactone, or as micelles or in liposomes for nasal or inhalation as spray or aerosolized form.

In one embodiment, the purpose of the invention is to block the viruses, such as (SARS-CoV-2), COVID-19 or their mutations, influenza, herpes, zoster, Zika, Epstein-bar, HIV etc. at different levels of entry in the cell or block the mechanisms involved in its replication and release of the virus including the virucidal activity by preventing attachment or of the viruses' glycoprotein with the glycosylated host protein on the cell membrane surface or inside the cell preventing its capsid formation by inhibiting viral reverse transcriptase, preventing the DNA or RNA transport to the nucleus, or the viral integrase and viral integration in the chromosome, or preventing viral protease to breakdown the cell protein to build viral capsid, or by inducing an innate immune response, such as stimulation of complement C1, C3, C5, toll-like receptors and NK cells and cytotoxic T cells. Other approaches are the use of venom peptides affecting the viral replication cycle, inhibiting viral attachment glycoprotein to the cells, such as ChTx and Scylla-toxin-based mimetics or cecropin A, Magainin or by preventing attachment of virus glycoprotein to CXCR4 and CCR5 co-receptors or disintegration of viral capsid or interfering with the reverse transcription using melittin peptides or preventing the viral assembly of the viral capsid using peptide hacate and interfering in the assembly of the viral capsid and in the organization of the polymerase complex or using peptides derived from Wasp venom to affect Zika virus, chikungunya, dengue, and HIV virus.

In one embodiment, the stabilized hypochlorous or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] solution is acid at a pH 3 to pH 9 and the concentration of 0.01% to about 0.05% or with mimetic heparin with or without Benzalkonium chloride in or with catechin combined with LMWH in a semifluorinated alkane or a suitable medium to block viral receptors, heparan sulfate and Sialic acid, present in the mucosa cells, endothelial cells or neuronal cells, or olfactory bulb and the thiol bound of the viruses, etc., as a slow release nanoparticles of lactic acid, polyglycolic acid, polycaprolactone, or as micelles or in liposomes and chitosan and encapsulated in a non-dissolvable compound given orally to pass through the stomach and is released by enzymatic action in the intestinal tract to release the medication and get absorbed in the intestine to kill the viruses such as (SARS-CoV-2), COVID-19 or their mutations locally preventing the intestinal side effect of viral infection.

In one embodiment, certain compounds can be used prophylactically as mouthwash or hand cleansing, nasal spray, such as hydrogen peroxide, povidone-iodine, ethanol, chlorhexidine, cetylpyridinium chloride, to disrupt the SARS-CoV-2 lipid envelope, COVID-19 lipid envelope, or their mutations, etc.

In one embodiment, for prophylaxis such as traveling by airplane, one can combine two or more antivirals with zinc, or povidone iodine, etc. or in a semifluorinated alkane or in a physiologic fluid in the form of slow release polymeric pluralities of nanoparticles, micelles liposomes, polyglycolic acid, or lactic acid, etc. administered through the nose or orally to last one week or more and release medication after administration in the form of spraying or nebulization by an intranasal route and inhalation to prevent viral attachment to the surface of the nose, throat, mucosa or lung alveoli or kill the incoming viruses or prevent their multiplication before reaching the brain and prevent their migration to the brain via the olfactory nerve.

In one embodiment, certain compounds can be used prophylactically as mouthwash or hand cleansing, such as hydrogen peroxide, povidone-iodine, ethanol, chlorhexidine, cetylpyridinium chloride, Hypochlorous acid, or chloramines, the stable N-chloro derivatives, or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] alone or in combination to disrupt the (SARS-CoV-2), COVID-19 or their mutations lipid envelope.

In one embodiment, the damage to the capillary endothelial cells causes accumulation of platelets and other blood cells causing vascular occlusion, pain, stroke, paralysis, etc.; therefore, in one embodiment, any treatment to combat viral or bacterial central nervous system (CNS) vasculitis or vasculitis in an autoimmune response, such as lupus or in immunotherapy of cancer, etc. should be treated also with oral or systemic anticoagulants, such as aspirin in low molecular weight heparin, and/or in severe conditions, anticoagulants, such as Coumadin, or heparin, low molecular weight heparin (Lovenox), without or with catechin in a semifluorinated alkane or a suitable medium as slow release nanoparticles of lactic acid, polyglycolic acid, polycaprolactone, or as micelles or in liposomes and chitosan with or without Benzalkonium chloride or to block viral receptors, heparan sulfate and Sialic acid, in the mucosa, endothelial cells or neuronal cells, or olfactory bulb, etc., as slow release nanoparticles of lactic acid (LA), polyglycolic acid (PGLA), polycaprolactone, or as micelles, or in liposomes and chitosan to prevent cellular damage by virus and to enhance nerve repair and prevent blood coagulation or TPA to dissolve the blood clot, etc. followed by plasmapheresis, and/or kidney dialysis to remove excessive cytokines.

In one embodiment, the cytokines can be measured by using either the saliva, expectorations, tear, urine, or nasal secretion, cerebrospinal fluid or aqueous fluid of the eye, or blood circulation, etc., the concentrations of cytokines, such as IL-1 and/or IL-6, IL-8 are higher in the inflammatory diseases, etc., and the increase or decrease of their concentrations are indicative of the progression of viral infection or its prognosis.

In the brain and spinal cord, microglial cells act as immune cells, such as macrophages and respond to any pathogen encountered.

In one embodiment, several viruses can affect the upper respiratory system and brain simultaneously, such as influenza viruses or SARS-CoV-2, COVID-19 viruses, or their mutations, and herpes simplex, mumps, or measles, EBV etc.

In one embodiment, the patient with early cases of viral CNS vasculitis can be treated with one or two or more anti-virals or IL-6 inhibitors, interleukin antagonists via inhalation using aerosolized or nebulized medication, in semifluorinated alkane, as polymeric slow release nanoparticles to cover the nasal passages to the brain from the olfactory epithelium to olfactory bulb, and subsequently to the posterior gyms rectus and the cerebrospinal fluid and simultaneously lower respiratory tract infection is treated as described here, while the presence of the virus and cytokines, such as IL-6, before and after therapy can be verified through the nasal secretion or cerebrospinal fluid (CSF), blood, etc. as prognostic indication of the disease process.

In one embodiment, the persistence of headache is a sign of brain vasculitis and increase in the intracranial pressure associated damage to pericytes of small brain capillaries leading to leakage of the blood enriched fibrinogen and accumulation and activation of microglial cells leading to loss of myelin and white matter and buildup of tau and amyloid oligomers, fibrils, and plaque and Alzheimer's disease or Parkinson's disease, dementia; in one embodiment, the nasal application or inhalation of one or more antivirals and anti-inflammatory agents, such as Rock inhibitors, Wnt inhibitors, GSK inhibitors, and integrin inhibitors with or without complement pathway inhibitors, such as C3 inhibitors—AMY-101 (NCT04395456) and APL-9 (NCT04402060); C5 inhibitors—eculizumab (NCT04346797 and NCT04355494), C1 esterase inhibitors, which block the classical complement pathway with anti-IL6 medication, such as Kevzara, tocilizumab, rituximab, etc., or antiviral, baloxavir marboxil, and antibiotics such as tetracycline derivatives a metalloproteinase inhibitor and/or low molecular weight heparin (Levonox) with or without catechin and LMWH in a semifluorinated alkane or a suitable medium to block viral receptors, heparan sulfate, and Sialic acid, as a slow release nanoparticles of lactic acid, polyglycolic acid, polycaprolactone, or as micelles, or in liposomes and chitosan or tissue plasminogen activator (tpa) in the form of nasal spray or aerosolized medication or nebulized medication to reduce the inflammatory process and low molecular weight heparin assists in clearing the fibrinogen and oligodendrocyte loss preventing future side effects of viral encephalitis, such as dementia, Alzheimer's disease, neuralgia, etc.

In one embodiment, viral infection of the lung and brain vasculitis, produce anoxia and ischemia through HIF-1 factor that induces angiogenesis. TiPARP is activated in the cell nucleus that eliminates the HIF-1alpha and TiPARP. Tamoxifen works similarly for the breast tumor and degrades HIF-1 and prevent ischemia and anoxia. In one embodiment, Tamoxifen is combined with an antiviral in a viral infection of the lung and viral brain encephalitis and brain vasculitis and cell pathway inhibitors, Wnt inhibitor, GSK inhibitors, and integrin inhibitors administered in a physiological solution or semifluorinated alkane or a physiological liquid or a suitable medium combined or sequentially through the nose inhalation by spraying, aerosolization, or nebulization to reach both brain and the lung tissue, reduce the inflammatory process and eliminate the side effects of the infection.

In one embodiment, in respiratory viral infection of the upper or lower respiratory system or brain is associated with significant fibrin formation, the treatment is given as nasal application or inhalation of one or more antivirals and anti-inflammatory agents, such as Rock inhibitors, Wnt inhibitors, GSK inhibitors, and integrin inhibitors with anti-IL6 medication, such as Kevzara, or nitric oxide (NO) donor (NONOate), tocilizumab, etc., or tPA tissue plasminogen activator in nanogram to microgram concentrations in the form of nasal spray or aerosolized medication or nebulized medication to reduce the inflammatory process and tPA assists in clearing the fibrinogen/fibrin preventing future side effects of viral encephalitis, or enhancing the clearing the lung from the fibrinous exudates initiated by the viral inflammatory disease. In one embodiment, Mucinex given orally will work synergistically to cleanse the lung alveoli.

In one embodiment, the TPA can be administered in a physiological solution or semifluorinated alkane or a physiological liquid or a suitable medium intravenously either to dissolve the blood clot in the vessels or prevent coronary stent clot formation.

In one embodiment, the brain vasculitis and viral infection produces headache as a sign of cranial vasculitis and increased intracranial pressure, in addition to other symptoms of fever, shiver, and neck stiffness, or nerve palsy, etc., release of viral cytokines and cellular and humoral immune response enhance the inflammatory process in the brain. In one embodiment, one treats the viral brain and upper respiratory infection by simultaneous administration of antiviral agents, with one or more anti-inflammatory cell pathway inhibitors to block the excessive inflammatory response of the brain tissue and its vasculature while maintaining a normal immune response, with one or more Rock inhibitors antitumor SB 772077B, potent Rho-kinase inhibitor; vasodilator SR 3677 dihydrochloride, potent, selective Rho-kinase (ROCK) inhibitor TC-S7001, potent and highly selective ROCK inhibitor Y-27632 dihydrochloride, Botox or botulinum toxin, ROCK2 inhibitor, KD025, Netarsudil, Fasudil, and its derivatives, and/or Wnt inhibitors, GSK inhibitors, integrin inhibitors, or IL-1 and/or IL-6, IL-8 inhibitors dissolved in liquid semifluorinated alkanes or other liquids as the drug, or in a polymeric slow release nanoparticles administered locally as a spray or evaporative solution or in evaporative aerosolized drops or nebulization that travels through the nasal cavity where the semifluorinated alkanes which is non-toxic or causes irritation to the tissue, rapidly evaporates leaving the medication(s) or slow release nanoparticles, such as polymeric lactic, glycolic acid, or in combination, or porous silicon or polycaprolactone, liposomes, micelles, etc. on the surface of these tissues, or travel to the brain through the olfactory or trigeminal nerves releasing the medications over time to the brain, or simultaneously to the mouth to reach the lung alveoli, and while on the way attaching to the mucosa, epithelial or endothelial cells of the trachea, bronchi and lung alveoli and its vasculature and simultaneous absorption of the medication through the nasal capillaries, and lung capillaries provide the delivery of the medication through the circulation to the heart, and brain to their inflamed vasculature by daily inhalation, for one week to three weeks, or the release of the medication from the nanoparticles continues for months or years to inhibit chronic inflammatory processes in the brain that is associated with silent dementia and Alzheimer's disease, Neuralgia, or Parkinson's disease depending on the location of the inflammation.

In one embodiment, the antiviral delivery and pathway inhibitors are conjugated with antibody coated nanoparticles made of pluralities of dimethyl fumarate (DMF), squalene, lanosterol or squalamine or their derivatives that per se are antibiotic/anti-inflammatory compounds, tetracycline and doxycycline, a metalloproteinase inhibitor, to reduce the excessive inflammatory immune response, combined with semifluorinated alkanes or a physiological solution as aerosolized drops or spray for intranasal administration to the lung, brain, and heart.

In one embodiment, the antiviral delivery and pathway inhibitors are conjugated with antibody coated nanoparticles made of pluralities of heparin or synthetic heparin mimetics or synthetic heparin, such as PG500 and polyphenols, such as catechins or hyaluronic acid or their derivatives that per se are anti-inflammatory compounds to reduce the excessive fibrin release or breakdown the fibrinogen and inflammatory immune response, combined with semifluorinated alkanes or a physiological solution as aerosolized drops or spray for intranasal administration to prevent blood clotting, closure of vasculature or coronary stent, etc.

In one embodiment, the nasal approach to the delivery of antivirals, pathway inhibitors or IL-6 inhibitors, etc. using a semifluorinated alkane compound or in physiologic fluid combined with slow release polymeric nanoparticles or antibody-coated nanoparticles can be considered as a systemic application of the drug delivery in viral diseases involving the lung, heart, and brain or their generalized vascular involvement (vasculitis) of the intestinal tract, brain or increased coagulopathy, a single disease complex that is best treated through judicious intranasal route or inhalation, since the major organs (e.g., heart, lung, intestine, and brain) are reached very fast and the lung absorption provide the circulation route to reach the rest of body's vasculature to be treated immediately and also long term with slow release polymeric nanoparticles.

In one embodiment, the administration of the inflammatory pathway inhibitors, such as a Rock inhibitor, Wnt inhibitor, GSK inhibitor, such as synthetic small-molecule ATP-competitive inhibitors, and substrate-competitive inhibitors, non-ATP-competitive inhibitors, where FRAT/GBP competes with Axin inhibiting GSK-3 activity or integrin inhibitors or IL-1 and/or IL-6 inhibitors via nasal administration and inhalation using a semifluorinated alkane compound or in physiologic fluid with polymeric slow release nanoparticles, block the severe inflammatory response of the brain tissue caused by the invasion of the pathogens, which stimulate glial cells proliferation and migration producing oligomers of amyloid that coalesce building fibrils, tau and amyloid plaques, and the medication over time prevents the consequences of the brain vasculitis and encephalopathy in viral diseases of the brain.

In one embodiment, the viral encephalitis, if not treated in time, causes slow simmering or sui generous inflammatory process that may not become recognized, in time, to be treated leading to glial response, production of oligomers of beta amyloid and to self-sustained progressive Alzheimer's disease years or decades later.

In one embodiment, one or two antivirals, such as Tamiflu, Baricitinib, Glidesivir, Favipiravir, Xofluza Remdesivir, nanoviricides, Lenacapavir/Gilead in picomolar concentrations or GS-CA1, Oya1, interferon, umifenovir, tamivir ribavirin, baloxavir can be used orally, systemically or with or without IL-6 inhibitors, etc. Intranasal and orally as prophylaxis of the viral infection in the winter season or when traveling, or flying etc.

In one embodiment, at least one antiviral is combined with one pathway inhibitor, such as Wnt inhibitor FH535, IWP-2, PNU-74654, IWR-1endo, IWR-exo, Demethoxycurcumin, CCTO36477, KY02111, WAY-316606, SFRP, IWP, LGK974, C59, Ant1.4Br/Ant 1.4C1, Ivermectin, Niclosamide, apicularen and bafilomycin, XAV939, XAV939, G007-LK and G244-LM, NSC668036, SB-216763, gemtuzumab, etc., small molecule Wnt inhibitor PKF118-310, Niclosamide with both antiviral and anti-inflammatory effect, Fasudil, Netarsudil, the Wnt/β-catenin pathway inhibitor or Rock inhibitors with an IL-6 inhibitor or Kevzara, or nitric oxide (NO) donor (NONOate), or Actems are used in combination with interferon which is normally produced by natural killer cells in the body to excite cellular immune response in the body where interferons or pegylated interferon act as antivirals in the upper and lower respiratory tract blocking the replication of the RNA and DNA of the viruses at an early stage of viral infection.

The interferons are released in the body as cytokines to excite protective immune such as natural killers, macrophages, major Histocompatibility complex, etc. The interferons act as an antiviral preventing the virus growth in the cells. Interferon or pegylated interferon attaches to the cell receptors of the nasal or throat of the airway system and brain vasculatures, etc. and prevents DNA or RNA of the virus from replicating, the medication is administered in a physiological solution or semifluorinated alkane or a physiological liquid or a suitable medium as a spray of aerosolized liquid or nebulized liquid with or without semifluorinated alkanes preferably at an early stage in the disease process and not if a cytokine storm is eminent.

In one embodiment, antivirals and pathway inhibitors, such as Wnt inhibitors, such as Ivermectin, Niclosamide, etc. can be given orally specially in children or when intestinal involvement is predicted or intranasal inhalation as slow release polymeric nanoparticles at a significantly lower concentration than systemic administration for both viral infection of the lung and brain vasculitis, etc.

In one embodiment, interferon enhances cellular response while cell pathway inhibitors such as Rock, Wnt, GSK, or integrin inhibitors such as such as abegrin, cilengitide, abciximab, tirofiban, natalizumab, eptifibatide, or risuteganib in a low concentration of 1 microgram to 10 micrograms as a solution and IL-6 inhibitor or Kevzara, and/or nitric oxide (NO) donor (NONOate) or Actems to inhibitors, retuaximab, tocilizumab, control the inflammatory process preventing a cytokine response.

In one embodiment, viruses may affect upper or lower respiratory system followed by a bacterial infection with pathogens such as *Streptococcus pneumonia, Haemophilus influenza, Staphylococcus aureus*, or *E. Coli*, etc. However, the bacterial encephalitis, or meningitis is caused more commonly through the circulation. In these cases, a combination use of an antibacterial and one or two antivirals and one pathway inhibitor with or without complement pathway inhibitors, such as C3 inhibitors—AMY-101 (NCT04395456) and APL-9 (NCT04402060); C5 inhibitors—eculizumab (NCT04346797 and NCT04355494); C1 esterase inhibitors, which block the classical complement pathway can be administered in a physiological solution or semifluorinated alkane or a physiological liquid or a suitable medium by inhalation and systemic administration of a non-toxic dose of the antibacterial, antibiotics, or refabutin, etc. medications.

In one embodiment, the TMPRSS2 inhibitor Camostat inhibits entry of the virus in the cells and one or two antivirals nasal combined with Rock inhibitors or GSK inhibitors, or integrin inhibitors, such as abegrin cilengitide, abciximab, tirofiban, natalizumab, eptifibatide, or risuteganib in a low concentration of 1 microgram to 10 micrograms as a solution with or without semifluorinated alkanes or as polymeric nanoparticles can be administered in a physiological solution or semifluorinated alkane or a physiological liquid, simultaneously or sequentially by inhalation for prophylactic as well and treatment of viral infection affecting the brain and its vasculature or the lung.

In one embodiment of viral encephalitis, one can combine intranasal admiration of two antivirals such as lopinavir and ritonavir or Baricitinib, Glidesivir, Favipiravir, Xofluza, Remdesivir, nanoviricides, Oya1, interferon, or pegylated interferon, umifenovir, tamivir, lopinavir, etc. with protease inhibitors such as NSAIDS, or cox-2 inhibitors celecoxib, propanoic acid derivatives, etc. that block the main protease of the virus (M-Pro) essential for virus replication or MicroRNAs or atovaquone with its antiviral effect against RNA viruses, or antisense molecule fomivirsen, antiherpes drugs inhibit viral replication with a Rock inhibitor, or Wnt inhibitor, GSK inhibitor, integrin inhibitor or an IL-6 inhibitor such as kevzara, rituximab, Melatonin, etc. in a semifluorinated alkane or a physiologic solution as polymeric slow release delivery as nasal spray of aerosolized, or nebulized drops to treat or use it as prophylaxis in susceptible patients or those who are exposed, such as health care workers etc., or first responders.

In one embodiment, in end stage viral encephalitis or lung infection, one can combine antivirals with Wnt inhibitors, or integrin inhibitors or Rock inhibitors with IL-6 inhibitors, a macrolide such as tacrolimus, mycophenolic acid, or cyclosporine administered in a physiological solution or semifluorinated alkane or a physiological liquid or a suitable medium intranasal with intravenous administration or orally to suppress cytokine storm with simultaneous kidney dialysis and blood dialysis or plasma electrophoresis.

In one embodiment, antivirals are administered in combination with MPA, an antiviral and TNF inhibitor, and LMWH, catechins, and a Wnt inhibitor, such as niclosamide or ivermectin, or melatonin in polymeric slow release nanoparticles with or without semifluorinated alkanes as a nasal spray or by inhaler to prevent or treat viral encephalitis or prevent the side effect of the viral infection of the brain or after traumatic brain injuries, such as Alzheimer's disease or Parkinson's disease, by eliminating the infection and reducing the endoplasmic reticulum stress in the neuronal cells.

In one embodiment, one administer intranasal antivirals along with medications that block the ACE-2 receptor to which viral particles attach as the compound hydroxyquinoline at low concentration of micro to milligrams, Rock inhibitors where rock inhibition reduces the blood pressure, and while reducing the angiotensin II and increases Ang (1-9) plasma levels and inhibiting the NOX4-Derived ROS-Mediated RhoA/Rho Kinase Pathway, or follicle stimulating hormone or finistride to inhibit testosterone production, along with IL-6 inhibitors or tocilizumab dissolved in a semifluorinated alkane or in a physiologic solution as polymeric slow release antibody coated polymeric nanoparticles as aerosolized delivery system, etc.

In one embodiment, the two viruses such as (SARS-CoV-2), COVID-19 or their mutations and a herpes virus is involved simultaneously or sequentially one can add two antivirals with ganciclovir or acyclovir or valacyclovir, Cidofovir, Vidarabine, Penciclovir, Foscarnet Fomivirsen Famciclovir or Oseltamivir phosphate, Rimantadine, Amantadine, Zanamivir, Telbivudine, Lamivudine, Entecavir, Emtricitabine, Adefovir and heparin mimics containing glucosamine saccharides/acrylamide to bind to 13-Secretase (BACE-1) involved in Alzheimer's disease (AD) administered with or without polyphenols, such as catechins, with or without fluvoxamine, selective serotonin reuptake inhibitors (SSRIs), or tetracycline derivatives, a metalloproteinase inhibitor, or doxycycline, etc., as an antibacterial and anti-inflammatory in a physiological solution or semifluorinated alkane or a physiological liquid or a suitable medium intranasally as slow release polymeric nanoparticles with or without semifluorinated alkanes with a Rock inhibitor and IL-6 inhibitor, or nitric oxide (NO), donor (NONOate) as antiviral and anti-cytokines such as or nitric oxide (NO) donor (NONOate), interleukin antagonists or DMF by inhalation, systemic, oral, topical locally to halt spread of the virus to the brain or its reactivation or to prevent continuation of inflammation as nasal inhalation, etc. in the brain leading to Alzheimer's disease, dementia, and neuralgia, etc.

In one embodiment, two or more antivirals that can be used with the described methodology as a cocktail, in the semifluorinated alkane as a cocktail of antivirals and with pathway inhibitors or complement inhibitors, such as: Fosfonet Sodium; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime, zinc, heparin, anionic polymers. Ganciclovir; Ganciclovir Sodium; Idoxuridine; Kethoxal; Lamivudine; Lobucavir; Memotine Hydrochloride; Methisazone, Adefovir; Alovudine; Alvircept Sudotox; Amantadine Hydrochloride; Aranotin; Arildone; Atevirdine Mesylate; Avridine, Acyclovir; Acyclovir Sodium; Desciclovir; Didanosine; Disoxaril; Edoxudine; Enviradene; Acemannan; Nevirapine; Penciclovir; Pirodavir; Ribavirin; Rimantadine Hydrochloride; Saquinavir Mesylate; Somantadine Hydrochloride; Sorivudine; Statolon; Stavudine; Enviroxime; Famciclovir; Famotine Hydrochloride; Fiacitabine; Fialuridine; Fosarilate; Foscarnet Sodium, Cidofovir; Cipamfylline; Cytarabine Hydrochloride; Delavirdine Mesylate, zanamivir, amantadine, and Palivizumab. Other examples of anti-viral agents include, but are not limited to Acemannan; Nevirapine; Penciclovir; Pirodavir; Ribavirin; Rimantadine Hydrochloride; Saquinavir Mesylate; Somantadine Hydrochloride; Sorivudine; Statolon; Stavudine, etc.

In one embodiment, with a viral infection, the antiviral can be given with an anti-inflammatory compound such as naltrexone, or disulfiram, combined with cox-2 inhibitors or Rock or Wnt or GSK inhibitors or anti-integrin intranasal with a semifluorinated or liquid solution with slow release nanoparticles or polylactic, polyglycolic, polycaprolactone, or porous silicon, micelles, or liposomes, etc. with or without IL-6 inhibitors.

In one embodiment of viral infection, the virus induces a storm cytokine response causing generalized vasculitis and thrombus formation, on treating this condition in addition to the antivirals such as the inhibitor Sofosbuvir, a polymerase inhibitor and ribavirin, umifenovir, tamivir, lopinavir etc., pathway inhibitors, such as Rock inhibitors, with inhibition of cytokine IL-6 with an inhibitor such as Kevzara or nitric oxide (NO), donor (NONOate), or rituximab intranasal administration with semifluorinated or liquid solution with slow release nanoparticles or polylactic, polyglycolic, polycaprolactone, or porous silicon, micelles, or liposomes, etc.

In one embodiment, the medications can be simultaneously administered in a physiological solution or semifluorinated alkane or a physiological liquid or medium orally, intravenously, and nasally as needed for therapy and/or as prophylaxis of the viral infection or when traveling, or flying by airplane, etc.

In one embodiment, one can administer prophylactically, antivirals nasal spray, aerosolized or nebulized form of zinc or oral zinc lozenges, or zinc at about 15 mg, vitamin D<than 4000 IU/day and/or with salt and lukewarm water or spray it as aerosolized or nebulized for nasal inhalation, or hydrogen peroxide at <3% concentration in combination with Listerine mouthwash at low concentration or gargle in a short time.

In one embodiment, the mouthwash Listerine in low concentration or diluted form can be applied to the nose, mouth or throat mucosa with salt water to eliminate viruses.

In one embodiment, povidone iodine toxicity to the eye was tested after injection in the eye 0.1 mL of 50, 100, 200, or 400 micrograms (microg) of PVP-I in one eye without toxic effect; higher concentrations of 100 milligram to 1000 milligram or more has been used routinely to sterilize the skin prior to surgery.

In one embodiment, povidone iodine at 400 micrograms to 10 milligrams or more can be used as inhalation/day through both nostrils for 1-14 days or using Q-tipped applicator with a mixture of 1-20% ethanol and 0.1-1% or more povidone iodide or other iodine preparations such as cadexomer, Inadine, tincture of iodine iodophor, lugol, iodine, with or without LMWH, etc. can be administered in a physiological solution or semifluorinated alkane or a physiological liquid or salt water to eliminate viruses and bacteria in the nose or respiratory tract.

In one embodiment, Povidone iodine 0.1% in salt water is combined with zinc <15 mg in a solution or ointment, etc. applied to the skin of the upper lip, nasal skin, and nose mucosa entrance to damage the invading viruses/bacteria before entering the nasal mucosal cells, etc. reducing the chance of the infection during traveling by plane, etc.

In one embodiment, nanoparticles of squalene nanoparticles combine with riboflavin in salt water 0.9% NaCl applied to the nose and exposure to a low level of UV radiation of 3 mW/cm2 for one minute damage the viral particles in the nose without crosslinking the nasal proteins.

In one embodiment, hypochlorous acid (HOCL) is stabilized at PH 5 and leas in salt water >0.9% NaCl can be applied as drops or spray or nebulized form locally or by inhalation to the nose and its surrounding tissue to eliminate viruses.

In one embodiment, certain compounds can be used prophylactically as mouthwash or hand cleansing, nasal spray, such as hydrogen peroxide, povidone-iodine, ethanol, chlorhexidine, cetylpyridinium chloride to disrupt the COVID-19 lipid envelope.

In one embodiment, for prophylaxis such as traveling by airplane or visiting a patient, or in the office, one can combine two or more antivirals with zinc, or povidone iodine, or another antiseptics, etc. or in semifluorinated alkane or in a physiologic fluid in form of slow release polymeric pluralities of nanoparticles, micelles, liposomes, polyglycolic acid, or lactic acid, etc. administered in form of spraying or nebulization by intranasal route and inhalation to last one week or more and release medication to prevent viral attachment to the surface of the nose, throat, mucosa, or lung alveoli, etc. or kill the incoming viruses or preventing their multiplication before reaching the brain and prevent their migration to the brain via olfactory nerve.

In one embodiment, the stabilized hypochlorous acid or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] solution has a pH 3 to pH 9 and a concentration of 0.02% to about 0.05% or in a semifluorinated alkane or liquid such as 1% or more NaCl solution as a slow release nanoparticles of lactic acid, polyglycolic acid, polycaprolactone or as micelles or in liposomes for nasal administration or inhalation as a spray or aerosolized form with or without antivirals.

In one embodiment, the stabilized hypochlorous acid or chloramines, the stable N-chloro derivatives or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT] at a concentration of 0.025% in 1% sodium chloride with electrolyzed water is obtained from Ecolox-Tech, Envirolite®, etc. without phosphates, or Phosphate Buffered Saline (PBS) and sodium Hypochloride, phosphate with or without a Rock inhibitor, at 1-20 microgram/ml or more, Wnt inhibitor at pico-nanogram/ml concentrations or more, GSK 50 microgram/ml inhibitor or statins at <100 microgram/ml concentration or integrin inhibitors at 25-200 microgram/ml or more concentration with one or more antivirals or bronchodilators.

In one embodiment, 60 milligrams of iron oxide administered in a physiological solution or semifluorinated alkane or a physiological liquid once every two days enhances the production of hemoglobin.

In one embodiment, the nose can be disinfected with intra-nasal Miramistin solution, an old non-toxic disinfectant that kills the bacteria and viruses without affecting the normal cells.

In one embodiment, one or more convalescent plasma's antibodies are used to coat or conjugate with slow release polymeric nanoparticles which seek and attach to the viruses; where the nanoparticles are made from lactic, polyglycolic acid, polycaprolactone, anhydrides, porous silicon, micelles, liposomes, etc. carrying medications, such as antivirals or pluralities of nanoparticles are used carrying two or more antivirals in a physiological solution or administered in a physiological solution or semifluorinated alkane or a physiological liquid or a suitable medium intra-nasally as spray or drops or nebulization for inhalation to treat the early stage viral infection and reduce both viral infection side effects of the infection in the brain or the lung.

In one embodiment, pluralities of one or more antibody-coated slow release polymeric nanoparticles, such as polylactic acid, polyglycolic acid, porous silicon, micelles, liposomes, polyanhydrides, polyesters, polycaprolactone with cell penetrating peptides carry antivirals, such as nelfinavir, or Remdesivir, etc. along with bronchodilators such as, emetine, hydroxychloroquine or its derivatives, salbutamol, obatoclax, albuterol, with or without Rock inhibitors, Wnt inhibitors, GSK inhibitors or integrin inhibitors, intra-nasally or through the mouth as inhalation, to enhance relaxation of the bronchi that bring air in the lung alveoli by relaxing the smooth muscles of the vessels of the lung and brain.

In one embodiment, a combination of antivirals and salbutamol, and IL-6 inhibitors, Rock inhibitors, Wnt inhibitors, GSK inhibitors, or integrin inhibitors, or nitric oxide (NO), donor (NONOate) with or without DMF to inhibit inflammatory processes of the brain or lung vessels leading to leakage of fibrinogen stimulating production of oligomeric beta-amyloid in the brain or fibrin in the lung and can slow down or inhibit formation of Alzheimer's plaques, tau and tangled fibrils or dementia, etc. or reduce oxygen absorption by the lung capillaries and hemoglobin.

In one embodiment, the combination of antivirals with or without tetracycline derivatives, a metalloproteinase inhibitor which antibacterial and an anti-inflammatory and/or nitric oxide (NO), donor (NONOate), with antibody-coated polymeric slow release nanoparticles, such as polylactic acid, polyglycolic acid, porous silicon, micelles, liposomes, polyanhydrides, polyesters, polycaprolactone and antivirals with pathway inhibitors to reduce the inflammation and with cell penetrating peptides or activatable cell penetrating peptides (ACPPs) or cyclodextrin or low-molecular-weight (2-5 kDa) polyethylene glycol, or low molecular weight heparin, synthetic heparin mimetics heparin mimics containing glucosamine saccharides/acrylamide to bind to 13-Secretase (BACE-1) involved in Alzheimer's disease (AD), or synthetic heparin, such as PG500, etc. or Epigallocatechin gallate (EGCG), a green tea catechin, that binds to heparan sulfate or in combination with low molecular weight heparin or heparin mimetics to bind to heparan sulfate and sialic acid preventing the viral attachment to viral cell receptors, such as Neuroplin-1 and ACE-2 receptors of the mucosa, endothelial cells or neuronal cells, or olfactory bulb, etc. as slow release nanoparticles of lactic acid, polyglycolic acid, polycaprolactone, or as micelles or in liposomes and chitosan administered in semifluorinated alkane or a suitable medium through inhalation or vapor, nasal spray or nebulization to reach the brain directly and lung endothelial cells and cells of alveoli directly to inhibit the intracellular viral replication, in the brain, and lung and kill them with minimal amount of antiviral medication compared to the systemic administration of the antiviral that requires production of a large amount of medication with its associated expenses and complications.

In one embodiment of a method of treating, reducing, or alleviating a medical condition in a patient, the method comprising administering to a patient in need thereof a biocompatible drug comprising one or more antiviral medications together with one or more green tee, oolong, Cinnamon, or orange with or without linoleic acid in the warm to boiling water or a nebulizer creating vapor containing the active ingredient of the cocktail for simultaneous inhalation of the vapor's components to inhibit attachment of viruses to ACE-2 receptors or neuropilins's receptors in the nasal pathway to the lung to through the olfactory nerve and trigeminal nerve to brain thereby preventing the viral attachment to enter the nasal or respiratory pathway to the alveoli cells and olfactory nerve or sensory trigeminal nerves, to gain access to the brain cell producing viral encephalitis, or lung infection, where the cocktail can be consumed orally after it is cooled down to be absorbed through the gut preventing damage to the intestine, liver, kidney and the brain through the blood circulation.

In one embodiment of a method of treating, reducing, or alleviating a medical condition in a patient, the method comprises administering to a patient in need thereof a biocompatible drug cocktail comprising one or more antiviral medications together with or without one or more green tee, oolong, Cinnamon, or orange with or without linoleic acid polyphenyls, epigallocatechin gallate catechins (EGCG) having antioxidants compounds cocktail also and catechins etc. found in black tea, or coffee, oolong, white tea, Pu-reh, Chamomile tea, the vegetable, such as fruits or coco, alone or in combinations as a cocktail, or in addition to it one or more antioxidants, antimicrobial, statins and immunomodulatory mangiferin, genistein, estradiol, berberine and baicalein, sulforaphane, with or without vitamin D and high doses of vitamin C, vitamin E, D, or with or without quercetin, curcumin, resveratrol, Alpha-lipoic acid, tocopherols and tocotrienols, carotenoids, glutathione tocopherols, carotenoids alone or with or without linoleic acid mixed in the warm to boiling water or a nebulizer to create a vapor containing the active ingredients for nasal inhalation of the components of the cocktail which are inhibiting attachment of viruses to ACE-2 receptors or neuropilins's receptors etc. thereby preventing the viral attachment or entering the nasal or respiratory pathway to the alveoli cells and olfactory nerve or sensory trigeminal nerves, to gain access to the brain cell producing viral encephalitis, where the cocktail can also be consumed orally after it is cooled down.

In one embodiment, phosphorylation of endoplasmic reticulum resident kinase (PERK) and increased eIF-2α phosphorylation is a marker of endoplasmic reticulum (ER) stress response. The intranasal application of inhibitors of phosphorylation with medications, such as Baricitinib, a Janus kinases inhibitor as anti-TNF and cycloheximide at low concentrations of nanogram/ml to 1-4 microgram/ml, or naproxen prevents/treats not only the viral growth and infection/inflammation in the lung and brain (encephalitis/Alzheimer disease) but also prevent ER stress induced protein misfolding, such as beta amyloid tangles or plaques, chronic inflammation and neuropathy.

In one embodiment, inhibitors of phosphorylation of endoplasmic reticulum resident kinase (PERK) a marker of endoplasmic reticulum (ER) stress response, and prevention of hyperphosphorylation of eIF-2α, such as with a short lasting cycloheximide in DMSO in nanogram/ml to 1-microgram/ml concentration or Baricitinib, a Janus kinases inhibitor as anti-TNF, or naproxen that interacts with the viral nucleocapsid and anti-inflammatory and an antiviral, such as remdesivir or favipiravir in semifluorinated alkanes is administered in combination with nitric oxide (NO), donor (NONOate), pathway inhibitors and LMWH with antivirals as a topical application or nebulization, spray in the nose to prevent or treat viral replication and protein misfolding in the brain diseases caused by viral encephalitis including influenza viruses, coronaviruses, e.g., (SARS-CoV-2), COVID-19, or their mutations herpes viruses, herpes zoster, Epstein Barr virus, cytomegalovirus and subsequent Alzheimer's disease formation, etc., the medications are used sequentially or combined or at different time of the day preferentially as a nasal inhalation, etc.

In one embodiment, other viruses that can be treated with the described methodology are certain RNA viruses that are antigens in vertebrate animals which include, but are not limited to, the following: members of the family Retroviridae, the genus Orbivirus Colorado Tick Fever virus), the genus Rotavirus (human rotavirus); the family Picornaviridae, including the genus Enterovirus, poliovirus, Coxsackie virus A and B, enteric cytopathic human orphan (ECHO) viruses, hepatitis A virus, Porcine enteroviruses, the genus Cardiovirus (Encephalomyocarditis virus) the genus Rhinovirus (Human rhinoviruses the genus Apthovirus; the family Calciviridae, Feline picornavirus and Norwalk virus; the family Togaviridae, including the genus Alphavirus, Ross river virus, Venezuelan equine encephalitis virus, Western equine encephalitis virus, the genus Flavirius, yellow fever virus; Dengue virus, Japanese encephalitis virus, St. Louis encephalitis virus, Murray Valley encephalitis virus, West Nile virus, Central European tick borne virus, Far Eastern tick borne virus, Omsk hemorrhagic fever virus), the genus Rubivirus (Rubella virus), the genus Pestivirus (Mucosal disease virus, the family Bunyaviridae, including the genus Bunyvirus (Bunyamwera and related viruses, California encephalitis group viruses), the genus Phlebovirus, Sandfly fever Sicilian virus, Rift Valley fever virus, the genus Nairovirus, hemorrhagic fever virus, and the genus Uukuvirus\the family Orthomyxoviridae, including the genus influenza virus (influenza virus type A, many human subtypes; Swine influenza virus, and Avian and Equine Influenza viruses; influenza type B many human subtypes, and influenza type C, the family paramyxoviridae, including the genus Paramyxovirus, Parainfluenza virus type I, Parainfluenza viruses types 2 to 5, Newcastle Disease Virus, Mumps virus, the genus Morbillivirus, Measles virus, subacute sclerosing panencephalitis virus, distemper virus, Rinderpest virus, the genus Pneumovirus respiratory syncytial virus (RSV), Bovine respiratory syncytial virus, forest virus, Sindbis virus, Chikungunya virus, O'Nyong-Nyong virus, Ross river virus, Venezuelan equine encephalitis virus, Western equine encephalitis virus, the genus Flavirius (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus Rubivirus (Rubella virus), the genus Pestivirus (Mucosal disease virus, Hog cholera virus, Border disease virus); the family Bunyaviridae, related viruses, California encephalitis group viruses, the genus Phlebovirus Sandfly fever Sicilian virus, Rift Valley fever, virus, the genus Nairovirus, Crimean-Congo hemorrhagic fever virus, Nairobi sheep disease virus), and the genus Uukuvirus (Uukuniemi and related viruses); the family Orthomyxoviridae, including the genus Influenza virus, Influenza virus type A, many human subtypes; Swine influenza virus, and Avian and Equine Influenza viruses; influenza type B and influenza type C the family paramyxoviridae, including the genus Paramyxovirus, Parainfluenza virus type I, Sendai virus, Hemadsorption virus, Parainfluenza viruses types 2 to 5, Newcastle Disease Virus, Mumps virus, the genus Morbillivirus, Measles virus, subacute sclerosing panencephalitis virus, distemper virus, Rinderpest virus, the genus Pneumovirus, respiratory syncytial virus (RSV), Bovine respiratory syncytial virus and Pneumonia virus of mic); the family Rhabdoviridae, including the genus Vesiculovirus (VSV), Chandipura virus, Flanders-Hart Park virus), the genus Lyssavirus (Rabies virus) (Marburg virus and Ebola virus); the family Arenaviridae, including Lymphocytic choriomeningitis virus (LCM), Tacaribe virus complex, and Lassa virus; the family Coronaviridae, including Infectious Bronchitis Virus (IBV), Mouse Hepatitis virus, Human enteric coronavirus, and Feline infectious peritonitis (Feline coronavirus). In addition, other viruses that can be treated with the described methodology are certain DNA viruses that are antigens in vertebrate animals which include, but are not limited to: the family Poxviridae, including the genus Orthopoxvirus (Variola major, Variola minor, Monkey pox Vaccinia, Cowpox, the family Herpesviridae, including the alpha-Herpesviruses, Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus, the Beta-herpesviruses Human cytomegalovirus and cytomegaloviruses of swine, monkeys and rodents; the gamma-herpes viruses, Epstein-Barr virus (EBV), Marek's disease virus, Herpes saimiri, Herpesvirus ateles, the family Adenoviridae, including the genus Mastadenovirus, Human subgroups A, B, C, D, E and ungrouped; simian adenoviruses, infectious canine hepatitis, (Avian adenoviruses); and non-cultivatable adenoviruses; the family Papoviridae, including the genus Papillomavirus, Human papilloma viruses, bovine papilloma viruses, various pathogenic papilloma viruses of other species), the genus Polyomavirus); the family Parvoviridae including the genus Adeno-associated viruses, the genus Parvovirus, bovine parvovirus, canine parvovirus, Aleutian mink disease virus, DNA viruses may include viruses that do not fit into the above families such as Creutzfeldt-Jacob disease viruses and chronic infectious neuropathic agents.

In one embodiment, one can administer antivirals with pathway inhibitors in combination with TNF alpha inhibitors, such as baricitinib, and Raf inhibitors, such as sorafenib, regorafenib, dabrafenib, with or without anti-VGEFs, aerosolized or in slow release polymeric nanoparticles with or without semifluorinated alkanes by nasal application, inhalation, etc. at low concentrations to inhibit inflammatory processes and excessive activation of glial cell stimulation in viral encephalitis or traumatic brain injuries while protecting the existing neuronal cells and preventing side effects, such as Alzheimer's disease or Parkinson's disease, etc.

In one embodiment, the combination of antivirals and salbutamol with antibody-coated nanoparticles, such as polylactic acid, polyglycolic acid, porous silicon, micelles, liposomes, polyanhydrides, polyesters, polycaprolactone with cell penetrating peptides or activatable cell penetrating peptides (ACPPs) or cyclodextrin or low molecular weight heparin, synthetic heparin mimetics, or synthetic heparin, such as PG500 and semifluorinated alkane or catechins alone or combined with low molecular weight heparin or heparin mimetics that bind to heparan sulfate or to sialic acid which are the component of ACE-2 and neuropilin-1 receptors of the mucosa, endothelial cells or neuronal cells, or olfactory bulb, etc. as slow release nanoparticles of lactic acid, polyglycolic acid, polycaprolactone, or as micelles or in liposomes and chitosan that the site where the influenza, (SARS-CoV-2), COVID-19 or their mutations and other viruses enter the cells, etc. in a hyaluronic acid solution at <1% concentration or LMWH are administered in a physiological solution or semifluorinated alkane or a physiological liquid through inhalation, or by an inhaler or through the nose to reach the brain directly and lung endothelial cells and remain there for a period of time before the semifluorinated alkane evaporates, leaving the antibody-coated polymeric slow release nanoparticles in place to penetrate the alveoli cells or brain vessels cells directly to inhibit the intracellular viral particles, and kill them with a minimal amount of antiviral medication compared to the systemic administration while the nanoparticles can deliver the medication for a long period of time, reducing the need for a production or availability of medication in a pandemic viral infection, while salbutamol and low molecular weight heparin or synthetic heparin mimetics and polyphenols, such as catechins and/or Probenecid inhibits Panex-1 and prevent formation of fibrin and beta-amyloid that encourages tau plaque and neurofibrillary formation as a precursor of dementia or Alzheimer's disease occurring after inflammatory processes of the brain.

In another embodiment, where the disease has progressed, the combination of inhalation and intravenous administration of antibody-coated polymeric slow release nanoparticles/antivirals with cell penetrating peptides or activatable cell penetrating peptides (ACPPs) or cyclodextrin, or polyethylene glycol, or low molecular weight heparin, micelles, etc. is given simultaneously intravenously or orally that enhances also the cellular immune response of the body directly in the gut, lung, or brain directly which clears the dead viruses or dead cells, etc. that can produce toxins and multi-system inflammatory disease in adults or children after viral infection.

In one embodiment, the combination of antivirals and salbutamol, adrenaline, hyaluronic acid, with antibody-coated polymeric slow release nanoparticles, such as polylactic acid, polyglycolic acid, porous silicon, PEG-PLA, micelles, liposomes, polyanhydrides, polyesters, polycaprolactone with cell penetrating peptides or activatable cell penetrating peptides (ACPPs) or cyclodextrin or epigallocatechin gallate (EGCG), that bind to heparan sulfate or to sialic acid preventing the viral attachment to its cell receptors or pegylated heparin or synthetic heparin mimetics, or synthetic heparin, such as PG500, or catechins alone or combined with low molecular weight heparin, or low molecular weight heparin (LMWH), or heparin mimetics that bind to heparan sulfate or to sialic acid which are the component of ACE-2 and neuropilin-1 receptors of the mucosa, endothelial cells or neuronal cells, or olfactory bulb etc. as a slow release nanoparticles of lactic acid, polyglycolic acid, polycaprolactone, or as micelles or in liposomes and chitosan that the site where the influenza, (SARS-CoV-2), COVID-19 or their mutations and other viruses enter the cells, etc. in nanoparticles, micelles, or liposomes are administered with protease (PLpro or Mpro, etc.) blocking agents, such as Ebselen, Ebseleno, or Ebselenum, and or glutathione peroxidase, GPx and superoxide dismutase (SOD)—metabolize oxidative toxic intermediates requiring zinc, selenium, manganese iron, copper, and for ideal catalytic activity applied in the nose etc., which also is an antiviral, antibacterial, anti-inflammatory, anti-prostaglandin, and neuroprotective effect, administered in a physiological solution or semifluorinated alkane or a physiological liquid or as vapor by inhalation through the nose, or through the mouth by an inhaler to reach the brain directly in lung, brain blood vessel endothelial cells, and remain in the nose, alveoli, brain endothelial cells, and to inhibit the replication of intracellular viruses, and kill them with minimal amount of antiviral medications compared to the systemic administration of the medications while improving breathing through the relaxation of bronchi smooth vessels and in the brain enhancing neuronal regeneration and prevention of amyloid plaque formation.

In one embodiment, the combination of antivirals with antibody-coated polymeric slow release nanoparticles, such as polylactic acid, polyglycolic acid, porous silicon, micelles, liposomes, polyanhydrides, polyesters, polycaprolactone with cell penetrating peptides or activatable cell penetrating peptides (ACPPs) or pegylated low-molecular-weight heparin or synthetic heparin mimetics or synthetic heparin, such as PG500, or epigallocatechin gallate (EGCG), that binds to sialic acid, combined low molecular weight heparin (LMWH) or heparin mimetics that bind to heparan sulfate or to sialic acid preventing the viral attachment to its cell receptors in slow release nanoparticles of lactic acid, polyglycolic acid, polycaprolactone, or as micelles or in liposomes and chitosan or cyclodextrin are administered with naturally or synthetically produced compounds to inhibit protease (PLpro or Mpro), such as Ebselen, and/or glutathione peroxidase and superoxide dismutase (SOD)—metabolize oxidative toxic intermediates requiring zinc, selenium, manganese iron, copper, and for ideal catalytic activity applied in the nose, blocking proteases, which also has an antiviral, antibacterial, anti-inflammatory, anti-prostaglandin, and neuroprotective effect, or preventing the (SARS-CoV-2), COVID-19 or their mutations spikes attachment to the cells, by administration in a semifluorinated alkane or a suitable medium through inhalation or through the mouth by an inhaler to reach the brain directly through the nose, lung, brain blood vessel endothelial cells and to remain in the nose, alveoli, brain endothelial cells for a longer period of time to inhibit the cell entry through the ACE-2 or preventing replication of intracellular viruses, and kill them with minimal amount of antiviral medications compared to the systemic administration for a long period of time for the patient to recover.

In one embodiment, one can examine and assess the degree of vascular and brain involvement or damage after viral brain involvement using an electroencephalogram prior and after administration of the antiviral and Rock inhibitors, etc. medications through the nose or orally or intravenously, with the administration of polymeric slow release nanoparticles carrying antivirals with or without Rock inhibitors, Wnt inhibitors, GSK inhibitors, or integrin inhibitors, etc. or salbutamol which indicates the functional recovery of the affected brain cells or treating seizure, sleep difficulty, etc.

In one embodiment, the combination of antivirals with antibody-coated polymeric slow release nanoparticles, such as polylactic acid, polyglycolic acid, porous silicon, PEG-PLA, micelles, liposomes, polyanhydrides, polyesters, polycaprolactone with cell penetrating peptides or activatable cell penetrating peptides (ACPPs) or cyclodextrin or pegylated nanoparticles or PEG-PLA or PGG-PGLA or PEG-Heparin, or synthetic heparin mimetics, or synthetic heparin, such as PG500, nanoparticles with polyphenols, such as catechins alone that bind to sialic acid or combined with low molecular weight heparin that bind to both heparan sulfate and to sialic acid which are the component of ACE-2 and neuropilin-1 receptors of the mucosa, endothelial cells or neuronal cells, or olfactory bulb, etc. that the site where the influenza, COVID-19 and other viruses enter the cells, etc. as slow release antibody-coated nanoparticles of lactic acid, polyglycolic acid, polycaprolactone, or as micelles or in liposomes and chitosan, etc. are administered in a physiological solution or semifluorinated alkane or a physiological liquid by spray or inhalation or through the nose, mouth by an inhaler in combination with bronchodilators, such as xanthine bronchodilators terbutaline, non-selective beta.-stimulants, isoprenaline, adrenaline, Sudafed, beta.sub.2-agonist fenoterol, formoterol, pirbuterol, reproterol, salbutamol, indacaterol, aminophylline and choline theophyllinate and anti-allergic agents, such as ketotifen, cromoglycate, and anti-inflammatory agents, such as Dexamethasone, fluticasone, betamethasone, budesonide, flunisolide, beclomethasone, dipropionate, ciclesonide, triamcinolone acetonide, etc., anticholinergic agents, ipratropium bromide, oxitropium bromide and tiotropiumetc, alone or in combinations as needed to treat viral brain infection, encephalitis or lung viral infections, such as influenza viruses or (SARS-CoV-2), COVID-19, or their mutations etc.

In one embodiment, with encephalitis viral infection, the vasculitis causes severe migraines, which are treated with the combination of antivirals with antibody-coated nanoparticles such as polylactic acid, polyglycolic acid, porous silicon, PEG-PLA, micelles, liposomes, polyanhydrides, polyesters, polycaprolactone with cell penetrating peptides or activatable cell penetrating peptides (ACPPs) or pegylated nanoparticles or PEG-PLA or PGG-PGLA or PEG-Heparin or synthetic heparin mimetics or synthetic heparin, such as PG500, or catechins alone or combined with low molecular weight heparin that bind to heparan sulfate or to sialic acid which are the component of ACE-2 and neuropilin-1 receptors of the mucosa, endothelial cells or neuronal cells, or olfactory bulb, etc. the site where the influenza, (SARS-CoV-2), COVID-19, or their mutations and other viruses enter the cells, etc. as slow release antibody-coated nanoparticles of lactic acid, polyglycolic acid, polycaprolactone, or as micelles or in liposomes and chitosan or nanoparticles or cyclodextrin administered in a physiological solution or semifluorinated alkane or a physiological liquid by spray or inhalation or through the mouth by an inhaler, in combination with bronchodilators, such as isoprenaline, adrenaline, Sudafed, salbutamol, albuterol, indacaterol, glycopyrrolate, formoterol, aminophylline or in combinations and choline theophylline and anti-inflammatory agents, such as Dexamethasone, fluticasone, betamethasone, Rock inhibitors, Wnt inhibitors, GSK inhibitors, or integrin inhibitors or in combinations, anticholinergic agents, ipratropium bromide, oxitropium bromide and tiotropiumetc, alone or in combinations with anti-migraine medications, such as almotriptan, rizatriptan, triptan through inhalation, or orally or NSAIDs, such as propionic acid derived non-steroidal agents.

In one embodiment, the combination of antivirals such as Remdesivir, zanamivir, ribavirin, flumist, ruprintrivir and pleconaril, Favipiravir, etc. and protease inhibitors with antibody-coated polymeric nanoparticles, such as polylactic acid, polyglycolic acid, porous silicon, PEG-PLA, micelles, liposomes, polyanhydrides, polyesters, polycaprolactone conjugated with or without cell penetrating peptides or activatable cell penetrating peptides (ACPPs) or cyclodextrin, or low-molecular-weight (2-5 kDa) polyethylene glycol or PEG-modified NPs densely coated by low MW PEG or Pluronic F-127 modified NPs, as PEG-polyacrylic acid, or papain or pegylated nanoparticles or PEG-PLA or PGG-PGLA or PEG-Heparin or synthetic heparin mimetics or synthetic heparin, such as PG500, or catechins alone or combined with low molecular weight heparin that bind to heparan sulfate or to sialic acid which are the component of ACE-2 and neuropilin-1 receptors of the mucosa, endothelial cells or neuronal cells, or olfactory bulb, etc. that the site where the influenza, COVID-19 and other viruses enter the cells, etc., as nanoparticles, PEG-LA, polysorbates are administered in a physiological solution or semifluorinated alkane or a physiological liquid as drops or spray, orally or intravenously in combination with anti-allergic agents, such as ketotifen, cromoglycate, and anti-inflammatory agents, such as Dexamethasone, fluticasone, budesonide, flunisolide, ciclesonide, beclomethasone, dipropionate, triamcinolone acetonide, fluorocinolone, betamethasone, etc., anticholinergic agents, ipratropium bromide, oxitropium bromide and tiotropiumetc, melatonin, alone or GABA inhibitors such as KDS2010, low molecular weight heparin (Lovenox) to simultaneously act as an antiviral (e.g., (SARS-CoV-2), COVID-19) or their mutations or antibacterial and to enhance nerve repair and prevent blood coagulation, NSAIDS in combinations with polyphenols, such as catechins as needed to treat intestinal viral infections (e.g., COVID-19) as inhalation therapy or through the mouth by an inhaler, with or without semifluorinated alkanes.

In one embodiment, end stage viral brain and lung infection antivirals are administered in a physiological solution or semifluorinated alkane or a physiological liquid or a suitable medium by inhalation or intravenously or orally in combination with anticoagulants, aspirin, Coumadin, non-coagulative low molecular weight heparin, or synthetic heparin mimetics or synthetic heparin, such as PG500, etc., and immunomodulators, Rock inhibitors, Wnt inhibitors, integrin inhibitors, cyclosporine, macrolide, mycophenolic acid, ascomycin, tacrolimus, etc. with GABA inhibitors, such as KDS2010, or melatonin that regulates the sleep-wake cycle or low molecular weight heparin (Lovenox) and polyphenols, such as catechins that bind to heparan sulfate or to sialic acid which are the component of ACE-2 and neuropilin-1 receptors of the mucosa, endothelial cells or neuronal cells, or olfactory bulb cells, etc. the site where the influenza, (SARS-CoV-2), COVID-19 or their mutations and other viruses enter the cells, etc. as a polymeric slow release nanoparticles of lactic acid, polyglycolic acid, polycaprolactone, or as micelles or in liposomes and chitosan to enhance nerve repair and prevent blood coagulation in antibody-coated polymeric slow release nanoparticles to combat an overactive immune response.

In one embodiment, when the viral infection is associated with a cytokine storm or multi-organ disease, blood electrophoresis, kidney dialysis, and/or dielectrophoresis are needed to remove excessive cytokine and killed cells and viruses, etc.

In the cells, TRIM proteins are generated by the interferon. A number of TRIMs are needed to block viral infections. Trim2 binds to the antibody conjugated non-enveloped virions in the infected cells and directs the virions to the proteasomes where the virions are degraded.

In one embodiment, since there are no antivirals for newly genetically modified viruses, the body's immune response including cellular response with killer cells is the only way to overcome a viral infection; the immune stimulation is beneficial at the early diseases process but excessive response damages the vital organs of the patient the so called multi-organ disease.

In one embodiment, to stimulate the immune response one can use viral-like particles along with serum antibody(s) obtained from convalescent person or an animal to conjugate with viral-like particles (VLP) that naturally produce a strong cellular immune response and interferon against any invading organism in this case the viral antigen that VLPs are conjugated with the viral antigen e.g., COVID-19 or their mutations, spike protein or multiple antigens, etc. to initiate humoral and cellular response against the recently propagated epidemic viral infection. In one embodiment, this methodology using methylene blue can be used to produce a vaccine in antibody-coated polymeric slow release nanoparticles to produce or enhance the immune system to fight the viral (e.g., COVID-19) infection in general or (SARS-CoV-2), COVID-19 or their mutations or other specific viruses, by inhalation or nasal drops or spray or aerosolized drops.

In one embodiment, using the antibody(s) coated VLPs used with the bethylen blue vaccinane production technology produces a strong cellular immune response by stimulating interferon production against any invading organism in this case the viral antigen, VLPs are conjugated with the viral antigen e.g., (SARS-CoV-2), COVID-19 or their mutations spike protein or RNA or multiple antigens, etc. to initiate humoral and cellular response against the recently propagated epidemic viral infection and natural killer cells that are culture grown with (SARS-CoV-2), COVID-19 or their mutations antigen(s) or protein(s) are administered in a physiological solution or semifluorinated alkane or a physiological liquid with or without antivirals simultaneously with or without Rock inhibitors, or Wnt inhibitors as ivermectin, niclosamide or integrin inhibitors, simultaneously or sequentially by inhalation, subcutaneously, intraperitoneally, intramuscularly or intravenously to initiate a cellular and humoral immune response against the (SARS-CoV-2), COVID-19 virus, or their mutations, or in immunosuppressed patient, where the natural killer cells attack the viruses to eliminate the infected cells and viruses.

In one embodiment, antibody-coated VLP that induces interferon production conjugated with spike protein of the virus is prepared with the known technology in the art for vaccination in antibody and CPP or Mucus penetrating agents coated polymeric slow release nanoparticles, with or without antivirals, and administered in a physiological solution or semifluorinated alkane or a physiological liquid intra-nasally, subcutaneously, or orally or systemically at low concentrations which can be repeated initially monthly, every three months, or six months or yearly by measuring the antibody or neutralizing antibody in a person.

In one embodiment, antibody-coated VLP that induces interferon production conjugated with fragments of RNA of the virus is prepared or after irradiation with UV light to crosslink it to lose its activity, but maintaining its antigenicity for vaccination in antibody (s), ACPP or MPP-coated polymeric slow release polymeric nanoparticles with or without antivirals simultaneously or sequentially and administered in a physiological solution or semifluorinated alkane or a physiological liquid intra-nasally, subcutaneously, or orally or systemically at low concentrations which can be repeated initially monthly, every three months, or six months or yearly by measuring the antibody or neutralizing antibody present in a person.

In one embodiment, using the spike protein or crosslinked DNA or RNA fragments of a number of viruses can be used with an antibody, CPP or MPP-coated VLP that enhance interferon production and to induce a humoral and cellular response against any viruses or other pathogens administered, in a physiological solution or semifluorinated alkane or a physiological liquid initially at very low but gradually increasing concentrations to render immune response against any organism.

In one embodiment, vaccination is performed with multiple viral antibodies, and CPP coated VLPs that induces interferon production conjugated with slow release polymeric nanoparticles with or without antivirals simultaneously or sequentially and administered in a physiological solution or semifluorinated alkane or a physiological liquid, etc. intra-nasally, subcutaneously, or orally or systemically at low concentrations which can be repeated initially monthly, every three months, or six months or yearly by measuring the antibody or neutralizing antibody present in a person.

In one embodiment, the VLPs can be coated with one or more viral (COVID-19) antibodies and another adjuvant, such as acrylic-acid-based adjuvant (ADJ) in antibody-coated polymeric slow release nanoparticles with or without antivirals, or catechins or Lovenox such as Remdesivir, favipiravir, etc. used in vaccine with and or an adjuvant production to create an incremental increase in immune response to the viruses, bacteria, etc. intramuscularly, by inhalation, intranasally without inducing a cytokine storm.

In one embodiment, the VLP or an adjuvant/antigen/antibody/Rock inhibitors, etc. vaccination is done with or without an antibody and ACPP-coated polymeric slow release of viral antibody-coated pluralities of nanoparticles alone or in an oxygenated semifluorinated alkane with adjuvants, such as Analgesic adjuvants, calcium phosphate hydroxide, aluminum phosphate, alum, aluminum hydroxide, paraffin oil, *Mycobacterium bovis*, squalene detergents, antivirals, catechins and/or Lovenox, antibiotics, such as tetracycline, a metalloproteinase inhibitor which are antibacterial and anti-inflammatory or doxycycline, Egg proteins, yeast proteins, Acidity regulators, or modified sugar molecules against viruses, such as Tamiflu, etc. in a semifluorinated alkane or a liquid for inhalation or intramuscularly, etc.

In one embodiment, the VLP/antigen/antibody/Rock inhibitors, etc. vaccination is done with or without antibody and ACPP, or MPP-coated polymeric slow release nanoparticles having dexamethasone or Rock inhibitors, Wnt inhibitors, integrin inhibitors, or GSK inhibitors with adjuvants such as Analgesic adjuvants, calcium phosphate hydroxide, aluminum phosphate, alum, aluminum hydroxide, paraffin oil, *Mycobacterium bovis*, squalene detergents, antiviral, antibiotics, antivirals with Tetracycline derivative medications, a metalloproteinase inhibitor which is antibacterial and anti-inflammatory include demeclocycline, doxycycline, Minocycline, Minocin, etc. to treat inflammatory viral lung or brain infection through the nasal inhalation, etc., Egg proteins, yeast proteins, acidity regulators, or modified sugar molecules against viruses, such as Tamiflu, green tee extracts etc. or other antivirals, such as baloxavir marboxil, combined with nanoparticles or polymeric slow release antibody-coated pluralities of nanoparticles coated with a virus, (SARS-CoV-2), COVID-19, or their mutations or influenza or other viruses in combination with LMWH/catechins, LMWH, heparin mimetics or viral-like or antibody coated viral like nanoparticles and an adjuvant such as acrylic-acid-based adjuvant (ADJ) to induce an immunity against the specific virus or treat specific viruses, etc. or vaccination for inhalation, or subcutaneous, intraperitoneal, or intramuscular or intravenous injection monthly, every three months, or six months or yearly by measuring the antibody or neutralizing antibody present in a person.

In one embodiment of viral lung or brain involvement the antibody, CPP or low-molecular-weight (2-5 kDa) polyethylene glycol or poloxamer, Lovenox-coated, VLP that induces interferon production is combined with or without polyphenols such as catechins with LMWH that block ACE-2 and neuropilin-1 receptors for the virus cell entry, and one of Rock inhibitors, Wnt inhibitors, GSK and/or integrin inhibitors, or with therapeutic medications, such an antiviral in a semifluorinated alkane or suitable medium administered by inhalation, with such as salbutamol, fenoterol, adrenalin, dobutamine, in antibody-coated polymeric slow release nanoparticles to reduce the side effect of vaccination and enhance recovery regardless of its application, intranasal, intramuscular, inhalation, or through the mouth by an inhaler, or intraperitoneal or intravenously.

In one embodiment, antivirals combined with antibody (monoclonal or polyclonal antibodies) coated or aptamer or mRNA or in combinations conjugated pluralities of nanoparticles or polymeric slow release nanoparticles coated against a virus, (SARS-CoV-2), COVID-19 or their mutations or influenza or other viruses in combination with LMWH, heparin mimetics/catechins, or a metalloproteinase inhibitor tetracycline derivatives which antibacterial and anti-inflammatory and antibody-coated viral-like nanoparticles or an adjuvant as a vaccine to induce interferon and an immune response to the antigens and a pathway inhibitor, with or without additional adjuvants to induce an immunity against the specific virus/bacteria, etc. or treat specific viruses while blocking excessive type 2 immune response.

In one embodiment, an adjuvant can be used or added to a vaccine to enhance the immune response including amorphous aluminum hydroxyphosphate sulfate (AAHS), aluminum hydroxide, aluminum phosphate, potassium aluminum sulfate (Alum), Oil in water emulsion made of squalene, Monophosphoryl lipid A (MPL), QS-21, extracted from the Chilean soapbark tree in liposomes, Cytosine phosphoguanine (CpG) a synthetic DNA mimicking viral bacteria genetic material, Glucopyranosyl Lipid Adjuvant-Stable Emulsion (GLA-SE), synthetic Toll-like receptor (TLR)4 agonist, adjuvant Fluzone®. The GLA-SE adjuvant Fluzone vaccine, or saponins, etc.

In one embodiment, one can start with VLP antigen/antibodies vaccination through the inhalation or variation of vaccines repeatedly combined with pathway inhibitors.

In one embodiment, one can start with one mRNA vaccine and move to second application of the same or another vaccine, one such as VLP antigen/antibodies or synthetic toll-like receptor agonist in a semifluorinated alkane or perfluorocarbon liquid through the inhalation or variation of vaccines repeatedly combined with pathway inhibitors in slow release polymeric nanoparticles.

In one embodiment to prevent vasculitis, one can administer two or more antivirals, combined with cell inflammatory pathway inhibitors, with LMWH, or heparin mimetic, linoleic acid etc. complement inhibitors, anti-inflammatory compounds, by inhalation, orally, systemically, intravenously, subcutaneously, intramuscularly, etc.

In one embodiment of viral encephalitis, one prevents Alzheimer's and Parkinson's disease and other viral-related CNS infections with an antiviral in combination with cell inflammatory pathway inhibitors and with LMWH, or a heparin mimetic, complement inhibitors and specific medications such as Bariticinib, Kezara, and with LMWH, or heparin mimetics, complement inhibitors, etc. and GSK inhibitors by inhalation, orally, systemically, intravenously, subcutaneously, intramuscularly, etc.

In one embodiment, the endoplasmic reticulum stress of the neuronal cell in viral diseases and also traumatic brain injuries, etc. is treated by adding anti inflammatory medications, such as such as Bariticinib, Kezara, to pathway inhibitors and combining ACE-2 inhibitors, neuropilin receptor blockage, catechins and linoleic acid, etc.

In one embodiment, as described with the use of methylene blue, for self-vaccination with a single dose unit or vaccine for nasal inhalation with one or multiple vaccines produced for numerous viruses that is obtained or ordered for home delivery from the pharmacists by doctor's prescription by inhalation, orally, systemically, intravenously, subcutaneously, intramuscularly, etc.

Example 12

After obtaining permission from the animal committee, two healthy female chimpanzees weighing 20 kg each, with a healthy body temperature of 37° C. were vaccinated, one by nasal inhalation/jet injector, and the other one by intramuscular injection of a vaccine made of treated (damaged) COVID-19 viruses which had grown in the cell culture media, with a solution of methylene blue at a concentration of 30 µg/ml in the dark environment for about two days. The samples of these treated viruses were placed in a cell culture and did not show any sign of growth. EM microscopy of the samples showed these viruses had damaged RNA genetic material with some breaks in the single stranded RNA. The animals tolerated the vaccination well without showing much of a malaise, their temperature rose less than one degree C. by the second day. Both animals developed neutralizing antibodies in their blood after two to three weeks. The animals were challenged one month after vaccination through nasal inhalation of the COVID-19. Except for a mild rise in the body temperature and increased neutralizing antibodies in their blood, which lasted for few months that followed, the animals did not show any other signs of infection.

Example 13

After obtaining permission from the animal committee, two healthy female chimpanzees weighing 20 kg each, with a healthy body temperature of 37° C. were inoculated with $10^5$ COVID-19 plaque forming units of the virus through the nose. The animal's temperature was monitored regularly for any sign of increase. As soon as the animal's temperature rose one degree C. above the normal temperature to 38 degrees C., and the animals appeared reluctant to play, a nose swab was taken from the animals and evaluated by PCR which became positive and the viruses were also grown on cell culture simultaneously. One animal received immediately an intravenous dose of 3 mg/Kg of a solution of methylene blue in a normal physiological solution intravenously daily after a short intramuscular anesthesia, if the temperature remained high and allowed to recover with monitoring his temperature for another day. A nasal swab was done daily for verification of the virus. The other animal having an increased body temperature and positive nasal swab, etc. was treated both by nasal inhalation with a methylene blue solution having 5 µg/ml methylene blue, by a jet injector/nebulizer two times daily and intravenous injection of the methylene blue at 3 mg/Kg dose. By three days, their body temperatures dropped to 37.3 degree C., and gradually normalized though the animal with combination therapy with nasal inhalation was less affected.

In one embodiment, the vaccine is produced by a combination of VLP, dead bacteria, and methylene blue, in combination with pathway inhibitors, etc. for self-administration by nasal inhalation or subcutaneously or intramuscularly as needed and single dose vaccines use or add this vaccine to other existing mRNA vaccines.

In one embodiment, pluralities of viral or a fragment of the viral S protein antibody(s) coated polymeric nanoparticles are conjugated with CPP, or ACPP and one or two antivirals to enhance cell penetration of the nanoparticle inside the cells to damage the viruses which have penetrated the cells by nasal or topical, or systemic administration.

In one embodiment, pluralities of ACE-2 or neuropilin receptors antibody(s) coated polymeric nanoparticles are conjugated with CPP, or ACPP, or heparin or catechins or linoleic acid and one or two antivirals to block the viruses to enter the cells via ACE-receptors or neuropilin receptors inside the cells by nasal or topical, or systemic administration.

In one embodiment, antivirals can be combined with Methylene blue, a phenothiazine dye, a cationic compound to enhance damage to the viruses, bacteria anionic RNA or DNA, and simultaneously acting as anti-oxidant and anti-depressant when given in combination with of one of the pathway inhibitors such as GSK inhibitors or GSK beta inhibitors in a solution or as polymeric slow release nanoparticles or in semifluorinated alkanes to be administered by systemic or preferentially by inhalation one or multiple times daily below the toxic dose of 1-2 mg/L to reach both the lung and the brain preventing or treating viral inflammatory disease of the lung or the brain, and preventing subsequent Alzheimer of Parkinson diseases and nerve damage and preventing or treating the tangled tau neurofibriles and preventing Tau protein's toxicity by activating plasma membrane calcium ATPase thus preventing endoplasmic reticulum (ER) stress response and unfolding the protein.

In one embodiment of vaccine preparation to avoid the use of formaldehyde or glutaraldehyde, which are toxic and crosslink the viral and bacterial membrane which are harvest from the viruses or bacterial for their protein for vaccine production and be used as prophylaxis or treatment of the viral or bacterial diseases such as SAR-Cov-2 or COVID-19, MCV, EBV, Zoster or Hopes viruses, coronavirus and its mutations, these organisms are grown in cell culture and harvested by centrifuge and filtration then exposed to concentrations of methylene blue with or without CPP or cyclodextrin or in combination with cysteine, etc., to enhance membrane penetration at concentration of above 1 mg/L to 50 mg/L or more for a period of about <30 minutes to 24 hours or more depending on the concentration of methylene blue alone without external light radiation to damage RNA or DNA of the virus while protecting the viral membrane and S-protein of the viruses for vaccination; since methylene blue passes easily through viral or bacterial membrane because of its cationic charge to attach to RNA and DNA with its anionic charge and oxidizes the Guanine in presence of oxygen, thereby damaging the RNA or DNA of the viruses or bacteria while leaving the viral capsid membrane or bacterial membrane intact to be used later alone or with other synthetic adjuvants such as Toll-like receptor 4, etc. for vaccination alone, preferably in combination with LMWH or heparin mimetic to prevent simultaneous blood clotting induced by Methylene blue and inhibit also the entrance of the virus inside a cell through the ACE-2 inhibitors for inhalation, oral etc.

In one embodiment, administration of this vaccine with or without antivirals, or LMWH or pathway inhibitors, nasally by spray or nebulation one can apply a light source of 670 nm for a short period of time through a fiber optic, the nasal cavity or oral cavity, throat, or through pharynx to kill the viruses directly.

In one embodiment, one administers stabilized hypochlorous acid, the stable N-chloro derivative, or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT], glutathione peroxidase, and slow release polymeric nanoparticles that carry at least two of the antiviral medications together with one or more cell pathway inhibitors and heparin or low molecular weight heparin, synthetic heparin mimetics, or in combination with polyphenols and its derivatives that bind to heparan sulfate, linoleic acid, catechins and/or to sialic acid thereby preventing the viral attachment to its cell receptors as slow release nanoparticles or antibody coated nanoparticles of lactic acid, polyglycolic acid, polycaprolactone, or as micelles, or in liposomes and chitosan; or as antibody-coated antiviral nanoparticles, such as gold or silver or zinc nanoparticles of 1-100 nm, preferably 1-10 nm in diameter, which act as antivirals and can penetrate the virus with or without methylene blue to damage the RNA or DNA of the virus and kill them.

In one embodiment, this preparation is used for administration in the nose as inhalation, in spray, or by an inhaler, or nebulized form or orally to treat viral encephalitis or lung inflammation or orally for intestinal tract involvement for treatment of the virus to kill one or more viruses that remain in the nose/pharynx/throat or in the intestine after vaccination, or after having recovered from a virus infection, and prevent their reactivation, or further virus transmission to the healthy people, or it can be used as prophylaxis.

In one embodiment, antibody-coated slow release polymeric nanoparticles that carry at least two of the antiviral medications together with one or more cell pathway inhibitors and heparin or low molecular weight heparin, synthetic heparin mimetics, or in combination with polyphenols and its derivatives that bind to heparan sulfate, linoleic acid, catechins and/or to sialic acid, thereby preventing the viral attachment to its cell receptors as a slow release nanoparticles or antibody coated nanoparticles of lactic acid, polyglycolic acid, polycaprolactone, or as micelles, or in liposomes and chitosan; or as antibody-coated antiviral nanoparticles, such as gold or silver or zinc nanoparticles of 1-100 nm, preferably 1-10 nm in diameter, which act as antivirals and can penetrate the virus with or without methylene blue to damage the RNA or DNA of the virus, and kill them or after they are heated with light radiation in the nose, etc. after inhalation.

In another embodiment, the method further comprises the steps of administering a stabilized hypochlorous acid, the stable N-chloro derivative, or chloramines, the stable N-chloro derivatives or N-chlorotaurine (NTC), dimethylated derivatives of NCT (N-chloro-2,2-dimethyltaurine [DM-NCT] and N,N-dichloro-2,2-dimethyltaurine [DM-NDCT], with antiviral medications together with pathway inhibitors and low molecular weight heparin or linoleic acid, and catechins conjugated with antibody-coated gold or silver or zinc nanoparticle of 1-100 nm preferably 1-10 nm in diameter which act as antiviral and can penetrate the virus conjugated with or without methylene blue for administration is in the nose as inhalation, in spray or nebulized form or orally to treat viral encephalitis or lung inflammation to kill one or more viruses that remain in the nose/pharynx/throat after vaccination or after having recovered from a virus infection to be eliminated by the above combinations to prevent reactivation or further virus transmission to the healthy people or as prophylaxis.

In one embodiment of vaccine production, the viruses are grown by incubating them in the cell culture, after the viruses invade the cells, using the cell machinery they grow to the degree that they can exit or burst the cell wall, at this stage the viruses are separated from the cells by filtration by passing them through the pores of less than 200 micron by the centrifugation. The intact viruses with their intact membranes and capsid containing the genetic component of the virus are incubated with a solution of methylene blue or combined with cell penetrating peptides or cyclodexterine, etc. at a desired concentration of 1 microgram/ml to 50 micrograms or more; the methylene blue with its positive charge penetrates the outer membrane of the virus entering the virus passing through the viral capsid and tightly attaches to the negatively charged RNA or DNA of the virus that in presence of the oxygen damages the Guanine of the RNA of DNA, which occurs rapidly at this stage or simultaneously one adds metallic nanoparticles of gold or silver, or zinc with the size of preferably <10 nm to one nanometer in diameter which have an antiviral effect with or without CPP or ACPP, which because of their size they penetrate the virus and attach to the DNA or RNA of the virus then entire viral culture is passed through a beam of laser radiation at 670 nm which is absorbed by the nanoparticles attached to RNA or DNA of the virus while it does not damage the proteins of the virus by creating only locally an increased temperature at the site of the nanoparticles damaging the RNA or DNA to which the positively charged nanoparticles are attached, this process might take less than one minute to a few minutes or more depending on the laser power and the spot size of the laser. At this stage, the DNA or RNA of the viruses are severely damaged while the viruses' membranes and their S-proteins and capsid proteins remain intact with their antigenic properties that can be harvested and utilized as a vaccine to be administered by inhalation, self-administration, injection intramuscularly, orally, etc. alone or in combination with other antivirals and cell pathway inhibitors such as Rock, GSK, integrin and Wnt inhibitors such as Ivermectin or Niclosamide, etc.

In one embodiment, the viral protein can also be combined with a synthetic adjuvants such as toll like receptor 4 or non-synthetic adjuvants, etc, to enhance the immune response of the patient or animals to the vaccine which can be used as nasal inhalation at repeated intervals as needed to induce sufficient immune response that can be checked for presence of neutralizing antibodies in the patient or the vaccine can be added to other vaccines such as mRNA vaccine, etc. to boost their effect or if the virus has mutated, and administered when needed as self-administration by inhalation through the nose, mouth and to vaccinate a large number of the population fast or the vaccine can be also injected initially as ordered by the physician, where the method simplifies the production and application of the vaccine application in a large population everywhere, specifically in developing countries, etc. the components can be premade to be used for any potential virus, etc. or the vaccine can be stored by freezing it in a regular refrigerator.

In one embodiment, the vaccines can be prepared from circulating tumor cells or tumor tissue from the cancerous circulating lyphocutes or tumor cells or obtained by biopsy from any part of the body to be grown in the tissue culture and treated the same way with methylene blue, etc or other appropriate dye and antibody-conjugated gold, silver or zinc nanoparticles of smaller than 10 microns, magnetic, paramagnetic or nonmagnetic, nanoparticles and can be killed in vitro for vaccine production with or without pathway inhibitors and antitumor medication etc. with or without external laser, or other source of energy if needed such as alternating magnetic field, the vaccine can administered to the patient locally or intra-arterially or intravenously, by inhalation, etc.

In one embodiment, in patients with viral infections, etc., such as COVID-19, there is an increased inflammatory process in the blood with release of cytokines causing a cytokine storm, etc. in these conditions anti-inflammatory compounds or inflammatory pathway inhibitors, such as Rock inhibitors, Wnt inhibitors, integrin inhibitors, and GSK inhibitor in antibody and CPP or PEG-coated polymeric slow release nanoparticles along with antiviral with or without DMF can be therapeutic or prophylactic if used by inhalation, orally, subcutaneously or intravenously or injected locally.

In one embodiment, anti-inflammatory compounds or inflammatory pathway inhibitors such as Rock inhibitors, Wnt inhibitors, integrin inhibitors, and GSK inhibitors along with antivirals can be combined with IL-1, IL-2, IL-6, and/or IL-17 inhibitors in antibody-coated and CPP or PEG conjugated polymeric slow release nanoparticles with LMWH/catechins as therapeutic or prophylactic if used by inhalation, orally, subcutaneously, intravenously, injected locally, or topically.

In one embodiment, anti-inflammatory compounds or inflammatory pathway inhibitors such as Rock inhibitors, Wnt inhibitors, integrin inhibitors and GSK inhibitors along with antivirals and/or GABA inhibitors such as KDS2010, low molecular weight heparin (Lovenox) to simultaneously act as antiviral (e.g., COVID-19) and other RNA viruses or anti-bacterial and/or synthetic heparin mimetics/catechins to block virus entry in the cells and probenecid Panex-1 inhibitor to enhance nerve repair and prevent blood coagulation and has an antiviral effect, with or without CPP-conjugated with pluralities of polymeric slow release antibody-coated pluralities of nanoparticles can be combined with IL-1 IL-2, IL-6, IL-17 inhibitors or a metalloproteinase inhibitor which are antibacterial, antiviral, and anti-inflammatory as therapeutic or prophylactic with extended release of the medication, if used by inhalation, orally, subcutaneously, or intravenously or injected locally or intraperitoneally.

In one embodiment, anti-inflammatory compounds or inflammatory pathway inhibitors, such as Rock inhibitors, Wnt inhibitors, integrin inhibitors and GSK inhibitors along TGF beta inhibitors, such as botulinum toxin at pictogram concentrations, with antiviral and/or protease inhibitors, such as indinavir, ritonavir, nelfinavir, darunavir, amprenavir, favipiravir, fosamprenavir, lopinavir, atazanavir, saquinavir, tipranavir, Apilimod or vacuolin-1 in polymeric slow release antibody-conjugated polymeric nanoparticles/CPP conjugated can be combined with IL-6, Kevzara, or Baricitinib, IL-17 inhibitors, antiviral mycophenolic acid as therapeutic or prophylactic with extended release of the medication if used by inhalation, or by an inhaler, orally, topically, subcutaneously, intravenously, or injected locally.

In one embodiment, anti-inflammatory compounds or inflammatory pathway inhibitors such as Rock inhibitors, Wnt inhibitors, integrin inhibitors and GSK inhibitors along with antiviral and/or protease inhibitors in ACPP conjugated polymeric slow release antibody-conjugated nanoparticles can be combined with IL-6 Kevzara, IL-17 inhibitors, antivirals, mycophenolic acid, as therapeutic or prophylactic with extended release of the medication if used by inhalation, or by an inhaler, orally, subcutaneously or intravenously or injected locally.

In one embodiment, anti-inflammatory compounds or inflammatory pathway inhibitors, such as Rock inhibitors, Wnt inhibitors, integrin inhibitors, and GSK inhibitors along with an antiviral, such as, favipiravir, ritonavir, Remdesivir, Burton tyrosine kinase inhibitor (BTK) ibrutinib, zanubritinib, acalabrutinib, or JAK-STAT, or JAK1/JAK2 inhibitor ruxolitinib, baricitinib, Pacritinib or inhibition of oxidative stress with Thalidomide and lenalidomide, PI3K/AKT/mTOR pathway inhibitors, Duvelisib, inhibitors of phosphorylation of endoplasmic reticulum resident kinase (PERK), Rapamycin, with or without complement pathway inhibitors, such as C3 inhibitors—AMY-101 (NCT04395456) and APL-9 (NCT04402060); C5 inhibitors—eculizumab (NCT04346797 and NCT04355494); C1 esterase inhibitors, which block the classical complement pathway and antiandrogen bicalutamide or anti-VEGFs avastin, dexamethasone, or tetracycline derivatives, metalloproteinase inhibitors which are antibacterial, antiviral, and anti-inflammatory or nitric oxide (NO) or donor (NONOate) in antibody-coated polymeric slow release pluralities of nanoparticles as a nasal spray or inhalation therapy in viral lung infection or viral encephalitis as anti-inflammatory agents to release the medication slowly without affecting other organs and treat or prevent an autoimmune response in various organs, such as type 1 diabetes, autoimmune encephalitis that becomes chronic leading to Alzheimer's disease and dementia, Bechet disease, temporal arteritis, Crohn's disease, unknown causes of uveitis and many chronic diseases.

In one embodiment, generalized damage to the brain, lung, retina blood vessels, and/or endothelial cells that caused blood clot formation and/or leakage of the capillaries is seen in fluorescein retinal angiography, etc. or large veins and arteries are reported. In one embodiment, anti-inflammatory compounds or inflammatory pathway inhibitors such as Rock inhibitors, Wnt inhibitors, integrin inhibitors, and GSK inhibitor along with an antiviral, such as ritonavir, Remdesivir, favipiravir, etc. are combined with antibody-coated polymeric slow release pluralities of nanoparticles are conjugated with dipyridamole, to treat endothelial cell damage or simultaneously or sequentially with GABA inhibitors such as KDS2010, probenecid a panx-1 inhibitor, low molecular weight heparin (Lovenox)/polyphenols, such as catechins, epicatechin (EC), epigallocatechin (EGC), epicatechin gallate (ECG), and epigallocatechin gallate (EGCG), to simultaneously prevent viral cell entry, act as an antiviral (e.g., COVID-19) and other viruses or anti-bacterial if present, such as a metalloproteinase inhibitor which is an antibacterial and an anti-inflammatory in a semifluorinated alkane or other medium, and to enhance nerve repair and prevent blood coagulation as a nasal spray or inhalation, or by an inhaler, or intravenous applications along with anti-blood coagulants, such as aspirin, Coumadin, low molecular weight heparin (Lovenox), or synthetic heparin mimetics, or synthetic heparin, such as PG500, non-anticoagulant low molecular weight pegylated heparin or non-anticoagulant low molecular weight heparin and to enhance nerve repair and prevent blood coagulation, etc.

In one embodiment, Protease inhibitors, such as Ulinastatin, leupeptin epsilon-aminocaproic acid, Aprotinin Camostat mesilate, etc., indinavir, fosamprenavir, Artemisinin, ritonavir, nelfinavir, amprenavir, lopinavir, saquinavir atazanavir, tipranavir, and darunavir, etc., block the viral attachment and entry in the cell, such as combined with a viral inhibitor such as Remdesivir, favipiravir, Ribavirin (RIB), etc. with or without $\alpha(1)$-antitrypsin (AA T), Stachyflin, acetylstachyflin, Thiobenzamide, and an anti-inflammatory agent, such as dexamethasone and/or pathway inhibitor, such as Rock inhibitor (e.g., Fasudil) and/or Wnt inhibitors (e.g., Niclosamide) with both an antiviral and anti-inflammatory effect, ivermectin, etc., GSK inhibitor, or integrin inhibitor conjugated with antibody-coated polymeric slow release nanoparticles with a physiological solution or semifluorinated alkane or low molecular weight heparin (Lovenox), or synthetic heparin mimetics, non-anticoagulant low molecular weight, pegylated heparin, or non-anticoagulant low molecular weight heparin administered as a spray, aerosolized through the nose, mouth or injected subcutaneously, intravenously in a non-toxic dose, as topical ointment for intranasal application, or as a dry powder or liquid formulations to be used for inhalation as aerosolized preparation.

In one embodiment, one or more antivirals are used with pluralities of heparin or anticoagulative or low molecular weight heparin to simultaneously act as antiviral, e.g., SARS-CoV-2, COVID-19, or their mutations or other RNA or DNA viruses and anti-bacterials, such as tetracycline derivatives, a metalloproteinase inhibitor which are antibacterial and anti-inflammatory or synthetic heparin mimetics or unfractionated heparins or synthetic heparin, such as PG500, conjugated with antibody-coated slow release polymeric pluralities of nanoparticles with or without and anti-VEGF (e.g., Avastin or Eylea) and are administered in a physiological solution or semifluorinated alkane or a physiological liquid as an aerosolized formulation for inhalation, or by an inhaler, subcutaneously, intramuscularly, or intravenously to treat early stage (SARS-CoV-2), COVID virus or other influenza viruses, or injected subcutaneously for treatment of Zika and or dengue viruses, Epstein Barr virus, viral encephalitis, etc., and reduce inflammatory processes in the body, eliminate the viruses in brain, in encephalitis or multi-organ disease after coronavirus infection, etc.

In one embodiment, a polymerase inhibitor, such as favipiravir (Faviflu), moroxydine, Azaindole VX-787, an inhibitor of PB2 and one or more protease inhibitors, such as Stachyflin, Doxycycline, acetylstachyflin, Thiobenzamide or darunavir, saquinavir, ritonavir, nelfinavir, Artemisinin, fosamprenavir, lopinavir, Faviflu, amprenavir, atazanavir, tipranavir, and one or more anti-inflammatory agents, such as dexamethasone and/or pathway inhibitor, such as a Rock inhibitor (Fasudil) and/or Wnt inhibitor (Niclosamide), ivermectin, etc., GSK inhibitor, or integrin inhibitor conjugated with antibody-coated polymeric slow release nanoparticles with a physiological solution or semifluorinated alkane administered in a physiological solution or semifluorinated alkane or a physiological liquid as a spray, aerosolized through the nose, mouth, or injected subcutaneously, intravenously in a non-toxic dose, or as topical ointment for intranasal application.

In one embodiment, a nuclear pathway inhibitor such as Leptomycin B is combined with an antiviral (including (SARS-CoV-2, COVID-19) or their mutations, such as Remdesivir, favipiravir and dexamethasone or Kevzara, or a pathway inhibitor such as a Wnt inhibitor such as Niclosamide with both an antiviral and anti-inflammatory effect, or synthetic heparin mimetics, or synthetic heparin, such as PG500, and GABA inhibitors such as KDS2010, low molecular weight heparin (Lovenox) or other non-anticoagulant low molecular weight heparin/catechins to simultaneously act as antiviral (e.g., against Covid-19), etc. and tetracycline derivatives, a metalloproteinase inhibitor which are antibacterial, antiviral, and anti-inflammatory or antibacterial by inhibiting the proteases and/or mycophenolic acid, an immunomodulator, with potent antiviral activity to enhance nerve repair and prevent blood coagulation, etc. conjugated with multiple antibody-coated slow release nanoparticles with a physiological solution or semifluorinated alkane or a physiological liquid administered as a spray, aerosolized through the nose, mouth or injected subcutaneously, intravenously, or orally in a non-toxic dose.

In one embodiment, a viral RNA and protein synthesis inhibitor such as Nucleozin or Cycloheximide or Naproxen and a polymerase inhibitor such as moroxydine are combined with an antiviral, such as remdesivir, Faviflu, Baricitinib, a Janus kinases inhibitor as anti-TNF and dexamethasone or a pathway inhibitor such as Wnt inhibitor such as niclosamide, etc. conjugated with multiple antibody-coated slow release slow release nanoparticles with a physiological solution or semifluorinated alkane administered as spray, aerosolized through the nose, mouth, or injected subcutaneously, intravenously in a non-toxic dose or as dry powder or liquid formulations to be used for inhalation as aerosolized preparation or ointment.

In one embodiment, a compound such as an influenza virus inhibitor such as sialidase is combined with a viral inhibitor such as Remdesivir, Favipiravir, Ribavirin (RIB), histone deacetylases (HDACs), such as Sodium Phenylbutyrate (PB) and Valproic Acid (VPA), etc. with or without $\alpha(1)$-antitrypsin (AA T), Stachyflin, acetylstachyflin, Thiobenzamide, and an anti-inflammatory agent such as dexamethasone and/or a pathway inhibitor, such as a Rock inhibitor (Fasudil) and/or Wnt inhibitor (Niclosamide), ivermectin, etc., GSK inhibitor, or integrin inhibitor conjugated with antibody-coated polymeric slow release nanoparticles with a physiological solution or semifluorinated alkane, or low molecular weight heparin (Lovenox), or synthetic heparin mimetics, non-anticoagulant low molecular weight pegylated heparin, or non-anticoagulant low molecular weight heparin/catechins administered as a spray, aerosolized through the nose, mouth, orally or injected subcutaneously, intravenously in a non-toxic dose for lung, brain or multi-organ diseases after coronavirus infection or other viral infections or Multisystem Inflammatory Syndrome in Children (MIS-C).

In one embodiment, a compound such as an influenza virus inhibitor, such as indinavir, fosamprenavir, Artemisinin, ritonavir, nelfinavir, amprenavir, lopinavir, saquinavir atazanavir, tipranavir, and darunavir, etc., block the viral attachment and entry in the cell, such as combined with a viral inhibitor such as Remdesivir, favipiravir, Ribavirin, GS-20 67, GS-CA1, polyphenol and its derivatives such as catechins and an anti-inflammatory agent, such as dexamethasone and/or a pathway inhibitor, such as a Rock inhibitor (Fasudil), etc. and/or Wnt inhibitor (Niclosamide), ivermectin, etc., GSK inhibitor, or integrin inhibitors conjugated with antibody-coated polymeric slow release pluralities of nanoparticles with a physiological solution or semifluorinated alkane, or low molecular weight heparin (Lovenox), or synthetic heparin mimetics, non-anticoagulant low molecular weight pegylated heparin, or non-anticoagulant low molecular weight heparin administered as a spray, aerosolized through the nose, mouth, orally or injected subcutaneously, intramuscularly, intravenously, by inhalation and/or combined with a known anti-inflammatory agent that can prevent pyroptosis of cells, such as dimethyl fumarate (DMF), administered orally, by injection or by inhalation in a slow release polymeric pluralities of nanoparticle format for a short period or time of 1-2 weeks as needed in a non-toxic dose of 100-1000 mg as needed for lung, brain, or multi-organ diseases after coronavirus infection, such as (SARS-CoV-2), COVID-19 or their mutations or other severe viral infections or with mycophenolic acid, an immunomodulator, with potent antiviral activity in Multisystem Inflammatory Syndrome in Children (MIS-C), DMF or Fumaric acid esters (FAEs) inhibit the activity of the transcription factor NF-κB and proinflammatory cytokines by T cells by its immunomodulatory mechanisms.

In another embodiment, in a systemic multisystem disease, where there is a genetic flaw in alpha-interferon, one administers synthetic interferons made by recombinant DNA technology with anti-inflammatory agents, such as doxycycline, a metalloproteinase inhibitor, which has an antibacterial and anti-inflammatory effect along with LMWH, polyphenol and its derivatives, such as catechins, NSAIDS or dexamethasone, with or without an anti-VEGF (e.g., Avastin or Eylea), one or more pathway inhibitors, such as Wnt, Rock, GSK, integrin inhibitors with TGF-alpha inhibitors with or without an anti-VEGF (e.g., Avastin or Eylea), with one or more antiviral agents, such as indinavir, molnupiravir, or MK-4482/EIDD-2801, and mycophenolic acid, an immunomodulator, with potent antiviral activity in a semifluorinated alkane of other suitable medium for inhalation, intramuscular, or intravenously.

In one embodiment of virals or COVID-19 disease or in multisystem disease, one administers LMWH, polyphenol and its derivatives, such as catechins, NSAIDS, doxycycline, one or more pathway inhibitors, such as Wnt, Rock, GSK, integrin inhibitors with TGF-alpha inhibitors, in addition to Pegaptanib sodium, with or without an anti-VEGF (e.g., Avastin or Eylea), a nucleotide polyethylene glycol RNA aptamer that inhibits angiogenesis that binds to $VEGF_{165}$, or another anti-VEGF with one or more antiviral agents or with ebselen and or glutathioneperoxidase and superoxide dismutase (SOD)—requiring additional zinc, or manganese, or heparin for ideal catalytic activity applied to the nasal passages, in a semifluorinated alkane or other suitable medium for inhalation, intramuscular, intravenously or inside a body cavity injection.

In one embodiment, one or more antivirals, such as Remdesivir, Ribavirin (RIB), histone deacetylases (HDACs), such as Sodium Phenylbutyrate (PB) and Valproic Acid (VPA) as an antiviral and protection of the liver and kidney, etc. are combined with NS1 inhibitors combined with MEK1 and MEK2, NFKB inhibitors, such as Bortezomib and glycosylation inhibitors, such as L-fructose and L-xylulose and one or more Rock inhibitors or Wnt inhibitors are combined with GSK inhibitors or integrin inhibitors conjugated with antibody-coated polymeric slow release nanoparticles with a physiological solution or semifluorinated alkane administered as a spray, aerosolized through the nose, mouth, at a non-toxic dose or as a dry powder or liquid formulations to be used for inhalation as aerosolized preparation.

In one embodiment, one or more antivirals, such as Remdesivir, Favipiravir, Ribavirin (RIB), oseltamivir, cyclosporine, etc. and an anti-oxidants or immunomodulators, such as calcitrol, Rolipram, a selective phosphodiesterase-4 (PDE-4) inhibitor to reduce bronchospasm, anti TNF alpha inhibitor Baricitinib, a Janus kinase inhibitor, interleukin antagonists, low molecular weight heparin, or synthetic heparin mimetics, an antiviral used in HIV infection, such as GS-6207, a long acting HIV capsid inhibitor, IL-6, Kevzara, PDE5 inhibitors sildenafil and tadalafil, enhance the level and action of cGMP, relax the smooth muscles of the lung or brain etc. improve tissue oxygenation and remove toxic proteins such as beta amyloid etc., IL10 inhibitors such as Canakinumab (Ilaris), GABA inhibitors such as KDS2010, low molecular weight heparin (Lovenox) to enhance nerve repair and prevent blood coagulation, NSAIDs ibuprofen, Dexamethasone, and one or more Rock inhibitors or Wnt inhibitors are combined with a GSK inhibitor or integrin inhibitor conjugated with antibody-coated polymeric slow release nanoparticles, where the antibody prevents the virus from entering the cells is administered with a physiological solution or semifluorinated alkane administered at a non-toxic dose in a physiological solution or semifluorinated alkane or a physiological liquid as a spray, aerosolized through the nose, mouth, intravenously or intramuscular or subcutaneously as needed in lung, brain or multi-organ diseases after coronavirus infection or other viral infections.

In one embodiment, the inflammatory viral diseases of the lung, brain, and other organs are treated as described in this application in addition with high oral doses of antioxidants such as ascorbic acid, Octyl gallate (octyl 3,4,5-trihydroxybenzoate), gallate (propyl 3,4,5-trihydroxybenzoate), Calcium 1-ascorbate Propyl 6-O-Palmitoyl-1-ascorbic acid (ascorbyl palmitate, natural or tocopherols, Synthetic α-tocopherol Synthetic γ-tocopherol Synthetic δ-tocopherol, tetracycline and/or mycophenolic acid, an immunomodulator, has potent antiviral activity or Baricitinib, etc. or an anti-inflammatory agent such as dimethyl fumarate (DMF), used orally or with or without and anti-VEGF by inhalation at low concentrations, inhibit pore formation and pyroptosis with its indiscriminate cellular destruction in the lung, brain, or multi-organ diseases after coronavirus infection or viral or (SARS-CoV-2), COVID-19 infections, etc. or severe inflammation of the lung or brain or intestinal tract inflammation, the so-called Multisystem Inflammatory Syndrome in Children (MIS-C) diseases, etc.

In one embodiment, a compound such as an influenza virus inhibitor such as sialidase is combined with a viral inhibitor such as Remdesivir, Favipiravir, Thiobenzamide, and an anti-inflammatory agent such as dexamethasone and/or a pathway inhibitor, such as Rock inhibitor (Fasudil) and/or Wnt inhibitor (Niclosamide), ivermectin, etc., GSK inhibitor, or integrin inhibitor conjugated with antibody-coated polymeric slow release nanoparticles, or conjugated with antibody-coated liposomes filled with low molecular weight heparin (Lovenox) or synthetic heparin mimetics or synthetic heparin, such as PG500, or non-anticoagulant low molecular weight pegylated heparin filled liposomes or PEG-PLA, micelles or non-anticoagulant low molecular weight heparins administered in a physiological solution or semifluorinated alkane or a physiological liquid as a spray, aerosolized through the nose, mouth, orally or injected subcutaneously, intravenously in a non-toxic dose or dry powder and liquid formulations is used for inhalation as a aerosolized preparation.

In one embodiment, one or two antivirals such as Remdesivir, Favipiravir, Ribavirin (RIB), oseltamivir, cyclosporine, and/or Niclosamide are combined with another antiviral heparin or low molecule weight heparin such as Lovenox or synthetic heparin mimetics which acts in blocking virus attachment and entrance to the cells or endothelial cells used with a Rock inhibitor (Fasudil) and/or Wnt inhibitor (Niclosamide), ivermectin, etc., GS K inhibitor, or integrin inhibitor conjugated with antibody-coated polymeric slow release nanoparticles, or conjugated with antibody-coated liposomes filled with low molecular weight heparin (Lovenox) or synthetic heparin mimetics or non-anticoagulant low molecular weight pegylated heparin-filled liposomes or micelles or non-anticoagulant low molecular weight heparins <600 KD or other heparins, such as recombinant heparin, high molecular weight heparin, low molecular weight heparin, unfractionated heparin, heparin fragments, heparin analogs, low-molecular-weight heparin-taurocholate 7 (LHT7) and sulfonated polysaccharides containing heparin activity, heparan sulfate. In one embodiment, heparin, sulfated heparin, or synthetic heparin, such as PG500, can be combined with catechins or cyclodextrin or conjugated with chitosan and poly(lactide-co-glycolide) complexes with or without other antivirals, such as faviflu, remdesivir, etc., to be used as nasal spray or combined with 0-pamitoyol to treat various viral infections, such as herpes simplex viruses of types 1 and 2), and the respiratory syncytial virus (SRV), influenza viruses (SARS-CoV-2), COVID-19, or their mutations human papilloma virus 16 (HVP-16), etc. administered in a physiological solution or semifluorinated alkane or a solvent such as polyethylene glycol or ethanol or a physiological liquid as a spray, aerosolized through the nose, mouth, orally, or injected subcutaneously, intravenously in a non-toxic dose, or as a dry powder and liquid formulations used for inhalation as a aerosolized preparation to inhibit viral invasion in the cell or its proliferation.

In one embodiment, giant papillary conjunctivitis (GPC) is treated with artificial tears while avoiding the use of a contact lens or administration of topical with an NSAID, such as Ketorolac 0.4%, etc. combined with low molecular weight heparin, e.g., enoxaparin or heparin mimetics.

In one embodiment, the viral infection, such as (SARS-CoV-2), COVID-19, or their mutations etc. is treated with a topical application of low molecular weight heparin, such as lovenox, etc. with cyclosporine A as an anti-inflammatory and antiviral agent and anti-fungal at 0.0000001%-5% concentration with or without antivirals such as Faviflu, Remdesivir, Favipiravir, etc. with or without Wnt inhibitors, such as ivermectin or niclosamide which work synergistically with heparin or heparin mimetics or heparin nanoparticles and Ebselen and/or glutathione peroxidase, and superoxide dismutase (SOD)—metabolize oxidative toxic intermediates requiring zinc, selenium, manganese iron, copper, and for ideal catalytic activity and LMWH to treat viral conjunctivitis and/or scleritis, vasculitis, retinitis, loss of the smell, cerebral vasculitis, or lung infection caused by (SARS-CoV-2), COVID-19 or their mutations virus, etc.

In one embodiment, the viral infection, such as (SARS-CoV-2), COVID-19, or their mutations etc. is treated with a topical, intranasal, inhalation, etc. application of low molecular weight heparin or heparin nanoparticles, such as Lovenox, etc., with cyclosporine A or Tacrolimus, or a mycophenolic acid, an immunomodulator, has potent antiviral activity and an anti-inflammatory and antiviral agents at 0,0000001%-5% concentration with or without other anti-inflammatory agents, such as colchicine or in combination with Panx1 inhibitor probenecid in viral vasculitis to protect neurons from damage in the brain or after refractive corneal surgery.

In one embodiment, low molecular weight heparin, synthetic heparin mimetics, or synthetic heparin, such as PG500, work synergistically with cyclosporine A, antiviral and antifungal, synergistically to treat topically blepharitis, and dry eye with or without Wnt inhibitors at a non-toxic concentration.

In one embodiment, low molecular weight heparin or heparin nanoparticles or antibody conjugated nanoparticles and/or microparticles of heparin mimetics, or synthetic heparin, such as PG500, PG 545, work synergistically with catechins or with cyclosporine A, and anti-fungal and/or mycophenolic acid an immunomodulator, with potent antiviral activity and an anti-inflammatory and antiviral agent where the antibody prevents the virus from entering the cells with or without a solution of stabilized hypochlorous acid at pH 6-8 or another medium in bacterial and viral infections of the lid and conjunctiva, etc.

In one embodiment, a topical application of low molecular weight heparin, such as Lovenox, or synthetic heparins, such as PG500, PG 545, etc. with cyclosporine A antiviral and anti-fungal at 0.0000001%-5% concentration with or without antivirals such as Faviflu, remdesivir, etc. with or without Wnt inhibitors such as ivermectin or niclosamide work synergistically to treat conjunctivitis and or scleritis caused by COVID-19 virus.

In one embodiment, one or two antivirals, such as Remdesivir, Favipiravir, Ribavirin (RIB), oseltamivir, histone deacetylases (HDACs), such as Sodium Phenylbutyrate (PB) and Valproic Acid (VPA), cyclosporine, mycophenolic acid as an anti-inflammatory and antiviral anti-fungal agent, and/or Niclosamide are combined with another antiviral heparin or heparin mimetics, such as PG500, or PG 545, or heparin nanoparticles or low molecule weight heparin, such as Lovenox, which acts in blocking numerous viruses attachment and entrance to the cells or endothelial cells used with a Rock inhibitor (Fasudil), TGF beta inhibitors, and/or Wnt inhibitor (Niclosamide), ivermectin, etc., GSK inhibitor, or integrin inhibitor conjugated with antibody-coated polymeric slow release nanoparticles, such as polylactic, polyglycolic or a combination or polycaprolactone, polyanhydride, etc., or conjugated with antibody-coated liposomes filled with low molecular weight heparin (LMWH), such as (Lovenox) or non-anticoagulant low molecular weight pegylated heparin-filled liposomes or micelles, heparin nanoparticles where antibody prevents the virus from entering the cells or non-anticoagulant low molecular weight heparins <6000 KD, other heparins for use such as recombinant heparin, high molecular weight heparin, low molecular weight heparin, unfractionated heparin, heparin fragments, heparin analogs, low-molecular-weight heparin-taurocholate 7 (LHT7) and sulfonated polysaccharides containing heparin activity, heparan sulfate, or heparin mimetics/catechins administered in a physiological solution or semifluorinated alkane or a physiological liquid as a spray, aerosolized through the nose, mouth, orally, or injected subcutaneously, intravenously in a non-toxic dose, or as a dry powder and liquid formulations is used for topical application, on the conjunctiva, intranasal inhalation as a aerosolized preparation to inhibit viral invasion in the cell or its proliferation in conjunctivitis, nasal, throat, pharynx, lung, or through the nasal sensory nerves to brain and brain vessel to prevent or treat vasculitis.

In one embodiment, LMWH or heparin nanoparticles or synthetic heparin or heparin mimetics, such as PG500, or PG 545, at 0.01 mg/ml to 30 mg/ml is used in combination with or without catechins and/or doxycycline with pH adjusted to 7.5 and a concentration of 0.1% to 2% is in blepharoconjunctivitis caused by bacterial infection, or antivirals in blepharoconjunctivitis as topical drops or spray.

In one embodiment, LMWH or heparin nanoparticles at 0.01 mg/ml to 30 mg/ml concentration is used topically in combination with one or two antivirals in blepharoconjunctivitis, such as in viral conjunctivitis, such as SARS-CoV-2, COVID-19, etc.

In one embodiment, LMWH or heparin nanoparticles or synthetic heparin, such as PG500, PG 545, etc. at 0.01 mg/ml to 30 mg/ml concentration and/or as a combination with or without catechins and doxycycline or with doxycycline with pH adjusted to 7.5 and concentration of 0.1% to 2% and/or triamcinolone at 400 microgram/0.1 ml are used topically in scleritis caused by a viral infection or in an autoimmune response to a pathogen.

In one embodiment, LMWH or pegylated heparin or heparin mimetics, such as PG500, PG 545 etc., nanoparticles is used topically in combination with a solution of sodium hypochlorite at concentrations 0.01-10%, stabilized to a pH of 5-10 preferably 7.5 to treat bacterial or viral conjunctivitis or viral keratoconjunctivitis, such as (SARS-CoV-2), COVID-19 or their mutations, HSV1-2, VZV or intranasally for upper or lower respiratory viral infection or viral encephalitis as prophylaxis or therapeutic.

In one embodiment, LMWH or heparin mimetic, such as PG500, PG 545, etc. is used topically for inhalation, intranasally, etc. in combination with hypochlorous acid or sodium hypochlorite or chloramines, the stable N-chloro derivatives or N-chlorotaurine (NCT), dimethylated derivatives of NCT (N-chloro-2,2-dimethyltaurine [DM-NCT] and N,N-dichloro-2,2-dimethyltaurine [DM-NDCT] or their nanoparticles sequentially in viral upper respiratory infection, such as (SARS-CoV-2), COVID-19, or their mutations influenza, HSV 1-2 or Epstein Bar virus or VZV, etc. infection or viral encephalitis, vasculitis with or without probenecid or histone deacetylases (HDACs), such as Sodium Phenylbutyrate (PB) and Valproic Acid (VPA).

In one embodiment, LMWH or pegylated heparin antibody-coated pluralities of nanoparticles or heparin mimetics, such as PG500, PG 545, etc., is used topically or for inhalation, intranasally, etc. in combination with anti-virals, such as Baricitinib, Glidesivir, Favipiravir, Xofluza Remdesivir, nanoviricides, Oya1, interferon, umifenovir, tamivir ribavirin, baloxavir in viral upper respiratory infection, such as (SARS-CoV-2), COVID-19, or their mutations influenza, HSV 1-2 or Epstein Bar virus or VZV, etc. infection or viral encephalitis or vasculitis.

In one embodiment, heparin, or sulfated heparin, or heparin mimetics with or without polyphenols with and without TGF beta inhibitors can be combined with cyclodextrin or conjugated with chitosan and poly(lactide-co-glycolide) complexes with or without other antivirals, such as faviflu, remdesivir, Baricitinib, Glidesivir, Favipiravir, Xofluza Remdesivir, nanoviricides, Oya1, interferon, Artemisinin, umifenovir, tamivir.ribavirin, baloxavir, etc., to be used as nasal spray or combined with 0-pamitoyol to treat various viral infections to the eye, nose, or respiratory tract, such as herpes simplex viruses of types 1 and 2), and the respiratory syncytial virus (SRV), influenza viruses, (SARS-CoV-2), COVID-19, or their mutations, human papilloma virus 16 (HVP16), etc.

In one embodiment, when internal eye structures are involved in SARS-CoV-2, COVID-19, or their mutations or other viruses, one administers non-toxic concentrations of Baricitinib, Glidesivir, Favipiravir, remdesivir, Artemisinin, etc. topically or injected inside in uveitis, retinitis and vasculitis with or without low molecular weight heparin.

In one embodiment, the GPC is treated with administering slow release polymeric nanoparticles carrying one or more cell pathway inhibitors, such as the Rock inhibitor Fasudil, wmt.IL6 or TGF-beta inhibitor such as Kavzara, Ivermectin or antiviral PLpro or Mpro inhibitors, such as Ebselen, Ebseleno, or Ebselen, and/or glutathione peroxidase and superoxide dismutase (SOD)—metabolize oxidative toxic intermediates requiring zinc, selenium, manganese iron, copper, and for ideal catalytic activity applied in the nose, conjunctiva and/or with NSAIDs or low molecular weight heparin or pegylated heparin antibody-coated pluralities of nanoparticles, such as Lovenox, Fragmin, dalteparin or non-anti-thrombotic heparin, or heparin mimetic such as PG500, PG 545, etc., unfractionated heparin, an antibiotic, such as tetracycline derivatives doxycycline, etc. or antiviral combinations.

In one embodiment, an intranasal application of low molecular weight heparin or heparin is administered with pluralities of nanoparticles and vasoconstricting agent, and Wnt inhibitors or mast cell stabilizer control itching and Astemizole an antihistaminic agent, at 0.1-0.5 microgram/ml for as inhalation or spray running nose and allergic response, in lid, conjunctiva, nose and throat, etc.

In one embodiment, a topical application of low molecular weight heparin, such as Lovenox or synthetic heparin, such as PG500, PG 545, etc., with cyclosporine or mycophenolic acid or Baricitinib as an anti-inflammatory and antiviral agent at a 0.0000001%-5% concentration or with Ebselen or doxycycline which also has an antiviral, antibacterial, anti-inflammatory, anti-prostaglandin, and neuroprotective effect, with or without antivirals, such as Faviflu, remdesivir, etc. and, vidarabine ointment, and trifluridine solution (Viroptic) or idoxuridine solution and ointment, work synergistic to treat conjunctivitis caused by bacteria and viruses or COVID-19 virus and dry eye.

In one embodiment, a topical application in the conjunctiva or nasal of low molecular weight heparin, such as Lovenox, or heparin antibody-coated pluralities of nanoparticles, etc. with probenecid or probenecid nanoparticles and/or with Ebselen and/or glutathione peroxidase and superoxide dismutase (SOD)—metabolize oxidative toxic intermediates requiring zinc, selenium, manganese iron, copper, and for ideal catalytic activity applied with mycophenolic acid/Doxycycline which acts as an antiviral, antibacterial, anti-inflammatory, anti-prostaglandin and neuroprotective as solution or ointment, work synergistically to treat ocular inflammation caused by bacteria and viruses or SARS-CoV-2, COVID-19 virus, or their mutations, and dry eye or after corneal refractive surgery.

In one embodiment, a topical application of low molecular weight heparin or antibody-coated heparin nanoparticles, or LMWH as Lovenox, etc., with administration of topical with an NASID, such as Ketorolac 0.4% in dry eye and blepharoconjunctivitis.

In one embodiment, a topical application of low molecular weight heparin or with or without antivirals or pegylated heparin antibody-coated pluralities of nanoparticles, such as Lovenox from 0.1 mg to 10 mg, etc. with mycophenolic acid, etc. at 0.0000001%-5% concentration work synergistically to treat dry eye, allergic blepharoconjunctivitis or Giant papillary conjunctivitis, and scleritis, etc.

In one embodiment, a topical application of low molecular weight heparin or pegylated heparin nanoparticles, such as Lovenox, or heparin mimetics, such as PG500, PG 545, etc., with or without antivirals, with ivermectin or niclosamide at picogram to microgram concentrations with or without antivirals, work synergistically to treat conjunctivitis caused by bacteria and viruses.

In one embodiment, a topical application of low molecular weight heparin, such as Lovenox or catechins of pegylated heparin or antibody-coated pluralities of nanoparticles or other non-anticoagulative heparins, where antibody, aptamer or mRNA conjugated with nanoparticles prevents the virus from entering the cells from 0.1 mg to 10 mg and Ebselen which also has an antiviral, antibacterial, anti-inflammatory, anti-prostaglandin and neuroprotective effect at a 0.00000001%-5% concentration with or without antivirals such as Favipiravir or an antibiotic, work synergistic to treat conjunctivitis caused by bacteria and viruses.

In one embodiment, a topical application of low molecular weight heparin, such as Lovenox, etc., from 0.01 mg to 10 mg with apilimod or vacuolin-1, or Wnt inhibitor or Rock inhibitor or probenecid at microgram to nanogram concentrations, work synergistically for neuronal growth of the cornea after refractive surgery, such as LASIK, Smile, or cataract surgery, etc.

In one embodiment, the conjunctivitis is treated initially with non-specific artificial tear drops and cold compress while more severe cases of bacterial infections are managed with antibiotic drops or ointments, such as Sulfacetamide, or ofloxacin or Polytrim, or Ciloxan (ciprofloxacin), combined or sequentially as anti-inflammatory agents, are useful except for steroid which requires exclusion of viral infection, anti-integrins or GSK-inhibitors, etc. Preference is given if viral infections, such as COVID-19 is suspected, to Wnt inhibitors, ivermectin, and an antiviral, such as acyclovir or valcyclovir or ebselen and to low molecular weight heparin or antibody-coated heparin nanoparticles if other viruses are involved.

In one embodiment of bacterial or viral conjunctivitis, Lovenox or low molecular weight heparin or non-anti-coagulant heparin can be used combined or sequentially as, from 0.1 mg to 10 mg or more daily alone because of its antiviral effect or in addition to other antivirals to treat diseases, such as the (SARS-CoV-2), COVID-19 or their mutations virus or herpes virus and other viruses, with antivirals such as Baricitinib, a Janus kinases inhibitor as an anti-TNF, Glidesivir, Favipiravir, Xofluza Remdesivir that blocks virus replication, nanoviricides, Oya1, interferon, umifenovir, tamivir ribavirin, baloxavir, histone deacetylases (HDACs), such as Sodium Phenylbutyrate (PB) and Valproic Acid (VPA), can be used orally, as a spray, intra-nasally, topically, by inhalation, or systemically with or without IL-6 inhibitors, etc. or Ebselen and or Ivermectin or other antivirals such as saquinavir, indinavir, ritonavir, nelfinavir, amprenavir, fosamprenavir, lopinavir, atazanavir, tipranavir, darunavir, etc.

In one embodiment of bacterial or viral conjunctivitis, Lovenox alone or in combination or sequentially as with ivermectin, or Ebselen and/or glutathione peroxidase and superoxide dismutase (SOD)—metabolize oxidative toxic intermediates requiring zinc, selenium, manganese iron, copper, and for ideal catalytic activity applied to the eye with mycophenolic acid, an immunomodulator, potent antiviral activity or an antibiotic, doxycycline or a capsid inhibitor GS-6207 (Lenacapavir), can be used in bacterial conjunctivitis or blepharoconjunctivitis because of their antibacterial effect, anti-viral effect, and its anti-inflammatory action or can be used in combination with an antibiotic or a disinfectant solution, such as hypochlorous acid or sodium hypochlorite or N-chlorotaurine (NTC), dimethylated derivatives of NCT (N-chloro-2,2-dimethyltaurine [DM-NCT] and N,N-dichloro-2,2-dimethyltaurine or their nanoparticles, which has also synergistic effect with low molecular weight heparin which as soothing effect in addition to antiviral or bacterial, and anti-inflammatory action in the nose, lung, or brain.

Hypochlorous acid (HCLO) and its anion hypochlorite (OCl⁻) is naturally produced compound by the white blood cells by the enzyme myeloperoxidase to eliminate invading bacteria, viruses, or fungi in the body. It penetrates the cell wall of the bacteria, protein, and nucleic acids to denature and deactivate them.

In one embodiment, stable Hypochlorous acid can be produced by either adding chlorine to the water to form hypochlorite, and ClO⁻ (HClO and ClO⁻ are oxidizers). Hypochlorous acid can also be made by electrolysis of salt (Na Cl) in water ($H_2O$) producing hypochlorous acid and sodium hydroxide (NAOH). Stable hypochlorous acid has a pH of 5-6. At pH 11-13, the chlorine is mostly in the form of hypochlorite solution, whereas at pH 5, most of the chlorine is present as hypochlorous acid (HOCl). The hypochlorous acid with a long shelf life can be produced.

In one embodiment, Hypochlorous acid at concentrations of <500-50 or less, parts per million is not toxic and can be used as topical drops or spray for conjunctivitis blepharitis keratitis, or intranasally as inhalation at a concentration of <50 parts per million.

In one embodiment, the viral conjunctivitis is treated combined or sequentially with topical administration of liquid or ointment of Baricitinib, a Janus kinase inhibitor as an anti-TNF, Glidesivir, Favipiravir, Xofluza Remdesivir, Artemisinin, nanoviricides, Oya1, interferon, umifenovir, tamivir ribavirin, baloxavir can be used topically, orally, systemically, or with or without IL-6 inhibitors, etc. and Lovenox and/or Ivermectin, and Ebselen nanoparticles with or without or N-chlorotaurine (NTC), dimethylated derivatives of NCT (N-chloro-2,2-dimethyltaurine [DM-NCT] and N,N-dichloro-2,2-dimethyltaurine nanoparticles.

In one embodiment, the viruses causing conjunctivitis can also be drained in the nose through the nasolacrimal duct and infect the nose, through and pharynx. In one embodiment, the conjunctival and the nasal cavities are treated combined or sequentially by drops using the described antivirals with antibody-coated pluralities of nanoparticles of low molecular with heparin as spray drops or inhalation simultaneous with the treatment of the conjunctiva with or without dimethylated derivatives of NCT (N-chloro-2,2-dimethyltaurine [DM-NCT] and N,N-dichloro-2,2-dimethyltaurine nanoparticles.

In one embodiment, all forms of Heparins, such as high molecular weight heparin or heparin nanoparticles, low molecular weight heparin, unfractionated heparin, heparin analogs, heparin mimics containing glucosamine saccharides and acrylamide, and sulfated polysaccharides containing heparin activity heparin fragments, recombinant heparin or pegylated heparin nanoparticles or heparin mimetics have similar blocking effect on the viruses, such as (SARS-CoV-2), COVID-19, or their mutations etc., bacteria and inflammation.

In one embodiment of bacterial or viral conjunctivitis, Lovenox can be used in bacterial conjunctivitis or blepharoconjunctivitis, because of its antibacterial effect, anti-viral effect, and its anti-inflammatory action or in combination or sequentially with NSAIDs such as Ketorolac 0.4% in allergic conjunctivitis as topical medication ointment or spray.

In one embodiment of bacterial or viral conjunctivitis, Lovenox can be used in bacterial conjunctivitis or blepharoconjunctivitis because of its antibacterial effect, anti-viral effect, and its anti-inflammatory action or dimethyl fumarate (DMF), or a Janus kinase inhibitor as an anti-TNF alpha with Ebselen and tetracyclines or glutathione peroxidase and superoxide dismutase (SOD)—requiring additional zinc, or manganese, for ideal catalytic activity applied to the conjunctiva, nasal passages or used orally or by injection or as inhalation in severe inflammatory conditions, such as multiple sclerosis, psoriasis, to inhibit protein Gasdermin D pore formation, and uncontrolled cellular damage or pyroptosis, in combination or sequentially with one or more antivirals, Favipiravir, Remdesivir, and/or molnupiravir or MK-4482/EIDD-2801 and/or a protease inhibitor, such as ritonavir, saquinavir, and indinavir administered in a physiological solution or semifluorinated alkane or a physiological liquid for inhalation with or without an inhaler in a COVID-19 upper or lower respiratory infection of its vasculitis in brain vasculitis, or multisystemic inflammatory disease or orally or intravenously or subcutaneously, etc., where the low molecular heparin attaches to the (SARS-CoV-2), COVID-19, or their mutations ACE-2 receptor and prevent or treat the infection.

In one embodiment of bacterial or viral conjunctivitis, Lovenox or Dalteparin can be used in bacterial conjunctivitis or blepharoconjunctivitis because of its antibacterial effect, anti-viral effect, and its anti-inflammatory action or in combination or sequentially with one or more antivirals Remdesivir, Favipiravir, or a protease inhibitor, such as ritonavir, saquinavir, and indinavir, molnupiravir or MK-4482/EIDD-2801 administered in a physiological solution or semifluorinated alkane with an additional solvent, such as polyethylene glycol (PEG) or ethanol, or a physiological liquid applied topically in the conjunctiva to treat a viral blepharoconjunctivitis or a viral keratitis, where the low molecular heparin or heparin mimetics attaches to the (SARS-CoV-2), COVID-19 or their mutations, ACE-2 receptor and prevent or treat the infection applied topically or using an inhaler.

In one embodiment, Lovenox or enoxaparin sodium solution is prepared at 10-100 mg/ml at pH of 5.5-7.5 administered in a physiological solution or semifluorinated alkane or a physiological liquid intra-nasally with a Rock inhibitor and or TGF beta inhibitors as slow release polymeric nanoparticles alone or in combination or sequentially with 1-2 antivirals and a decongestant administered in a physiological solution or semifluorinated alkane or a physiological liquid intra-nasally or by an inhaler to treat (SARS-CoV-2), COVID-19 or their mutations as prophylaxis or therapy.

In one embodiment, Lovenox or enoxaparin sodium solution or heparin nanoparticles or pegylated heparin nanoparticles, or heparin mimetics is prepared at 1-100 mg/ml at pH of 5.5-7.5 alone as powder, inhalation dose from 0.1 mg to 20 mg or more daily solution or polymeric nanoparticles for slow release poly (lactic glycolic) acid or in combination or sequentially with 1-2 antivirals and a decongestant administered in a physiological solution or semifluorinated alkane or a physiological liquid intra-nasally or by an inhaler to treat COVID-19 as prophylaxis or therapy.

In one embodiment, Lovenox or enoxaparin sodium solution or pegylated emoxaparin nanoparticles, or heparin mimetics, such as PG-500 or PG-545, are prepared at 1-100 mg/ml at pH of 5.5-7.5 alone as powder, or spray for Inhalation dose from 0.1 mg to 20 mg or more daily solution or polymeric nanoparticles for slow release or in combination or sequentially with 1-2 or more antivirals, Wnt inhibitor ivermectin or niclosamide, GSK inhibitor or anti-integrins and a decongestant administered in a physiological solution or semifluorinated alkane with an additional solvent, such as polyethylene glycol (PEG) or ethanol or a physiological liquid intra-nasally or by an inhaler, such as a delivery device selected from the group consisting of a nebulizer, an inhaler, or an aerolizer, ultrasonic nebulizer, jet nebulizer, to treat (SARS-CoV-2), COVID-19 or their mutations and other viral respiratory diseases as prophylaxis or therapy.

In one embodiment, Lovenox or enoxaparin sodium or pegylated enoxaparin nanoparticles or heparin mimetics solution is prepared at 1-100 mg/ml at pH of 5.5-7.5 alone as powder, inhalation dose from 0.1 mg to 20 mg or more daily solution or polymeric antibody-coated pluralities of nanoparticles for slow release or in combination or sequentially with 1-2 or more antivirals, Wnt inhibitor ivermectin or niclosamide, GSK inhibitor or anti-integrins or TNF alpha inhibitors Baricitinib, a Janus kinases inhibitor, and/or IL-1β inhibitors, such as canakinumab or DMF, and a decongestant with or without stabilized hypochlorous acid solution at pH 5-7 or sodium hypochlorite solution or administered in a physiological solution or semifluorinated alkane with an additional solvent such as polyethylene glycol (PEG) or alcohol or a physiological liquid intra-nasally with or without an antibiotic ointment applied to the nasal passages or by an inhaler, ultrasonic nebulizer, jet nebulizer to treat (SARS-CoV-2), COVID-19 or their mutations or other viruses as prophylaxis or therapy of respiratory viral infection or viral encephalitis or severe vasculitis.

In one embodiment, Lovenox or enoxaparin sodium solution or anther Anticoagulants heparin is prepared at 1-100 mg/ml at a pH of 5.5-7.5 alone or in combination or sequentially with 1-2 antivirals such as remdesivir and one protease inhibitor or other anti-virals, such as ganciclovir or acyclovir or valacyclovir, Cidofovir, Vidarabine, Penciclovir, Foscarnet Fomivirsen Famciclovir or Oseltamivir phosphate, Rimantadine, Amantadine, Zanamivir, Telbivudine, Lamivudine, Entecavir, Emtricitabine, capsid inhibitor GS-6207 (Lenacapavir), Adefovir, IL6 inhibitor, administered in a physiological solution or semifluorinated alkane or a physiological liquid intranasally as slow release polymeric nanoparticles for topical application in viral keratitis as topical drops, spray or inhalation in inflammatory vasculitis of the brain or the lung or topical application in the eye.

In one embodiment, Lovenox or enoxaparin sodium solution or another anticoagulant, heparin or heparin nanoparticles is prepared at 10-100 mg/ml at a pH of 5.5-7.5 as powder, solution or polymeric nanoparticles for slow release, alone or in combination or sequentially with 1-2 antivirals and remdesivir that blocks virus replication and one protease inhibitor or other anti-virals with or without stabilized hypochlorous acid, NCT of up to 0.5 mM concentration or sodium hypochlorite for inhalation or topic intranasal application, in treatment of viral diseases of the eye, nose, upper and lower respiratory disease and viral cerebral vasculitis or orally with or without DMF for intestinal complication of COVID-19.

In one embodiment, Lovenox or enoxaparin sodium solution or another anticoagulant, heparin or heparin or heparin mimics containing glucosamine saccharides and acrylamide antibody-coated nanoparticles is prepared at 10-100 mg/ml at a pH of 5.5-7.5 as powder, solution or in combination or sequentially with 1-2 or more antivirals and remdesivir that blocks virus replication and one protease inhibitor or other anti-virals with or without stabilized hypochlorous acid (NaCLO), N-chlorotaurine (NTC), dimethylated derivatives of NCT (N-chloro-2,2-dimethyltaurine [DM-NCT] and N,N-dichloro-2,2-dimethyltaurine [DM-NDCT] nanoparticles or sodium hypochlorite at 0.05-1.5 wt %; or more or hypochlorous acid (HCLO) in combination with water or semifluorinated alkanes at similar concentrations or stabilized hypochlorous acid 0.10% for inhalation or for topic intranasal application along with an antibiotic ointment applied with or without Ebselen and or glutathione peroxidase and superoxide dismutase (SOD)—requiring additional zinc, or manganese, for ideal catalytic activity applied to the nasal passages, in treatment of viral, bacterial diseases of the eye, nose, upper and lower respiratory disease and viral cerebral vasculitis where endothelial cell of the vessels are damaged by the released cytokine, or orally for intestinal complication of (SARS-CoV-2), COVID-19 or their mutations in Multisystem Inflammatory Syndrome in Children (MIS-C).

In one embodiment, low molecular weight heparin or pegylated heparin nanoparticles at 0.01 mg to 300 mg·ml solution, preferably 0.05-0.1 wt % or 1-10 mg/ml is used alone or in combination with DMF at microgram to milligram concentrations, doxycycline at concentrations of 0.5%-10% doxycycline alone or in combination with sodium hypochlorite of 0.001-2 wt % or hypochlorous acid, N-chlorotaurine (NTC), dimethylated derivatives of NCT (N-chloro-2,2-dimethyltaurine [DM-NCT] and N,N-dichloro-2,2-dimethyltaurine [DM-NDCT] nanoparticles, or with or without probenecid in water or semifluorinated alkanes with additional solvents, such as polyethylene glycol (PEG) or ethanol as topical, mucosal, oral, intranasal, inhalation, etc. an antibiotic ointment, such as doxycycline, applied to the nasal passages to treat bacterial or viral conjunctivitis or nasal and respiratory tract, influenza, COVID-19, etc., viral, RNA or DNA viruses including prions or bacterial respiratory infection or cerebral vasculitis, necrotizing scleritis, encephalitis, intestinal multisystem disease in (SARS-CoV-2), COVID-19, or their mutations In one embodiment, low molecular weight heparin or heparin antibody-coated pluralities of nanoparticles at 0.01 mg to 300 mg·ml solution, preferably 0.05-0.1 wt % or 1-10 mg/ml is used alone or in combination with doxycycline at concentrations of 0.5%-10% doxycycline alone or with dexamethasone 400-2000 mg/ml in combination or sequentially in water of semifluorinated alkanes with or without probenecid as topical, mucosal, oral, intranasal, tetracycline derivatives, an antibiotic ointment etc. applied to the nasal passages by inhalation, etc. act simultaneously as an antiviral, antibacterial, and an anti-inflammatory in respiratory viral infections, anti-inflammatory or as topical drops in the eye for ocular and adnexal inflammation or uveitis or scleritis.

In one embodiment, low molecular weight heparin or heparin mimics containing glucosamine saccharides and acrylamide to bind to 13-Secretase (BACE-1) involved in Alzheimer's disease (AD) or pegylated heparin nanoparticles at 0.01 mg to 300 mg·ml solution, preferably 0.05-0.1 wt % or 1-10 mg/ml is used as spray or aerosolized for inhalation alone or in combination with doxycycline at concentrations of 0.5%-10% doxycycline alone or with dexamethasone 400-2000 mg/ml in water or semifluorinated alkanes with an additional solvent, such as polyethylene glycol (PEG) or alcohol as topical, mucosal, oral, intranasal, inhalation, or the use of inhalator to treat vascular endothelial cell damage in the lung or in the brain, etc. by preventing COVID-19 or other viruses to attach to the endothelial cell wall, prevent complement factors activation, and causing damage and subsequent attachment of the platelets and blood clot formation.

In one embodiment, one administers subcutaneously or intravenously, etc. low molecular weight heparin or heparin mimetics combined with LY6E, a naturally occurring protein in the body, to prevent the virus attachment to the ACE-2 receptors and inhibition of virus to enter the endothelial cells and damage them in respiratory viral infection or viral brain encephalitis through an inhalation preparation or intravenously or subcutaneously.

In one embodiment of a case of conjunctivitis or viral or bacterial respiratory or brain infection, one can administer topically or spray for inhalation a combination or sequentially with mycophenolic acid an IL-17 inhibitor or cyclosporine as antiviral and anti-inflammatory and an antiviral agent in a 0.5-1 mg/ml physiological solution or semifluorinated alkanes, as emulsion or micelles or nanomicelles, liposomes, or oil in water, with 0.001-20 or more mg/ml of low molecular weight heparin or heparin mimetics, or heparin antibody-coated pluralities of nanoparticles and at least one or more antivirals, in combination or sequentially topically or for inhalation or with Lifitegrast at concentration of 1 mg/ml or dexamethasone, at 10 microgram/ml to 4 mg/ml one-three times to five times a day or more or 1-2 drops a day, with doxycycline and minocycline to reduce bacterial spread, and act as anti-inflammatory agents, etc.

In one embodiment, all accessible body cavities involved with a viral or bacterial infection, such as the bladder, uterus, abdominal cavity, eye, or CNS cavities or in the joint or subcutaneously can be treated with non-toxic doses of the above described preparations in a non-toxic dose along with TNF alpha inhibitor Baricitinib, a Janus kinase inhibitor or IL-beta inhibitors or DMF in a physiological solution or semifluorinated alkane or a physiological liquid by intracavity administration or injection or intravenously or intraarterial as is needed and prevent post encephalitis induced dementia.

In one embodiment using intranasal delivery to the brain takes a shorter and faster route than the systemic administration. Since the blood vessel are separated from the brain by the presence of the blood brain barrier. In addition the nasal delivery bypasses the general circulation that brings polymeric slow release nanoparticles to the liver where they are taken up from circulation and never reach the brain.

In one embodiment, at least two antivirals used in an appropriate medium at a lower concentration that is administered alone to increase effectiveness of the preparation against the viral infection while reducing their toxicity and treat a viral infection.

In one embodiment, at least two antivirals PEGylated or non-PEGylated are combined with one or more protease inhibitors or polymerase inhibitors with LMWH, or mycophenolic acid to increase effectiveness of the preparation against the viral infection while reducing their toxicity and treat a viral infection.

In one embodiment, at least two antivirals are combined with anti-inflammatory agents such as Baricitinib, DMF, complement inhibitors (C1,C3,C5) and one pathway inhibitor sequentially or as a cocktail at reduced concentrations to increase their efficacy and reduced their side effects.

In one embodiment, at least two antivirals are combined or applied sequentially with LMWH or a heparin mimetic with catechins to prevent attachment of the virus to the cell membrane receptors, the medication is administered intravenous or inside a body cavity or preferably as a spray, inhalation through an inhaler, through the nose such as nebulizer, a dry powder inhaler, liquid or suspension inhaler, breath actuated nebulizer, injector, topically, orally, intramuscularly, locally, or as described by Peyman U.S. Pat. Nos. 7,678,078 and 10,272,035, where the container is filled with a defined amount of semifluorinated alkane and nanoparticle emulsion and appropriate medication using compressed oxygen instead of air to spray the semifluorinated/medication as a fine spray or in nebulized form in the nasal cavity or mouth while the person inhales.

Any of the features, attributes, or steps of the above described embodiments and variations can be used in combination with any of the other features, attributes, and steps and routes of administration of the above described embodiments and variations as desired.

Although the invention has been shown and described with respect to a certain embodiment or embodiments, it is apparent that this invention can be embodied in many different forms and that many other modifications and variations are possible without departing from the spirit and scope of this invention.

Moreover, while exemplary embodiments have been described herein, one of ordinary skill in the art will readily appreciate that the exemplary embodiments set forth above are merely illustrative in nature and should not be construed as to limit the claims in any manner. Rather, the scope of the invention is defined only by the appended claims and their equivalents, and not, by the preceding description.

The invention claimed is:

1. A method of treating a respiratory infection caused by SARS-CoV-2 or a variant of SARS-CoV-2, in a human in need thereof, the method comprising:
   administering to the human, via nasal inhalation, a pharmaceutical composition comprising effective amounts of remdesivir and umifenovir; and
   co-administering to the human an effective amount of a cell pathway inhibitor selected from the group consisting of a rho-associated protein kinase (ROCK) inhibitor, a Wnt inhibitor, a glycogen synthase kinase 3 (GSK-3) inhibitor, an integrin inhibitor, an interleukin-1 (IL-1) inhibitor, an interleukin-6 (IL-6) inhibitor, a transforming growth factor beta (TGFB) inhibitor, and combinations thereof.

2. The method according to claim 1, wherein the pharmaceutical composition further comprises a semifluorinated alkane and polymeric slow release nanoparticles or microparticles as a carrier.

3. The method according to claim 2, wherein the polymeric slow release nanoparticles or microparticles are conjugated with a viral specific antibody.

4. The method according to claim 1, wherein the method further comprises:
co-administering one or more protease inhibitors to the human.

5. The method according to claim 1, wherein the method further comprises:
co-administering tocilizumab or tamoxifen to the human.

6. The method according to claim 1, wherein the cell pathway inhibitor is administered to the human by nasal inhalation.

7. The method according to claim 1, wherein the method further comprises:
co-administering interferon or pegylated interferon to the human.

8. The method according to claim 1, wherein the method further comprises:
co-administering a TMPRSS2 inhibitor, an ACE-2 inhibitor, and/or a neuropilin inhibitor to the human.

9. The method according to claim 1, wherein the method further comprises:
co-administering a low molecular weight heparin or synthetic heparin mimetics in combination with a macrolide to the human.

10. The method according to claim 9, wherein the macrolide comprises cyclosporine A.

11. The method according to claim 1, wherein the method further comprises co-administering a polyphenol to the human.

12. The method according to claim 11, wherein the polyphenol is selected from the group consisting of epigallocatechin gallate (EGCG), green tea, and catechin.

13. The method according to claim 1, wherein the method further comprises:

co-administering a polyclonal antibody cocktail to the human.

14. The method according to claim 1, wherein the method further comprises:

co-administering methylene blue to the human.

15. The method according to claim 1, wherein the method further comprises:

co-administering a low molecular weight heparin to the human.

16. The method according to claim 1, wherein the method further comprises:

co-administering dimethyl fumarate to the human.

17. The method according to claim 1, wherein the method further comprises:

co-administering mycophenolic acid or metalloproteinase inhibitors to the human.

18. The method according to claim 1, wherein the method further comprises:

co-administering an anti-vascular endothelial growth factor medication to the human.

19. The method according to claim 1, wherein the cell pathway inhibitor is a rho-associated protein kinase (ROCK) inhibitor.

20. The method according to claim 1, wherein the cell pathway inhibitor is a Wnt inhibitor.

21. The method according to claim 1, wherein the cell pathway inhibitor is a glycogen synthase kinase 3 (GSK-3) inhibitor.

22. The method according to claim 1, wherein the cell pathway inhibitor is an integrin inhibitor.

23. A method of treating, reducing, or alleviating a medical condition in a patient, the method comprising:

administering to a patient in need thereof a biocompatible drug comprising one or more antiviral medications together with one or more cell pathway inhibitors, the patient having a respiratory tract inflammatory disease and at least one of a central nervous system inflammatory disease and vasculitis, the one or more antiviral medications performing at least two of the following functions: (i) preventing an attachment of viruses to cell walls, (ii) blocking a penetration of the viruses into cells, (iii) inhibiting virus replication by damaging nucleic acids of the viruses, (iv) interfering in assembly of viral capsids, and (v) inhibiting viral reverse transcriptase, and the one or more cell pathway inhibitors blocking an inflammatory response of inflamed lung, brain, and/or vascular tissue without inhibiting an immune response of the patient;

administering methylene blue, which acts as antioxidant and converts methemoglobin to hemoglobin and acts as an antiviral at a concentration of 0.25-2 mg/liter or less than 1 nM concentration, together with the one or more antiviral medications and the one or more cell pathway inhibitors;

administering low molecular weight heparin to the patient to prevent blood coagulation; and performing dialysis, hemodialysis, or serum electrophoresis to remove unwanted toxins and creatinine and simultaneously acting to prevent blood clotting after administration of the methylene blue and the low molecular weight heparin;

wherein the administration of the biocompatible drug to the patient treats the respiratory tract inflammatory disease and the at least one of the central nervous system inflammatory disease and the vasculitis, reduces the symptoms associated with the respiratory tract inflammatory disease and the at least one of the central nervous system inflammatory disease and the vasculitis, and/or alleviates the respiratory tract inflammatory disease and the at least one of the central nervous system inflammatory disease and the vasculitis; and wherein the methylene blue together with the one or more antiviral medications and the one or more cell pathway inhibitors are conjugated with pluralities of gold nanoparticles to enhance viral damage upon administration to the patient.

* * * * *